US008431376B2

(12) United States Patent
Jarvis et al.

(10) Patent No.: US 8,431,376 B2
(45) Date of Patent: Apr. 30, 2013

(54) BACTERIAL REPLICATION SYSTEMS AND METHODS

(75) Inventors: Thale Cross Jarvis, Boulder, CO (US); Charles S. McHenry, Denver, CO (US); Nebojsa Janjic, Boulder, CO (US); Garry Dallmann, Boulder, CO (US); James M. Bullard, Longmont, CO (US); Stacie Bell, Louisville, CO (US); Glenn Sanders, Boulder, CO (US); Frank Dean, Broomfield, CO (US)

(73) Assignee: The Regents of the University of Colorado, Denver, CO (US)

( * ) Notice: Subject to any disclaimer, the term of this patent is extended or adjusted under 35 U.S.C. 154(b) by 1138 days.

(21) Appl. No.: 11/568,286

(22) PCT Filed: Apr. 26, 2005

(86) PCT No.: PCT/US2005/015548
§ 371 (c)(1),
(2), (4) Date: Sep. 29, 2009

(87) PCT Pub. No.: WO2006/071255
PCT Pub. Date: Jul. 6, 2006

(65) Prior Publication Data
US 2010/0028862 A1    Feb. 4, 2010

Related U.S. Application Data

(60) Provisional application No. 60/565,612, filed on Apr. 26, 2004, provisional application No. 60/568,890, filed on May 7, 2004, provisional application No. 60/569,540, filed on May 7, 2004, provisional application No. 60/607,550, filed on Sep. 8, 2004, provisional application No. 60/609,662, filed on Sep. 14, 2004, provisional application No. 60/623,564, filed on Oct. 28, 2004, provisional application No. 60/623,566, filed on Oct. 28, 2004, provisional application No. 60/623,562, filed on Oct. 28, 2004, provisional application No. 60/641,706, filed on Jan. 6, 2005.

(51) Int. Cl.
*C12N 9/00* (2006.01)

(52) U.S. Cl.
USPC .......................................................... 435/183

(58) Field of Classification Search ........................ None
See application file for complete search history.

(56) References Cited

U.S. PATENT DOCUMENTS

| | | | |
|---|---|---|---|
| 5,583,026 | A | 12/1996 | O'Donnell |
| 5,668,004 | A | 9/1997 | O'Donnell |
| 2003/0129633 | A1 | 7/2003 | O'Donnell et al. |
| 2003/0219737 | A1 | 11/2003 | Bullard et al. |
| 2004/0235766 | A1* | 11/2004 | Bullard et al. .................. 514/44 |

FOREIGN PATENT DOCUMENTS

| | | |
|---|---|---|
| WO | WO 02/34936 | 5/2002 |
| WO | WO 02/092769 | 11/2002 |
| WO | WO 02092769 A2 * | 11/2002 |

OTHER PUBLICATIONS

Bullard et al. (2002) A Three-domain Structure for the delta Subunit of the DNA Polymerase III Holoenzyme; delta Domain III Binds delta' and Assembles into the DnaX Complex. *J. Biol. Chem.* 277: 13246-13256.
Carter et al. (1992) Molecular Cloning Sequencing and Overexpression of the Structural Gene Encoding the δ Subunit of *Escherichia coli* DNA Polymerase III Holoenzyme. J Bacteriol 174: 7013-7025.
Carter et al. (1993) Identification, Isolation, and Characterization of the Structural Gene Encoding the δ' Subunit of *Escherichia coli* DNA Polymerase III Holoenzyme. *J Bacteriol* 175: 3812-3822.
Cull and McHenry (1990) Preparation of Extracts from Prokaryotes. *Methods Enzymol.* 12: 147-154 Academic Press, New York.
Dallmann et al. (1995) DnaX Complex of *Escherichia coli* DNA Polymerase III Holoenzyme: Physical Characterization of the DnaX Subunits and Complexes. *J Biol Chem* 270: 29563-29569.
Glover and McHenry (1998) *J. Biol. Chem.* 273, 23476-23484.
Johanson et al. (1986) Chemical Characterization and Purification of the β Subunit of the DNA Polymerase III Holoenzyme From an Overproducing Strain. *J. Biol. Chem.* 261, 11460-11465.
Kelman et al. (1998) *EMBO J.* 17, 2436-2449.
Kim and McHenry (1996) In Vivo Assembly of Overproduced DNA Polymerase III: Overproduction, Purification, and Characterization of the α, α-ε, and α-ε-θ Subunits. *J. Biol. Chem.* 271: 20681-20689.
Lohman et al. (1986) *Biochemistry* 25, 21-25.
Masai and Arai (1995) Dna-A Dependent Assembly of the ABC Primosome at the A Site, a Single-Stranded DNA Hairpin-Containing a dnaA Box. *Eur. J. Biochem.* 230:384-395.
Masai et al. (1990) The ABC primosome: A Novel Priming System Employing dnaA, dnaB, dnaC and Primase on a Hairpin Containing a dnaA Box Sequence. *J. Biol. Chem.* 265:15134-15144.
McHenry and Crow (1979) DNA Polymerase III of *Escherichia coli*: Purification and Identification of Subunits. *J. Biol. Chem.* 254: 1748-1753.
Meinkoth et al. (1984) *Anal. Biochem.* 138, 267-284.
Olson et al. (1995) DnaX-Complex of *Escherichia coli* DNA Polymerase III Holoenzyme: The χψ Complex Functions by Increasing the Affinity of τ and γ for δ-δ' to a Physiologically Relevant Range. *J. Biol. Chem.* 270: 29570-29577.
Pritchard et al. (1996) In Vivo Assembly of the τ-Complex of the DNA Polymerase III Holoenzyme Expressed from a Five-Gene Artificial Operon: Cleavage of the τ-Complex to Form a Mixed γ-τ-Complex by the OmpT Protease. *J. Biol. Chem.* 271: 10291-10298.

(Continued)

*Primary Examiner* — Christopher M. Babic
(74) *Attorney, Agent, or Firm* — Swanson & Bratschun, L.L.C.

(57) ABSTRACT

Reconstituted bacterial replication assemblies and methods for their use are provided.

1 Claim, 17 Drawing Sheets

OTHER PUBLICATIONS

Sambrook et al., Molecular Cloning: A Laboratory Manual, Cold Spring Harbor Labs Press, 1989.
Seville et al. (1996) Fluorometric Assay for DNA Polymerases and Reverse Transcriptase. *Biotechniques* 21: 664-672.
Stamford et al. (1992) *Biochim. Biophys. Acta* 1132, 17-25.
Swart and Griep (1993) *J. Biol. Chem.* 268, 12970-12976.
Tsuchihashi and Kornberg (1990) Translational Frameshifting Generates the γ Subunit of DNA Polymerase III Holoenzyme. *Proc. Natl. Acad. Sci. U.S.A.* 87: 2516-2520.

* cited by examiner

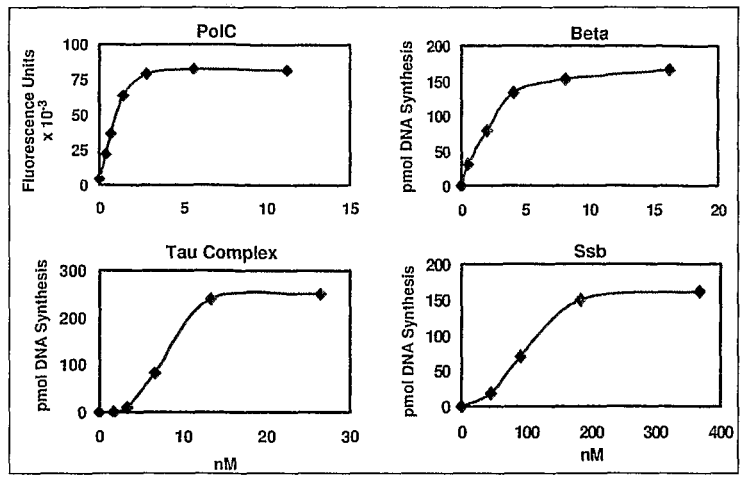
Figure 9A, B, C, D
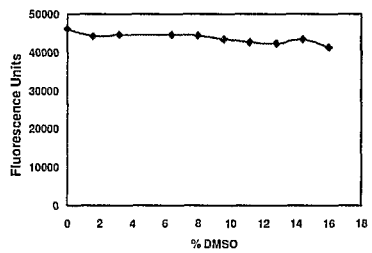
Figure 10A
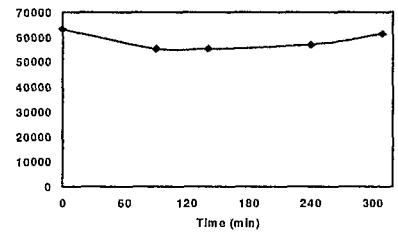
Figure 10B
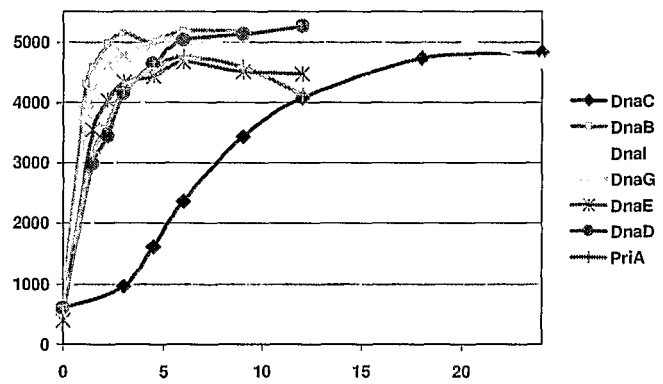
Figure 11

PA4679 nucleotide sequence (*Pseudomonas aeruginosa* genome sequence range 5248771-5248070)
GTGCCTGTGCGTGCGCGCGCCGCGATCGATGCGCCGCAGGCCCGCGTCCCGCAAGCCGAGGCGCC
GGCCAGCGCGCCGAGCGTGGCTCCCGCCGCGCCCGTGGAAGGCCGGGGGATCCCGATCAGCCTGC
CGAAGCCGGGCGCCCCGGCGGCGAAGAAAGCCGAGCCGGTCGCGCCGGTCGAAGAGGCCCCGGC
CGAGTCGCCGGCGGTCCAGGCCCCGCCGCCGCGCTTCGCCTTGCAACTGCTGCAGGCGGGCTCCTG
CACCCTGCTGGTCGAACTGCCCACCGGCGAACCCTTCGCCAGCCGCGATCCGGGTTACCTGCTGCT
GCGCGACCTGCTGCGCGCCGCCGGCCTGCCGGACAGCCCGCGGCTGATCGGCGAACCGGTACGCT
GGCCGCTGCTGGCGCGCGGCAACCTCGACCAGGGGCCGCAGGCGGCCCTGGAGTTCGTCCAGAGC
TTCGTCGCCGCGCGCATGGAGGAGAGCGAGCGTAGCCGCTGCCTGTGGTTGGTCGGCCTGCCGGC
GATCCGCTTCGCCGGCGAGGGCGACGAGGGCAGCCTGTTCCGCGAGCTGCAGGTGGACGGTCTGG
GCGCAACCTGGGCCGTGCCAGGCCTGGAAGCCCTCATGGAAGAACCCGCCCTCAAGGGCGAGCTG
TGGCGCGCCATGCGCCGTGTCCGTCAGCGCTGGTCGAGCGAGATTCAATGA (SEQ ID NO:29)

Predicted amino acid sequence of protein encoded by PA4679:
MPVRARAAIDAPQARVPQAEAPASAPSVAPAAPVEGRGIPISLPKPGAPAAKKAEPVAPVEEAPAESPA
VQAPPPRFALQLLQAGSCTLLVELPTGEPFASRDPGYLLLRDLLRAAGLPDSPRLIGEPVRWPLLARGNL
DQGPQAALEFVQSFVAARMEESERSRCLWLVGLPAIRFAGEGDEGSLFRELQVDGLGATWAVPGLEA
LMEEPALKGELWRAMRRVRQRWSSEIQ (SEQ ID NO:31)

Figure 25A

PA4679N32 nucleotide sequence (*Pseudomonas aeruginosa* genome sequence range 5248867-5248070)
**ATGCAGATAACCAGTTGGCTGCCCCGCCAGCCGTTGCCGTTCGCCGCACCCTCGCGGCCGG
AGTTGCTGGAGACCCCGCCCCGGGAAGAGCCGGCGGT**GCCTGTGCGTGCGCGCGCCGCGATCG
ATGCGCCGCAGGCCCGCGTCCCGCAAGCCGAGGCGCCGGCCAGCGCGCCGAGCGTGGCTCCCGCC
GCGCCCGTGGAAGGCCGGGGGATCCCGATCAGCCTGCCGAAGCCGGGCGCGCCCCGGCGGCGAAGA
AAGCCGAGCCGGTCGCGCCGGTCGAAGAGGCCCCGGCCGAGTCGCCGGCGGTCCAGGCCCCGCCG
CCGCGCTTCGCCTTGCAACTGCTGCAGGCGGGCTCCTGCACCCTGCTGGTCGAACTGCCCACCGGC
GAACCCTTCGCCAGCCGCGATCCGGGTTACCTGCTGCTGCGCGACCTGCTGCGCGCCGCCGGCCTG
CCGGACAGCCCGCGGCTGATCGGCGAACCGGTACGCTGGCCGCTGCTGGCGCGCGGCAACCTCGA
CCAGGGGCCGCAGGCGGCCCTGGAGTTCGTCCAGAGCTTCGTCGCCGCGCGCATGGAGGAGAGCG
AGCGTAGCCGCTGCCTGTGGTTGGTCGGCCTGCCGGCGATCCGCTTCGCCGGCGAGGGCGACGAG
GGCAGCCTGTTCCGCGAGCTGCAGGTGGACGGTCTGGGCGCAACCTGGGCCGTGCCAGGCCTGGA
AGCCCTCATGGAAGAACCCGCCCTCAAGGGCGAGCTGTGGCGCGCCATGCGCCGTGTCCGTCAGC
GCTGGTCGAGCGAGATTCAATGA (SEQ ID NO:32)

Predicted amino acid sequence of the protein encoded by PA4679N32:
MQITSWLPRQPLPFAAPSRPELLETPPREEPAVPVRARAAIDAPQARVPQAEAPASAPSVAPAAPVE
GRGIPISLPKPGAPAAKKAEPVAPVEEAPAESPAVQAPPPRFALQLLQAGSCTLLVELPTGEPFASRDPG
YLLLRDLLRAAGLPDSPRLIGEPVRWPLLARGNLDQGPQAALEFVQSFVAARMEESERSRCLWLVGLP
AIRFAGEGDEGSLFRELQVDGLGATWAVPGLEALMEEPALKGELWRAMRRVRQRWSSEIQ (SEQ ID
NO:34)

Figure 25B

PA4679N45 nucleotide sequence (*Pseudomonas aeruginosa* genome sequence range 5248906-5248070):
*TTGATCGAAGAACAGCGTCGCCGCGCCTTCCTGGGCGCGA TGCAGATAACCAGTTGGCTGCCCC
GCCAGCCGTTGCCGTTCGCCGCACCCTCGCGGCCGGAGTTGCTGGAGACCCCGCCCCGGGA*
AGAGCCGGCGGTGCCTGTGCGTGCGCGCGCCGCGATCGATGCGCCGCAGGCCCGCGTCCCGCAA
GCCGAGGCGCCGGCCAGCGCGCCGAGCGTGGCTCCCGCCGCGCCCGTGGAAGGCCGGGGGATCCC
GATCAGCCTGCCGAAGCCGGGCGCCCCGGCGGCGAAGAAAGCCGAGCCGGTCGCGCCGGTCGAA
GAGGCCCCGGCCGAGTCGCCGGCGGTCCAGGCCCCGCCGCCGCGCTTCGCCTTGCAACTGCTGCA
GGCGGGCTCCTGCACCCTGCTGGTCGAACTGCCCACCGGCGAACCCTTCGCCAGCCGCGATCCGGG
TTACCTGCTGCTGCGCGACCTGCTGCGCGCCGCCGGCCTGCCGGACAGCCCGCGGCTGATCGGCGA
ACCGGTACGCTGGCCGCTGCTGGCGCGCGGCAACCTCGACCAGGGGCCGCAGGCGGCCCTGGAGT
TCGTCCAGAGCTTCGTCGCCGCGCGCATGGAGGAGAGCGAGCGTAGCCGCTGCCTGTGGTTGGTC
GGCCTGCCGGCGATCCGCTTCGCCGGCGAGGGCGACGAGGGCAGCCTGTTCCGCGAGCTGCAGGT
GGACGGTCTGGGCGCAACCTGGGCCGTGCCAGGCCTGGAAGCCCTCATGGAAGAACCCGCCCTCA
AGGGCGAGCTGTGGCGCGCCATGCGCCGTGTCCGTCAGCGCTGGTCGAGCGAGATTCAATGA
(SEQ ID NO:35)

Predicted amino acid sequence of the protein encoded by PA4679N45:
*LIEEQRRRAFLGAMQITSWLPRQPLPFAAPSRPELLETPPREEPA*VPVRARAAIDAPQARVPQAEAP
ASAPSVAPAAPVEGRGIPISLPKPGAPAAKKAEPVAPVEEAPAESPAVQAPPPRFALQLLQAGSCTLLVE
LPTGEPFASRDPGYLLLRDLLRAAGLPDSPRLIGEPVRWPLLARGNLDQGPQAALEFVQSFVAARMEES
ERSRCLWLVGLPAIRFAGEGDEGSLFRELQVDGLGATWAVPGLEALMEEPALKGELWRAMRRVRQR
WSSEIQ (SEQ ID NO:37)

Figure 25C

| PolC Peptide | Amino Acid Sequence |
|---|---|
| Upper Band | MTEQQKFKVL |
| Middle Band | MKAEKAKQQD |
| Lower Band | MMMSDIEEIK |

Figure 32

```
     ThrGluLysL euGluLysMe tLysAlaGlu LysAlaLysG lnGlnAspAsn
568  ACAGAGAAAC TTGAAAAAAT GAAAGCTGAA AAAGCGAAAC AACAAGATAA
     TGTCTCTTTG AACTTTTTTA CTTTCGACTT TTTCGCTTTG TTGTTCTATT
```

Figure 33

```
     ThrGluLysL euGluLysMe tLysAlaGlu LysAlaLysG lnGlnAspAsn
568  ACTGAAAAAC TTGAAAAAAT GAAAGCTGAA AAAGCGAAAC AACAAGATAA
     TGACTTTTTG AACTTTTTTA CTTTCGACTT TTTCGCTTTG TTGTTCTATT
```

Figure 34

```
     .IleArgAsp LeuValMetM etMetSerAs pIleGluGlu IleLysLys.
918  TATTAGAGAT TTAGTTATGA TGATGTCTGA TATTGAAGAG ATTAAAAAAG
     ATAATCTCTA AATCAATACT ACTACAGACT ATAACTTCTC TAATTTTTTC
```

Figure 35

```
        .IleArgAsp LeuValMetM etMetSerAs pIleGluGlu IleLysLys.
918     TATTCGCGAT TTAGTTATGA TGATGTCTGA TATTGAAGAG ATTAAAAAAG
        ATAAGCGCTA AATCAATACT ACTACAGACT ATAACTTCTC TAATTTTTC
```

1. Fraction I
2. A.S. 30-50%
3. Heparin pool
4. DEAE pool
5. Q Sepharose pool
6. Gel Filtration pool
7. Size Markers

BACTERIAL REPLICATION SYSTEMS AND METHODS

RELATED APPLICATIONS

This application is a 35 U.S.C. §371 national phase application of PCT/US2005/015548 (WO2006-071255) filed Apr. 26, 2005, entitled "Bacterial Replication Systems and Methods," which application claims priority to U.S. Provisional Application Ser. No. 60/565,612 filed Apr. 26, 2004; U.S. Provisional Application Ser. No. 60/568,890 filed May 7, 2004; U.S. Provisional Application Ser. No. 60/569,540 filed May 7, 2004; U.S. Provisional Application Ser. No. 60/607,550 filed Sep. 8, 2004; U.S. Provisional Application Ser. No. 60/641,706 filed Jan. 6, 2005; U.S. Provisional Application Ser. No. 60/623,564 filed Oct. 28, 2004; U.S. Provisional Application Ser. No. 60/609,662 filed Sep. 14, 2004; U.S. Provisional Application Ser. No. 60/623,566 filed Oct. 28, 2004; and U.S. Provisional Application Ser. No. 60/623,562 filed Oct. 28, 2004.

FIELD OF THE INVENTION

The present invention relates to bacterial DNA polymerase subunit proteins bacterial DNA replication systems and their use in screening potential antibacterial compounds.

BACKGROUND OF THE INVENTION

The fundamental mechanisms of DNA replication have been conserved throughout biology. The chemistry and direction of synthesis, the requirement for RNA primers, the mechanisms of semi-discontinuous replication with Okazaki fragments on the lagging strand and the need for well-defined origins are shared. The basic features of the replicative apparatus are also shared. All cells, both eukaryotic and prokaryotic, contain multiple DNA polymerases. Yet, only a subset of these polymerases can function as the replicative catalytic subunit.

In *E. coli*, Pol III holoenzyme is composed of ten different types of subunits that function in concert to perform highly rapid and processive DNA chain elongation from a primed template. The $\alpha$ subunit serves as the polymerization subunit; $\epsilon$ catalyzes a 3'-5' exonuclease activity that is necessary for proofreading. $\theta$ binds to the N-terminal region of $\epsilon$. Together, $\alpha$, $\epsilon$ and $\theta$ associate tightly to form Pol III. The $\beta$ subunit confers high processivity. It consists of a bracelet-shaped molecule that clamps around DNA, contacting the polymerase and preventing it from falling off of the template, ensuring high processivity. The asymmetric DnaX complex is responsible for transferring the sliding clamp onto a primer-terminus in an ATP-dependent reaction. The native holoenzyme appears to employ a DnaX complex containing two copies of the $\tau$ subunit and one copy of the shorter $\gamma$ variant along with ancillary subunits ($\tau_2\gamma_1\delta\delta'\chi\psi$). The dnaX gene expresses two related proteins; $\tau$ is the full length protein and $\gamma$ is a truncated version formed by frameshifting during translation of dnaX. $\tau$ binds the $\alpha$ subunit of DNA polymerase III and causes it to dimerize, forming the scaffold upon which other auxiliary proteins can assemble to form a dimeric replicative complex. $\delta$ and $\delta'$ are required for processive elongation in addition to their role in initiation complex formation. $\chi$ forms a 1:1 heterodimeric complex with $\psi$. $\chi\psi$ binds tightly to domain III of $\gamma$, while $\chi$ alone does not bind to $\gamma$. The interaction of $\psi$ and $\gamma$ is probably mediated through the conserved N-terminal region of $\psi$. $\chi\psi$ confers resistance to high salt on DNA synthesis catalyzed by holoenzyme, and this salt resistance requires the presence of SSB. $\chi$ interacts with C-terminus of SSB and enhances the binding of SSB to DNA, thereby preventing premature dissociation of SSB from the lagging strand and increasing holoenzyme processivity.

Bacterial DNA replication has long been recognized as an attractive target system for new antibacterials. It is an essential process and stalled DNA replication can trigger cell death. The bacterial DNA replication complex is target-rich and involves as much as 6% of the essential proteins in bacteria, and its proper functioning is based on multiple, dynamic enzyme-substrate, protein-protein, and protein-DNA interactions. Replication proteins tend to be highly conserved among bacteria but substantially different from eukaryotic systems at the amino acid sequence level, which may facilitate the identification of compounds that selectively disrupt bacterial DNA replication. With only a few copies per cell, the replication complex is a significant point of pathogen susceptibility and even very low concentrations of an inhibitor can shut down DNA replication.

*Pseudomonas aeruginosa* is a gram-negative bacterium is omnipresent in the environment in large part due to its propensity to grow on many different surfaces including tissues from plants and animals, rocks, soil as well as synthetic materials such as contact lens, surgical instruments and catheters. *Pseudomonas aeruginosa* causes a wide range of infections including bacteremia in urinary tract infections, burn victims and patients on respirators. In hospitals, *Pseudomonas aeruginosa* is responsible for about one-seventh of all infections with multidrug-resistant strains being increasingly common. The most serious medical problem caused by *Pseudomonas aeruginosa* are lung infections associated with cystic fibrosis (CF).

To date, published work relating to DNA replication in *P. aeruginosa* has focused on either characterization of the origin of replication or on the biophysical properties of the single-stranded binding protein (SSB).

Inhibition of bacterial DNA polymerase holoenzymes and other DNA replication-related processes will be beneficial in the treatment of bacterial infections especially against those organisms that have developed resistance to existing chemotherapeutics.

SUMMARY OF THE INVENTION

The present invention provides methods for identifying compounds that modulate the activity of a bacterial replication assembly, comprising contacting a DNA molecule capable of being replicated with a bacterial replication assembly with a test compound to form a reaction mixture; subjecting the reaction mixture to conditions, which in the absence of the compound, effect nucleic acid polymerization; and comparing the nucleic acid polymerization in the presence of the test compound with the nucleic acid polymerization in the absence of the test compound, wherein a change in the activity of the bacterial replication assembly in the presence of the test compound is indicative of a compound that modulates the activity of the bacterial replication assembly.

The present invention also provides methods for identifying compounds that modulate the activity of a bacterial replication assembly, comprising contacting each of a plurality of DNA molecules capable of being replicated with a bacterial replication assembly with a different test compound to form a plurality of reaction mixtures; subjecting the reaction mixtures to conditions, which in the absence of the compounds, effect nucleic acid polymerization; and comparing the nucleic acid polymerization in the presence of the test compounds with the nucleic acid polymerization in the absence of the test compounds, wherein a change in the activity of the bacterial replication assembly in the presence of any one compound is indicative of a compound that modulates the activity of the bacterial replication assembly.

In some embodiments, the bacterial replication assembly is selected from the group consisting of an *S. pyogenes* bacterial replication assembly, an *S. aureus* bacterial replication assembly, a *Y. pestis* bacterial replication assembly, a *P. aeruginosa* bacterial replication assembly, a *B. subtilis* bacterial replication assembly, and an *E. coli* bacterial replication assembly.

The present invention also provides a reconstituted bacterial replication assembly capable of functioning in a test for identifying compounds that modulate the ability of bacterial replication assembly to replicate DNA. In some embodiments, the reconstituted bacterial replication assembly comprises isolated DNA Polymerase III holoenzyme subunit proteins, including *Yersinia pestis* subunit proteins, *Staphylococcus aureus* subunit proteins, *Streptococcus pyogenes* subunit proteins, or *Pseudomonas aeruginosa* subunit proteins.

The present invention also provides a method of synthesizing a DNA molecule comprising contacting a DNA molecule with a bacterial replication assembly and one or more dNTPs under conditions sufficient to synthesize a second DNA molecule complementary to all or a portion of said first DNA molecule, wherein said bacterial replication assembly is selected from the group consisting of an *S. pyogenes* bacterial replication assembly, an *S. aureus* bacterial replication assembly, a *Y. pestis* bacterial replication assembly, a *P. aeruginosa* bacterial replication assembly, a *B. subtilis* bacterial replication assembly, and an *E. coli* bacterial replication assembly.

The bacterial replication assemblies may comprises one or more isolated bacterial proteins, including PolC, $\alpha$, $\epsilon$, $\theta$, $\tau$, $\gamma$, $\delta$, $\delta'$, $\chi$, $\psi$, $\beta$, PriA, DnaA, DnaB, DnaC, DnaD, DnaI, DnaG, and SSB.

BRIEF DESCRIPTION OF THE FIGURES

FIG. 9A shows the results of a titration of *S. aureus* PolC in a reconstitution assay. FIG. 9B shows the results of a titration of *S. aureus* beta in a reconstitution assay. FIG. 9C shows the results of a titration of *S. aureus* tau complex in a reconstitution assay. FIG. 9D shows the results of a titration of *S. aureus* SSB in a reconstitution assay.

FIG. 10A shows the results of a titration of DMSO in an *S. aureus* reconstitution assay. FIG. 10B shows the results of an *S. aureus* reconstitution assay after the proteins were stored on ice at various times.

FIG. 11 show a titration of various components using the *Bacillus subtilis* primosome-dependent replication assay.

FIG. 15A shows titration of pol III core in the presence of excess $\tau$-complex and $\beta_2$. FIG. 15B shows titration of $\tau$-complex in the presence of excess $\tau$-complex and $\beta_2$. FIG. 15C shows titration of $\beta_2$ in the presence of excess pol III core and $\tau$-complex.

with (filled squares) or without (hollow squares) a saturating amount of E. coli χψ (12 μg/ml).

Figure 22:
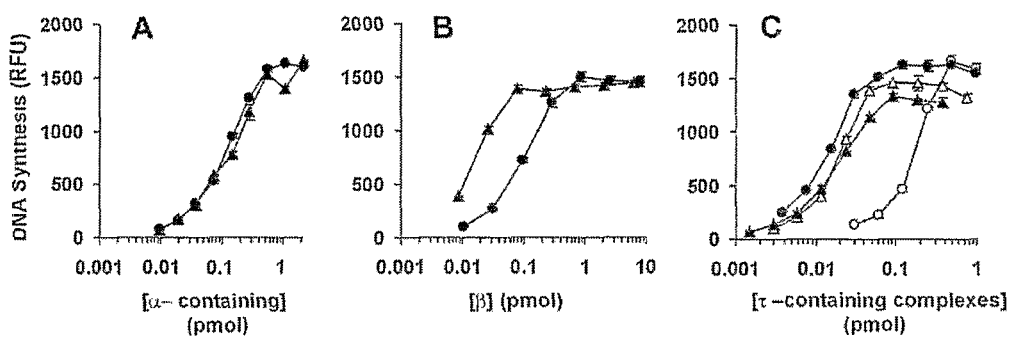

FIG. 22 shows substitution of P. aeruginosa components in E. coli Holoenzyme reconstitution assays. DNA synthesis by E. coli Pol III holoenzyme was measured using PicoGreen® detection of dsDNA synthesized. 25 μL reactions were performed for 5 minutes at 22° C. using templates preannealed with DNA oligonucleotide primer as described in Example 26. Reactions contained saturating levels of each E. coli component with the exception of the component being titrated. Saturating levels were: 0.9 pmol Pol III (6 μg/ml), 1.1 pmol $\beta_2$ (3.6 μg/ml), 0.6 pmol $\tau_3\delta\delta'\chi\psi$ (8 μg/ml), 11 pmol $SSB_4$ (33 μg/ml) and where indicated 10 pmol χψ (12 μg/ml). A, (filled triangles) Titration of E. coli Pol III. (filled circles) Titration of P. aeruginosa αε. B, (filled triangles) Titration of E. coli β. (filled circles) Titration of P. aeruginosa β. C, (hollow triangles) Titration of E. coli $\tau_3\delta\delta'$. (filled triangles) Titration of E. coli $\tau_3\delta\delta'\chi\psi$. (hollow circles) Titration of P. aeruginosa $\tau_3\delta\delta'$. (filled circles) Titration of P. aeruginosa $\tau_3\delta\delta'\chi\psi$ in the presence of saturating amounts E. coli χψ.

Figure 23:
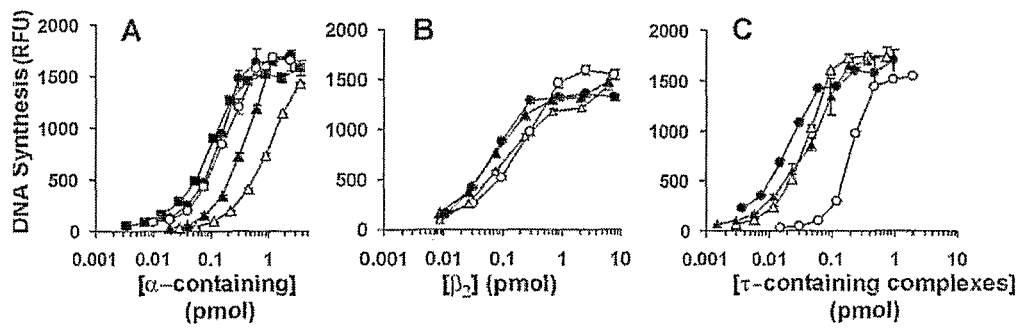

FIG. 23 shows substitution of E. coli components in P. aeruginosa Holoenzyme reconstitution assays. DNA synthesis by P. aeruginosa Pol III holoenzyme was measured as described in the legend to FIG. 22. Reactions contained saturating levels of each P. aeruginosa component with the exception of the component being titrated; saturating levels were 5 pmol αε (32 μg/ml), 3.6 pmol β (12 μg/ml), 1.1 pmol $\tau_3\delta\delta'$ (13 μg/ml), 9 pmol SSB (27 μg/ml) and where indicated 10 pmol E. coli χψ (12 μg/ml). A, (hollow triangles) Titration of P. aeruginosa αε. (filled triangles) Titration of P. aeruginosa αε in the presence of E. coli χψ (filled squares) Titration of P. aeruginosa αε in an assay where E. coli $\tau_3\delta\delta'\chi\psi$ substituted for P. aeruginosa $\tau_3\delta\delta'$. (filled circles) Titration of E. coli Pol III. (hollow circles) Titration of E. coli Pol III in the presence of E. coli χψ. B, (hollow triangles) Titration of E. coli β. (filled triangles) Titration of E. coli β in the presence of E. coli χψ. (hollow circles) Titration of P. aeruginosa β. (filled circles) Titration of P. aeruginosa β in the presence of E. coli χψ. C, (hollow triangles) Titration of E. coli $\tau_3\delta\delta'$. (filled triangles) Titration of E. coli $\tau_3\delta\delta'\chi\psi$. (hollow circles) Titration of P. aeruginosa $\tau_3\delta\delta'$. (filled circles) Titration of P. aeruginosa $\tau_3\delta\delta'$ in the presence of saturating amounts E. coli χψ.

Figure 24:
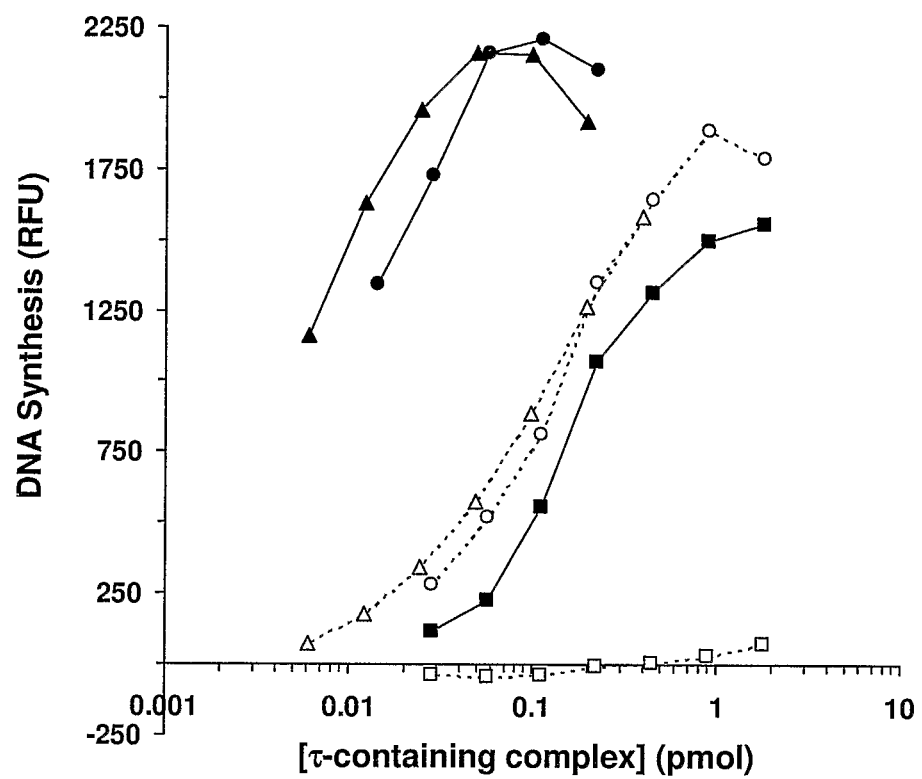

FIG. 24 shows activity of native DnaX complex. DNA synthesis activity was measured by the PicoGreen® assay at 22° C. using templates pre-primed with E. coli DnaG and SSB as described in Example 33. Reactions contained saturating levels of P. aeruginosa αε (14 μg/ml) and β (13 μg/ml). Titration of P. aeruginosa $\tau_3\delta\delta'$ in the presence of 300 mM potassium glutamate (hollow squares) or no added monovalent salt (filled squares). Titration of P. aeruginosa $\tau_3\delta\delta'$ in the presence of saturating amounts of E. coli χψ and 300 mM potassium glutamate (hollow circles) or no added monovalent salt (filled circles). Titration of native P. aeruginosa DnaX complex in the presence 300 mM potassium glutamate (hollow triangles) or no added monovalent salt (filled triangles).

FIG. 25 shows nucleotide sequences for ψ gene candidates and predicted protein products. A, PA4679 nucleotide sequence and translated polypeptide. B, PA4679N32 nucleotide sequence and translated polypeptide. Additional upstream sequence relative to PA4679 shown in bold. C, PA4679N45 nucleotide sequence and translated polypeptide. Additional upstream sequence relative to PA4679 shown in bold. Additional upstream sequence relative to PA4679N32 shown in italics.

Figure 26:
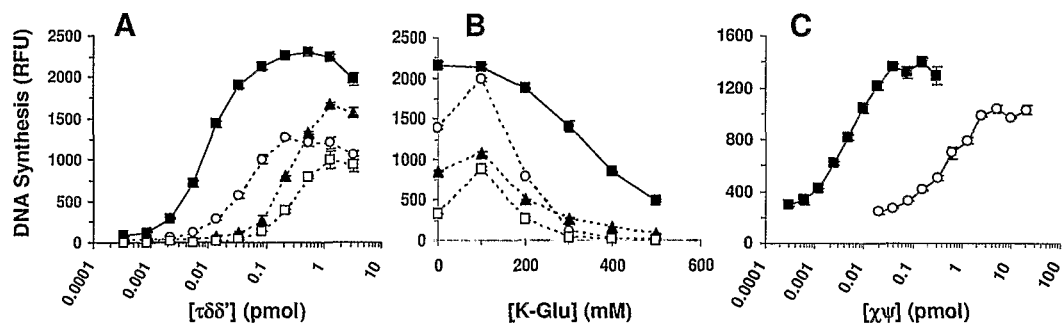

FIG. 26 shows the effects of P. aeruginosa χψ on pol III Holoenzyme Activity. DNA synthesis for 30 minutes at 22° C. was measured by the PicoGreen® assay as described in Example 33. A, Titration of P. aeruginosa $\tau_3\delta\delta'$ in the presence of saturating concentrations of P. aeruginosa αε, β, and DnaG (8, 2, and 4 μg/ml, respectively). Where indicated, χψ and SSB were present at saturating concentrations (2 and 13 μg/ml, respectively). (hollow squares) neither χψ nor SSB, (filled triangles) with SSB, (hollow circles) with χψ, (filled squares) with χψ and SSB. B, Titration of potassium glutamate in holoenzyme reactions containing P. aeruginosa αε, β, DnaG and χψ and/or SSB as described in A. P. aeruginosa $\tau_3\delta\delta'$ was present at sub-saturating level (0.7 ug/ml=0.09 pmol). C, Titration of P. aeruginosa χψ (filled squares) or E. coli χψ (hollow circles) in the presence of 200 mM potassium glutamate and P. aeruginosa αε, β, DnaG and SSB (as given in A) and a sub-saturating concentration of P. aeruginosa $\tau_3\delta\delta'$ (0.36 μg/ml, 0.044 pmol).

Figure 27:
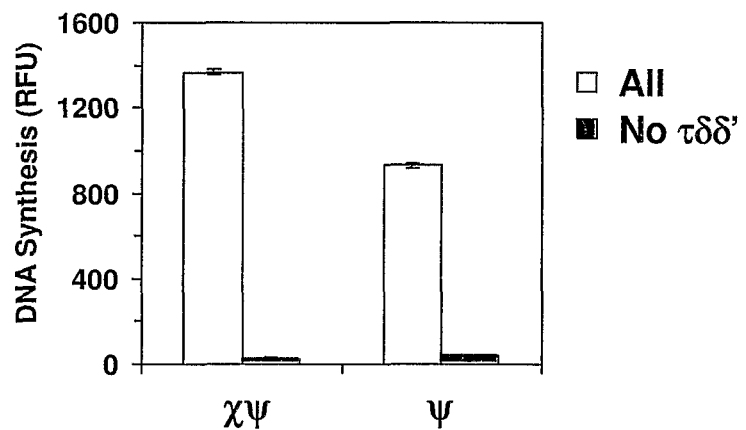

FIG. 27 shows activity of P. aeruginosa χψ Versus ψ Alone. DNA synthesis for 30 minutes at 22° C. was measured by the PicoGreen® assay as described in Example 33 in the presence of 200 mM potassium glutamate and saturating concentrations of P. aeruginosa αε, β, SSB and DnaG (8, 2, 13 and 4 μg/ml, respectively). Saturating levels of χψ (10 μg/ml) versus ψ alone (10 μg/ml) were compared in the presence or absence of sub-saturating $\tau_3\delta\delta'$ (0.7 μg/ml).

Figure 28:
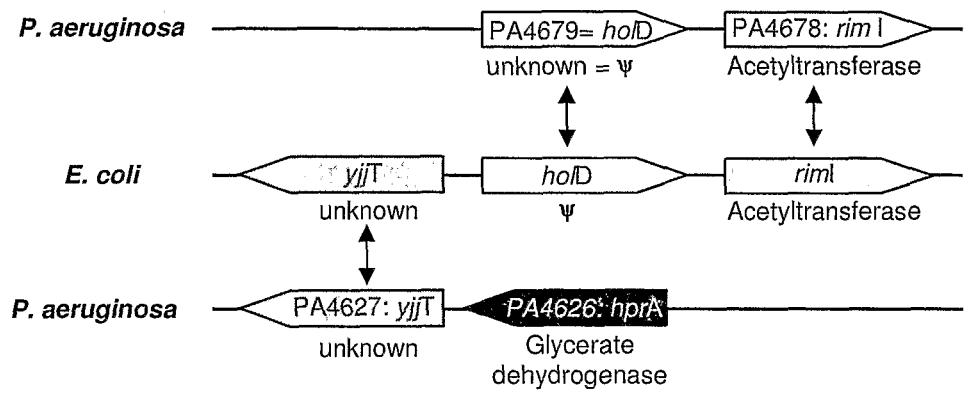

FIG. 28 shows the genomic sequence context of E. coli holD. The genes immediately adjacent to the E. Coli holD gene, rimI and yjjT, were aligned with their counterparts in P. aeruginosa. The neighboring genes to rimI and yjjT in P. aeruginosa are shown.

Figure 29:
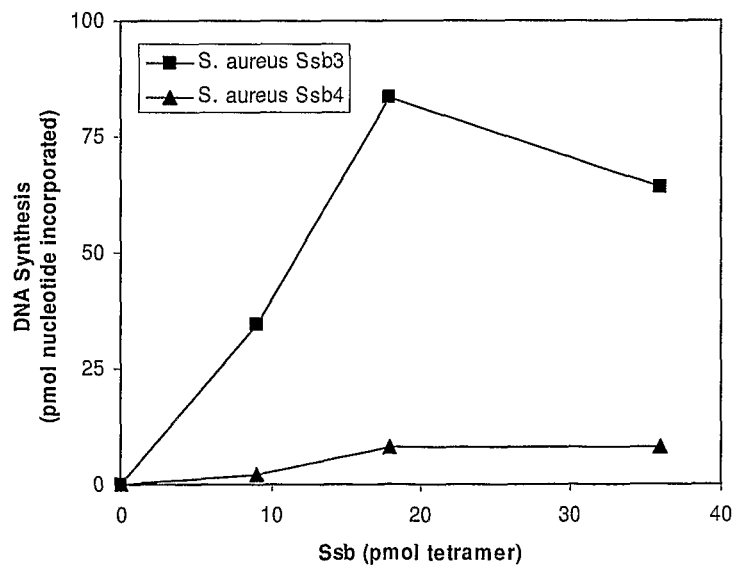

FIG. 29 shows the dependence of S. aureus DNA Synthesis on SSb3 and Ssb4 from S. aureus.

Figure 30:
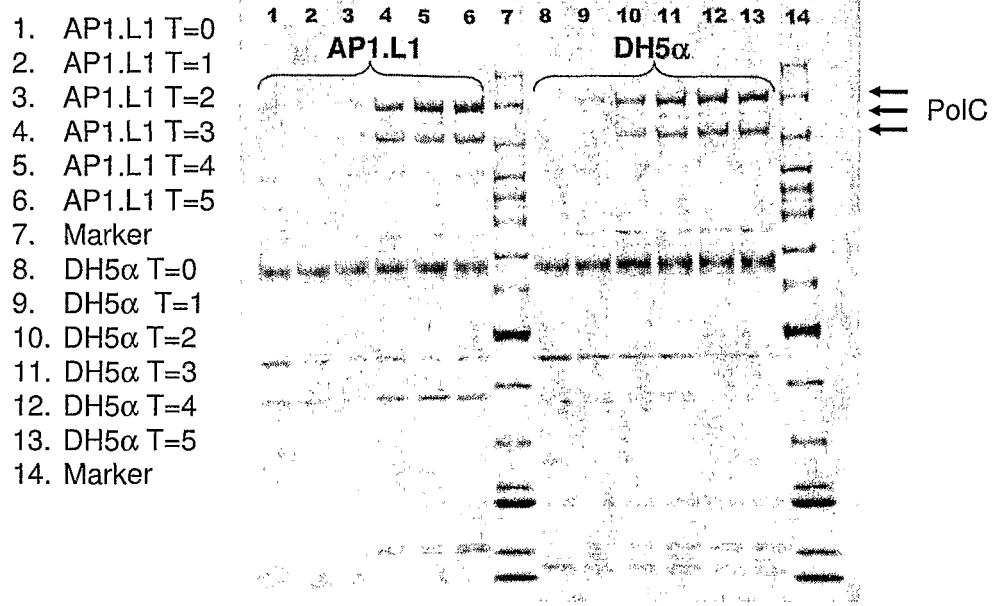

FIG. 30 shows analysis of S. aureus polC expression by SDS-PAGE.

Figure 31:
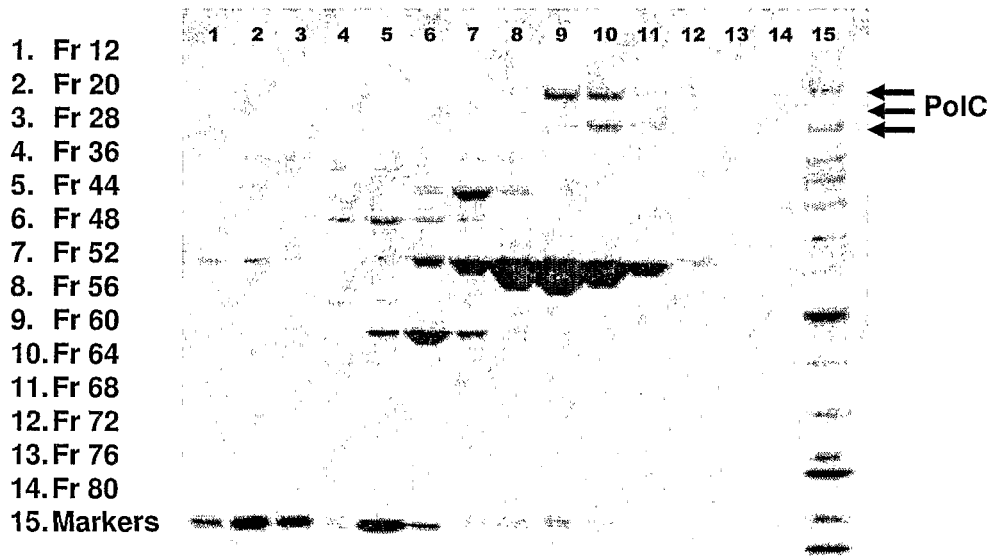

FIG. 31 shows analysis of DEAE Sepharose fractions containing S. aureus PolC by SDS-PAGE.

FIG. 32 shows amino Terminal Amino Acid Sequences of Three PolC Peptides.

FIG. 33 shows a portion of the S. aureus polC coding region showing nucleotides 568-617 and translated amino acid sequence. Nucleotides are numbered from the first nucleotide of the initiator codon.

FIG. 34 shows a portion of the S. aureus polC coding region showing nucleotides 568-617, translated amino acid sequence, and two nucleotide sequence alterations.

FIG. 35 shows a portion of the S. aureus polC coding region showing nucleotides 918-967 and translated amino acid sequence.

Figures 36, 37:
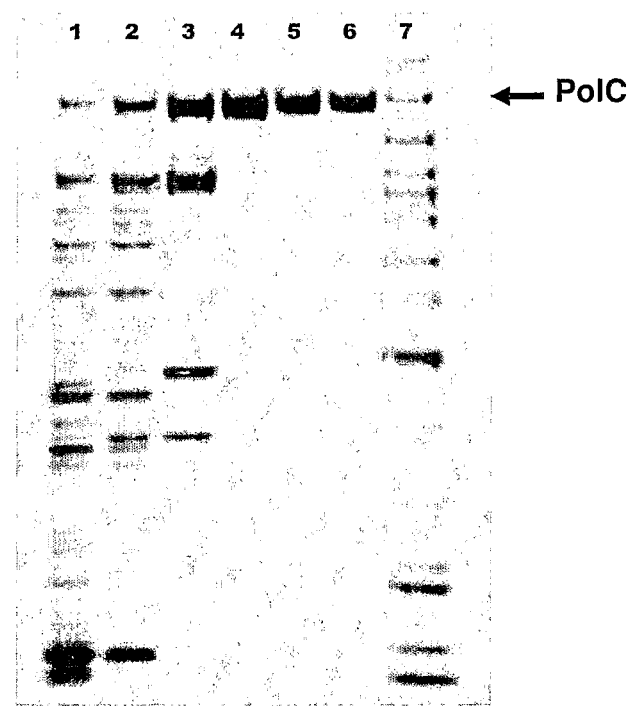

FIG. 36 shows a portion of the S. aureus polC coding region showing nucleotides 918-967, translated amino acid sequence, and two nucleotide sequence alterations.

FIG. 37 shows analysis by SDS-polyacrylamide gel electrophoresis of protein fractions arising during the purification of S. aureus PolC.

DETAILED DESCRIPTION OF THE INVENTION

The present invention relates to gene and amino acid sequences encoding DNA polymerase III holoenzyme subunits and structural genes from Pseudomonas aeruginosa and Staphylococcus aureus, as well a other replication related proteins from these organisms. As used herein, the term "gene" refers to a nucleic acid (e.g., DNA) sequence that comprises coding sequences necessary for the production of a polypeptide or precursor (e.g., DNA polymerase III holoenzyme or holoenzyme subunit, as appropriate). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The term "gene" encompasses both cDNA and genomic forms of a gene. A genomic form or clone of a gene contains the coding region interrupted with non-coding sequences termed "intervening regions" or "intervening sequences." The mRNA functions during translation to specify the sequence or order of amino acids in a nascent polypeptide. As used herein, the term "DNA polymerase III holoenzyme" refers to the entire DNA polymerase III entity (i.e., all of the polymerase subunits, as well as the other associated accessory proteins required for processive replication of a chromosome or genome), while "DNA polymerase III" is just the polymerase core [α, ε, θ subunits in *E. coli*]). "DNA polymerase III holoenzyme subunit" is used in reference to any of the subunit entities that comprise the DNA polymerase III holoenzyme. Thus, the term "DNA polymerase III holoenzyme" encompasses "DNA polymerase III" and "DNA polymerase III subunits." Subunits include, but may not be limited to DnaE (α), PolC (α), DnaN (β), DnaX (τ and/or γ), HolA (δ), HolB (δ'), HolC (χ), HolD (ψ), SSB, DnaG and DnaB proteins. The subunit HolD is also referred to herein as "psi". Identification of some of these subunits has been previously described in U.S. patent application Ser. No. 10/476,597, filed May 14, 2001, entitled "System for Discovery of Agents that Block *Yersinia Pestis* and *Pseudomonas Aeruginosa* DNA Replication," and published as International Patent Application Publication WO 02/092769. The disclosure of U.S. patent application Ser. No. 10/476,597, and all patents, patent applications, and publications referred to herein, are incorporated herein by reference in their entirety.

One skilled in the art will realize, that in certain cases, the gene sequences of the present invention will initiate with UUG or GUG rather than AUG, and will code for Met (rather than the canonical Leu or Val).

In *E. coli*, ψ is a binding partner to χ, and both associate with γ, τ, δ, and δ' to form the DnaX complex. In *P. aeruginosa*, the holC gene, encoding χ, was tentatively identified based on homology, but the holD gene, encoding ψ, was not found. The sequence of ψ is not highly conserved across proteobacteria. More than a dozen bacterial species exist in which χ was apparent, while ψ was not have been identified. The apparent lack of identifiable ψ subunits in these bacteria and in *P. aeruginosa* may reflect sequence divergence rather than actual absence of the subunit.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited proteins.

One embodiment of the present invention is an isolated DNA polymerase III holoenzyme subunit protein. According to the present invention, an isolated, or biologically pure, protein, is a protein that has been removed from its natural environment. As such, "isolated" and "biologically pure" do not necessarily reflect the extent to which the protein has been purified. An isolated *Pseudomonas aeruginosa* or *Staphylococcus aureus* DNA polymerase III holoenzyme subunit protein of the present invention can be obtained from its natural source, can be produced using recombinant DNA technology or can be produced by chemical synthesis. As used herein, an isolated *Pseudomonas aeruginosa* or *Staphylococcus aureus* DNA polymerase III holoenzyme subunit protein can be a full-length protein or any homologue of such a protein.

Proteins include *S. aureus* PolC (α), represented by amino acid sequence SEQ ID NO:45, DnaQ (ε), represented by amino acid sequence SEQ ID NO:50, DnaN (β), represented by amino acid sequence SEQ ID NO:40, DnaX (τ), represented by amino acid sequence SEQ ID NO:70, HolA (δ), represented by amino acid sequence SEQ ID NO:65, HolB (δ'), represented by amino acid sequence SEQ ID NO:60, DnaE, represented by amino acid sequence SEQ ID NO:55, DnaG (primase), represented by amino acid sequence SEQ ID NO:78, and/or ssb, represented by amino acid sequence SEQ ID NO:93, as well as proteins that are encoded by nucleic acid molecules that are allelic variants of the nucleic acid molecules that encode proteins having any of those SEQ ID NO's.

Proteins of the present invention include *Staphylococcus aureus* DNA polymerase III holoenzyme subunits, including the DNA polymerase DnaE subunit protein, PolC (α) subunit protein, DnaN (β) subunit protein, DnaQ (ε) subunit protein, DnaX (τ) subunit protein, HolA (δ) subunit protein, and HolB (δ') subunit protein; and ssb and DnaG proteins; a homolog of such proteins (including, but not limited to the encoded proteins, full-length proteins, processed proteins, fusion proteins and multivalent proteins thereof) as well as proteins that are truncated homologs of proteins that include at least portions of the aforementioned proteins. One DNA polymerase III holoenzyme subunit protein of the present invention is *Pseudomonas aeruginosa* DNA polymerase III holoenzyme subunit, including the DNA polymerase ψ subunit protein, or a homolog of ψ (including, but not limited to the encoded proteins, full-length proteins, processed proteins, fusion proteins and multivalent proteins thereof) as well as proteins that are truncated homologs of proteins that include at least portions of the aforementioned proteins. In one embodiment, a DNA polymerase III ψ subunit protein has a molecular weight of about 32-33 kDa as determined by Tris-glycine SDS PAGE. DNA polymerase III ψ subunit proteins include amino acid sequence SEQ ID NO:37 (FIG. 25C), as well as proteins that are encoded by nucleic acid molecules that are allelic variants of the nucleic acid molecules that encode proteins having SEQ ID NO:37. Examples of methods to produce such proteins are disclosed herein. In one embodiment, DnaE is capable of extending primed DNA in a gap-filling polymerase assay. DnaE alone is capable supporting DNA synthesis (replication) using primed M13 template. DnaE was tested for any stimulation or change in activity with the addition of *S. aureus* beta and Tau complex components but no difference was observed. So, DNA synthesis in these reactions is only dependent of the DnaE protein alone, and not on the other components. This is not necessarily expected, as PolC and DnaE share some amino acid sequence similarity, and PolC shows stimulation with beta and Tau Complex.

In another embodiment DnaN is capable of stimulation of the processitivity of the DNA polymerase in the presence of DnaN in a processivity stimulation assay. In another embodiment, DnaX is capable of hydrolyzing ATP in a DNA-dependent manner. In another embodiment, HolA and HolB in the presence of DnaX are capable of loading DnaN onto primed DNA template. In another embodiment, PolC, DnaN, DnaX, HolA HolB, and ssb are capable of assembling into a functional DNA replicase that can perform rapid and processive DNA synthesis on RNA- or DNA-primed long single-stranded DNA templates.

In some embodiments, *Pseudomonas aeruginosa* DNA polymerase III ψ subunit protein is capable of performing the function of that subunit in a functional assay. In one embodiment, a "τ-complex" ($\tau_3\delta\delta'\chi\psi$) is capable of loading β onto primed DNA. In one embodiment, a clamp loader complex ($\tau_3\delta\delta'\chi\psi$) sets the β processivity clamp on the primer-terminus functional DNA replicase. In some embodiments, a replicase comprising ψ can perform rapid and processive DNA synthesis on RNA- or DNA-primed long single-stranded DNA templates. In another embodiment, χ forms a 1:1 heterodimeric complex with ψ. In another embodiment, χψ binds to τ. In another embodiment, ψ stimulates the ATPase or replication functions of τ. In another embodiment, χψ confers resistance to high salt on DNA synthesis catalyzed by holoenzyme, in the presence of SSB. In another embodiment, ψ increases the specific activity of $\tau_3\delta\delta'$. In another embodiment, ψ increases the specific activity of αε.

Examples of such assays are detailed in the Examples section. The ability of such protein subunits to function in an activity detection assay suggests the utility of such proteins and mimetopes in an assay to screen for antibacterial drug candidates that inhibit *Pseudomonas aeruginosa* or *Staphylococcus aureus* replicase. As used herein, "replicase" means an enzyme that duplicates a DNA polynucleotide sequence.

The phrase "capable of performing the function of that subunit in a functional assay" means that the protein has at least about 10% of the activity of the natural protein subunit in the functional assay. In other embodiments, has at least about 20% of the activity of the natural protein subunit in the functional assay. In other embodiments, has at least about 30% of the activity of the natural protein subunit in the functional assay. In other embodiments, has at least about 40% of the activity of the natural protein subunit in the functional assay. In other embodiments, has at least about 50% of the activity of the natural protein subunit in the functional assay. In other embodiments, the protein has at least about 60% of the activity of the natural protein subunit in the functional assay. In other embodiments, the protein has at least about 70% of the activity of the natural protein subunit in the functional assay. In other embodiments, the protein has at least about 80% of the activity of the natural protein subunit in the functional assay. In other embodiments, the protein has at least about 90% of the activity of the natural protein subunit in the functional assay.

As used herein, an isolated protein of the present invention can be a full-length protein or any homolog of such a protein, such as a protein in which amino acids have been deleted, inserted, inverted, substituted and/or derivatized (e.g., by glycosylation, phosphorylation, acetylation, myristoylation, prenylation, palmitoylation, amidation and/or addition of glycerophosphatidyl inositol) such that the homolog comprises a protein having an amino acid sequence that is sufficiently similar to a natural *Pseudomonas aeruginosa* or *Staphylococcus aureus* DNA polymerase protein that a nucleic acid sequence encoding the homolog is capable of hybridizing under stringent conditions to (i.e., with) the complement of a nucleic acid sequence encoding the corresponding natural *Pseudomonas aeruginosa* or *Staphylococcus aureus* DNA polymerase amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., Molecular Cloning: A Laboratory Manual, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, Anal. Biochem. 138, 267-284; Meinkoth et al., ibid., is incorporated by reference herein in its entirety. In other embodiments, hybridization conditions will permit isolation of nucleic acid molecules having at least about 80% nucleic acid sequence identity with the nucleic acid molecule being used to probe. In other embodiments, hybridization conditions will permit isolation of nucleic acid molecules having at least about 90% nucleic acid sequence identity with the nucleic acid molecule being used to probe. In other embodiments, hybridization conditions will permit isolation of nucleic acid molecules having at least about 95% nucleic acid sequence identity with the nucleic acid molecule being used to probe.

The minimal size of a protein homolog of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protease protein homolog of the present invention is from about 12 to about 18 nucleotides in length. There is no limit on the maximal size of such a nucleic acid molecule in that the nucleic acid molecule can include a portion of a gene, an entire gene, or multiple genes, or portions thereof. Similarly, the minimal size of a polymerase protein homolog of the present invention is from about 4 to about 6 amino acids in length, with some sizes depending on whether a full-length, multivalent (i.e., fusion protein having more than one domain each of which has a function), or functional portions of such proteins are desired. Polymerase protein homologs of the present invention may have activity corresponding to the natural subunit.

A protein homolog of the present invention can be the result of allelic variation of a natural gene encoding *Pseudomonas aeruginosa* or *Staphylococcus aureus* DNA polymerase III holoenzyme subunit. A natural gene refers to the form of the gene found most often in nature. Protein homologs can be produced using techniques known in the art including, but not limited to, direct modifications to a gene encoding a protein using, for example, classic or recombinant DNA techniques to effect random or targeted mutagenesis. Isolated proteins of the present invention, including homologs, can be identified in a straight-forward manner by the proteins ability to perform the protein's specified function. Examples of such techniques are delineated in the Examples section.

The present invention also includes mimetopes of *Pseudomonas aeruginosa* and *Staphylococcus aureus* DNA polymerase holoenzyme III subunit proteins. In accordance with the present invention, a mimetope refers to any compound that is able to mimic the ability of an isolated *Pseudomonas aeruginosa* or *Staphylococcus aureus* protein of the present invention to perform the function of that subunit in a functional assay. A mimetope can be a peptide that has been modified to decrease its susceptibility to degradation but that still retains functional ability. Other examples of mimetopes include, but are not limited to, anti-idiotypic antibodies or fragments thereof, that include at least one binding site that mimics one or more epitopes of an isolated protein of the present invention; non-proteinaceous immunogenic portions of an isolated protein (e.g., carbohydrate structures); and synthetic or natural organic molecules, including nucleic acids, that have a structure similar to at least one epitope of an isolated protein of the present invention. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the present invention is a fusion protein that includes a *Pseudomonas aeruginosa* or *Staphylococcus aureus* protein-containing domain attached to a fusion segment. As used herein, the term "fusion protein" refers to a chimeric protein containing the protein of interest (i.e., DNA polymerase III holoenzyme or holoenzyme subunit and fragments thereof) joined to an exogenous protein fragment (the fusion partner which consists of a non-DNA polymerase III holoenzyme or holoenzyme subunit protein). The fusion partner may enhance solubility of the DNA polymerase III holoenzyme or holoenzyme subunit protein as expressed in a host cell, may provide an affinity tag to allow purification of the recombinant fusion protein from the host cell or culture supernatant, or both. If desired, the fusion protein may be removed from the protein of interest (i.e., DNA polymerase III holoenzyme, holoenzyme subunit protein, or fragments thereof) by a variety of enzymatic or chemical means known to the art. Inclusion of a fusion segment as part of a *Pseudomonas aeruginosa* or *Staphylococcus aureus* DNA polymerase holoenzyme III ψ subunit of the present invention can enhance the protein's stability during production, storage and/or use. Depending on the segment's characteristics, a fusion segment can also act as an immunopotentiator to enhance the immune response mounted by an animal immunized with *Pseudomonas aeruginosa* or *Staphylococcus aureus* protein containing such a fusion segment. Furthermore, a fusion segment can function as a tool to simplify purification of *Pseudomonas aeruginosa* or *Staphylococcus aureus* protein, such as to enable purification of the resultant fusion protein using affinity chromatography. A suitable fusion segment can be a domain of any size that has the desired function (e.g., imparts increased stability, imparts increased immunogenicity to a protein, and/or simplifies purification of a protein). It is within the scope of the present invention to use one or more fusion segments. Fusion segments can be joined to amino and/or carboxyl termini of the *Pseudomonas aeruginosa* or *Staphylococcus aureus* protein-containing domain of the protein. Linkages between fusion segments and *Pseudomonas aeruginosa* or *Staphylococcus aureus* protein-containing domains of fusion proteins can be susceptible to cleavage in order to enable straight-forward recovery of the *Pseudomonas aeruginosa* or *Staphylococcus aureus* protein-containing domains of such proteins. Fusion proteins may be produced by culturing a recombinant cell transformed with a fusion nucleic acid molecule that encodes a protein including the fusion segment attached to either the carboxyl and/or amino terminal end of a *Pseudomonas aeruginosa* or *Staphylococcus aureus* protein-containing domain.

Fusion segments that may be used in the present invention include a glutathione binding domain, such as glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, $F_c$ receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). Other fusion segments include metal binding domains, such as a poly-histidine segment; a maltose binding domain; and a hexahistidine/biotin binding peptide.

Another embodiment of the present invention is an isolated nucleic acid molecule that hybridizes under stringent hybridization conditions with at least one of the *Pseudomonas aeruginosa* or *Staphylococcus aureus* DNA polymerase III holoenzyme subunit genes of the present invention. One *Pseudomonas aeruginosa* gene is holD, and includes nucleic acid sequence SEQ ID NO:35 (FIG. 25C), which encodes a ψ subunit protein including SEQ ID NO:37.

One *S. aureus* gene is dnaE, and includes nucleic acid sequence SEQ ID NO:53, which encodes a dnaE subunit protein including SEQ ID NO:55. Another *S. aureus* gene is polC, and includes nucleic acid sequence SEQ ID NO:43 and SEQ ID NO:101, which encode a PolC protein including SEQ ID NO:45. Another *S. aureus* gene is dnaQ, and includes nucleic acid sequence SEQ ID NO:48, which encodes a dnaQ protein including SEQ ID NO:50. Another *S. aureus* gene is dnaN, and includes nucleic acid sequence SEQ ID NO:38, which encodes a DNA polymerase III β-subunit protein including SEQ ID NO:40. Another *S. aureus* gene is dnaX, and includes nucleic acid sequence SEQ ID NO:68, which encodes a dnaX protein including SEQ ID NO:70. Another *S. aureus* gene is holA, and includes nucleic acid sequence SEQ ID NO:63, which encodes a δ subunit protein including SEQ ID NO:65. Another *S. aureus* gene is holB, and includes nucleic acid sequence SEQ ID NO:58, which encodes a δ' subunit protein including SEQ ID NO:60. Another *S. aureus* gene is dnaG, and includes nucleic acid sequence SEQ ID NO:76, which encodes a dnaG subunit protein including SEQ ID NO:78. Another *S. aureus* gene is ssb, and includes nucleic acid sequence SEQ ID NO:91, which encodes a ssb subunit protein including SEQ ID NO:93.

It should be noted that since nucleic acid sequencing technology is not entirely error-free, sequences presented herein, at best, represent an apparent nucleic acid sequence of the nucleic acid molecules encoding a *Pseudomonas aeruginosa* or *Staphylococcus aureus* DNA polymerase holoenzyme protein of the present invention. A nucleic acid molecule of the present invention can include an isolated natural gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with one of the aforementioned genes under stringent hybridization conditions.

In one embodiment, hybridization conditions will permit isolation of nucleic acid molecules having at least about 70% nucleic acid sequence identity with the nucleic acid molecule being used to probe. In some embodiments, hybridization conditions will permit isolation of nucleic acid molecules having at least about 80% nucleic acid sequence identity with the nucleic acid molecule being used to probe. In other embodiments, hybridization conditions will permit isolation of nucleic acid molecules having at least about 90% nucleic acid sequence identity with the nucleic acid molecule being used to probe. In other embodiments, hybridization conditions will permit isolation of nucleic acid molecules having at least about 95% nucleic acid sequence identity with the nucleic acid molecule being used to probe.

In accordance with the present invention, an isolated nucleic acid molecule is a nucleic acid molecule that is identified and separated from at least one contaminant nucleic acid with which it is ordinarily associated in its natural source. Isolated nucleic acid molecules are thus present in a form or setting that is different from that in which it is found in nature. In contrast, non-isolated nucleic acids as nucleic acids such as DNA and RNA found in the state they exist in nature. The isolated nucleic acid molecule may be present in single-stranded or double-stranded form. When an isolated nucleic acid molecule is to be utilized to express a protein, the nucleic acid molecule will contain at a minimum the sense or coding strand (i.e., the oligonucleotide or polynucleotide may single-stranded), but may contain both the sense and antisense strands (i.e., the oligonucleotide or polynucleotide may be double-stranded). "Isolated" does not reflect the extent to which the nucleic acid molecule has been purified. An isolated nucleic acid molecule can include DNA, RNA, or derivatives of either DNA or RNA.

An isolated *Pseudomonas aeruginosa* or *Staphylococcus aureus* nucleic acid molecule of the present invention can be obtained from its natural source either as an entire (i.e., complete) gene or a portion thereof capable of forming a stable hybrid with that gene. An isolated *Pseudomonas aeruginosa* or *Staphylococcus aureus* nucleic acid molecule can also be produced using recombinant DNA technology (e.g., polymerase chain reaction (PCR) amplification, cloning) or chemical synthesis. Isolated *Pseudomonas aeruginosa* or *Staphylococcus aureus* DNA polymerase III holoenzyme ψ subunit nucleic acid molecules include natural nucleic acid molecules and homologs thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a protein of the present invention or to form stable hybrids under stringent conditions with natural gene isolates.

A *Pseudomonas aeruginosa* or *Staphylococcus aureus* nucleic acid molecule homolog can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the function of the protein encoded by the nucleic acid (e.g., ability to elicit an immune response against at least one epitope of a *Pseudomonas aeruginosa* or *Staphylococcus aureus* protein, ability to bind to immune serum) and/or by hybridization with a *Pseudomonas aeruginosa* DNA polymerase III holoenzyme ψ subunit gene.

The present invention also provides methods for detection of nucleic acid molecules encoding at least a portion of DNA polymerase III holoenzyme, or DNA polymerase III holoenzyme subunit in a biological sample comprising the steps of: a) hybridizing at least a portion of a nucleic acid molecule of the present invention to nucleic acid material of a biological sample, thereby forming a hybridization complex, and b) detecting the hybridization complex, wherein the presence of the complex correlates with the presence of a polynucleotide encoding at least a portion of DNA polymerase III holoenzyme or DNA polymerase III holoenzyme subunit in the biological sample. In other embodiments, hybridization conditions will permit isolation of nucleic acid molecules having at least about 80% nucleic acid sequence identity with the nucleic acid molecule being used to probe. In other embodiments, hybridization conditions will permit isolation of nucleic acid molecules having at least about 90% nucleic acid sequence identity with the nucleic acid molecule being used to probe. In other embodiments, hybridization conditions will permit isolation of nucleic acid molecules having at least about 95% nucleic acid sequence identity with the nucleic acid molecule being used to probe. In other embodiment of the methods, the nucleic acid material of the biological sample is amplified by the polymerase chain reaction.

The present invention also includes a recombinant vector, which includes at least one *Pseudomonas aeruginosa* or *Staphylococcus aureus* nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that may be derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of *Pseudomonas aeruginosa* or *Staphylococcus aureus* nucleic acid molecules of the present invention. One type of recombinant vector, referred to herein as a recombinant molecule and described in more detail below, can be used in the expression of nucleic acid molecules of the present invention. Recombinant vectors may be capable of replicating in the transformed cell.

Isolated *Pseudomonas aeruginosa* or *Staphylococcus aureus* proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable nucleic acid molecules with which to transform a cell are as disclosed herein for suitable *Pseudomonas aeruginosa* or *Staphylococcus aureus* nucleic acid molecules per se. Nucleic acid molecules to include in recombinant cells of the present invention include *Pseudomonas aeruginosa* holD, and *Staphylococcus aureus* polC, dnaN, dnaQ, dnaE, holA, holB, dnaX, dnaG, and ssb.

Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing *Pseudomonas aeruginosa* or *Staphylococcus aureus* proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), insect, other animal and plant cells. Host cells include bacterial, mycobacterial, yeast, insect and mammalian cells. Other host cells include *Escherichia*, such as *Escherichia coli*, including DH5α, MGC1030 and AP1.L1 strains. Other host cells are *Pseudomonas aeruginosa* and *Staphylococcus aureus* including attenuated strains with reduced pathogenicity.

A recombinant cell may be produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. The term "vehicle" is sometimes used interchangeably with "vector." The expression vector may also be capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Expression vectors of the present invention may direct gene expression in bacterial, yeast, insect and mammalian cells and in the cell types heretofore disclosed.

Recombinant molecules of the present invention may also (a) contain secretory signals (i.e., signal segment nucleic acid sequences) to enable an expressed *Pseudomonas aeruginosa* or *Staphylococcus aureus* protein of the present invention to be secreted from the cell that produces the protein and/or (b) contain fusion sequences which lead to the expression of nucleic acid molecules of the present invention as fusion proteins. Eukaryotic recombinant molecules may include intervening and/or untranslated sequences surrounding and/or within the nucleic acid sequences of nucleic acid molecules of the present invention.

Suitable signal segments include natural signal segments or any heterologous signal segment capable of directing the secretion of a protein of the present invention. Signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Transcription control sequences include those which function in bacterial, yeast, insect and mammalian cells, such as, but not limited to, pA1, tac, lac, tip, trc, oxy-pro, omp/lpp, rrnB, bacteriophage lambda (λ), bacteriophage T7, T7lac, bacteriophage T3, bacteriophage SP6, bacteriophage SP01, metallothionein, α-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with *Pseudomonas aeruginosa* or *Staphylococcus aureus*.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A recombinant cell of the present invention includes any cell transformed with at least one of any nucleic acid molecule of the present invention. Recombinant cells of the present invention can also be co-transformed with one or more recombinant molecules including *Pseudomonas aeruginosa* or *Staphylococcus aureus* nucleic acid molecules encoding one or more proteins of the present invention. In some embodiments, the recombinant molecule of the present invention is pA1-SA-dnaN, pA1-SA-polC, pA1-SA-polCrevised, pA1-SA-dnaQ pA1-SA-dnaE, pA1-SA-dnaQE, pA1-SA-holB, pA1-SA-holA, pA1-SA-dnaX, pA1-SA-BAX, pA1-SA-dnaG, or pA1-SA-ssb#3.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a *Pseudomonas aeruginosa* or *Staphylococcus aureus* protein of the present invention. Such a medium is typically an aqueous medium comprising assimilable carbon, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention may be retrieved in "substantially pure" form. As used herein, "substantially pure" refers to a purity that allows for the effective use of the protein as a therapeutic composition or diagnostic.

The present invention also includes isolated antibodies capable of selectively binding to a *Pseudomonas aeruginosa* or *Staphylococcus aureus* protein of the present invention or to a mimetope thereof. Such antibodies are also referred to herein as anti-*Pseudomonas aeruginosa* antibodies and anti-*Staphylococcus aureus* antibodies.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Antibodies may be raised in response to proteins, or mimetopes thereof, that are encoded, at least in part, by a nucleic acid molecule of the present invention. Methods to generate and detect antibodies are known in the art. See, e.g., Harlow and Lane, *Antibodies: A Laboratory Manual*, Cold Spring Harbor Laboratory Press, Cold Spring Harbor, N.Y., incorporated by reference herein in its entirety.

One method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce *Pseudomonas aeruginosa* or *Staphylococcus aureus* proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from bacteria susceptible to treatment by such antibodies, including *Pseudomonas aeruginosa* or *Staphylococcus aureus*, (b) as reagents in assays to detect infection by such bacteria and/or (c) as tools to screen expression libraries and/or to recover desired proteins of the present invention from a mixture of proteins and other contaminants. Furthermore, antibodies of the present invention can be used to target cytotoxic agents to bacteria of the present invention in order to directly kill such bacteria. Targeting can be accomplished by conjugating (i.e., stably joining) such antibodies to the cytotoxic agents using techniques known to those skilled in the art. Suitable cytotoxic agents are known to those skilled in the art. Suitable cytotoxic agents include, but are not limited to: double-chain toxins (i.e., toxins having A and B chains), such as diphtheria toxin, ricin toxin, *Pseudomonas* exotoxin, modeccin toxin, abrin toxin, and shiga toxin; single-chain toxins, such as pokeweed antiviral protein, α-amanitin, and ribosome inhibiting proteins; and chemical toxins, such as melphalan, methotrexate, nitrogen mustard, doxorubicin and daunomycin. Double-chain toxins may be modified to include the toxic domain and translocation domain of the toxin but lack the toxin's intrinsic cell binding domain.

The present invention also provides methods for detecting DNA polymerase III comprising: providing in any order, a sample suspected of containing DNA polymerase III, and antibody capable of specifically binding to at least a portion of the DNA polymerase III; mixing the sample and the antibody under conditions wherein the antibody can bind to the DNA polymerase III; and detecting the binding. In alternative embodiments, the organism is *Pseudomonas aeruginosa*. Methods for detecting proteins with antibodies are well known to those skilled in the art, see, for example Harlow and Lane, ibid., and include immunoblot assays, immunoprecipitation assays, enzyme immunoassays (e.g., ELISA), radioimmunoassays, immunofluorescent antibody assays and immunoelectron microscopy.

The present invention also provides methods for detection of nucleic acid molecules encoding at least a portion of DNA polymerase III holoenzyme, or DNA polymerase III holoenzyme subunit, or other replication related protein in a biological sample comprising the steps of: a) hybridizing at least a portion of a nucleic acid molecule of the present invention to nucleic acid material of a biological sample, thereby forming a hybridization complex, and b) detecting the hybridization complex, wherein the presence of the complex correlates with the presence of a polynucleotide encoding at least a portion of DNA polymerase III holoenzyme, DNA polymerase III holoenzyme subunit, or replication-related in the biological sample. In alternative embodiment of the methods, the nucleic acid material of the biological sample is amplified by the polymerase chain reaction.

The present invention also provides methods for detecting DNA polymerase III holoenzyme or holoenzyme ψ subunit expression, including expression of abnormal or mutated DNA polymerase III holoenzyme or holoenzyme subunit proteins or gene sequences comprising the steps of a) providing a test sample suspected of containing DNA polymerase III holoenzyme or DNA polymerase III holoenzyme ψ subunit protein, as appropriate; and b) comparing the test DNA polymerase III holoenzyme or holoenzyme ψ subunit, in the sample with the quantitated DNA polymerase III holoenzyme or holoenzyme ψ subunit in the control to determine the relative concentration of the test DNA polymerase III holoenzyme or holoenzyme ψ subunit in the sample. In addition, the methods may be conducted using any suitable means to determine the relative concentration of DNA polymerase holoenzyme or holoenzyme ψ subunit in the test and control samples. Examples of such methods may be found in the Examples section.

The present invention also provides methods for detecting DNA polymerase III holoenzyme, holoenzyme subunit, ssb or dnaG expression, including expression of abnormal or mutated DNA polymerase III holoenzyme, holoenzyme subunit proteins, other replication related proteins, or gene sequences comprising the steps of a) providing a test sample suspected of containing DNA polymerase III holoenzyme, DNA polymerase III holoenzyme subunit protein, dnaG, ssb, as appropriate; and b) comparing the test sample with the a control to determine the relative concentration of the test enzyme or protein in the sample. In addition, the methods may be conducted using any suitable means to determine the relative concentration of proteins in the test and control samples. Examples of such methods may be found in the Examples section.

Another embodiment of the present invention is a method for detecting functional activity of *Pseudomonas aeruginosa* DNA polymerase III protein ψ subunits. One method is the detection of activity comprising a) providing a test sample suspected of containing DNA polymerase III holoenzyme ψ subunit protein; and b) comparing the activity of the test holoenzyme ψ subunit in the sample with a quantitated DNA polymerase III holoenzyme ψ subunit in a control to determine the relative activity of the test DNA polymerase III holoenzyme ψ subunit in the sample. In one embodiment, the activity is "τ-complex" ($\tau_3\delta\delta'\chi\psi$) loading β onto primed DNA. In one embodiment, the activity is a clamp loader complex ($\tau_2\gamma1\delta\delta'\chi\psi$) setting the β processivity clamp on the primer-terminus functional DNA replicase. In some embodiments, the activity is a replicase comprising ψ can performing rapid and processive DNA synthesis on RNA- or DNA-primed long single-stranded DNA templates. In another embodiment, the activity is χ forming a 1:1 heterodimeric complex with ψ. In another embodiment, the activity is χψ binding to τ. In another embodiment, the activity is ψ stimulating the ATPase or replication functions of γ. In another embodiment, the activity is χψ conferring resistance to high salt on DNA synthesis catalyzed by holoenzyme, in the presence of SSB. In another embodiment, the activity is increasing the specific activity of $\tau_3\delta\delta'$. In another embodiment, the activity is increasing the specific activity of αε.

This invention provides methods for the assembly of a complete *Pseudomonas aeruginosa* chromosomal DNA replication elongation system. This invention also provides methods for the expression and purification of the 9 centrally important components of the *Pseudomonas aeruginosa* DNA polymerase III holoenzyme. This invention further provides a *Pseudomonas aeruginosa* minimal processive replicase. This invention also provides methods for the use of the fully reconstituted *Pseudomonas aeruginosa* replication system in a high-throughput screening format to identify compounds that are active as inhibitors of *Pseudomonas* DNA replication. Examples of such methods may be found in the Examples section.

In *E. coli*, the reconstituted holoenzyme reaction is only moderately stimulated by the presence of χψ. Thus, it was expected that a functional holoenzyme could be reconstituted from *P. aeruginosa* in the absence of χψ. Each identified replicase gene was amplified from *P. aeruginosa* genomic DNA by PCR and inserted in vectors for expression in *E. coli* as detailed in Example 13. All of the proteins were expressed as native polypeptides without inclusion of any tag (fusion) sequences. Proteins that function in a complex in *E. coli* were expressed in operons. Thus, dnaX, holA and holB were co-expressed, and dnaE was co-expressed with dnaQ. Expression vectors were transfected into fermentation strains, and induction conditions were optimized to give maximum expression and solubility of the recombinant proteins. Cells were grown in large scale in a fermentor, and processed as described in Example 14. Formation of a subassembly of the *P. aeruginosa* Pol III holoenzyme that contained α, ε, τ, δ and δ' is described in Example 24. Reconstitution of DNA Polymerase III Holoenzyme Activity with αε, β, $\tau_3\delta\delta'$ and SSB is described in Example 23.

Thus, this invention describes the expression and purification of key components of the Pol III holoenzyme from *P. aeruginosa*. These proteins were sufficient to reconstitute an efficient DNA elongation reaction from a primed single-stranded DNA template. In the *E. coli* system, addition of β to Pol III in the absence of the DnaX complex results in a modest increase in processivity. Thus, the stimulation of *P. aeruginosa* αε activity observed here with addition of *P. aeruginosa* β seemed consistent with the expected functions of these proteins. We also observed a modest stimulation of αε activity with addition of $\tau_3\delta\delta'$ in the absence of β. Stimulation of Pol III by τ, in the absence of other subunits has also been observed in the *E. coli* system. However, in the *P. aeruginosa* system, the combined presence of αε, $\tau_3\delta\delta'$ and β is necessary to achieve highly efficient DNA synthesis. We found that when *E. coli* χψ was added to a reaction containing sub-saturating levels of $\tau_3\delta\delta'$, DNA synthesis could be stimulated dramatically to the same level as observed with saturating amounts of $\tau_3\delta\delta'$ in the absence of χψ. In the absence of χψ, the *P. aeruginosa* reconstituted system was very sensitive to salt, with very little DNA synthesis seen at salt levels within a physiological range (>200 mM glutamate). Addition of *E. coli* χψ markedly increased the salt tolerance of the reaction to a level more typical of a replicase. Neither *E. coli* χ alone, nor tagged *P. aeruginosa* χ, was able to stimulate the synthesis reaction. These results suggest the existence of ψ counterpart in *P. aeruginosa* and highlight its potentially important functional contributions. This system represents a minimal elongation system; lack of the χψ component can be overcome by driving the binding equilibrium with high levels of $\tau_3\delta\delta'$. One contribution of χψ is to increase the affinity of the remaining DnaX complex components for one another. Identification of the *P. aeruginosa* ψ subunit is therefore an important addition to the current system, and enhances the dependence of the system on each individual component, allowing one to work at lower $\tau_3\delta\delta'$ concentrations. *P. aeruginosa* αε was able to substitute efficiently for *E. coli* Pol III to reconstitute Pol III holoenzyme in the presence of the required *E. coli* auxiliary proteins. *P. aeruginosa* $\tau_3\delta\delta'$ by itself was 10-fold less effective at limiting concentrations, but full activity could be attained by either addition of more $\tau_3\delta\delta'$ or by addition of saturating levels of *E. coli* χψ. These observations would be consistent with the subunit interactions of *P. aeruginosa* $\tau_3\delta\delta'$ being weaker than their *E. coli* counterpart and their mutual affinities being increased by binding of *E. coli* χψ. *P. aeruginosa* β is 10-fold less effective at limiting concentrations, but full synthesis is attained when higher levels are added. This would be consistent with a diminished affinity for *E. coli* holoenzyme subunits—either Pol III or DnaX complex with which β interacts. All *E. coli* Pol III holoenzyme components, Pol III, β or $\tau_3\delta\delta'$, were able to substitute completely for the corresponding *P. aeruginosa* component in the presence of the required *P. aeruginosa* auxiliary proteins. The striking finding was that *E. Coli* $\tau_3\delta\delta'$ and Pol III worked better than the *P. aeruginosa* components. The relative "defect" in *P. aeruginosa* $\tau_3\delta\delta'$ could be restored by the addition of saturating *E. coli* χψ, consistent with a diminished affinity of *P. aeruginosa* $\tau_3\delta\delta'$ subunits for one another, as discussed above. The "defect" in *P. aeruginosa* αε could be partially corrected by addition of high levels of *E. coli* χψ. Since *P. aeruginosa* αε fully substituted for *E. coli* Pol III in *E. coli* Pol III holoenzyme reconstitution assays, we expected a component of the *E. coli* assay to fully restore *P. aeruginosa* αε activity. In hybrid assays, we found that *E. coli* DnaX complex ($\tau_3\delta\delta'$χψ) restored full activity to *P. aeruginosa* αε in the *P. aeruginosa* holoenzyme reconstitution assay. Interestingly, *E. Coli* $\tau_3\delta\delta'$ was also able to restore full activity to *P. aeruginosa* αε in the *P. aeruginosa* holoenzyme reconstitution assay. These results suggest that *P. aeruginosa* αε lacks a function present in *E. coli* Pol III (αεθ) and that *E. coli* DnaX complex contains a function not present in *P. aeruginosa* $\tau_3\delta\delta'$. The latter function was hypothesized to be contained in authentic *P. aeruginosa* χψ.

Purification of native DnaX complex from *P. aeruginosa* was performed as described in Example 27-Example 29. The composition of native DnaX complex was accomplished by analyzing Fraction VI by SDS-PAGE. The polypeptides present in Fraction VI were excised and identified by peptide mass fingerprinting. The results are shown in Table 23 along with the approximate abundance of each band estimated by densitometry. The complex contained all of the expected components of the DnaX complex from *P. aeruginosa* in roughly the expected stoichiometries, and also the α and ε subunits of DNA polymerase III holoenzyme. Thus, although DnaX activity was being monitored as a guide to purification, the complex that was purified actually resembled the pol III* subassembly that has been isolated from *E. coli*. In fact, Fraction IV showed Pol III* activity when assayed in the presence of β but in the absence of exogenously added Pol III core. In addition, SSB was present in this complex; in *E. Coli*, SSB has been shown to associate with Pol III* but only in the presence of χψ. An approximately 32 kD protein of unknown function was identified that appeared to be present in stoichiometrically equivalent levels relative to the χ, δ and δ' subunits. This protein was encoded by *P. aeruginosa* gene PA4679 and appeared to be a candidate for the ψ subunit.

As annotated in the *Pseudomonas* genome project, which has its own web site, PA4679 encodes a protein of 233 amino acids with a predicted molecular mass of 24.9 kD. The apparent molecular mass of the native polypeptide based on gel mobility, however, was 32-33 kD. While this discrepancy could have been an SDS-PAGE artifact, mechanisms that would produce a larger native protein product were also considered. Translational readthrough was not likely since several other in-frame termination codons would be encountered in rapid succession. A $^+1$ translational frameshift near the predicted C-terminus would add 49 amino acids, a change of approximately the right magnitude; a $^-1$ frameshift would add 149 amino acids, giving a much larger protein product. We also considered whether the translational start site was correctly annotated. There was an in-frame upstream AUG that would encode a protein with 32 additional amino acids at the N-terminus, for a total molecular mass of 28.5 kD. Further upstream, initiation at an in-frame UUG would add 45 amino acids to the N-terminus, for a total molecular mass of 30.0 kD. Sequence similarity between these upstream translated regions and conserved hypothetical proteins in *Pseudomonas putida* and *Pseudomonas syringae* supported the upstream translational start hypothesis but we were unable to obtain N-terminal amino acid sequence of the native protein despite several attempts. Peptide mass fingerprinting of the native protein did not reveal any peptides consistent with either of the translational frameshift models, but did detect several peptides consistent with the upstream start hypotheses. The actual N-terminal peptide was not observed, however, leaving the exact translational start site ambiguous. Therefore we cloned and expressed three versions of the ψ candidate gene, denoted PA4679 for the original gene, and PA4679N32 and PA4679N45, respectively, for the 32 amino acid and 45 amino acid N-terminal extensions, as described in Example 30. Nucleotide sequences and the translated protein products are shown in FIG. 25. Each of the three ψ candidate proteins was capable of binding to immobilized tagged *P. aeruginosa* χ. The longer version of the gene and the alignment of the protein with proteins encoded by related genes are annotated in The Institute for Genome Research database under gene NT03PA5405. The three proteins migrated on SDS-PAGE at approximately the expected sizes relative to molecular weight markers. The largest of the three proteins (encoded by PA4679N45) showed comparable mobility to the native polypeptide. Only the largest of the three showed χψ activity, confirming that PA4679N45 corresponds to the *E. coli* holD gene and encodes the ψ subunit of DNA polymerase III holoenzyme. The observed stimulation of holoenzyme activity by the affinity purified χ and ψ was completely dependent on the presence of $\tau_3\delta\delta'$, indicating that the stimulation results from formation of a fully functional DnaX complex.

The present invention also provides a *P. aeruginosa* χψ complex. An inducible expression vector was constructed that co-expressed PA4679N45 and the holC gene from *P. aeruginosa* as described in Example 30. Untagged χ and ψ could thereby be expressed in *E. coli* and purified as a complex. χψ was purified based on stimulation of DNA synthesis activity in *P. aeruginosa* DNA polymerase III holoenzyme reconstitution assays containing sub-saturating $\tau_3\delta\delta'$ (see Example 32).

When $\tau_3\delta\delta'$ was titrated at low salt, both $\chi\psi$ and SSB were required to achieve optimal holoenzyme activity (FIG. 26A). In the absence of either $\chi\psi$ or SSB, high levels of $\tau_3\delta\delta'$ were required for activity. Addition of $\chi\psi$ alone increased the apparent specific activity of the DnaX complex approximately 10-fold, but did not increase the maximal extent of the reaction; addition of SSB alone increased the maximal extent of the reaction to an intermediate level, but did not alter the apparent specific activity. Addition of both $\chi\psi$ and SSB increased the apparent specific activity >50-fold, and doubled the maximal extent of the reaction. The presence of $\chi\psi$ facilitated efficient DNA synthesis at elevated salt (FIG. 26B). At salt concentrations $\leq$100 mM, a substantial stimulation was seen upon addition of $\chi\psi$ in the absence of SSB. In the physiological salt range ($\geq$200 mM), however, there was clearly a synergistic effect in which both SSB and $\chi\psi$ were required to achieve maximal synthesis. Titration of *P. aeruginosa* $\chi\psi$ (FIG. 26C) achieved maximal stimulation at a 1:1 stoichiometric ratio with $\tau_3\delta\delta'$, while approximately 100-fold molar excess of *E. coli* $\chi\psi$ was required to achieve similar levels of stimulation. These results indicated that the cognate $\chi\psi$ bound much more tightly to $\tau_3\delta\delta'$ compared to the non-cognate $\chi\psi$.

*P. aeruginosa* $\psi$ was expressed in *E. coli* in the absence of $\chi$. Initial purification was accomplished by precipitation of crude lysates with 40% ammonium sulfate. The ability of $\psi$ to stimulate holoenzyme DNA synthesis activity was assessed in comparison to a $\chi\psi$ 40% ammonium sulfate fraction (FIG. 27). $\psi$ alone gave a substantial stimulation of holoenzyme activity, although the total magnitude of the stimulation was lower than that attained in the presence of $\psi$ and $\chi$. Both activities were completely dependent on the presence of $\tau_3\delta\delta'$.

The nearest neighbor genes to *E. coli* holD are rimI, encoding an acetyl transferase, and yjjT, encoding a protein of unknown function. The rimI and yjjT counterparts in *P. aeruginosa* were identified based on homology. Then their neighboring genes, in the positions corresponding to holD, were examined. The *P. aeruginosa* gene immediately adjacent to yjjT is hprA, encoding a glycerate dehydrogenase. The *P. aeruginosa* gene immediately adjacent to rimI is PA4679, of previously unknown function, which we have shown to be holD, encoding the $\psi$ subunit of DNA polymerase III holoenzyme. Thus the holD and rimI genes have comparable genomic sequence positions in *E. coli* and *P. aeruginosa*. See FIG. 28.

The $\psi$ subunits encoded by *E. coli* and *P. aeruginosa* holD show little overall sequence similarity (ranging from 8-22% identity depending on which alignment algorithm was used). Local regions of similarity can be found that appear to correspond to regions important for interactions with other components of the holoenzyme complex. For example, in the *E. coli* $\chi\psi$ crystal structure (Gulbis et al., (2004) Crystal structure of the chi:psi sub-assembly of the *Escherichia coli* DNA polymerase clamp-loader complex" *Eur J Biochem* 271:439-449), two helical regions in $\psi$, $\alpha$1 and $\alpha$4, form the interface with $\chi$. $\alpha$1 helical region from *E. coli* $\psi$ aligns with a region in *P. aeruginosa* $\psi$, showing 50% identity and 64% similarity over a 14 amino segment; $\alpha$4 shows 27% identity and 73% similarity over an 11 amino region. It has been postulated that the disordered but highly conserved N-terminus of $\psi$ forms an interface with the clamp loader complex. This region shows only 42% identity and 58% similarity between *E. coli* and *P. aeruginosa* $\psi$.

Each identified *S. aureus* replicase gene was amplified from *S. aureus* genomic DNA by PCR and inserted in vectors for expression in *E. coli* as detailed in Example 36. All of the proteins were expressed as native polypeptides without inclusion of any tag (fusion) sequences. Proteins that function in a complex in *E. coli* were expressed in operons. Thus, dnaX, holA and holB were co-expressed, and dnaE was co-expressed with dnaQ. Expression vectors were transfected into fermentation strains, and induction conditions were optimized to give maximum expression and solubility of the recombinant proteins. Cells were grown in large scale in a fermentor, and processed as described in Example 39. Formation of a subassembly of the *S. aureus* Pol III holoenzyme that contained PolC, $\beta$, $\tau$, $\delta$ and $\delta'$ ($\tau$, $\delta$ and $\delta'$ are present as $\tau$-complex) as well as SSB is described in Example 38D.

Thus, this invention describes the expression and purification of key components of the Pol III holoenzyme from *S. aureus*. These proteins were sufficient to reconstitute an efficient DNA elongation reaction from a primed single-stranded DNA template.

The present invention provides reconstituted bacterial replication assemblies. As used herein, a bacterial replication assembly is a collection of proteins essential for DNA replication in a given system. In general, a bacterial replication assembly is comprised of isolated proteins or isolated complexes of proteins. According to the present invention, an isolated, or biologically pure, protein, is a protein that has been removed from its natural environment. As such, "isolated" and "biologically pure" do not necessarily reflect the extent to which the protein has been purified. An isolated subunit protein is obtained from its natural source, produced using recombinant DNA technology or produced by chemical synthesis, for example. Bacterial replication assemblies of the present invention include reconstituted polymerase III holoenzyme assemblies, reconstituted replicase assemblies, reconstituted bacterial origin of replication assemblies, and reconstituted primosome-dependent replication restart assemblies. The assemblies are useful for screening compounds that modulate the activity of the aforementioned assemblies. A bacterial replication system has not previously been targeted in large part because its complexity poses a technological barrier to setting up drug screening assays. In addition, since activity of many individual subunits depends on proper association with other components of the replication apparatus, target-based assays using single subunits are generally not feasible. A substantial portion of the system must therefore be reconstituted for drug screening.

In some embodiments it is possible to use replication protein subunits derived from a single organism. In other embodiments, the various subunits may be derived from one or more organisms. Replication proteins from Gram positive bacteria and from Gram negative bacteria can be interchanged for one another in certain embodiments. Hence, they can function as mixtures. Suitable *E. coli* replication proteins are the subunits of its Pol III holoenzyme which are described in U.S. Pat. Nos. 5,583,026 and 5,668,004 to O'Donnell. The disclosure of these patents, as well as the disclosure of all patents and publications referred to herein, are hereby incorporated by reference herein in their entirety.

The DNA Polymerase III holoenzyme of bacteria contains approximately 10 subunits that undergo marked changes in protein-protein association during each of the steps of the complex reaction they catalyze. Since all of these proteins must function together, the multitude of distinct interactions and catalytic events all provide targets for antibacterial action and thus provide a multiple of the proteins present as targets. As used herein, the term "DNA polymerase III holoenzyme"

refers to the entire DNA polymerase III entity (i.e., all of the polymerase subunits, as well as the other associated accessory proteins required for processive replication of a chromosome or genome), or a subassembly of the entire entity, such as just the core [α, ε, θ] for type I DNA Polymerase IIIs (encoded by dnaE gene) (sometimes referred to herein as "DNA polymerase III") or just an α catalytic subunit for type II DNA Polymerase IIIs (encoded by polC gene) that includes and epsilon-like sequence within the same polypeptide chain. "DNA polymerase III holoenzyme subunit" is used in reference to any of the subunit entities that comprise the DNA polymerase III holoenzyme. Thus, the term "DNA polymerase III" encompasses "DNA polymerase III holoenzyme subunits" and "DNA polymerase III subunits." Subunits include, but are not limited to, DnaX or τ (and γ from some organisms, including, but not limited to, many proteobacteria), HolA or δ, HolB or δ' proteins, DnaN or β proteins, DnaE or α subunit of DNA polymerase III-type I, PolC or α subunit of DNA polymerase III-type II and DnaQ or ε proteins. The subunits are organized into 3 subassemblies 1) Pol III core, 2) Clamp Loader ATPase and 3) Sliding clamp processivity factor. Pol III HE's are held together by multiple protein-protein interactions among subunits; these interactions are sufficiently strong to permit isolation of the oligomeric enzyme from wild-type Gram(-) bacteria. Other proteins, such as SSB and primase are implicated in replication and used in replication assemblies as described herein. Such proteins may be described in general as DNA polymerase holoenzyme subunit proteins, even though they are not part of the 10-subunit complex.

The present invention describes methods for synthesizing DNA using the bacterial replication assemblies of the present invention. Examples of such methods are found in the Examples section. In general, the method comprises incubating a DNA molecule in the presence of a bacterial replication assembly and one or more dNTPs under conditions sufficient to synthesize a second DNA molecule complementary to all or a portion of said first DNA molecule.

The present invention describes a method of identifying compounds which modulate the activity of bacterial replication assembly. This method is carried out by forming a reaction mixture that includes a primed DNA molecule, a bacterial replication assembly, a candidate compound, a dNTP or up to 4 different dNTPs, ATP or up to 4 different rNTPs; subjecting the reaction mixture to conditions effective to achieve nucleic acid polymerization in the absence of the candidate compound; analyzing the reaction mixture for the presence or absence of nucleic acid polymerization extension products and comparing the activity of the replicase in the presence of the test compound with the activity of the assembly in the absence of the test compound. A change in the activity of the assembly in the presence of the test compound is indicative of a compound that modulates the activity of the assembly.

Accordingly, the present invention also provides bacterial replication screening assemblies. A bacterial replication screening assembly comprises a bacterial replication assembly of the present invention, template DNA, a dNTP or up to 4 different dNTPs, and ATP or up to 4 different rNTPs. Certain bacterial replication screening assemblies include additional components, as described herein. The invention also provides replication protein assembly-specific assays, methods of identifying and making such assemblies, and their use in a variety of diagnostic and therapeutic applications.

This invention also provides methods for the use of the reconstituted bacterial replication assemblies in a high-throughput screening format to identify compounds that are active as modulators of DNA replication. As used herein, modulators of bacterial DNA replication are compounds that interact with the replication assembly thereby altering the ability of the replication assembly to replicate DNA. In some embodiments, the modulator inhibits the activity of the replication assembly. In the screening methods, the function of replication assemblies is quantified in the presence of different chemical test compounds. A chemical compound that inhibits the function of the assembly (e.g., inhibits DNA synthesis) is a candidate antibiotic. This method comprises the steps of a) providing a test compound suspected of modulating the function of a bacterial DNA replicase, b) detecting DNA replication in a test reaction, and c) comparing the test to a DNA replication control, wherein the amount of replication correlates with the modulatory effect of the test compound.

A wide variety of labels may be employed for detection. Essentially any label that provides for detection of DNA product, loss of DNA substrate, conversion of a nucleotide substrate, or bound protein is useful. The label may provide for direct detection such as radioactivity, fluorescence, luminescence, optical, or electron density, etc. or indirect detection such as an epitope tag, an enzyme, etc. The label may be appended to the protein (e.g., a phosphate group comprising a radioactive isotope of phosphorous), or incorporated into the DNA substrate or the protein structure (e.g., a methionine residue comprising a radioactive isotope of sulfur). A variety of methods may be used to detect the label depending on the nature of the label and other assay components. For example, the label may be detected bound to the solid substrate, or a portion of the bound complex containing the label may be separated from the solid substrate, and thereafter the label detected. Labels may be directly detected through optical or electron density, radioactive emissions, nonradiative energy transfer, fluorescence emission, etc. or indirectly detected with antibody conjugates, etc. For example, in the case of radioactive labels, emissions may be detected directly (e.g., with particle counters) or indirectly (e.g., with scintillation cocktails and counters). Radiation-based and simple fluorescence-based assays with PicoGreen® in a high-throughput screening format are described herein.

A wide variety of assays for activity and binding agents are provided, including DNA synthesis, DNA replication initiation, and primosome dependent DNA replication, for example. The replication protein assemblies used to identify modulators, are composed of more than one isolated subunit, of partially pure or pure form, which are typically, but not necessarily, recombinantly produced. The replication protein may be part of a fusion product with another peptide or polypeptide (e.g., a polypeptide that is capable of providing or enhancing protein-protein binding, stability under assay conditions (e.g., a tag for detection or anchoring), etc.). The assay mixtures comprise a natural intracellular replication protein-binding target such as DNA, another protein, NTP, or dNTP. For binding assays, while native binding targets may be used, it is possible in some embodiments to use portions (e.g., peptides, nucleic acid fragments) thereof so long as the portion provides binding affinity and avidity to the subject replication protein conveniently measurable in the assay. The assay mixture also comprises a candidate pharmacological agent. Generally, a plurality of assay mixtures are run in parallel with different agent concentrations to obtain a differential response to the various concentrations. Typically, one of these concentrations serves as a negative control (i.e., at zero concentration or below the limits of assay detection). Additional controls are often present such as a positive control, a dose response curve, use of known inhibitors, use of control heterologous proteins, etc. Candidate agents encompass numerous chemical classes, though typically they are organic compounds; preferably they are small organic compounds and are obtained from a wide variety of sources, including libraries of synthetic or natural compounds. A variety of other reagents may also be included in the mixture. These include reagents like salts, buffers, neutral proteins (e.g., albumin, detergents, etc.) which may be used to facilitate optimal binding and/or reduce nonspecific or background intersactions, etc. Also, reagents that otherwise improve the efficiency of the assay (e.g., protease inhibitors, nuclease inhibitors, antimicrobial agents, etc.) may be used.

This technology also includes efficient high-throughput approaches for deconvolution and efficient identification of the specific target. Such assays are more efficient compared to the more traditional screening assays using single target enzymes since activities of each of the proteins that comprise the holoenzyme are targeted simultaneously. Examples of such methods may be found in the Examples section.

Parallel target screens can be used for the identification of hits with broad-spectrum and narrow-spectrum specificity. Several screening systems, including Gram-negative and Gram-positive systems, have been developed using reconstituted replicases. In some embodiments, a reconstituted eukaryotic replicase will be used to identify 'hits' with broad and narrow spectrum potential and to eliminate compounds with toxic potential that inhibit the eukaryotic (DNA polymerase δ, PCNA, RFC, RPA) replication system. For example, a compound that inhibits a Gram-negative and Gram-positive replicase without inhibiting the eukaryotic replicase provides a potential candidate that can be developed into a broad-spectrum antibacterial. This strategy can be reversed (i.e., identify a compound that inhibits one Gram-negative replicase without inhibiting a different Gram-negative replicase) to obtain antibacterials that are useful for treatment of specific chronic infections where the ideal antibacterial drug would be fairly specific and not lead to the elimination of normal, nonpathogenic flora. Compounds that specifically inhibit replication of pathogens are useful as drugs to benefit infected patients.

In general, subunit proteins used in reconstituted systems are either purified from wild-type cells or genes, or the subunits were cloned, and subunits overexpressed and purified as described in the Examples. The reconstituted systems are tested for the ability to replicate DNA. Each reconstituted system is then optimized for high-throughput screening.

In one embodiment, the invention provides a reconstituted bacterial replication assembly from a Gram negative organism, including an assembly from *Yersinia pestis*. The *Y. pestis* polymerase III holoenzyme contains 10 subunits in the stoichiometry $(\alpha\epsilon\theta)_2\tau_2\gamma\delta\delta'\chi\psi(\beta_2)$. The *Y. pestis* reconstituted bacterial replication assemblies comprises $\alpha, \epsilon, \theta, \tau, \gamma, \delta, \delta', \chi, \psi, \beta$, SSB, and primase.

TABLE 1

Summary of bacterial replication assembly components.

| Gene | | | | |
|---|---|---|---|---|
| *E. coli*, *Y. pestis* | *S. pyogenes* | Protein | Function | Subassembly |
| dna E | dnaE | α | Replicative DNA polymerase | Polymerase core |
| — | polC | PolC | Replicative DNA polymerase/exonuclease | |

TABLE 1-continued

Summary of bacterial replication assembly components.

| Gene | | | | |
|---|---|---|---|---|
| *E. coli*, *Y. pestis* | *S. pyogenes* | Protein | Function | Subassembly |
| dna Q | — | ε | 3'→ 5' proofreading exonuclease | |
| hol E | — | θ | No known function | |
| dna X | dna X | τ/γ | ATPase that loads β₂ onto DNA | Clamp loader |
| hol A | hol A | δ | Essential part of DnaX complex, binds β | |
| hol B | hol B | δ' | Essential part of DnaX complex | |
| hol C | — | χ | Interacts with SSB | |
| hol D | — | ψ | Increases the affinity of DnaX for δ' | |
| dna N | dna N | β | Processivity factor | Clamp |
| ssb | ssb | SSB | Single-stranded DNA binding protein | SSB |
| dnaG | dnaG | Primase | Synthesis of RNA primers | Primosome |

*Y. pestis* DNA replication proteins and protein complexes, *E. coli* SSB, DnaG primase and β, were cloned and expressed in *E. coli* using standard protein overexpression vectors. *E. coli* DNA polymerase III* $((\alpha\epsilon\theta)_2\tau_2\gamma\delta\delta'\chi\psi)$ was purified as the native complex from wild-type cells. Proteins and protein complexes were purified using standard column chromatography similar to that described for the homologous *E. coli* proteins.

In one embodiment, the invention provides a reconstituted bacterial replication assembly from a gram positive organism, including a bacterial replication assembly from *Streptococcus pyogenes*. *S. pyogenes* DNA replication proteins and protein complexes were cloned and expressed in *E. coli* using standard protein overexpression vectors. Proteins and protein complexes were purified using standard column chromatography similar to that described for the homologous *E. coli* proteins. The *S. pyogenes* reconstituted bacterial replication assemblies comprise PolC, τ, γ, δ, δ', χ, ψ, β, SSB, and primase.

A high throughput screen (Table 2) of a total of 758,032 compounds across the 3 HTS assay yielded excellent Z- and Z prime factors (Z: 0.68-0.76; Z': 0.81-0.83), high average Signal/Background ratios (10-12-fold), manageable primary hit rates (0.2-0.7%), and excellent confirmation rates (30-60%). The HTS campaign resulted in 978, 238 and 644 confirmed hits from the *Y. pestis, E. coli* and *S. pyogenes* HTS assays. These 1,860 confirmed hits actually represent a total of 1,319 distinct compounds due to common hits between HTS assays.

TABLE 2

Results of high throughput screen in three systems.

| Statistic | *Y. pestis* HTS | *E. coli* HTS | *S. pyogenes* HTS |
|---|---|---|---|
| Signal/Background | 9.6 ± 1.2 | 11.1 ± 1.4 | 11.8 ± 2.1 |
| Z-Factor | 0.68 ± 0.12 | 0.75 ± 0.15 | 0.76 ± 0.12 |
| Z'-Factor | 0.81 ± 0.08 | 0.83 ± 0.14 | 0.82 ± 0.09 |
| Compounds Tested | 277070 | 199876 | 281086 |
| Compound Concentration | 32 µM | 24 µM | 32 µM |
| Primary Hits | 1724 | 493 | 1846 |
| Hit Rate | 0.62% | 0.25% | 0.66% |

TABLE 2-continued

Results of high throughput screen in three systems.

| Statistic | Y. pestis HTS | E. coli HTS | S. pyogenes HTS |
| --- | --- | --- | --- |
| Confirmed Hits | 978 | 238 | 644 |
| Confirmation Rate | 56.7% | 48.3% | 34.9% |

In one embodiment, the invention provides a reconstituted replicase from *Staphylococcus aureus*. The *S. aureus* replicase comprises six proteins: PolC, β, τ, δ, δ', and SSB. Five *S. aureus* genes were identified in the NCBI database by homology to previously identified genes from *S. pyogenes*. The gene for the δ subunit, however, had too little sequence similarity to be identified by simple homology. Instead, the gene for δ was only identified by an iterative ψ-BLAST search, as described in United States Patent Application Publication No. US-2003-0219737. All *S. aureus* proteins were over expressed in *E. coli* and purified using standard column chromatography.

A high throughput screening assay was developed using the purified factors to detect inhibitors of DNA synthesis. The reaction products were detected after the addition of PicoGreen®, a fluorescent stain for quantitating double-stranded DNA. The DNA synthesis assay was dependent on all six proteins and was optimized for screening so that inhibition of PolC, Beta, or Tau Complex activity would be the linear range for inhibition of DNA synthesis. The optimized assay performed well in either 96- or 384-well formats and was used to screen over 150,000 compounds. It has a good signal-to-noise ratio (7.490), with a Z-factor of 0.593 and a Z'-factor of 0.700. The overall hit rate was 0.80%.

TABLE 3

Summary of results from *S. aureus* high throughput screening assay

| Compounds Screened | 165,933 |
| --- | --- |
| Primary hits | 1,320 |
| Unique to Sau System | 1,019 |
| Cherry picked for confirmation | 796 |
| Confirmed hits | 202 |
| Primary hit rate | 0.80% (1,320/165,933) |
| Adjusted hit rate | 0.48% (796/165,933) |
| Confirmation rate | 15.3% (202/1,320) |
| Adjusted confirmation rate | 25.4% (202/796) |
| Signal/background | 7.49 ± 0.87 |

TABLE 3-continued

Summary of results from *S. aureus* high throughput screening assay

| Z-factor | 0.59 ± 0.11 |
| --- | --- |
| Z'-factor | 0.70 ± 0.09 |

In one embodiment, the invention provides a reconstituted bacterial replication assembly from *Pseudomonas aeruginosa*. The components of pol III holoenzyme and primase from *P. aeruginosa* were PCR-cloned from genomic DNA, overexpressed and purified as described in U.S. Provisional Patent Application Ser No. 60/623,564, filed on Oct. 28, 2004. As disclosed in this application, the identity of the ψ subunit was not apparent based on sequence homology. Native DnaX complex from *P. aeruginosa* was purified and the ψ subunit was identified on this basis. Addition of χ and ψ to the reaction increased the specific activity of $\tau_3\delta\delta$. χψ also conferred higher salt tolerance, allowing the holoenzyme to function efficiently under physiological salt conditions. In the absence of χψ, a modest dependence on β is observed at limiting core (αε) concentrations. χψ conferred increased dependence on β. χψ conferred greater dependence on both β and SSB. There was a virtually complete dependence on all other components. The *P. aeruginosa* bacterial replication assembly comprises α, ε, τ, δ, δ', χ, ψ, β, SSB, and primase.

TABLE 3

Summary of *P. Aeruginosa* bacterial replication assembly.

| P. Aeruginosa Gene Name | P. Aeruginosa Gene Number | Protein Encoded | No. Amino Acids | % Identity/Similarity to E. coli Protein |
| --- | --- | --- | --- | --- |
| dnaE | PA3640 | DnaE (α) polymerase | 1,173 | 58/71 |
| dnaQ | PA1816 | DnaQ (ε) exonuclease | 246 | 51/66 |
| dnaN | PA0002 | DnaN (β) sliding clamp | 367 | 56/71 |
| dnaX | PA1532 | DnaX (τ) clamp loader | 681 | 42/53 |
| holA | PA3989 | HolA (δ) clamp loader accessory | 345 | 31/44 |
| holB | PA2961 | HolB (δ') clamp loader accessory | 328 | 29/45 |
| holC | PA3832 | HolC (χ) clamp loader accessory | 142 | 30/47 |
| ssb | PA4232 | SSB single-stranded DNA binding | 165 | 56/62 |

Table 4 below shows HTS statistics for screening of compounds libraries in the presence or absence of χψ. The HTS assay proved to be quite robust. Inclusion of 0.2 mg/mL bovine serum albumin (BSA) in the reaction buffer lowered the overall number of hits by approximately 60%. Many compounds showed a higher magnitude of inhibition of the holoenzyme reaction in the presence χψ compared to holoenzyme without χψ, and new classes of compounds were identified that only inhibited in the presence χψ.

TABLE 4

HTS statistics for screening of compounds libraries in the presence or absence of χψ

| Statistic | Without χψ | With χψ |
| --- | --- | --- |
| Signal/background | 11.3 ± 1.0 | 8.9 ± 1.3 |
| z-factor | 0.57 ± 0.20 | 0.34 ± 0.22 |
| z'-factor | 0.73 ± 0.10 | 0.61 ± 0.09 |
| Compounds tested | 181,120 | 126,043 |
| Primary hit rate | 1.95% | 3.92% |
| Confirmation rate | 39% | 65% |

In one embodiment, the invention provides a reconstituted E. coli bacterial origin of replication assembly. Although DNA replication is an essential process for proliferation of all cell types, in bacteria, DNA replication is initiated by a mechanism which set bacterial cells apart from their eukaryotic counterpart. The unique initiation mechanism provides a potential target for novel antibacterial agents. The E. coli chromosomal DNA replication initiates bi-directionally at a specific sequence, oriC. The minimal origin region required was isolated by determining the smallest oriC segment that could drive replication. This minimal E. coli oriC sequence is highly conserved has several distinctive DNA sequence features. There are four copies of the sequence 5'-TTAT(C/A)CACA-3' (SEQ ID NO: 1) in the form of two inverted repeats. The position of these sequences, denoted R1-R4, is also highly conserved. This repeated sequence was shown to be the binding site for the DnaA protein and is referred to as a DnaA box. Directly to the left of the DnaA boxes is a series of three A+T-rich 13 mers. This region plays a critical role in the process of localized denaturation required to initiate DNA replication.

The pathway of initiation at oriC has been established, primarily through the efforts directed by Arthur Kornberg. DnaA binds to the origin to form a nucleoprotein complex. DnaA is an ATPase; only the ATP-bound form is competent to execute subsequent steps in the process of initiation at oriC. In the presence of ATP, the DnaA protein unwinds the A+T-rich 13 mers. The replication fork helicase, DnaB, is now guided into position onto the single strands of the denatured region via a protein-protein interaction with DnaA. DnaB exists in solution as an inactive complex with DnaC. This is presumably to prevent loading of DnaB onto regions of the chromosome other than the origin. It has been shown that transfer of DnaB to DNA is mediated by DnaC first binding to DNA. Once DnaB is transferred to the DNA, however, DnaC dissociates and is not found at the replication fork. The next step is the attraction of the primase, DnaG, to the DNA by virtue of a protein-protein interaction with DnaB. The first primer that is made attracts DNA polymerase III holoenzyme, the specialized multi-subunit polymerase, and catalyzes the initiation of leading-strand synthesis.

The origin region would be difficult to utilize in the development of a high throughput screen due to size of the region. However, a system based on the initial system developed by Arai and Kaguni has been developed that has allowed for the successful DnaA and DnaB-dependent reconstitution of the origin complex (Masai, et al., The ABC primosome: A novel priming system employing dnaA, dnaB, dnaC and primase on a hairpin containing a dnaA box sequence. J Biol Chem; 1990; 265:15134-15144; Masai, & Arai, Dna-A dependent assembly of the ABC primosome at the A site, a single-stranded DNA hairpin-containing a dnaA box. Eur J Biochem; 1995; 230:384-395). The initiation of replication can be conveniently monitored by measuring the conversion of bacteriophage M13 single-stranded DNA template to the duplex replicative form. Basically, DnaA, DnaB and DnaC interact with a M13 single-strand DNA possessing a DnaA box within a hairpin.

The reconstituted bacterial replication assembly for the E. coli origin of replication comprises DnaA, DnaB, DnaC, primase, SSB. Additional components include $\alpha$, $\epsilon$, $\theta$, $\tau$, $\delta$, $\delta'$, $\psi$, and $\chi$. $\alpha$, $\epsilon$, $\theta$, $\tau$, $\delta$, $\delta'$, $\psi$, and $\chi$ are present as Core polymerase ($\alpha\epsilon\theta$) and $\tau$ complex ($\tau_2\gamma\delta\delta'\chi\psi$). Expression and purification were optimized for the five proteins and two protein complexes needed at the origin. The assay is DnaA, DnaB and DnaC dependent, however, the DnaC dependence is unique in that it (along with SSB) are critical for balancing the equilibrium between the DnaA-dependent mechanism and general priming. If a compound targets DnaC, the general priming mechanism takes over and a false negative would result. Therefore, other screening assays will be required to identify DnaC targeted compounds. DnaA binding has been verified by nitrocellulose filter binding a gel shift analysis. The reconstituted origin assay has been termed ECDNAA.

The reaction modeling the replication initiation event provides a robust, reproducible HTS assay. A high throughput screen of ~230,000 compounds in the ECDNAA assay yielded average Z- and Z prime factors of 0.49 and 0.68 respectively, an average S/B of 9.3, an overall hit rate of 0.92%, and an overall confirmation rate of 4.8%. Of the confirmed hits, there are compounds that demonstrate both biochemical specificity and microbiological activity.

TABLE 5

Summary of HTS statistics for the E. coli origin of replication

| | |
|---|---|
| Compounds Evaluated | 231,804 |
| Signal/Background | 9.3 |
| Z-Factor | 0.486 |
| Z'Factor | 0.607 |
| No. of Primary Hits | 2,136 |
| No. of "Cherry-picked" | 1,574 |
| Hit Rate | 0.92% |
| No. of Confirmed Hits | 75 |
| Confirmed Hit Rate | 4.76% |

The invention also provides a reconstituted primosome-dependent replication restart assembly from gram-positive organism. Primosome-dependent replication restart is an integral part of the replication process. Genes that encode the protein components of the primosome are, like those of the replication apparatus, essential and therefore represent candidate targets for antibacterial drugs. The Gram-positive primosome-dependent replication restart assembly comprises PriA, DnaB, DnaC, DnaD, DnaI, DnaG (primase), and SSB.

TABLE 6

Analysis of gram-positive primosome-dependent replication restart assembly

| Gram-negative (E. coli) | Gram-positive (B. subtilis) | Function in Priming | Gene essential in B. subtilis? (candidate drug target?) |
|---|---|---|---|
| PAS site | ssiA | Primosome assembly site | N/A |
| PriA | PriA | Initiator (stalled forks and PAS sites) | Yes |
| DnaT, PriB, PriC | DnaD | Adaptor | Yes |
| DnaB | DnaC | Helicase | Yes |
| DnaC | DnaI, DnaB | Helicase loader | Yes |
| DnaG | DnaG | Primase | Yes |

Additional components in the bacterial replication screening assembly include Bacillus subtilis-encoded single-stranded DNA-binding protein, a plasmidic primosome assembly site (PAS), and DNA polymerase.

The primosome-dependent replication reaction in vitro is robust, reproducible, and DMSO-resistant. A screen of a 10,000 compound test library in duplicate produced a Z' of 0.64, and a predicted confidence rate of 60% at a 50% inhibition cut-off (below, second from right). A screen of roughly 200,000 compounds has produced a Z' of 0.64, an average S/B of 8.88, an overall hit rate of 2.92%, and an overall confirmation rate of 40%. A majority of hits are unique to the B. subtilis primosome. More than 200 compounds exhibit an IC50 of less than 20 μM, and more than 75 compounds exhibit MIC's of 32 μg/ml or less.

TABLE 7

Summary of HTS statistics for gram-positive primosome-dependent replication restart assembly

| | |
|---|---|
| Compounds screened | 202,742 |
| Average Z' | 0.64 |
| Primary hits | 5,914 |
| Hit rate (50% cutoff) | 2.92% |
| Unique to Bs primosome | 4,866 |
| Cherry-picked | 4,295 |
| Confirmed | 1,788 |
| Confirmation rate | 41.3% |
| $IC_{50}$'s measured | 877 |
| $IC_{50}$'s under 20 μM | 193 |
| MIC's measured | 342 |
| MIC's under 32 μg/ml | 78 |

The results show that it is possible to do HTS with complex multiple-target systems. The diversity of enzymatic activities present in any single HTS assay is predicted to save expensive resources that otherwise would be spent on multiple single-protein screens. Another advantage is that the more physiological setting of enzymes within multi-protein complexes as found in vivo provide multiple protein-protein and protein-nucleic acid interactions as additional targets as well as more in vivo relevant protein conformations than would otherwise be the case in single component systems.

5-Benzylidene-2-thioxo-thiazolidin-4-ones have recently been identified as a new series of antibacterial agents. These compounds were tested in high-throughput screening assays from *S. pyogenes*, and *Y. pestis* as described in the Examples. These compounds demonstrated inhibition of DNA polymerase holoenzyme that correlated well with pathogen-specific antibacterial activity. Nitro-substituted analogs were found to have a specific substitution requirement for DNA Polymerase holoenzyme activity. The structure activity relationship for compounds screened is shown in the following tables.

TABLE 8

Activity of 5-Benzylidene-2-thioxo-thiazolidin-4-ones

| STRUCTURE | $IC_{50}$ S. pyog. (μM) | $IC_{50}$ Y. pestis (μM) |
|---|---|---|
| 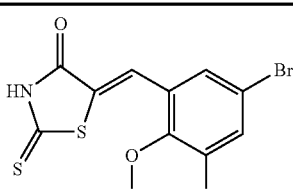 | 18.07 | 31.42 |
| 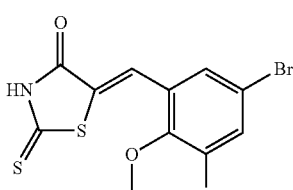 | 13.47 | 22.26 |

TABLE 8-continued

Activity of 5-Benzylidene-2-thioxo-thiazolidin-4-ones

| STRUCTURE | $IC_{50}$ S. pyog. (μM) | $IC_{50}$ Y. pestis (μM) |
|---|---|---|
| 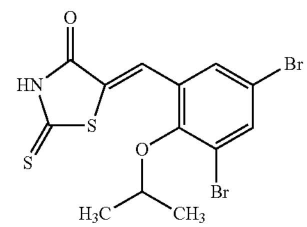 [SMILES: CC(C)Oc1c(Br)cc(Br)cc1/C=C1\SC(=S)NC1=O] | 7.11 | 18.81 |
| 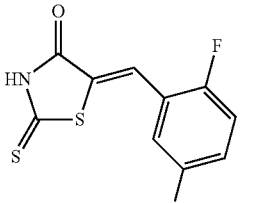 | >320.00 | >320.00 |
| 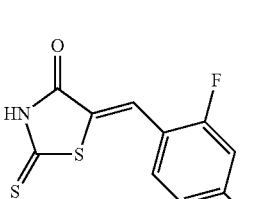 | 14.2 | 21.99 |
|  | >320.00 | >320.00 |
| 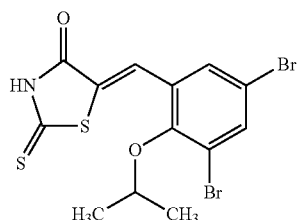 | 64.52 | 95.91 |
| 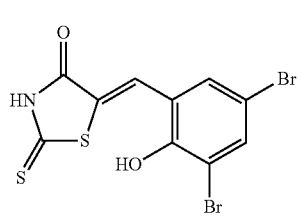 [SMILES: O=C1NC(=S)S/C1=C\c1cc(Br)cc(Br)c1O] | 60.05 | 28.46 |

TABLE 8-continued

Activity of 5-Benzylidene-2-thioxo-thiazolidin-4-ones

| STRUCTURE | IC$_{50}$ S. pyog. (µM) | IC$_{50}$ Y. pestis (µM) |
|---|---|---|
| (2,4,5-trifluorobenzylidene) | 120.87 | 202.81 |
| (2-fluoro-3-chlorobenzylidene) | 79.88 | 122.58 |
| (2-fluoro-3-methoxybenzylidene) | 276.55 | 54.14 |
| (2,6-dimethoxybenzylidene) | >320.00 | 185.58 |
| (2,6-dimethylbenzylidene) | 270.83 | 302.14 |
| (2,6-dichlorobenzylidene) | 102.28 | 161.61 |
| (2-(4-chlorophenylthio)-4-nitrobenzylidene) | 3.53 | 4.62 |
| (2-(4-tert-butylphenoxy)-5-nitrobenzylidene) | 4.38 | 7.03 |
| (2-(trifluoromethoxy)-5-nitrobenzylidene) | 96.03 | 52.85 |
| (2-(cyclohexylthio)-5-nitrobenzylidene) | 8.73 | 9.94 |
| (2-methoxy-5-nitrobenzylidene) | 89.04 | 126.32 |
| (3-nitro-4-methoxybenzylidene) | >320.00 | 48.93 |

TABLE 8-continued

Activity of 5-Benzylidene-2-thioxo-thiazolidin-4-ones

| STRUCTURE | IC$_{50}$ S. pyog. (μM) | IC$_{50}$ Y. pestis (μM) |
|---|---|---|
| 3-nitro-4-morpholinobenzylidene derivative | >320.00 | >320.00 |
| 2-nitro-4-chlorobenzylidene derivative | 133.04 | 63.92 |
| 2-nitro-5-chlorobenzylidene derivative | 162.73 | 267.27 |
| 2-methoxy-6-fluorobenzylidene derivative | >320.00 | 194.62 |
| 2-fluoro-5-methoxybenzylidene derivative | 192.95 | 179.41 |
| 3,4-difluorobenzylidene derivative | 181.26 | 241.01 |
| 2,5-difluorobenzylidene derivative | 210.52 | 320 |
| 2,6-difluorobenzylidene derivative | >320.00 | 196.34 |
| 2,3-difluorobenzylidene derivative | 214.31 | 211.54 |
| 2,4-difluorobenzylidene derivative | 288.15 | 315.09 |
| 2-fluoro-5-trifluoromethylbenzylidene derivative | 45.09 | 108.4 |
| 2-fluoro-3-trifluoromethylbenzylidene derivative | 67.92 | 165.76 |
| 2-fluoro-4,5-dimethoxybenzylidene derivative | >320.00 | >320.00 |

TABLE 8-continued

Activity of 5-Benzylidene-2-thioxo-thiazolidin-4-ones

| STRUCTURE | IC$_{50}$ S. pyog. (μM) | IC$_{50}$ Y. pestis (μM) |
|---|---|---|
| (3,4-dichlorobenzylidene, 2-thioxo) | 37.25 | 61.59 |
| (3,4-dichlorobenzylidene, 2-methylimino) | 111.87 | 286.11 |
| (3,4-dichlorobenzylidene, 2-imino) | 145.49 | 115.65 |
| (3,4-dichlorobenzylidene, 2-thioxo) | >320.00 | >320.00 |
| (2-piperidinyl-5-nitrobenzylidene, 2-thioxo) | 23.72 | 41.21 |
| (2-morpholinyl-5-nitrobenzylidene, 2-thioxo) | 191.61 | 107.74 |
| (2-fluoro-5-nitrobenzylidene, 2-thioxo) | 89.72 | 101.35 |
| (2-chloro-5-nitrobenzylidene, 2-thioxo) | 81.62 | 88.86 |
| (3-nitro-4-chlorobenzylidene, 2-thioxo) | 24.15 | 27.15 |
| (6-nitro-benzodioxole, 2-thioxo) | 98.35 | 143.91 |
| (2-nitro-4,5-dimethoxybenzylidene, 2-thioxo) | >320.00 | >320.00 |
| (2-nitro-4-dimethylaminobenzylidene, 2-thioxo) | 44.41 | 22.56 |

TABLE 8-continued

Activity of 5-Benzylidene-2-thioxo-thiazolidin-4-ones

| STRUCTURE | IC$_{50}$ S. pyog. (μM) | IC$_{50}$ Y. pestis (μM) |
|---|---|---|
| (structure shown) | 320 | 161.64 |

In particular, 5-[2-(4-Chloro-phenylsulfanyl)-5-nitro-benzylidene]-2-thioxo-thiazolidin-4-one:

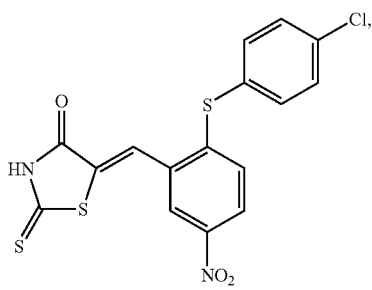

was identified as a Pol III holoenzyme inhibitor that displayed low μM activity (3-7 μM) against post gram positive and gram negative derived enzymes. The present invention also includes the use of modulators of bacterial DNA replication that reduce the replication activity of a bacterial DNA replicase to reduce bacterial infection of animals, plants, humans and the surrounding environment. As used herein, modulators of bacterial DNA replication are compounds that interact with the replicase thereby altering the ability of replicase to replicate DNA. A preferred modulator inhibits replication.

Novel replication protein-specific antibodies and other natural intracellular binding agents identified with assays such as one- and two-hybrid screens, non-natural intracellular binding agents identified in screens of chemical libraries, etc. are also included. Generally, replication protein-specificity of the binding agent is shown by equilibrium constants or values that approximate equilibrium constants such as the concentration that inhibits a reaction 50% (IC$_{50}$). Such agents are capable of selectively binding a replication protein (i.e., with an equilibrium association constant at least about $10^7 M^{-1}$, preferably, at least about $10^8 M^{-1}$, more preferably, at least about $10^9 M^{-1}$). A wide variety of cell-based and cell-free assays may be used to demonstrate replication protein-specific activity, binding, gel shift assays, immunoassays, etc.

The resultant mixture is incubated under conditions whereby, but for the presence of the candidate pharmacological agent, the replication protein specifically binds the cellular binding target, portion, or analog. The mixture of components can be added in any order that provides for the requisite bindings.

Incubations may be performed at any temperature which facilitates optimal binding, typically between 4° C. and 40° C., more commonly between 15° C. and 37° C. Incubation periods are likewise selected for optimal binding but also minimized to facilitate rapid, high-throughput screening, and are typically between 0.1 and 10 hours, preferably less than 5 hours, more preferably less than 1 hour.

After incubation, the presence or absence of activity or specific binding between the replication protein and one or more binding targets is detected by any convenient way. For cell-free activity and binding type assays, a separation step may be used to separate the activity product or the bound from unbound components.

Separation may be effected by precipitation (e.g., immunoprecipitation or acid precipitation of a nucleic acid product), immobilization (e.g., on a solid substrate such as a microtiter plate), etc., followed by washing. Many assays that do not require separation are also possible such as use of europium conjugation in proximity assays, fluorescence increases upon double stranded DNA synthesis in the presence of dyes that increase fluorescence upon intercalating in double-stranded DNA, scintillation proximity assays or a detection system that is dependent on a reaction product or loss of substrate.

Detection may be effected in any convenient way. For cell-free activity and binding assays, one of the components usually comprises or is coupled to a label.

The present invention also includes a test kit to identify a compound capable of modulating DNA polymerase III replicase activity. Such a test kit includes components for a reconstituted bacterial replication system and a means for determining the extent of modulation of DNA replication activity in the presence of (i.e., effected by) a putative modulatory or inhibitory compound.

For completeness, various aspects of the invention are set out in the following numbered clauses:

1. An isolated P. aeruginosa DNA polymerase ψ subunit protein, wherein the ψ subunit protein is selected from the group consisting of:
   a) an amino acid sequence represented by SEQ ID NO:37; and
   b) an amino acid sequence having at least 95% sequence identity to an amino acid sequence represented by SEQ ID NO:37.

2. An isolated polypeptide selected from the group consisting of a polypeptide encoded by a nucleic acid molecule represented by SEQ ID NO:35 and a polypeptide encoded by a nucleic acid molecule having at least 85% homology to a nucleic acid molecule represented by SEQ ID NO:35.

3. An isolated nucleic acid molecule selected from the group consisting of a nucleic acid molecule represented by SEQ ID NO:35 and a nucleic acid molecule having at least 85% homology to a nucleic acid molecule represented by SEQ ID NO:35.

4. An antibody, wherein the antibody is capable of specifically binding to at least one antigenic determinant on the protein encoded by an amino acid sequence selected from the group consisting of
   a) an amino acid sequence represented by SEQ ID NO:37; and
   b) an amino acid sequence selected from the group consisting of an amino acid sequence having at least 95% sequence identity to an amino acid sequence represented in a).

5. The antibody of Clause 4, wherein the antibody type is selected from the group consisting of polyclonal, monoclonal, chimeric, single chain, $F_{ab}$ fragments, and an $F_{ab}$ expression library.

6. A method for producing anti-DNA polymerase III subunit antibodies comprising exposing an animal having immunocompetent cells to an immunogen comprising at least an antigentic portion of P. aeruginosa ψ subunit.

7. The method of Clause 6, further comprising the step of harvesting the antibodies.

8. The method of Clause 6, further comprising fusing the immunocompetent cells with an immortal cell line under conditions such that a hybridoma is produced.

9. A method for detecting a P. aeruginosa DNA polymerase III subunit protein comprising,
   a) providing in any order, a sample suspected of containing P. aeruginosa DNA polymerase III, an antibody capable of specifically binding to at least a portion of the P. aeruginosa DNA polymerase III ψ subunit protein;
   b) mixing the sample and the antibody under conditions wherein the antibody can bind to the P. aeruginosa DNA polymerase III; and
   c) detecting the binding.

10. A recombinant molecule comprising at least a portion of a P. aeruginosa DNA polymerase III holD nucleic acid molecule.

11. The recombinant molecule of Clause 10, wherein the nucleic acid molecule is operably linked to a transcription control element.

12. The recombinant molecule of Clause 11, wherein the transcription control element is pA1 or T7 promoter.

13. The recombinant molecule of Clause 10, wherein the recombinant molecule comprises pET14b-PA-L4679, pET14b-PA-L4679HolC.

14. A recombinant molecule comprising at least a portion of a P. aeruginosa DNA polymerase III holC nucleic acid molecule and at least a portion of a P. aeruginosa DNA polymerase III holD nucleic acid molecule.

15. The recombinant molecule of Clause 14, wherein the holC and holD nucleic acid molecules are operably linked to a transcription control element.

16. The recombinant molecule of Clause 15, wherein the transcription control element is pA1 or T7 promoter.

17. The recombinant molecule of Clause 16, wherein the recombinant molecule comprises, pET14b-PA-L4679HolC.

18. A method of identifying compounds that modulate the activity of a DnaX complex and a β subunit in stimulating a DNA polymerase replicase comprising
   a) contacting a primed DNA (which may be coated with SSB) with a DNA polymerase replicase, a β subunit, and a τ complex (or subunit or subassembly of the DnaX complex) in the presence of the candidate pharmaceutical, and dNTPs (or modified dNTPs) to form a reaction mixture
   b) subjecting the reaction mixture to conditions effective to achieve nucleic acid polymerization in the absence of the candidate compound; and
   c) comparing the nucleic acid polymerization in the presence of the test compound with the nucleic acid polymerization in the absence of the test compound, wherein a change in the nucleic acid polymerization in the presence of the test compound is indicative of a compound that modulates the activity of a DnaX complex and a β subunit, wherein said DnaX complex comprises a P. aeruginosa DNA polymerase III ψ subunit protein.

19. The method of Clause 18, wherein said P. aeruginosa DNA polymerase III subunit protein is encoded by a nucleic acid molecule selected from the group consisting of
   a) SEQ ID NO:35; and
   b) a protein comprising a homologue of a protein of a), wherein said homologue encodes a protein containing one or more amino acid deletions, substitutions, or insertions, and wherein said protein performs the function of a natural subunit protein in a bacterial replication assay; and
   c) an isolated bacterial nucleic acid molecule which is fully complementary to any said nucleic acid molecule recited in a).

20. The method of Clause 18, wherein said DnaX complex further comprises a P. aeruginosa DNA polymerase III χ subunit protein.

21. A method to identify compounds that modulate the ability of a β subunit and a DnaX complex (or a subunit or subassembly of the DnaX complex) to interact comprising
   a) contacting the β subunit with the DnaX complex (or subunit or subassembly of the DnaX complex) in the presence of the compounds to form a reaction mixture;
   b) subjecting the reaction mixture to conditions under which the DnaX complex (or the subunit or subassembly of the DnaX complex) and the β subunit would interact in the absence of the compound; and
   c) comparing the extent of interaction in the presence of the test compound with the extent of interaction in the absence of the test compound, wherein a change in the interaction between the β subunit and the DnaX complex (or the subunit or subassembly of the DnaX complex) is indicative of a compound that modulates the interaction,
   wherein said DnaX complex (or subunit or subassembly of the DnaX complex) comprises a P. aeruginosa DNA polymerase ψ III subunit protein.

22. The method of Clause 21, wherein said P. aeruginosa DNA polymerase III subunit protein is encoded by a nucleic acid molecule selected from the group consisting of
   a) SEQ ID NO:36; and
   b) a protein comprising a homologue of a protein of a), wherein said homologue encodes a protein containing one or more amino acid deletions, substitutions, or insertions, and wherein said protein performs the function of a natural subunit protein in a bacterial replication assay; and
   c) an isolated bacterial nucleic acid molecule which is fully complementary to any said nucleic acid molecule recited in a).

23. The method of Clause 21, wherein said DnaX complex further comprises a P. aeruginosa DNA polymerase III χ subunit protein.

24. A method to identify compounds that modulate the ability of a DnaX complex (or a subassembly of the DnaX complex) to assemble a β subunit onto a DNA molecule comprising:
   a) contacting a circular primed DNA molecule (which may be coated with SSB) with the DnaX complex (or the subassembly thereof) and the β subunit in the presence of the compound, and ATP or dATP to form a reaction mixture
   b) subjecting the reaction mixture to conditions under which the DnaX complex (or subassembly) assembles the β subunit on the DNA molecule absent the compound; and
   c) comparing extent of assembly in the presence of the test with the extent of assembly in the absence of the test compound, wherein a change in the amount of β subunit on the DNA molecule is indicative of a compound that modulates the ability of a DnaX complex (or a subassembly of the DnaX complex) to assemble a β subunit onto a DNA molecule,
   wherein the DnaX complex (or a subassembly of the DnaX complex) comprises a P. aeruginosa DNA polymerase III ψ subunit protein.

25. The method of Clause 24, wherein said P. aeruginosa DNA polymerase III subunit protein is encoded by a nucleic acid molecule selected from the group consisting of a) SEQ ID NO:36; and b) a protein comprising a homologue of a protein of a), wherein said homologue encodes a protein containing one or more amino acid deletions, substitutions, or insertions, and wherein said protein performs the function of a natural subunit protein in a bacterial replication assay; and c) an isolated bacterial nucleic acid molecule which is fully complementary to any said nucleic acid molecule recited in a).

26. The method of Clause 24, wherein said DnaX complex further comprises a P. aeruginosa DNA polymerase III χ subunit protein.

27. A method to identify compounds that modulate the ability of a DnaX complex (or a subunit (s) of the DnaX complex) to disassemble a β subunit from a DNA molecule comprising a) contacting a DNA molecule onto which the β subunit has been assembled in the presence of the compound, to form a reaction mixture;

b) subjecting the reaction mixture to conditions under which the DnaX complex (or a subunit (s) or subassembly of the DnaX complex) disassembles the β subunit from the DNA molecule absent the compound; and c) comparing the extent of assembly in the presence of the test compound with the extent of assembly in the absence of the test compound, wherein a change in the amount of β subunit on the DNA molecule is indicative of a compound that modulates the ability of a DnaX complex (or a subassembly of the DnaX complex) to disassemble a β subunit onto a DNA molecule, wherein the DnaX complex (or a subassembly of the DnaX complex) comprises a P. aeruginosa DNA polymerase III ψ subunit protein.

28. The method of Clause 27, wherein said DNA polymerase III subunit protein is encoded by a nucleic acid molecule selected from the group consisting of a) SEQ ID NO:36; and b) a protein comprising a homologue of a protein of a), wherein said homologue encodes a protein containing one or more amino acid deletions, substitutions, or insertions, and wherein said protein performs the function of a natural subunit protein in a bacterial replication assay; and c) an isolated bacterial nucleic acid molecule which is fully complementary to any said nucleic acid molecule recited in a).

29. The method of Clause 27, wherein said DnaX complex further comprises a P. aeruginosa DNA polymerase III χ subunit protein.

30. A method of synthesizing a DNA molecule comprising
a) hybridizing a primer to a first DNA molecule; and
b) incubating said DNA molecule in the presence of a DNA polymerase replicase and one or more dNTPs under conditions sufficient to synthesize a second DNA molecule complementary to all or a portion of said first DNA molecule;
wherein said DNA polymerase replicase comprises a P. aeruginosa DNA polymerase III ψ subunit protein.

31. The method of Clause 30, wherein said DNA polymerase complex further comprises a P. aeruginosa DNA polymerase III χ subunit protein.

32. An isolated bacterial DNA polymerase SSB protein, wherein the SSB selected from the group consisting of:
a) an amino acid sequence represented by SEQ ID NO:93; and
b) an amino acid sequence having at least 95% sequence identity to an amino acid sequence represented by SEQ ID NO:93.

33. An isolated polypeptide selected from the group consisting of a polypeptide encoded by a nucleic acid molecule represented by SEQ ID NO:91 and a polypeptide encoded by a nucleic acid molecule having at least 85% homology to a nucleic acid molecule represented by SEQ ID NO:91.

34. The isolated polypeptide of Clause 33, wherein the polypeptide is capable of extending primed DNA in a M13Gori polymerase assay.

35. An isolated nucleic acid molecule selected from the group consisting of a nucleic acid molecule represented by SEQ ID NO:91 and a nucleic acid molecule having at least 85% homology to a nucleic acid molecule represented by SEQ ID NO:91.

36. An antibody, wherein the antibody is capable of specifically binding to at least one antigenic determinant on the protein encoded by an amino acid sequence selected from the group consisting of a) an amino acid sequence represented by SEQ ID NO:93; and b) an amino acid sequence selected from the group consisting of an amino acid sequence having at least 95% sequence identity to an amino acid sequence represented in a).

37. The antibody of Clause 36, wherein the antibody type is selected from the group consisting of polyclonal, monoclonal, chimeric, single chain, $F_{ab}$ fragments, and an $F_{ab}$ expression library.

38. A method for producing anti-DNA polymerase III subunit antibodies comprising exposing an animal having immunocompetent cells to an immunogen comprising at least an antigentic portion of DNA polymerase SSB protein.

39. The method of Clause 38, further comprising the step of harvesting the antibodies.

40. The method of Clause 38, further comprising fusing the immunocompetent cells with an immortal cell line under conditions such that a hybridoma is produced.

41. A method for detecting an S. aureus DNA polymerase III subunit protein comprising, a) providing in any order, a sample suspected of containing S. aureus DNA polymerase III, an antibody capable of specifically binding to at least a portion of the S. aureus DNA polymerase III subunit protein;

b) mixing the sample and the antibody under conditions wherein the antibody can bind to the S. aureus DNA polymerase III; and c) detecting the binding.

42. A recombinant molecule selected from the group consisting of a recombinant molecule comprising at least a portion of an S. aureus DNA polymerase III ssb nucleic acid molecule.

43. The recombinant molecule of Clause 42, wherein the nucleic acid molecule is operably linked to a transcription control element.

44. The recombinant molecule of Clause 43, wherein the transcription control element is pA1.

45. The recombinant molecule of Clause 43, wherein the transcription control element is an RBS.

46. The recombinant molecule of Clause 42, wherein the recombinant molecule is selected from the group consisting of pA1-SA-ssb#3.

47. A method of synthesizing a DNA molecule comprising
a) hybridizing a primer to a first DNA molecule; and
b) incubating said DNA molecule in the presence of a DNA polymerase replicase and one or more dNTPs under conditions sufficient to synthesize a second DNA molecule complementary to all or a portion of said first DNA molecule;

wherein said DNA polymerase replicase comprises an isolated *S. aureus* SSB protein.

48. A method for identifying a compound that modulates the activity of a bacterial replication assembly, comprising:

a) contacting a DNA molecule capable of being replicated with a bacterial replication assembly with a test compound to form a reaction mixture;

b) subjecting the reaction mixture to conditions, which in the absence of the compound, effect nucleic acid polymerization; and c) comparing the nucleic acid polymerization in the presence of the test compound with the nucleic acid polymerization in the absence of the test compound, wherein a change in the activity of the bacterial replication assembly in the presence of the test compound is indicative of a compound that modulates the activity of the bacterial replication assembly.

49. The method of clause 48, wherein the bacterial replication assembly is selected from the group consisting of an *S. pyogenes* bacterial replication assembly, an *S. aureus* bacterial replication assembly, a *Y. pestis* bacterial replication assembly, a *P. aeruginosa* bacterial replication assembly, a *B. subtilis* bacterial replication assembly, and an *E. coli* bacterial replication assembly.

50. The method of clause 49, wherein the *S. pyogenes* bacterial replication assembly comprises isolated *S. pyogenes* PolC, $\tau$, $\gamma$, $\delta$, $\delta'$, $\chi$, $\psi$, $\beta$, SSB and primase proteins.

51. The method of clause 49, wherein the *S. aureus* bacterial replication assembly comprises isolated *S. aureus* PolC, $\beta$, $\tau$, $\delta$, $\delta'$ and SSB proteins.

52. The method of clause 49, wherein the *Y. pestis* bacterial replication assembly comprises isolated *Y. pestis* $\alpha$, $\epsilon$, $\theta$, $\tau$, $\gamma$, $\delta$, $\delta'$, $\chi$, $\psi$, $\beta$, SSB and primase proteins.

53. The method of clause 49, wherein the *P. aeruginosa* bacterial replication assembly comprises isolated *P. aeruginosa* $\alpha$, $\epsilon$, $\tau$, $\gamma$, $\delta$, $\delta'$, $\chi$, $\psi$, $\beta$, SSB and primase proteins.

54. The method of clause 49, wherein the *B. subtilis* bacterial replication assembly comprises isolated *B. subtilis* PriA, DnaB, DnaC, DnaD, DnaI, DnaG (primase), and SSB proteins.

55. The method of clause 54, wherein said *B. subtilis* bacterial replication assembly further comprises DNA polymerase.

56. The method of clause 54, wherein said DNA molecule comprises a plasmidic primosome assembly site (PAS).

57. The method of clause 49, wherein the *E. coli* bacterial replication assembly comprises isolated *E. coli* DnaA, DnaB, DnaC, primase, and SSB proteins.

58. The method of clause 57, wherein the *E. Coli* bacterial replication assembly further comprises DNA polymerase.

59. The method of clause 57, wherein said DNA molecule comprises an A site.

60. A method for identifying a compound that modulates the activity of a bacterial replication assembly, comprising:

a) contacting a each of a plurality of DNA molecules capable of being replicated with a bacterial replication assembly with a different test compound to form a plurality of reaction mixtures;

b) subjecting the reaction mixtures to conditions, which in the absence of the compounds, effect nucleic acid polymerization; and c) comparing the nucleic acid polymerization in the presence of the test compounds with the nucleic acid polymerization in the absence of the test compounds, wherein a change in the activity of the bacterial replication assembly in the presence of any one compound is indicative of a compound that modulates the activity of the bacterial replication assembly.

61. The method of clause 60, wherein the bacterial replication assembly is selected from the group consisting of an *S. pyogenes* bacterial replication assembly, an *S. aureus* bacterial replication assembly, a *Y. pestis* bacterial replication assembly, a *P. aeruginosa* bacterial replication assembly, a *B. subtilis* bacterial replication assembly, and an *E. coli* bacterial replication assembly.

62. The method of clause 61, wherein the *S. pyogenes* bacterial replication assembly comprises isolated *S. pyogenes* PolC, $\tau$, $\gamma$, $\delta$, $\delta'$, $\chi$, $\psi$, $\beta$, SSB and proteins.

63. The method of clause 61, wherein the *S. aureus* bacterial replication assembly comprises isolated *S. aureus* PolC, $\beta$, $\tau$, $\delta$, $\delta'$ and SSB proteins.

64. The method of clause 61, wherein the *Y. pestis* bacterial replication assembly comprises isolated *Y. pestis* $\alpha$, $\epsilon$, $\theta$, $\tau$, $\gamma$, $\delta$, $\delta'$, $\chi$, $\psi$, $\beta$ and SSB proteins.

65. The method of clause 61, wherein the *P. aeruginosa* bacterial replication assembly comprises isolated *P. aeruginosa* $\alpha$, $\epsilon$, $\tau$, $\gamma$, $\delta$, $\delta'$, $\chi$, $\psi$, $\beta$, SSB and primase proteins.

66. The method of clause 61, wherein the *B. subtilis* bacterial replication assembly comprises isolated *B. subtilis* PriA, DnaB, DnaC, DnaD, DnaI, DnaG (primase), and SSB proteins.

67. The method of clause 66, wherein said *B. subtilis* bacterial replication assembly further comprises DNA polymerase.

68. The method of clause 66, wherein said DNA molecule comprises a plasmidic primosome assembly site (PAS).

69. The method of clause 61, wherein the *E. Coli* bacterial replication assembly comprises isolated *E. coli* DnaA, DnaB, DnaC, primase, and SSB proteins.

70. The method of clause 69, wherein the *E. coli* bacterial replication assembly further comprises DNA polymerase.

71. The method of clause 69, wherein said DNA molecule comprises an A site.

72. A reconstituted bacterial replication assembly capable of functioning in a test for identifying compounds that modulate the ability of bacterial replication assembly to replicate DNA.

73. The reconstituted bacterial replication assembly of clause 72, wherein the reconstituted bacterial replication assembly comprises isolated DNA Polymerase III holoenzyme subunit proteins, wherein subunit proteins are proteins selected from the group consisting of *Yersinia pestis* subunit proteins, *Staphylococcus aureus* subunit proteins, *Streptococcus pyogenes* subunit proteins, and *Pseudomonas aeruginosa* subunit proteins.

74. The bacterial replication assembly of clause 73 comprising isolated *Y. pestis* DNA polymerase III holoenzyme subunit proteins $\alpha$, $\epsilon$, $\theta$, $\tau$, $\gamma$, $\delta$, $\delta'$, $\chi$, $\psi$, $\beta$ and SSB, and primase.

75. The bacterial replication assembly of clause 73 comprising isolated *S. aureus* DNA polymerase III holoenzyme subunit proteins PolC, $\beta$, $\tau$, $\delta$, $\delta'$ and SSB.

76. The bacterial replication assembly of clause 73 comprising isolated *S. pyogenes* DNA polymerase III holoenzyme subunit proteins PolC, $\tau$, $\gamma$, $\delta$, $\delta'$, $\beta$; and SSB.

77. The bacterial replication assembly of clause 73, comprising isolated *P. aeruginosa* DNA polymerase III holoenzyme subunit proteins $\alpha$, $\epsilon$, $\tau$, $\gamma$, $\delta$, $\delta'$, $\chi$, $\psi$, $\beta$; and SSB and primase.

78. The bacterial replication assembly of clause 72, comprising isolated *B. subtilis* PriA, DnaB, DnaC, DnaD, DnaI, DnaG, and SSB proteins.

79. The bacterial replication assembly of clause 78, further comprising DNA polymerase.

80. The bacterial replication assembly of clause 78, further comprising a DNA molecule comprising a plasmidic primosome assembly site (PAS).

81. The bacterial replication assembly of clause 72, comprising isolated E. coli DnaA, DnaB, DnaC, primase, SSB proteins.

82. The bacterial replication assembly of clause 81, further comprising DNA polymerase.

83. The bacterial replication assembly of clause 81, further comprising a DNA molecule comprising an A site.

84. A method of synthesizing a DNA molecule comprising contacting a DNA molecule with a bacterial replication assembly and one or more dNTPs under conditions sufficient to synthesize a second DNA molecule complementary to all or a portion of said first DNA molecule, wherein said bacterial replication assembly is selected from the group consisting of an S. pyogenes bacterial replication assembly, an S. aureus bacterial replication assembly, a Y. pestis bacterial replication assembly, a P. aeruginosa bacterial replication assembly, a B. subtilis bacterial replication assembly, and an E. coli bacterial replication assembly.

85. The method of clause 84, wherein the S. pyogenes bacterial replication assembly comprises isolated S. pyogenes PolC, $\tau$, $\gamma$, $\delta$, $\delta'$, $\beta$, SSB and proteins.

86. The method of clause 84, wherein the S. aureus bacterial replication assembly comprises isolated S. aureus PolC, $\beta$, $\tau$, $\delta$, $\delta'$ and SSB proteins.

87. The method of clause 84, wherein the Y. pestis bacterial replication assembly comprises isolated Y. pestis $\alpha$, $\epsilon$, $\theta$, $\tau$, $\gamma$, $\delta$, $\delta'$, $\chi$, $\psi$, $\beta$, SSB and primase proteins.

88. The method of clause 84, wherein the P. aeruginosa bacterial replication assembly comprises isolated P. aeruginosa $\alpha$, $\epsilon$, $\tau$, $\gamma$, $\delta$, $\delta'$, $\chi$, $\psi$, $\beta$, SSB and primase proteins.

89. The method of clause 84, wherein the B. subtilis bacterial replication assembly comprises isolated B. subtilis PriA, DnaB, DnaC, DnaD, DnaI, DnaG (primase), and SSB proteins.

90. The method of clause 89, wherein said B. subtilis bacterial replication assembly further comprises DNA polymerase.

91. The method of clause 89, wherein said DNA molecule comprises a plasmidic primosome assembly site (PAS).

EXAMPLES

The following examples are provided for illustrative purposes only and are not intended to limit the scope of the invention.

Example 1

Y. pestis Bacterial Replication Assembly

Y. pestis subunits were cloned and expressed as described in copending U.S. patent application Ser. No. 10/476,597, entitled "System For Discovery Of Agents That Block Yersinia Pestis And Pseudomonas Aeruginosa DNA Replication", published as International Patent Application Publication WO 02/092769.

Large-Scale Preparation of Y. pestis DNA Polymerase III Holoenzyme Proteins and Associated Proteins.

To generate sufficient amounts of the Y. pestis DNA polymerase III proteins (and associated subunits), we adapted the previously reported procedures for large-scale preparation of E. coli homologs (Cull, M. and McHenry, C. S. (1990) Preparation of Extracts from Prokaryotes. Academic Press, New York). Briefly, cells transformed with expression vectors encoding Y. pestis proteins were grown in the presence of ampicillin, then induced to express their respective recombinant proteins by addition of IPTG. After an incubation period to allow further growth, cells were harvested, frozen by directly pouring them into liquid nitrogen, and stored at −20° C. Lysis was accomplished via creation of spheroplasts by treatment of cells with lysozyme in the presence of 10% sucrose, followed by a brief heat pulse as previously described. The presence of 18 mM spermidine kept the nucleoid condensed within partially disrupted cells and displaced DNA binding proteins. DNA-free supernatant (Fr I) was collected by centrifugation.

Figure 1:
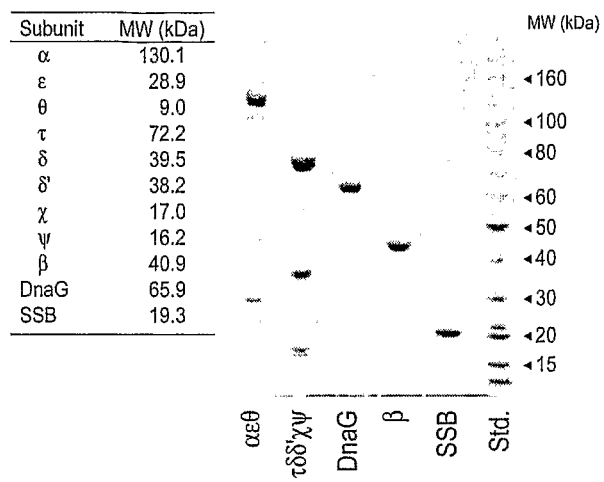
FIG. 1 shows a summary SDS-polyacrylamide gel for purified components of the *Y. pestis* DNA polymerase III holoenzyme complex and associated proteins.

Purification protocols were based on those previously reported for recombinant E. coli homologs. (Johanson, K. O., Haynes, T. E., and McHenry, C. S. (1986) J. Biol. Chem. 261, 11460-11465; Glover, B. P. and McHenry, C. S. (1998) J. Biol. Chem. 273, 23476-23484; Kelman, Z., Yuzhakov, A., Andjelkovic, J., and O'Donnell, M. (1998) EMBO J. 17, 2436-2449; Lohman, T. M., Green, J. M., and Beyer, R. S. (1986) Biochemistry 25, 21-25; Stamford, N. P. J., Lilley, P. E., and Dixon, N. E. (1992) Biochim. Biophys. Acta 1132, 17-25). Critical procedures included ammonium sulfate precipitation, various chromatography steps, and gel filtration. At each step of the purification process, the purity of Y. pestis proteins was analyzed by SDS polyacrylamide gel electrophoresis; a summary gel is provided in FIG. 1.

In order to assess the relative abundance of subunits expressed using multi-gene vectors, gels were subjected to densitometry scans. A densitometry scan of the protein bands in pol III core Fraction VI indicated that the ratio of $\alpha$, $\epsilon$, and $\theta$ in the core complex is 1:1:1. A scan of the protein bands in DnaX complex Fraction V indicated that the ratio of $\tau$, $\delta$-$\delta'$, and $\chi\psi$ in the core complex was 3:1:1, respectively, consistent with the stoichiometry $\tau_3\delta\delta'\chi\psi$. Finally, to ensure that the purification process did not result in loss of functional activity of the protein, the protein yield (all proteins) and activity (all proteins except SSB) were characterized at each of the purification steps. Purification was associated with substantial increases in specific activity.

Large-Scale Preparation of Y. pestis DNA Polymerase III Holoenzyme Proteins and Associated Subunits.

We adapted the previously reported procedures (Cull, M. and McHenry, C. S. (1990) Preparation of Extracts from Prokaryotes. Academic Press, New York) for large-scale preparation of recombinant E. coli DNA polymerase III proteins (and associated subunits) for the generation of sufficient amounts of the Y. pestis homologs for functional analyses. Briefly, cells transformed with expression vectors encoding Y. pestis proteins were grown in the presence of ampicillin, then induced to express their respective recombinant proteins by addition of IPTG. After an incubation period to allow further growth, cells were harvested, frozen by directly pouring them into liquid nitrogen, and stored at −20° C. Lysis was accomplished via creation of spheroplasts by treatment of cells with lysozyme in the presence of 10% sucrose followed by a brief heat pulse as previously described (Cull, M. and McHenry, C. S. (1990) Preparation of Extracts from Prokaryotes. Academic Press, New York). The presence of 18 mM spermidine kept the nucleoid condensed within partially disrupted cells and displaced DNA binding proteins. DNA-free supernatant (Fr I) was collected by centrifugation.

Purification of Y. pestis Pol III Core ($\alpha\epsilon\theta$).

Figure 2:
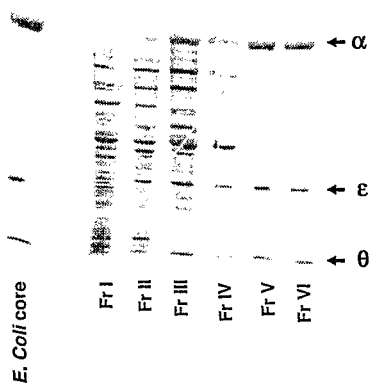
FIG. 2 shows a summary SDS-polyacrylamide gel analysis of each step in the purification of *Y. pestis* pol III core.
Figure 3:
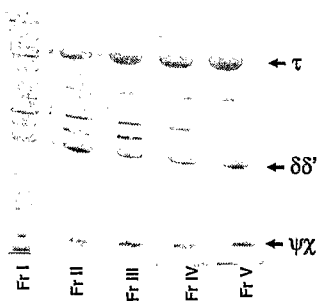
FIG. 3 shows a summary SDS-polyacrylamide gel analysis of each step in the purification of *Y. pestis* DnaX complex.
Figure 4:
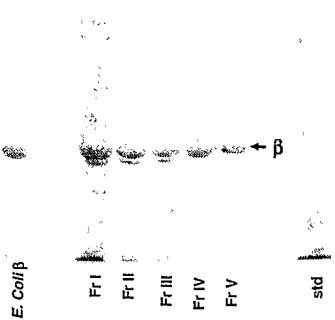
FIG. 4 shows a summary SDS-polyacrylamide gel analysis of each step in the purification of *Y. pestis* processivity factor ($\beta_2$).

The procedure developed for purifying the recombinant pol III core corresponding to that from E. coli (35) was adapted for purifying the recombinant Y. pestis pol III core. Briefly, the protein pellet from an ammonium sulfate precipitation step (45% saturation) was subjected to DEAE- Sepharose chromatography and was eluted with a gradient of increasing ionic strength. Polymerase activity eluted in a single peak. The protein in the peak fractions was subjected to hydroxylapatite chromatography and was eluted with a $KPO_4$ gradient. Active fractions were pooled and subjected to P-11 phosphocellulose chromatography. Active fractions eluted in a salt gradient were concentrated and gel filtered through a Sephacryl®S-200 column. Fractions containing the single activity peak of the purified protein were pooled, aliquoted and stored at −80° C. At each step of the purification process, the purity of *Y. pestis* core was analyzed by SDS polyacrylamide gel electrophoresis. A summary gel of the pooled protein for each purification step is shown in FIG. 2. Details of the precise chromatographic conditions for pol III and other purifications in this application are included in our interim progress reports.

Densitometry scan of the protein bands in Fr VI indicate that the ratio of α, ϵ, and θ in the core complex is 1:1:1, respectively. To ensure that the purification process did not result in loss of functional activity of the protein, the protein yield and activity were characterized at each of the purification steps and the results are summarized in Table 9. Activity was based on the stimulation of DNA synthesis by samples containing *Y. pestis* pol III core in the presence of *E. coli* DnaX complex and β subunits using *E. coli* DnaG primase-primed singled-stranded M13Gori DNA template. The ability of the pol III core from *Y. pestis* to reconstitute polymerase activity in in vitro assays employing the DnaX complex and β subunit from *E. coli* was established previously.

TABLE 9

Purification of *Yersinia pestis* DNA polymerase III.

| Fraction | Protein (mg) | Protein concentration (mg/ml) | Activity (Units) | Specific Activity (Units/mg) |
|---|---|---|---|---|
| Fr I | 22000 | 17.3 | — | — |
| Fr II (AS) | 5440 | 2.6 | $1.3 \times 10^9$ | $2.4 \times 10^5$ |
| Fr III (DEAE) | 900 | 2.1 | $2.0 \times 10^9$ | $2.2 \times 10^6$ |
| Fr IV (HAP) | 370 | 1.3 | $8.6 \times 10^8$ | $2.3 \times 10^6$ |
| Fr V (P-Cellulose) | 57 | 9.5 | $6.0 \times 10^8$ | $1.1 \times 10^7$ |
| Fr VI (S-200) | 51 | 4.3 | $5.8 \times 10^8$ | $1.1 \times 10^7$ |

Purification of *Y. pestis* DnaX Complex ($\tau_3\delta\delta'\chi\psi$).

The purification scheme for recombinant *E. coli* DnaX complex (Pritchard, A. E., Dallmann, H. G., and McHenry, C. S. (1996) *J. Biol. Chem.* 271, 10291-10298) was adapted for purifying the *Y. pestis* DnaX complex. Briefly, the protein pellet from an ammonium sulfate precipitation step (30% saturation) was dissolved and subjected to DEAE-Sepharose chromatography and eluted with a salt gradient. Active fractions were pooled and subjected to hydroxylapatite chromatography. Active fractions eluting in a gradient of increasing phosphate concentration were concentrated by ammonium sulfate precipitation, redissolved and gel filtered through a Sephacryl S-200 column. The single peak of activity was pooled, aliquoted and stored at −80° C. A summary SDS polyacrylamide gel of the pooled protein for each purification step is in FIG. 3.

Densitometry scan of the protein bands in Fr V indicate that the ratio of τ, δ/δ', and χ/ψ in the core complex is 3:1:1, respectively, consistent with the stoichiometry $\tau_3\delta\delta'\chi\psi$. The protein concentration and activity were also characterized at each purification step (Table 10). Activity was based on the stimulation of DNA synthesis by samples containing *Y. pestis* τ-complex in the presence of *E. coli* pol III core and β subunits using *E. coli* DnaG primase-primed singled-stranded M13Gori DNA.

TABLE 10

Purification of *Yersinia pestis* DnaX complex.

| Fraction | Protein (mg) | Protein concentration (mg/ml) | Activity (Units) | Specific Activity (Units/mg) |
|---|---|---|---|---|
| Fr I | 30460 | 18.5 | — | — |
| Fr II (AS) | 2665 | 5.6 | $3.2 \times 10^9$ | $1.2 \times 10^6$ |
| Fr III (DEAE) | 1138 | 3.1 | $2.8 \times 10^{10}$ | $2.5 \times 10^7$ |
| Fr IV (HAP) | 427 | 61.1 | $6.8 \times 10^{10}$ | $1.6 \times 10^7$ |
| Fr V (S-200) | 352 | 11.0 | $2.2 \times 10^{10}$ | $6.3 \times 10^7$ |

Purification of *Y. pestis* Processivity Factor (Beta).

The purification scheme for the recombinant β subunit of the *E. coli* DNA polymerase III holoenzyme (Johanson, K. O., Haynes, T. E., and McHenry, C. S. (1986) *J. Biol. Chem.* 261, 11460-11465) was adapted for purifying the recombinant β subunit of *Y. pestis*. Briefly, pellet from an ammonium sulfate precipitation step (70% saturation) was redissolved and subjected to DEAE-Sepharose chromatography. After a wash step, active $\beta_2$ was eluted with a salt gradient. The resulting protein was subjected to hydroxyl-apatite chromatography and eluted with a phosphate gradient. Active fractions were pooled and subjected to gel filtration through a Sephacryl S-200 column. The peak fractions were pooled to form Fr V, aliquoted, and stored at −80° C. A summary SDS polyacrylamide gel of the pooled protein for each purification step is shown in FIG. 4.

Protein concentration and activity were also characterized at each purification step (Table 11). The reconstitution assays contained samples of *Y. pestis* β subunit with *E. coli* pol III core, DnaX complex and DnaG primase-primed singled-stranded M13Gori DNA.

TABLE 11

Purification of *Yersinia pestis* β.

| Fraction | Protein (mg) | Protein concentration (mg/ml) | Activity (Units) | Specific Activity (Units/mg) |
|---|---|---|---|---|
| Fr I | 2610 | 34.8 | — | — |
| Fr II (AS) | 2164 | 10.8 | $1.6 \times 10^{10}$ | $7.4 \times 10^6$ |
| Fr III (DEAE) | 632 | 1.4 | $1.0 \times 10^{10}$ | $1.6 \times 10^7$ |
| Fr IV (HAP) | 411 | 58.7 | $9.5 \times 10^9$ | $2.3 \times 10^7$ |
| Fr V (S-200) | 440 | 20 | $1.3 \times 10^{10}$ | $3.0 \times 10^7$ |

Cloning, Expression and Purification of *Y. pestis* SSB.

Single-stranded binding protein (SSB) plays an essential role in facilitating rapid and processive elongation of the DNA polymerase holoenzyme. A binding interaction between the holoenzyme and SSB stimulate enzymatic activity by keeping the enzyme in proximity to its substrate during DNA synthesis. In *E. coli*, this binding interaction is mediated by χψ subunits (Glover, B. P. and McHenry, C. S. (1998) *J. Biol. Chem.* 273, 23476-23484; Kelman, Z., Yuzhakov, A., Andjelkovic, J., and O'Donnell, M. (1998) *EMBO J.* 17, 2436-2449). SSB may also facilitate DNA synthesis by preventing the formation of stable secondary structures (that potentially block polymerases lacking strand displacement activity) within the single-stranded template.

We have identified the SSB gene from the *Y. pestis* genome by sequence similarity with the corresponding *E. coli* gene. PCR amplification of the ssb gene from *Y. pestis* genomic DNA allowed us to insert it into the vector pA1-CB-NcoI (producing pA1-YP-SSB plasmid), and we optimized conditions for the large-scale growth of *E. coli* containing the pA1-YP-SSB plasmid. Time growth analysis for optimal expression of *Y. pestis* SSB and determination of optimal ammonium sulfate precipitation conditions were also performed as described above for the holoenzyme components.

Purification of *Y. pestis* SSB.

Figure 5:
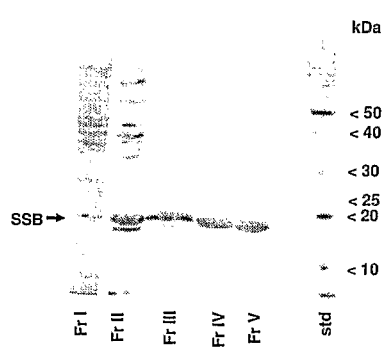
FIG. 5 shows a summary gel analysis of *Y. pestis* SSB purification.

The purification scheme for the recombinant SSB of the *E. coli* DNA polymerase III holoenzyme (Lohman, T. M., Green, J. M., and Beyer, R. S. (1986) *Biochemistry* 25, 21-25) was adapted for purifying recombinant *Y. pestis* SSB. Cells were lysed and protein precipitated by addition of ammonium sulfate (30% saturation), as described for the preceding purifications. Redissolved protein was subjected to chromatography over a Blue Dextran-Sepharose column and eluted with steps of increasing concentrations (0.1-4 M) of NaCl. Active fractions were pooled and subjected to hydroxylapatite chromatography, being eluted by increasing concentrations of phosphate in a gradient. Active fractions were concentrated by ammonium sulfate precipitation, redissolved in a minimal volume of buffer and gel filtered through Sephacryl S-200. Active fractions were pooled, aliquoted and stored at −80° C. A summary gel of the pooled protein for each purification step is shown in FIG. 5. The protein yield at each purification step is shown in Table 12.

TABLE 12

Purification of *Y. pestis* SSB.

| Fraction | Protein (mg) | Protein concentration (mg/ml) |
|---|---|---|
| Fr I | 40000 | 17 |
| Fr II (AS) | 810 | 8 |
| Fr III (Blue dextran) | 150 | 0.15 |
| Fr IV (HAP) | 120 | 3.3 |
| Fr V (S-200) | 120 | 12 |

Cloning, Expression and Purification of *Y. pestis* DnaG Primase.

We identified the dnaG gene from the *Y. pestis* genome by sequence similarity with the corresponding *E. coli* gene, amplified it by PCR inserted it into the vector pA1-CB-NcoI (producing pA1-YP-dnaG plasmid). Optimization of time growth and ammonium sulfate precipitation conditions were performed as described above for the holoenzyme components and the large-scale growth of *E. Coli* containing the pA1-YP-dnaG plasmid was performed as described for *Y. pestis* SSB.

Purification of *Y. pestis* DnaG.

Figure 6:
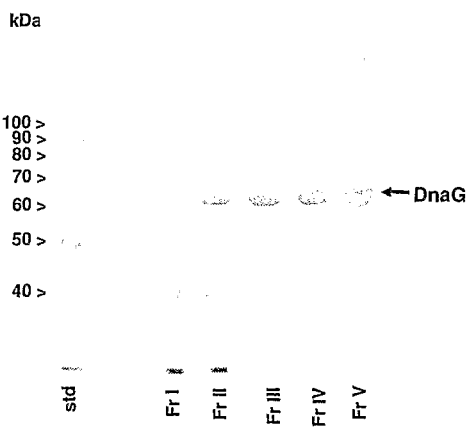
FIG. 6 shows a summary SDS-polyacrylamide gel analysis of each step in the purification of *Y. pestis* DnaG primase.

The purification scheme for the recombinant DnaG of the *E. coli* DNA polymerase III holoenzyme (Stamford, N. P. J., Lilley, P. E., and Dixon, N. E. (1992) *Biochim. Biophys. Acta* 1132, 17-25) was adapted for purifying recombinant *Y. pestis* DnaG. Briefly, cells were lysed and DnaG activity was precipitated by addition of ammonium sulfate to 45% saturation. Protein was redissolved and subjected to phosphocellulose chromatography. Active fractions eluting in a salt gradient were pooled and subjected to hydroxylapatite chromatography. Active fractions eluting in a gradient of increasing phosphate were concentrated by ammonium sulfate precipitation, redissolved and gel-filtered through Sephacryl S-200. Peak fractions were pooled to form Fr V. This sample was aliquoted and stored at −80° C. A summary gel of the pooled protein for each purification step is shown in FIG. 6.

The protein yield and activity were also characterized at each purification step (Table 13). Activity of DnaG primase was determined in a reconstitution assay using *Y. pestis* pol III core, τ-complex, β subunit and SSB.

TABLE 13

Purification of *Yersinia pestis* DnaG primase.

| Fraction | Protein (mg) | Protein concentration (mg/ml) | Activity (Units) | Specific Activity (Units/mg) |
|---|---|---|---|---|
| Fr I | 31302 | 22.5 | $3.6 \times 10^9$ | $1.0 \times 10^5$ |
| Fr II (AS) | 7461 | 10.8 | $2.8 \times 10^{10}$ | $3.8 \times 10^6$ |
| Fr III (P-11) | 1150 | 1.3 | $8.8 \times 10^8$ | $0.8 \times 10^6$ |
| Fr IV (HAP) | 274 | 39 | $2.1 \times 10^8$ | $0.7 \times 10^6$ |
| Fr V (S-200) | 131 | 6.6 | $7.6 \times 10^8$ | $5.8 \times 10^6$ |

Amino Acid Sequence Analysis of all Components of the *Y. pestis* DNA Replication Apparatus.

To ensure that the purified recombinant *Y. pestis* replication proteins were not significantly contaminated by *E. coli* replication proteins, samples from each of the purified *Y. pestis* proteins were subjected to N-terminus amino acid sequencing analysis by Edman degradation at the Molecular Resource Center of the National Jewish Medical and Research Center in Denver, Colo. All proteins sequenced contained the expected amino-terminal sequence and were free of their *E. coli* counterparts to the level of detection.

Example 2

*S. pyogenes* Bacterial Replication Assembly

*S. pyogenes* subunit cloning and expression is also described in International Patent Application Publication WO 02/34936, entitled "Novel *S. Pyogenes* DNA Polymerase III Holoenzyme Nucleic Acid Molecules and Proteins."

A. *S. pyogenes* PolC:

A small scale (pilot) preparation of *S. pyogenes* PolC indicated the use of two columns, a hydroxylapatite and a Q-sepharose for the greatest yield of pure protein (>95%) with the most activity. The large scale preparation is described below. Starting with 100 g of cells containing overexpressed *S. pyogenes* PolC a FrI was prepared. The cell lysis was prepared in the presence of protease inhibitors and 0.1 mM PMSF. 0.258 g/ml of ammonium sulfate (45% saturation) was added to FrI and the precipitated protein was collected by centrifugation. The *S. pyogenes* PolC was contained in the precipitated proteins. The protein pellets were dissolved in buffer I (50 mM Imidazole, (pH 6.8), 10% glycerol, 5 mM DTT, 0.1 mM PMSF). Additional buffer was added to adjust the conductivity of the sample to that of the column and loaded onto a hydroxylapatite column (250 ml) equilibrated in the same buffer plus 50 mM NaCl. The column was washed with 5 CV of the equilibration buffer and the protein was then eluted (6.5 ml/min) in 10 CV of the same buffer containing a 10-250 mM gradient of $KPO_4$. 6% of the protein was in the column flow-through and 5% in the column wash. However, there was no activity observed in the column flow-through or the wash. Fractions were analyzed by SDS-polyacrylamide gel electrophoresis (shown below).

Fractions 40-56 were pooled (425 ml) and resulted in retention of 75% of the total activity seen in FrII, but a 3-fold increase in specific activity. The pool was diluted (to 800 ml) to the conductivity of the Q-Sepharose column using buffer T (50 mM Tris-HCl, (pH 7.5), 20% glycerol, 0.5 mM EDTA, 5 mM DTT, 0.1 mM PMSF) and then loaded (0.6 ml/min)

directly onto a Q-Sepharose column (200 ml) equilibrated using buffer T/100 mM NaCl. The column was then washed (5 CV) with the same buffer. 6% of the protein was in the column flow-through and 5% in the column wash. There was no activity detected in either the column flow or wash. The protein was eluted (10 CV) in the same buffer containing a 100-400 mM NaCl gradient. Fractions were analyzed by SDS-polyacrylamide gel electrophoresis Fractions 52-61 were pooled (250 ml, 370 g protein) and resulted in retention of approximately 150% of the total activity present in Fr II. There was a 6.5-fold increase in specific activity compared to the load and a 17-fold increase compared to FrII. The steps of purification of S. pyogenes PolC (EP-43) are summarized in table 14.

TABLE 14

Summary of S. pyogenes PolC purification

| Fraction | Volume (ml) | Protein (mg) | Activity (units) | Conc. (mg/ml) | Activity (U/μl) | Sp. Activity (U/mg) | Recovery (% Activity) | Recovery (% Protein) |
|---|---|---|---|---|---|---|---|---|
| FrI (cell lysate) | 390 | 18026 | — | 46 | — | — | — | — |
| FrII AS cut | 1000 | 3528 | $1.1 \times 10^8$ | 3.5 | 120 | $3 \times 10^4$ | 100 | 100 |
| FrIII (Hydroxylapatite) | 800 | 1017 | $8.0 \times 10^7$ | 1.3 | 100 | $8 \times 10^4$ | 75 | 30 |
| FrIV (Q-Sepharose) | 250 | 371 | $1.7 \times 10^8$ | 1.5 | 700 | $5 \times 10^5$ | 150 | 10 |
| EP-43 (aliquots) | 250 | 371 | $1.7 \times 10^8$ | 1.5 | 700 | $5 \times 10^5$ | 150 | 10 |

Figure 7:
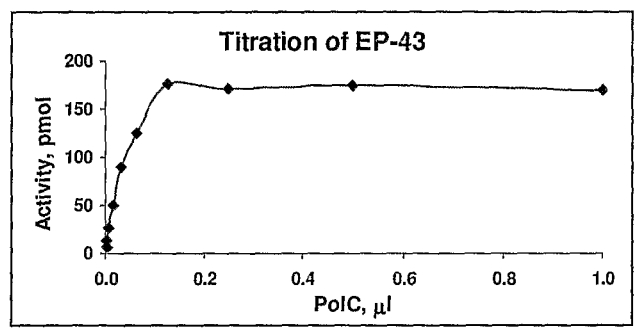
FIG. 7 shows the results of a titration of *S. pyogenes* PolC in a reconstitution assay.

S. pyogenes PolC was assayed by titrating the PolC into reconstitution assays as shown in FIG. 7.

B. S. pyogenes τ-Complex:

A pilot or small scale purification of S. pyogenes τ-complex was carried out using a heparin column followed by a hydroxylapatite and finally a gel filtration (S-200) column. Although this pilot purification did not result in a pure protein, it gave us confidence that by varying elution conditions on the different columns we could produce a homogenous τ-complex. Therefore we proceeded with a large scale purification of the τ-complex.

First, starting with 400 g of cells containing over-expressed S. pyogenes τ-complex a FrI was produced. 16.4 g/ml of ammonium sulfate (30% saturation) was added to FrI and the precipitated protein was collected by centrifugation. Some endogenous proteins including E. coli SSB was removed by this step. The supernatant was retained and 8.1 g/ml of ammonium sulfate (43% saturation) was added and the additional precipitated protein was collected by centrifugation. The S. pyogenes τ-complex was contained in the precipitated protein. The protein pellet was dissolved in 50 mM Tris, pH 7.5; 10% Glycerol, 0.5 mM EDTA, 1 mM PMSF, and 5 mM DTT and loaded onto a 500 ml Heparin column. The column was washed with three column volumes of the above buffer with 75 mM NaCl. The S. pyogenes τ-complex was eluted from the column using a ten column volume gradient of the same buffer going from 75 mM NaCl to 250 mM NaCl. The activity and protein profile of the fractions eluted from the heparin column are shown below. The fractions were analyzed by SDS-polyacrylamide gel electrophoresis.

Fractions 47-61 were pooled and loaded directly onto a 50 mL hydroxylapatite column equilibrated in 50 mM Imidazole, pH 6.8; 10% Glycerol, 50 mM NaCl, and 5 mM DTT. The column was washed with four column volumes of the above buffer with 20 mM potassium phosphate, pH 6.8. Elution of the protein was accomplished by running a ten column volume gradient of the same buffer containing 20 mM potassium phosphate going up to 140 mM potassium phosphate. The activity and protein profile of the fractions eluted from the hydroxylapatite column are shown below. The fractions were analyzed by SDS-polyacrylamide gel electrophoresis. The pool was concentrated using PEG and quick-frozen and stored at −86°.

In the final step the concentrated sample was thawed and loaded onto a 140 ml (1:50 ration) gel filtration (S-200) column equilibrated in 50 mM Tris, pH 7.5; 10% Glycerol, 0.5 mM EDTA, 50 mM NaCl, and 2 mM DTT. The fractions were analyzed by SDS-polyacrylamide gel electrophoresis. Fractions 26-28 were pooled, aliquoted and stored at −80° C.

The summary of the different steps in the purification process is shown below in Table 15.

TABLE 15

Summary of S. pyogenes τ-complex Purification

| Fraction | Total Activity (U) | Activity (U/uL) | Total Volume (mL) | Total Protein (mg) | Total Conc. (mg/mL) | SA (U/mg) | % Activity | % Protein |
|---|---|---|---|---|---|---|---|---|
| Fr I | | | 1125 | 22192 | 19.7 | | | |
| Fr II (Heparin Load) | 1.7E+09 | 1680 | 1000 | 4119 | 4.10 | 4.1E+05 | 100 | 100 |
| 500 mL Heparin Pool | 3.9E+08 | 627 | 625 | 240.6 | 0.4 | 1.6E+06 | 23 | 6 |
| 40 mL HA Pool | 1.2E+08 | 3067 | 40 | 29.4 | 0.7 | 4.1E+06 | 7 | 1 |
| G.F. Pool | 3.5E+07 | 3541 | 10 | 14.9 | 1.50 | 2.4E+06 | 2 | .36 |

Each step of the purification process was analyzed by SDS-polyacrylamide gel electrophoresis on a summary gel.

C. Reconstitution Assay:

In order to monitor purification, the standard assay used for the *E. coli* DNA polymerase III holoenzyme, synthesis on a long single-stranded circular template primed by an RNA primer was modified. Assays (25 µl) contained 19 µl of a master mix: 1 µl MgOAc, 2.7 µl M13 Gori (240 µM, nt) annealed to a DNA primer (30 mer), 3 µl dNTP mix (400 µM dATP, dCTP, dGTP and 150 µM [3H]-dTTP (100 cpm/pmol), 12.3 µl EDB (50 mM HEPES (pH 7.5), 20% glycerol, 0.02% NP40, 0.2 mg/ml BSA). To this was added 4 µl of enzyme mix (0.08 µM *S. pyogenes* clamp-loader complex (DnaX, δ and δ') (Sp. Act. $4.3 \times 10^6$), 0.46 µM *S. pyogenes* PolC (Sp. Act. $0.5 \times 10^6$), and 0.18 µM *S. pyogenes* $\beta_2$ (Sp. Act. $10 \times 10^6$). To this was added 2 µl of different concentrations of *S. pyogenes* SSB. The reactions contained approximately 550 pmol of primed-template (total nucleotides). Reactions were initiated by combining the enzyme mix the primed-template mix and the SSB sample and incubating for 10 min at room temperature. The reactions were terminated by placing the reaction tubes on ice and adding 2 drops of 0.2 M NaPP$_i$ and 4 ml 10% TCA. The solution was filtered under vacuum through Whatman GF/C glass microfibre filters. The filters were then washed with 2×4 ml of 1M HCl/0.2 M NaPP$_i$ and 1 ml 95% EtOH and dried using a heat lamp. The pmol of nucleotides incorporated were quantified by scintillation counting.

D. Purification of SSB:

Beginning with 800 g cells, FrI (3100 ml, 12.2 mg/ml) was prepared according to the procedure described above. FrII (245 ml, 1.4 mg/ml) was prepared as described above by adding 415.4 g of ammonium sulfate (25% saturation) to FrI and recovering precipitated protein by centrifuging and re-suspension of protein pellet in 230 ml of Buffer T (50 mM Tris-HCl, (pH 7.5), 20% glycerol, 1 mM EDTA, and 5 mM DTT). FrII was loaded onto a Blue Dextran Sepharose column (250 ml) (for procedure for making Blue Dextran Sepharose, see below). FrII was loaded onto the column (5 ml/min). The column was then washed with: 250 ml (1 cv) of Buffer T/0.1 M NaCl; 500 ml (2 cv) of Buffer T/0.5 M NaCl; 500 ml (2 cv) of Buffer T/1 M NaCl; 250 ml (1 cv) Buffer T/2 M NaCl; 750 ml (3 cv) BufferT/4 M NaCl. Fractions (20 ml) were collected beginning with the Buffer T/0.5 M NaCl wash. The fractions were analyzed by protein and by SDS-PAGE (10% Bis/Tris/MES buffer). Fractions 44-56 (260 ml, 0.53 mg/ml) were pooled.

The Blue Dextran pool was loaded (gravity flow) directly onto a Hydroxylapatite column (30 ml) equilibrated in Imidazole buffer (50 mM Imidazole, (pH 6.8), 20% glycerol, 1 M NaCl, 5 mM DTT). The column was then washed (gravity flow) with 60 ml of Imidazole buffer (2 cv). The protein was eluted from the column in 150 ml (5 cv) of Imidazole buffer containing 70 mM KPO$_4$. Fractions (2 ml) 24-34 were pooled (20 ml, 4.5 mg/ml) and AS precipitated in 50% saturated AS at 4° C. Ammonium sulfated (0.291 g/ml sample) was added for each nil of the Hydroxylapatite pool over a 15 min interval at 4° C. The mixture was stirred for an additional 30 min at 4° C. The precipitate was collected by centrifugation (23,000×g, 45 min, 0° C.).

Figure 8:
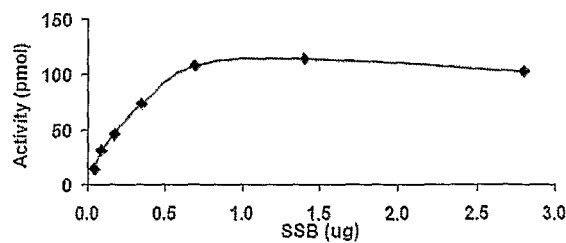
FIG. 8 shows the results of a titration of *S. pyogenes* SSB in a reconstitution assay.

The resulting protein pellets were re-suspended in 6 ml of buffer containing 25 mM Hepes (pH 7.5), 0.1 mM EDTA, 5.0 mM DTT and 10% glycerol. The pellet refused to go into suspension. Another 9 ml of buffer was added and the sample still would not go into solution. The sample was centrifuged as above, the supernatant decanted and 5 ml of buffer was added. The sample immediately went into solution. If this purification is carried out again, the first AS pellet should be washed in the above buffer to remove residual AS and the supernatant discarded and then re-suspend the pellet in the buffer after the residual AS has been completely removed. Since the *S. pyogenes* SSB precipitates at such a low concentration of AS (25%), this is required to re-suspend the pellet in a small volume. The sample was then loaded onto an S-200 Sephacryl column (100 ml, 1:25 ratio d:h) and the protein eluted from the column at 0.1 ml/min and fractions containing 2.0 ml each were collected. The fractions were analyzed by protein assays and by SDS-PAGE. Fractions 22-80 were pooled. The volume of the pool was reduced from 114 ml to 29 ml (0.7 mg/ml) using PEG 8000. The sample was then analyzed by reconstitution assays (FIG. 8). The steps in the purification are summarized in Table 16.

TABLE 16

Summary of *S. pyogenes* SSB purification

|  | mg/mL | mL | mg | % Protein |
|---|---|---|---|---|
| Fr I | 12.2 | 3100 | 37895 |  |
| BD Load (Fr II) | 1.41 | 245 | 345 | 100 |
| BD Pool (HA Load) | 0.53 | 260 | 137.7 | 40 |
| HA Pool | 4.51 | 20 | 90.2 | 26 |
| G.F. Pool | 0.2 | 114 | 25 | 7 |
| Conc. (EP-53) | 0.7 | 29 | 20 | 6 |

SSB should not be precipitated by ammonium sulfate after the Blue Dextran column, as it will not precipitate and the sample will be lost.

D. Preparation of Blue Dextran-Sepharose:

Wash 1 L of Sepharose 4B with 6 L of distilled water and re-suspend resin in cold distilled water so that the final volume is 3 L. Pack the beaker containing the re-suspended Sepharose 4B in ice in a fume hood. Dissolve 50 g of cyanogens bromide in 100 ml of cold dimethylformamide and add it to the Sepharose suspension. Stir the suspension (using an overhead stirrer) continuously for 1 h and do not allow the temperature to rise above 2° C. Adjust the speed of the stirrer to the slowest setting that will keep the material in suspension. Do not use a magnetic stirrer with a stir bar. Monitor and maintain the pH of the suspension throughout the hour. The pH should be between 10.5-11.5. Make adjustments by drop wise addition of 5.0 N NaOH. Quickly filter the suspension in a 3000 ml Buchner funnel and wash with 15 L of cold distilled water followed by 4 L of cold 0.1 M NaHCO$_3$. Re-suspend the Sepharose resin in 2 L of 0.1 M NaHCO$_3$ with the overhead stirrer. Slowly add 20 g of Blue Dextran. Keep suspension stirring overnight at 4° C. Adjust the speed of the stirrer to the slowest setting that will keep the material in suspension. Collect the Blue Dextran Sepharose on a Buchner funnel, wash with 15 L of cold distilled water and re-suspend in approximately 1 L of 1 M KCl/0.02% sodium azide buffer. Store at ° C. Do not store in the presence of a nucleophile. Prior to using the resin, pack column and wash with at least 10 column volumes of Buffer T/2 M KCl until the eluent is clear. This eliminates any non-covalently bound Blue Dextran that could leach off the resin during chromatography. Immediately after use, store resin in 2 M KCl/0.02% sodium azide. Store at 4° C.

E. Purification of *S. pyogenes* dnaN Gene Product (β Subunit)

Storage Buffer: 10 mM Tris-HCl, pH 6.5, 5 mM NaOAc, 2% glycerol, 0.1 mM EDTA, 5 mM NaCl, and 5 mM DTT. Over-producing Strain: pA1-StN/MGC1030. Strain pA1-StN/MGC1030 was grown in a 250 L to produce a large-scale growth of cells for purification of *S. pyogenes* DnaN.

Frozen cells were lysed by adding 225 g of a 1:1 suspension of frozen cells (112 g cells) in Tris-sucrose which had been stored at −20° C. to 308 ml Tris-sucrose buffer that had been pre-warmed to 45° C. (2.75 ml/g of cells). To the stirred mixture, 5.6 ml of 0.5 M 1,4-dithiothreitol (DTT) (0.05 ml/g of cells) and 28.1 ml of lysis buffer (2M NaCl, 0.3M spermidine in Tris-sucrose adjusted to pH 7.5) (0.25 ml/g of cells) was added. The pH of the slurry was tested with pH paper and adjusted to pH 7.5 by the addition of 3 ml of 2 M Tris base. Lysozyme (224 mg) was added in 5 ml of Tris-sucrose buffer (2 mg lysozyme/g of cells). The slurry was distributed into 250 ml centrifuge bottles after stirring 5 min and incubated at 4° C. for 1 hour. The 250 ml centrifuge bottles were then placed in a 37° C. swirling water bath and gently inverted every 30 seconds for 4 minutes. The insoluble cellular components were removed by centrifugation (23,000×g, 60 min, 4° C.). The recovered supernatant (430 ml) constituted Fraction I (16.1 mg/ml).

To 205 ml of Fraction I, ammonium sulfate (0.243 g to each initial ml of Fraction I-43% saturation) was added over a 15 min interval. The mixture was stirred for an additional 30 min at 4° C. and the precipitate collected by centrifugation (23,000×g, 60 min, 4° C.). Ammonium sulfate was added to the resulting supernatant (0.072 g to each ml of 43% supernatant, yielding 55% saturation) over a 15 min interval. The mixture was again stirred for 30 min at 4° C. and the precipitate collected by centrifugation (23,000×g, 60 min, 4° C.). The pellet containing the 43-55% cut was resuspended in 20 ml of Buffer A (see below) and frozen at −80° C. The resuspended pellet constituted Fraction II (46.0 mg/ml) (Table 17).

TABLE 17

Summary of Ammonium Sulfate Fractionation

| Fraction | Protein | % | Units | % | SA (U/mg) |
|---|---|---|---|---|---|
| AS 0-43 | 790.3 | 23.9 | $1.6 \times 10^8$ | 7.2 | $2.0 \times 10^5$ |
| AS 43-55 | 1655.2 | 50.0 | $15.8 \times 10^8$ | 72.6 | $9.5 \times 10^5$ |
| AS 55 Supt | 867.6 | 26.2 | $4.4 \times 10^8$ | 20.1 | $5.1 \times 10^5$ |
| Total | 3313.1 | | $21.8 \times 10^8$ | | |

Fraction II was dialyzed (10 kDa MW cut off Spectra/Por® dialysis membrane) against 1 L of Buffer A (50 mM Tris-HCl, pH 7.5, 10% glycerol, 0.5 mM EDTA, 25 mM NaCl, and 5 mM DTT). After 2 hours the dialysis buffer was changed and dialysis continued for an additional 2 hours. The conductivity of the resulting dialysate was 42400 μS. Dialyzed Fraction II (1655 mg) was diluted 5-fold with buffer A without NaCl to a conductivity of 11700 μS (equivalent to 75 mM NaCl) and loaded onto a Q Sepharose™ High Performance column (300 ml) equilibrated in buffer A at a flow rate of 4 ml/min. The column was washed with 450 ml of buffer A at a flow rate of 4 ml/min. The protein was eluted in 3000 ml of buffer A using a 25-525 mM sodium chloride (NaCl) gradient at a flow rate of 2.8 ml/min. The eluate was collected in 22 ml fractions and analyzed for protein, for ability to support DNA synthesis in the Recon assay, and by electrophoresis onto 4-12% SDS-PAGE gels (8×6.8×0.1 cm). The protein assay was carried out using BSA as a standard. The Recon assay was performed in EDB buffer for 5 minutes at 30° C. in a 25 μl volume, using S. pyogenes PolC(RP 28) and S. pyogenes tau complex (RP 27) at saturating concentrations, and using previously frozen primase mix made with E. coli primase (RP29) and E. coli SSB (RP30). Protein gels were stained with Coomassie Brilliant Blue. The S. pyogenes β-subunit eluted in a single peak between fractions 55-57 (Fraction III; 65 ml; 2.1 mg/ml).

Fraction III (65 ml, 135 mg) was loaded onto a hydroxylapatite column (30 ml; Hypatite C, Clarkson Chemical Company) equilibrated in buffer B (50 mM imidazole, pH 6.8, 10% glycerol, 50 mM NaCl, 5 mM DTT, 1 mM NaCl, no EDTA) at a flow rate of 0.5 ml/min. The column was washed with 60 ml of buffer B at a flow rate of 0.5 ml/min. The protein was eluted in 300 ml of buffer B using a 0-300 mM potassium phosphate buffer (KPB, pH 6.8) gradient at a flow rate of 0.5 ml/min. The eluate was collected in 4.5 ml fractions and analyzed by protein and activity assays. The fractions were also analyzed using SDS-PAGE. The S. pyogenes β-subunit eluted as a peak early in the gradient, and partially overlapped contaminating proteins. Fractions 43-50 containing S. pyogenes β subunit were pooled (Fraction IV; 36 ml; 1.6 mg/ml).

An SP Sepharose™ High Performance column (20 ml) was equilibrated in 10 mM NaOAc (pH 5.5), 5 mM DTT. Fraction IV containing S. pyogenes β-subunit was diluted 10-fold with 10 mM NaOAc (pH 5.5), 5 mM DTT to adjust the conductivity to that of the column (360 ml final volume) and with 2.28 ml of 0.2 M acetic acid to adjust the pH of the solution to 5.5. The diluent and the acetic acid were mixed prior to the diluting of the protein. The diluted sample was loaded onto the column at a flow rate of 78 ml/hr. No precipitate formed during the four hours that the protein was being loaded onto the column. The column was washed with 35 ml of 10 mM NaOAc (pH 5.5), 5 mM DTT at a flow rate of 78 ml/hr. The sample was eluted from the column in 250 ml of a 10 mM NaOAc (pH 5.5), 5 mM DTT to 0.2× buffer A (10 mM Tris-HCl, pH 7.5, 2% glycerol, 0.1 mM EDTA, 5 mM NaCl, and 5 mM DTT) gradient at a flow rate of 78 ml/hr. The eluate was collected in 4 ml fractions. The protein concentrations and activity were determined and the fractions were analyzed using SDS-PAGE. The S. pyogenes β-subunit eluted as peak midway through the pH gradient. Fractions 16-19 containing S. pyogenes β subunit were pooled (Fraction V; 15 ml; 2.0 mg/ml).

The active SP Sepharose fractions (Fraction V) were pooled to yield the final purified preparation. A summary of the purification fractions is given in Table 18. The protein makeup from each step in the purification scheme was analyzed by SDS-Polyacrylamide gel electrophoresis.

TABLE 18

S. pyogenes β Purification Summary

| Fraction | Volume (ml) | Protein Conc. (mg/ml) | Total Protein (mg) | Activity (units) | Specific Activity (units/mg) |
|---|---|---|---|---|---|
| Fr I (lysate) | 205 | 19.9 | 4079 | nd | nd |
| Fr II (AS 43-55%) | 36 | 31.3 | 1128 | $2.6 \times 10^9$ | $2.3 \times 10^6$ |
| Fr III (Q Sepharose ™) | 65 | 2.4 | 156 | $1.3 \times 10^9$ | $8.5 \times 10^6$ |
| Fr IV (Hydroxylapatite) | 36 | 1.9 | 69 | $5.5 \times 10^8$ | $8.0 \times 10^6$ |
| Fr V (SP Sepharose ™) | 15 | 2.0 | 30 | $3.1 \times 10^8$ | $1.0 \times 10^7$ |

Example 3

Expression and Purification of B. subtilis Proteins

Five B. subtilis genes were identified in the NCBI database by homology to previously identified genes from S. pyogenes. The gene for the δ subunit, however, had too little sequence similarity to be identified by simple homology. Instead, the gene for δ was only identified by an iterative ψ-BLAST search, as described in United States Patent Application Publication No. US-2003-0219737. All *B. subtilis* proteins were over expressed in *E. coli* and purified using standard column chromatography.

A. Expression and purification of *B. subtilis* PriA.

Overproducing cells are grown in F medium in a 200 liter fermenter, and induced at an optical density at 600 nanometers of 2.0. Cells are grown for an additional 2 hours, then harvested by centrifugation. Cell pellets are stored as a 50% weight/volume slurry in a solution consisting of 50 mM Tris-HCl pH 8.0 and 10% w/v sucrose. The resulting paste is frozen at −20° C. *Bacillus subtilis* PriA overproduces well in *E. coli* and the majority of it is soluble. It seems to be a "sticky" enzyme and elutes from most columns in broad or multiple peaks. Hence the chromatographic methods employed in its purification generally employ step gradients rather than linear gradients. Frozen cells are lysed by adding 180 g of a 1:1 suspension of frozen cells (90 g cells) in Tris-sucrose which had been stored at −20° C. to 247.5 ml of Tris-Sucrose Buffer that had been pre-warmed to 45° C. (2.75 ml/g of cells). To the stirring mixture, 4.5 ml of 0.5M 1,4-dithiothreitol (DTT) (0.05 ml/g of cells) and 22.5 ml of lysis buffer (2M NaCl, 0.3M spermidine in Tris-sucrose adjusted to pH 7.5) (0.25 ml/g of cells) was added. The pH of the mixture is tested with pH paper and adjusted to pH 8.2 by the addition of about 3 ml of 2M Tris Base. Lysozyme (90 mg) is added in 3 ml of Tris-sucrose buffer (1 mg Lysozyme/g of cells). The mixture was distributed into 250 ml centrifuge bottles and incubated at 4° C. for 1 hour. The bottles are then placed into a 37° C. water bath and gently inverted every 30 seconds for 4 minutes. The insoluble cellular components are removed by centrifugation (13000×g fo, 60 min, 4° C.). The recovered supernatant comprises Fraction I. 0.31 grains of ammonium sulfate per ml of Fraction I are added (55% saturation). The ammonium sulfate is added over a period of 30 minutes while stirring and then let stir for another 30 minute at 4° C. The suspension is transferred to 250 ml GSA bottles and spun at 12K for 30 minutes minimum to 1 hour. The supernatant is discarded. Suspended pellets comprise Fraction II. A 150 ml column of Heparin-Sepharose is equilibrated in Buffer T (40 mM Tris pH 7.5, 1 mM EDTA pH 8, 0.25 mM EGTA pH 7.5, 10% glycerol, and 1 mM DTT)+200 mM NaCl. The conductivity of Fraction II is adjusted to that of Buffer T+200 mM NaCl by the addition of Buffer T containing no added salt. Owing to the "stickiness" of PriA, and taking advantage of its tenacious binding to heparin, PriA is loaded at relatively high salt concentration and eluted with a step rather than a gradient. The buffer is changed over during chromatography to one that contains no metal chelators, as the next step is chromatography on hydroxylapatite. Diluted Fraction II is loaded onto the Heparin-Sepharose column and washed with 6 column volumes of Buffer T+400 mM NaCl and 3 column volumes of Buffer H (40 mM Hepes pH 7.5, 10% glycerol, and 1 mM DTT)+400 mM NaCl. The washes must not be truncated, as contaminants do continue to leach off. PriA is eluted from the column with a step-gradient of Buffer H+800 mM NaCl. The eluate is assayed for PriA by SDS-PAGE, and the best fractions are pooled. The pool comprises Fraction III. A column of hydroxylapatite is poured (1 ml resin for every 2 mg protein in Fraction III). The column is equilibrated in Buffer H+400 mM NaCl. Fraction III is loaded directly onto the HAP column without dialysis or dilution. The column is washed with 5 column volumes of Buffer H+400 mM NaCl. A gradient, from Buffer H+400 mM NaCl to Buffer H+400 mM NaCl+200 mM potassium phosphate is run over 10 column volumes. PriA elutes at about 120 mM Kpi by conductivity. Fractions are assayed by SDS gel and PriA-containing fractions are pooled. This material comprises Fraction IV. Fraction IV is dialyzed overnight against T buffer+20% glycerol+100 mM NaCl, then aliquotted. The aliquotted material is tested for single-stranded and double-stranded endonuclease activity, and activity in the *Bacillus subtilis* primosome-dependent replication assay is verified.

B. Expression and Purification of *B. subtilis* DnaD.

Overproducing cells are grown in F medium in a 200 liter fermenter, and induced at an optical density at 600 nanometers of 2.0. Cells are grown for an additional 2 hours, then harvested by centrifugation. Cell pellets are stored as a 50% weight/volume slurry in a solution consisting of 50 mM Tris-HCl pH 8.0 and 10% w/v sucrose. Frozen cells are lysed by adding 1800 g of a 1:1 suspension of frozen cells (900 g cells) in Tris-sucrose which had been stored at −20° C. to 2475 ml of Tris-Sucrose Buffer that had been pre-warmed to 45° C. (2.75 ml/g of cells). To the stirring mixture, 45 ml of 0.5M 1,4-dithiothreitol (DTT) (0.05 ml/g of cells) and 225 ml of lysis buffer (2M NaCl, 0.3M spermidine in Tris-sucrose adjusted to pH 7.5) (0.25 ml/g of cells) was added. The pH of the mixture is tested with pH paper and adjusted to pH 8.2 by the addition of 30 ml of 2M Tris base. Lysozyme (900 mg) is added in 30 ml of Tris-sucrose buffer (1 mg lysozyme/g of cells). The mixture was distributed into 500 ml centrifuge bottles and incubated at 4° C. for 1 hour. The bottles are then placed into a 37° C. water bath and gently inverted every 30 seconds for 4 minutes. The insoluble cellular components were removed by centrifugation (13000×G, 60 min, 4° C.). The recovered supernatant comprises Fraction I. Ammonium sulfate (0.226 g/ml of Fraction I, 45% saturation) is then added over a period of 30 minutes. The mixture is stirred for an additional 30 minutes at 4° C. The mixture are distributed into 500 ml bottles and centrifuged for 30-45 minutes (13000×g, 4° C.). The supernatant is discarded. The pellet is resuspended in 150 ml of 200 mM NaCl+Buffer T (40 mM Tris pH 7.5, 1 mM EDTA pH 8, 0.5 mM EGTA pH 7.5, 10% glycerol and 1 mM 1,4-dithiothreitol (DTT). The resuspended pellet comprises Fraction II. Fraction II is then put into SS-34 tubes and spun for 30 minutes (12,000 rpm, 4° C.) to remove insoluble material. The supernatant is then dialyzed (10 kDa MW cut off Spectra/Por® dialysis membrane) overnight against 4 liters of 80 mM NaCl+Buffer T. The dialysate is spun down in SS-34 centrifuge tubes for 30 minutes (12,000 rpm, 4° C.) DnaD is contained in the pellet and is resuspended in 100 ml of 200 mM NaCl+Buffer T. One volume of Buffer T without added NaCl is added to the mixture and stirred for 30 minutes at 4° C. The mixture is put into SS-34 tubes and spun for 30 minutes (12,000 rpm, 4° C.) The pellet, containing dnaD, is resuspended in 150 ml of 200 mM NaCl (any lower salt concentration and dnaD precipitates)+Buffer T. The resuspended pellets comprise Fraction III. Fraction III is loaded onto a Heparin Sepharose column equilibrated in Buffer A (Buffer T+200 mM NaCl). The column is washed with 5 column volumes of Buffer A. DnaD is eluted in a gradient from Buffer A to 100% Buffer B (Buffer T+1M NaCl) over 10 column volumes. The fractions are analyzed by SDS-PAGE. DnaD elutes as a peak early in the gradient (about 380 mM NaCl) along with a small amount of contaminant. Fractions containing DnaD are pooled and concentrated by dialysis against dry polyethylene glycol (nominally 12,000 MW) until the concentration is about 2 mg/ml. The pool is dialyzed overnight against 500 mM NaCl+Buffer T. Activity is verified by titration in the *Bacillus subtilis* primosome-dependent replication reaction, and the material is tested for single- and double-stranded endonuclease activity.

C. Expression and Purification of *B. subtilis* DnaI.

Overproducing cells are grown in F medium in a 200 liter fermenter, and induced at an optical density at 600 nanometers of 2.0. Cells are grown for an additional 2 hours, then harvested by centrifugation. Cell pellets are stored as a 50% weight/volume slurry in a solution consisting of 50 mM Tris-HCl pH 8.0 and 10% w/v sucrose. Fraction III is dialyzed overnight against Buffer T with no added salt. Dialyzed Fraction III is loaded onto a Heparin Sepharose Column that has been equilibrated with no-salt Buffer T. The column is washed with 5 column volumes of Buffer A (no salt Buffer T). Proteins are eluted in a gradient from Buffer A to 100% Buffer B (1M NaCl+Buffer T). *B. subtilis* dnaI elutes as a peak early in the gradient (about 150 mM NaCl). Fractions are analyzed using SDS-PAGE. Fractions containing DnaI are pooled This pool constitutes Fraction IV. Fraction IV conductivity is adjusted to that of Buffer A (50 mM NaCl+Buffer T) using Buffer T. Fraction IV is loaded onto a Q sepharose column that has been equilibrated with Buffer A. The column is washed with 5 column volumes of Buffer A. Proteins are eluted in a gradient from Buffer A to 100% Buffer B (1M NaCl+Buffer T). *B. subtilis* dual elutes as a peak early in the gradient (200 mM NaCl). Fractions are analyzed using SDS-PAGE DnaI-containing fractions are pooled. This pool constitutes Fraction V. Fraction V is dialyzed against Buffer T+50 mM NaCl, tested for single- and double-stranded endonuclease activity, and tested for activity in the *B. subtilis* primosome-dependent DNA replication assay.

D. Expression and Purification of *B. subtilis* dnaC.

Note that overproduction of soluble *B. subtilis* dnaC requires co-expression of *B. subtilis* dnaI. Both proteins are purified from a single overproduction run. Over producing cells are grown in F medium in a 200 liter fermenter, and induced at an optical density at 600 nanometers of 2.0. Cells are grown for an additional 2 hours, then harvested by centrifugation. Cell pellets are stored as a 50% weight/volume slurry in a solution consisting of 50 mM Tris-HCl pH 8.0 and 10% w/v sucrose Frozen cells are lysed by adding 1800 g of a 1:1 suspension of frozen cells (900 g cells) in Tris-Sucrose which had been stored at −20° C. to 2475 ml of Tris-Sucrose Buffer pre-warmed to 45° C. (2.75 ml/g of cells). To the stirring mixture, 45 ml of 0.5M 1,4-dithiothreitol (DTT) (0.05 ml/g of cells) and 225 ml of lysis buffer (2M NaCl, 0.3M Spermidine in Tris-Sucrose adjusted to pH 7.5) (0.25 ml/g of cells) are added. 45 ml of 0.5M EDTA pH 8 and 45 ml of 0.25M EGTA pH 7.5 are then added. The pH of the mixture is adjusted to 8.2 by the addition of 2M Tris Base. Lysozyme (900 mg) is added in 30 ml of Tris-Sucrose buffer (1 mg/g of cells) and 45 ml of 0.1M PMSF (dissolved in Isopropanol) is added. The mixture is distributed into 500 ml centrifuge bottles and incubated on ice (4° C.) for an hour. The bottles are then placed in a 37° C. water bath and gently inverted every 30 seconds for 4 minutes. The insoluble cellular components are removed by centrifugation (12,000 rpm, 60 min, 4° C.). The recovered supernatant comprises Fraction I. Ammonium sulfate (0.184 g/ml of Fraction I, 32.5% saturation) is then added over a period of 30 minutes. The mixture is stirred for an additional 30 minutes and then transferred to 500 ml bottles and centrifuged for 30-60 minutes (13000×g, 4° C.). The supernatant is discarded and the precipitate is backwashed with ⅛× Fraction I volume of buffer T' (40 mM Tris, 10% glycerol, 1 mM EDTA, 0.25 mM EGTA, 1 mM DTT) supplemented with 0.17 g/ml ammonium sulfate. This material is dialyzed overnight in the above buffer supplemented with 50 mM NaCl. The dialysate comprises Fraction II. Fraction II is centrifuged at 10,000×g for 30 minutes to remove insoluble material. Fraction II (350 mg) is then loaded onto a Q sepharose column equilibrated with Buffer A (50 mM NaCl+Buffer T). The column is washed with Buffer A for 5 column volumes. Proteins are eluted in a gradient that went from Buffer A to 100% Buffer B (1M NaCl+Buffer T). *B. subtilis* dnaC elutes as a peak in the middle of the gradient (about 450 mM NaCl). Fractions are analyzed using SDS-PAGE. Best fractions are pooled, dialyzed overnight against 50 mM NaCl+Buffer T, analyzed for single- and double-stranded endonuclease activity, and assayed for activity in the *B. subtilis* primosome-dependent replication assay. Note that contaminants have consistently co-purified with DnaC on every column subsequently tested, hence we now employ this single-column purification procedure.

E. Expression and Purification of *B. subtilis* dnaB.

Overproducing cells are grown in F medium in a 200 liter fermenter, and induced at an optical density at 600 nanometers of 2.0. Cells are grown for an additional 2 hours, then harvested by centrifugation. Cell pellets are stored as a 50% weight/volume slurry in a solution consisting of 50 mM Tris-HCl pH 8.0 and 10% w/v sucrose. Frozen cells are lysed by adding 1800 g of a 1:1 suspension of frozen cells (900 g cells) in Tris-sucrose which had been stored at −20° C. to 2475 ml of Tris-Sucrose Buffer that had been pre-warmed to 45° C. (2.75 ml/g of cells). To the stirring mixture, 45 ml of 0.5M 1,4-dithiothreitol (DTT) (0.05 ml/g of cells) and 225 ml of lysis buffer (2M NaCl, 0.3M spermidine in Tris-sucrose adjusted to pH 7.5) (0.25 ml/g of cells) was added. The pH of the mixture is tested with pH paper and adjusted to pH 8.2 by the addition of 2M Tris Base. Lysozyme (900 mg) is added in 30 ml of Tris-sucrose buffer (1 mg lysozyme/g of cells). The mixture was distributed into 500 ml centrifuge bottles and incubated at 4° C. for 1 hour. The bottles are then placed into a 37° C. water bath and gently inverted every 30 seconds for 4 minutes. The insoluble cellular components were removed by centrifugation (13000×G, 60 min, 4° C.). The recovered supernatant (3700 ml) comprises Fraction I. Ammonium sulfate (0.226 g/ml of Fraction I, 40% saturation) is then added over a period of 30 minutes. The mixture is stirred for an additional 30 minutes at 4° C. The mixture are distributed into 500 ml bottles and centrifuged for 30-45 minutes (13000×g, 4° C.). The supernatant is discarded. The pellet is resuspended in 50 ml of no salt Buffer T (50 mM Tris pH 7.5, 1 mM EDTA pH 8, 0.25 mM EGTA pH 7.5, 10% Glycerol and 1 mM DTT). The suspended pellet comprises Fraction II. The conductivity of Fraction II is then adjusted with no-salt Buffer T to that of Buffer A (50 mM NaCl+Buffer T). A Q sepharose column is equilibrated with Buffer A. Fraction II is loaded onto the Q sepharose column, then the column is washed with 5 column volumes of Buffer A. Proteins are eluted with a gradient from Buffer A to 50% Buffer B (1M NaCl+Buffer T) over 10 column volumes. *B. subtilis* dnaB elutes as a peak halfway through the gradient (about 250 mM NaCl). The fractions are analyzed by SDS-PAGE and the best fractions are pooled. The pooled fractions comprise Fraction III.

Fraction III is dialyzed overnight against 50 mM NaCl+ Hepes Buffer (40 mM Hepes pH 7.5, 10% Glycerol, 0.1 mM EDTA, and 1 mM DTT). A 50 ml Heparin Sepharose column is being equilibrated with 5 column volumes of Buffer A (50 mM NaCl+Hepes Buffer). Dialyzed Fraction III is loaded onto the Heparin column and the column is washed with 5 column volumes of Buffer A. Proteins are eluted with a gradient from Buffer A to 100% Buffer B (1M NaCl+Hepes Buffer). *B. subtilis* dnaB elutes as a peak early in the gradient (200 mM NaCl). Fractions were analyzed using SDS-PAGE and the best fractions are pooled The pooled fractions comprise Fraction IV. Fraction IV is diluted with saturated ammonium sulfate (3.9M) to bring its conductivity up to that of Buffer A (1M ammonium sulfate in Hepes Buffer). A butyl-Sepharose column is equilibrated with Buffer A. The equilibrated Fraction IV is then loaded onto the column. The column is washed with 50% Buffer B (no salt Hepes Buffer) for 5 column volumes. A gradient from 50% Buffer B to 100% Buffer B is then run. B. subtilis dnaB elutes as a peak late in the gradient (200 mM Ammonium Sulfate). The fractions are analyzed by SDS-PAGE and the best fractions are pooled. The pool comprises Fraction V. Fraction V is dialyzed overnight against 50 mM NaCl+Buffer T (50 mM Tris pH 7.5, 1 mM EDTA pH 8, 0.25 mM EGTA pH 7.5, 20% Glycerol and 1 mM DTT). The dialyzed pool is tested for single- and double-stranded endonuclease activity and tested for activity in the B. subtilis primosome-dependent replication assay.

F. Expression and Purification of B. subtilis DnaG.

Overproducing cells are grown in F medium in a 200 liter fermenter, and induced at an optical density at 600 nanometers of 2.0. Cells are grown for an additional 2 hours, then harvested by centrifugation. Cell pellets are stored as a 50% weight/volume slurry in a solution consisting of 50 mM Tris-HCl pH 8.0 and 10% w/v sucrose. Frozen cells are lysed by adding 180 g of a 1:1 suspension of frozen cells (90 g cells) in Tris-Sucrose which had been stored at −20° C. to 247.5 ml of Tris-Sucrose that has been pre-warmed to 45° C. (2.75 ml/g of cells). To the stirring mixture, 4.5 ml of 0.5M 1,4-dithiothreitol (DTT) (0.05 ml/g of cells) and 22.5 ml of lysis buffer (2M NaCl, 0.3M spermidine in Tris-sucrose adjusted to pH 7.5) (0.25 ml/g of cells) was added. Also, to the stirring mixture, 4.5 ml of 0.5M EDTA pH 8.0 and 4.5 ml of 0.25M EGTA pH 7.5. The pH of the mixture was adjusted to pH 8.2 by the addition 2M Tris Base. Lysozyme (90 mg) was added in 10 ml of Tris-sucrose buffer (1 mg Lysozyme/g of cells). The mixture are distributed into 500 ml centrifuge bottles and incubated at 4° C. for 1 hour. The bottles are then placed into a 37° C. water bath and gently inverted every 30 seconds for 4 minutes. The insoluble cellular components are removed by centrifugation (13000×g, 60 min, 4° C.). The supernatant constituted Fraction I. Ammonium sulfate (0.291 gr/ml of Fraction I, 58% saturation) is added slowly over a period of 30 minutes. The mixture is then stirred for an additional 30 minutes at 4° C. The mixture is distributed into 500 ml bottles and centrifuged for 30-60 minutes (13000×g, 4° C.). The supernatant is discarded and the pellet is resuspended in no-salt Hepes Buffer 1 (40 mM Hepes pH 7.5, 10% Glycerol, and 1 mM 1,4-dithiothreitol (DTT)). The resuspended pellet comprises Fraction II. Fraction II is then centrifuged for 30 minutes at 10,000×g to remove insoluble material. The conductivity is adjusted with no-salt Hepes Buffer to the conductivity of Buffer A (Hepes buffer+75 mM NaCl). A Q sepharose column is equilibrated with Buffer A (75 mM NaCl+Hepes Buffer). Fraction II is loaded onto the Q sepharose column and washed with 5 column volumes of Buffer A. Proteins are eluted with a gradient from 100% Buffer A to 100% Buffer B (1M NaCl+Hepes Buffer 1) over 10 column volumes. Fractions are analyzed by SDS-PAGE. B. subtilis DnaG elutes as a peak early in the gradient (about 107 mM NaCl). The best fractions are pooled, and the pool comprises Fraction III. The conductivity of Fraction III is adjusted with no salt Hepes Buffer to that of Buffer A (200 mM NaCl, 40 mM Hepes pH 7.5, 10% Glycerol and 1 mM 1,4-dithiothreitol (DTT)). Fraction III is loaded onto a Hydroxyl Apatite column equilibrated in Buffer A. The column is washed with 5 column volumes of Buffer A. Proteins are eluted in with a gradient from 100% Buffer A to 100% Buffer B (200 mM potassium phosphate pH 7.0+Buffer A) over 10 column volumes. Fractions were analyzed by SDS-PAGE. B. subtilis DnaG elutes as a peak in the middle of the gradient (about 90 mM potassium phosphate) along with some contaminants. The best fractions are pooled. The pool comprises Fraction IV.

Fraction IV is desalted on a G50 desalting column equilibrated in 50 mM NaCl+Hepes Buffer 2 (40 mM Hepes pH 7.5, 0.5 mM EDTA pH 8.0, 0.25 mM EGTA pH 7.5, 10% Glycerol and 1,4-dithiothreitol (DTT)). Desalted Fraction IV is loaded onto a Heparin Sepharose column that has been equilibrated with Buffer A (75 mM NaCl+Hepes Buffer 2). The column is washed with 5 column volumes of Buffer A. Proteins are eluted with a gradient that from 100% Buffer A to 100% Buffer B (1M NaCl+Hepes Buffer 2) over 10 column volumes. Fractions are analyzed using SDS-PAGE. B. subtilis dnaG elutes as a peak early in the gradient (about 250 mM NaCl) with one minor contaminant (we believe it is likely a breakdown product of dnaG). Fractions containing B. subtilis DnaG are pooled and comprise Fraction V. Glycerol is added to a final concentration of 20% v/v, and the material is tested for single- and double-stranded endonuclease activity, and for activity in the B. subtilis primosome-dependent replication assay.

G. Expression and Purification of B. subtilis SSB1

Overproducing cells are grown in F medium in a 200 liter fermenter, and induced at an optical density at 600 nanometers of 2.0. Cells are grown for an additional 2 hours, then harvested by centrifugation. Cell pellets are stored as a 50% weight/volume slurry in a solution consisting of 50 mM Tris-HCl pH 8.0 and 10% w/v sucrose. Frozen cells are lysed by adding 1800 g of a 1:1 suspension of frozen cells (900 g cells) in Tris-sucrose which had been stored at −20° C. to 2475 ml of Tris-Sucrose Buffer that had been pre-warmed to 45° C. (2.75 ml/g of cells). To the stirring mixture, 45 ml of 0.5M 1,4-dithiothreitol (DTT) (0.05 ml/g of cells) and 225 ml of lysis buffer (2M NaCl, 0.3M spermidine in Tris-sucrose adjusted to pH 7.5) (0.25 ml/g of cells) was added. The pH of the mixture is tested with pH paper and adjusted to pH 8.2 by the addition of 30 ml of 2M Tris Base. Lysozyme (900 mg) is added in 30 ml of Tris-sucrose buffer (1 mg lysozyme/g of cells). The mixture was distributed into 500 ml centrifuge bottles and incubated at 4° C. for 1 hour. The bottles are then placed into a 37° C. water bath and gently inverted every 30 seconds for 4 minutes. The insoluble cellular components were removed by centrifugation (13000×g, 60 min, 4° C.). The recovered supernatant comprises Fraction I. Ammonium sulfate (0.226 g/ml of Fraction I, 40% saturation) is then added over a period of 30 minutes. The mixture is stirred for an additional 30 minutes at 4° C. The mixture is distributed into 500 ml bottles and centrifuged for 30-45 minutes (13000×g, 4° C.). The supernatant is discarded. The pellet was washed with ⅛ the original Fraction I volume with buffer T supplemented with 0.2 g/ml ammonium sulfate. The mixture is placed into 250 ml centrifuge bottles and spun for 30 minutes at 13000×g for 30 minutes at 4 degrees C. Pellets are suspended in 200 ml of 150 mM NaCl in Buffer T (50 mM Tris pH 7.5, 1 mM EDTA pH 8.0, 20% Glycerol and 1 mM DTT). The suspended material comprises Fraction II. A 450 ml Blue Dextran Column is equilibrated with 3000 ml of 150 mM NaCl in Buffer T. Fraction II conductivity is adjusted to that of 150 mM NaCl in Buffer T, then loaded onto the Blue Dextran column. The column is washed with 500 ml of 150 mM NaCl in Buffer T, with 1000 ml of 400 mM NaCl in Buffer T and with 500 ml of 1M NaCl plus Buffer T. Proteins are eluted with 1000 ml of 2M NaCl in Buffer T. Remaining proteins, including B. subtilis SSB1, are eluted with 1500 ml of 4M NaCl in Buffer T. Fractions are analyzed by SDS PAGE gels. Pooled fractions comprise Fraction III. Fraction III is loaded onto a Hydroxyl Apatite Column equilibrated with Buffer A (50 mM Imidazole pH 6.8, 1M NaCl, 20% Glycerol and 1 mM DTT). The column is washed with 5 column volumes of Buffer A. Proteins are eluted with a gradient that went from 100% Buffer A to 100% Buffer B (Imidazole Buffer+100 mM Potassium Phosphate pH 7). *B. subtilis* SSB 1 elutes late in the gradient, at about 70 mM Potassium. Fractions are analyzed using SDS-PAGE, and the best fractions are pooled. This pool constitutes Fraction IV. Fraction IV is dialyzed against dry polyethylene glycol (MW nominally 10,000 to a concentration of about 2 mg/ml and is assayed for single- and double-stranded endonuclease activity.

H. Expression and Purification of DnaE.

Purification of *Bacillus subtilis* DnaE is relatively straightforward, since it overproduces vigorously and is relatively well-behaved. The protein does have a tendency to precipitate at higher concentrations and lower ionic strength (>1 mg./ml and <300 mM NaCl). Expected yield is about 5 mg BsDnaE per liter culture medium. Cells growth and induction are as follows: cells are grown in F medium+1% glucose at 37 degrees to OD600=0.6. IPTG is added to 0.5 mM and growth is continued for an additional 2 hours. Cells are harvested by centrifugation, and stored at −20° C. as a 50% slurry in Tris-sucrose. Cells are thawed and lysed by the addition of 2.75 mls of Tris-sucrose per gram cells, pre-warmed to 45 C. 0.5 M DTT is added to 5 mM final concentration, 0.5M EDTA is added to 5 mM final concentration, 0.25M EGTA is added to 2.5 mM. 0.25 mls lysis solution per gram cells are added and the pH adjusted to 8.0, using pH paper. Freshly prepared lysozyme is added to 200 ug/ml final concentration, the mixture is transferred to centrifuge bottles and incubated on ice for 1 hour. The bottles are immersed in a 37 C water bath for 2-6 minutes with agitation every 30 seconds. Bottles are then centrifuged for 1 hour at 13000×g. The supernatant comprises Fraction I. Ammonium sulfate (0.25 g/ml Fraction I, 45% saturation) is added slowly over 30 minutes, and stirring is continued for 30 minutes. The mixture is then centrifuged 30 minutes. The pellet is suspended in roughly 0.5 ml/gram cells H' buffer (40 mM Hepes-NaOH pH 7.8, 0.5 mM EDTA, 0.25 mM EGTA, 1 mM DTT, 10% glycerol). The resuspended pellet comprises Fraction II. Fraction II is dialyzed overnight against H' buffer+300 mM NaCl. A Q-sepharose column (1 ml resin/10 mg protein) is equilibrated in H'+60 mM NaCl. Fraction II is diluted 5-fold in H' buffer without added NaCl and loaded onto the column. The column is washed with 4 volumes H'+100 mM NaCl, and developed with a gradient to 500 mM NaCl over 10 column volumes. *B. subtilis* DnaE elutes at about 220 mM NaCl. Fractions are analyzed by SDS gel and the best fractions are pooled. The pool comprises Fraction III. A heparin agarose column (1 ml resin per 5 mg protein is equilibrated in H'+50 mM NaCl. Fraction III is diluted with H' w/o NaCl to a conductivity equivalent to H'+50 mM NaCl (about 5-fold). The diluted Fraction III is loaded onto the heparin-agarose column, then washed with 4 column volumes H'+100 mM NaCl. The column is developed with 10 column volumes H' to 500 mM NaCl. DnaE elutes in a broad peak centered at about 250 mM NaCl. Fractions are analyzed by SDS gel and best fractions are pooled. Specific activity should be about $5 \times 10^5$ units per mg. The pooled fractions comprise Fraction IV. A Q-Separose column is equilibrated with H' (or T') buffer, as before. Maximum load is 10 mg/ml resin. Fraction IV is diluted 5-fold with H' or T' buffer without added salt, to a conductivity equivalent to H' or T'+50 mM NaCl. The column is loaded, washed, and developed with a gradient as done to obtain Fraction III. DnaE will again elute in a sharp peak at about 220 mM NaCl. Fractions are assayed by SDS gel and the best fractions are pooled. Glycerol is added to a final concentration of 20% v/v, and NaCl to a final concentration of 300 mM. The final material (Fraction V) is assayed for gap-filling activity (it should be in the neighborhood of $5 \times 10^5$ units/mg), for activity in the *B. subtilis* primosome-dependent replication assay, and tested for single- and double-stranded endonuclease activity.

I. Activity assays.

Briefly, DNA synthesis activity was monitored during purification of components using the *Bacillus subtilis* primosome-dependent replication assay. M13 single-stranded bacteriophage DNA bearing a Gram-positive primosome assembly site (PAS) was used as template DNA. An enzyme mix containing *B. subtilis* PriA, DnaD, DnaB, DnaC, DnaI, primase (DnaG), and DnaE (DNA polymerase) was prepared. Restart reactions were reconstituted by incubating the enzyme mix with *B. subtilis* SSB 1-coated ssiA primosome assembly (PAS) site-bearing single-stranded DNA substrate. Assembly of a protein complex at the ssiA PAS site culminates in the synthesis of an RNA primer. The RNA primer is then elongated by DnaE DNA polymerase, converting single-stranded substrate to duplex form. Measurements were for a 25 µL reaction volume for 15-60 minutes at 30° C. Incorporation of [$^3$H]-dTTP was measured by TCA precipitation on GF-C filters. Enzyme titrations were performed to determine the linear range of the assay. In some cases where it was not necessary to determine absolute incorporation rates, formation of dsDNA was measured by fluorescent detection of dsDNA using PicoGreen® (Molecular Probes) (Seville, et al. (1996) "Fluorometric Assay for DNA Polymerases and Reverse Transcriptase" Biotechniques 21: 664-672). Enzyme concentrations were set at the knee of each curve as shown in FIG. 11 and ranged from 2.5 to 18 nM.

Figure 12A:
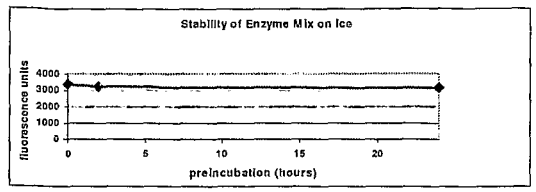
FIG. 12A shows the results of *Bacillus subtilis* primosome-dependent replication assay after the proteins were stored on ice for various times.
Figure 12B:
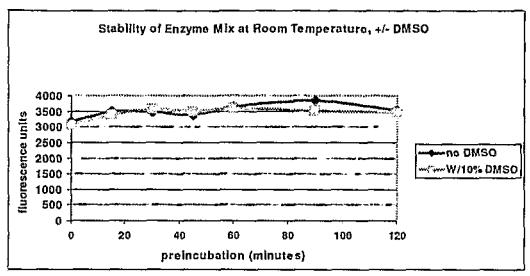
FIG. 12B shows the results of *Bacillus subtilis* primosome-dependent replication assay after the proteins were stored at room temperature for various times.
Figure 12C:
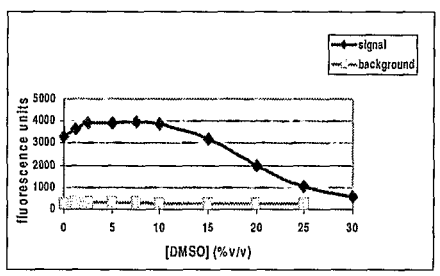
FIG. 12C shows the results of a titration of DMSO in the *Bacillus subtilis* primosome-dependent replication assay.

Optimization of assay parameters was performed as described for other bacterial replication assemblies. Results are shown in FIG. 12.

Example 4

Other Proteins Utilized in DNA Replication Activity and HTS Assays

*E. coli* holoenzyme components, DNA polymerase III*, and primase were prepared and purified according to previously published procedures.

*E. coli* β was purified as follows. Frozen cells were lysed by adding Tris-sucrose buffer that had been pre-warmed to 45° C. to 100 g of "popcorn" stored at −20° C.). To the stirred mixture, 2.5 mL of 0.5 M DTT (0.05 mL/g of cells and lysis buffer (2M NaCl, 0.3M spermidine in Tris-sucrose, pH 7.5) were added. 2 mL of 0.5M EDTA was then added. The pH of the slurry was tested with pH paper and adjusted to pH 8 by the addition of Tris base. Lysozyme (7.5 mg) was added in 10 mL of Tris-sucrose buffer. The slurry was placed into a centrifuge bottle after stirring 5 min and incubated at 4° C. for 1 hour. The centrifuge bottle was then placed in a 37° C. water bath and gently inverted every 30 seconds for 4 minutes. The insoluble cellular components were removed by centrifugation. The recovered supernatant constituted Fraction I.

To Fraction I, ammonium sulfate to a 40% saturation over a 30 min interval. The mixture was stirred for an additional 20 min at 4° C. and the precipitate collected by centrifugation. Ammonium sulfate was added to the resulting supernatant of 40% supernatant, yielding 70% saturation over a 30 min interval. The mixture was again stirred for 20 min at 4° C. and the precipitate collected by centrifugation. The pellet containing the 40-70% was resuspended in (Fraction II) and further diluted to 2000 mL of Buffer $A_0$ (50 mM Tris, pH 7.5, 0.25 M EDTA) to reach a conductivity below that measured for Buffer $A_{25}$ ($A_0$+25 mM NaCl).

Diluted Fraction II was loaded onto a 100 mL DEAE column (Amersham DEAE sepharose Fast Flow, 1.6×10 cm) pre-equilibrated with Buffer $A_{25}$ at a flow rate of 1 mL/min. *E. coli* β was eluted with a 25-500 mM NaCl gradient (Fraction III) at a flow rate of 1.28 mL/min. The eluate was collected and analyzed for protein concentration and for DNA synthesis in the M13gori *E. coli* holoenzyme assay, and by gel electrophoresis. The *E. coli* β-subunit eluted in a single peak.

Fraction III was diluted with Buffer $IA_0$ (50 mM imidazole, pH 6.8, 10% glycerol, 5 mM DTT) to a conductivity which was lower than Buffer $IA_{KP10}$ and loaded onto a hydroxylapatite column (60 mL; Hypatite C, Clarkson Chemical Company) equilibrated in Buffer $IA_{KP10}$ at a flow rate of 0.4-0.8 mL/min. The column was washed with 30 mL of Buffer $IA_{KP10}$ at a flow rate of 0.5 mL/min. The protein was eluted in a 600 mL gradient from 10-150 mM potassium phosphate (pH 6.8) at a flow rate of 0.4 mL/min. The eluate was collected and analyzed by protein concentration determination, gel electrophoresis and activity assays. The β-subunit eluted as a single peak early in the gradient. Fractions containing the *E. coli* β subunit were pooled (Fraction IV).

One-half HAP pool was ammonium sulfate precipitated at 70% saturation and isolated by centrifugation. The pellet was resuspended in Gel Filtration Buffer (25 mM HEPES, 5 mM EDTA, 10% glycerol, 5 mM DTT, 150 mM NaCl) and loaded onto a HiLoad 16/60 Superdex 200 column equilibrated in Gel Filtration Buffer utilizing a Pharmacia AKTA FPLC system (1.5 CV). The eluate was and the protein concentration and activity were determined and the fractions were analyzed using gel electrophoresis. The *E. coli* β-subunit eluted as a single peak. A duplicate attempt was made and the elutions were combined following analysis (Fraction V).

Titration of the β subunit was carried out in the presence of excess levels of Core complex and tau complex. The minimum amount of β subunit that allowed the reaction to reach a plateau was 0.011 μg, which corresponds to a concentration of 0.005 μM β.

*E. coli* SSB was purified as follows. The advantage of the purification was the vastly improved expression of a new construct in Rosetta cells. Frozen cells were lysed by adding Tris-sucrose buffer that had been pre-warmed to 45° C. to cell paste which had been stored at −20° C. to). To the mixture, DTT was added and the mix was stirred for 2 hours. The cell paste is more difficult to resuspend and dissolution should be fully confirmed prior to continuing with the purification steps. Lysis buffer (2M NaCl, 0.3M spermidine in Tris-sucrose, pH 7.5) was added. EDTA was then added. The pH of the slurry was tested with pH paper and adjusted to pH 8 by the addition of Tris base. Lysozyme in Tris-sucrose buffer was added. The slurry was placed into centrifuge bottles and incubated on ice for 1 hour. The insoluble cellular components were removed by centrifugation. The recovered supernatant constituted Fraction I.

To Fraction I, ammonium sulfate was added to a 19% saturation level over a 30-minute interval. The mixture was stirred for an additional 30 minutes at 4° C. and the precipitate collected by centrifugation.

The pellets containing the SSB (Fraction II) were resuspended in Buffer A (50 mM imidazole, pH 6.8, 10% glycerol, 5 mM DTT, 200 mM NaCl) and dialyzed overnight in the same buffer. Following dialysis, the sample was loaded onto a hydroxyapetite (HAP) column (Hypatite C, Clarkson Chemical Company; 180 mL) pre-equilibrated with Buffer A at a flow rate of 0.5 mL/minute. The column was washed and the SSB was then eluted from the HAP column with a potassium phosphate buffer gradient (0 mM-150 mM). The eluate was collected analyzed for protein concentration and by gel electrophoresis as described above. SSB eluted as a single, broad peak was pooled (Fraction III). The SSB was again pelleted by ammonium sulfate (50%) and dialyzed into a final storage buffer (20 mM Tris-HCl, pH 7.5, 0.1 mM EDTA, 20% glycerol, 1 mM DTT, 200 mM NaCl). Following dialysis, the final SSB was centrifuged to remove insoluble material, analyzed for protein concentration and purity (as described above), aliquoted into cryogenic vials, snapfrozen in $N_2(l)$, and stored at −80° C.

Example 5

*E. coli* Origin of Replication Bacterial Replication Assembly

A. Construction of Overexpression Vectors.

The sequences of each gene were identified in the NCBI database by a homology search based on known sequences, unless noted otherwise. Cloning of the genes entailed PCR amplifying from bacterial genomic DNA, followed by insertion into expression vectors. All of the expression vectors utilized for origin specific proteins (DnaA, DnaB, and DnaC) were pET vectors (Novagen) under the control of the highly inducible T7 promoter. This was also the case for SSB which was a novel construction, expression and purification methodology for this system. The polymerase proteins were a native purification, while the β subunit and primase were expressed under the influence of the pA1 vector. When appropriate, *E. coli* low usage codons in the bacterial genes were altered to high usage codons, and non-AUG start codons were changed to AUG, to facilitate efficient translation in *E. coli*. A plasmid containing a pBR322 origin of replication, a gene expressing the lacIQ repressor protein, and the semi-synthetic promoter, pA1, which is repressed by lacI, was used. The polylinker region was modified to introduce appropriate restriction sites to facilitate insertion of the desired bacterial genes.

B. Cell Growth and Lysis.

Expression vectors were transferred into appropriate fermentation strains, and the strain giving optimal protein expression was chosen for large scale growth. In the case of the origin specific proteins, BL21 DE3 pLysS cells were utilized for optimal expression. These proteins can be toxic to the bacterial cell viability and slow the growth of the expressing cells. The pLysS cells offer more stringent expression control and regulation. For SSB, the protein is not toxic to the cells so Rosetta cells were used to provide a very high yield of protein.

C. Activity Assays

Activity assays for replication origin reconstitution were modified and optimized from initial origin assays described in Masai, et al., "The ABC primosome: A novel priming system employing dnaA, dnaB, dnaC and primase on a hairpin containing a dnaA box sequence." *J Biol Chem;* 1990; 265:15134-15144; Masai & Arai, "Dna-A dependent assembly of the ABC primosome at the A site, a single-stranded DNA hairpin-containing a dnaA box." *Eur J Biochem;* 1995; 230:384-395 and Carr & Kaguni, "The following changes allowed for a more efficient reaction with every component optimized for DnaA and DnaB dependence and conversion of the origin reconstitution to a high-throughput screening (HTS) format. The protein purifications were improved for DnaA and DnaB to increase the purity, activity and yield. New expression constructs were created for DnaC and SSB which increases the level of expression to provide the amount of protein needed for HTS. Excipients were included in the reaction mix to improve DMSO tolerance so that the presence of compound for analysis did not affect the origin reconstitution system.

Briefly, a 306-nucleotide region with a hairpin containing a DnaA binding sequence was cloned into M13 single-stranded phage DNA was used as template DNA. A large scale preparation of the M13 DNA template was performed and an improved purification developed. Replication origin proteins were purified to homogeneity (see Purification Examples below) and the activity evaluated in independent assays. The origin reconstitution assay was done as follows. To a mix with DnaA and reaction buffer (which contains magnesium and ATP for optimal DnaA function and stability), primase, Pol III*, β and finally DnaB and DnaC were added. A solution containing single-stranded DNA template, deoxy-nucleotides, and SSB was added to initiate the reaction. In cases, where compound was evaluated, the DMSO-solubilized compound was added to the enzyme mix prior to reaction initiation. The format was the same for HTS as well. The reconstitution reactions were in a final reaction volume of 25 µL and were conducted for 45 minutes at room temperature. Incorporation of [$^3$H]-dTTP was measured by TCA precipitation on GF-C filters. Enzyme titrations were performed to determine the linear range of the assay, and specific activities were calculated using points in the linear range. Relative to the component being assayed, other components were used at saturating concentrations. In some cases where it was not necessary to determine absolute incorporation rates, formation of dsDNA was measured by fluorescent detection of dsDNA using PicoGreen® (Molecular Probes) (Seville, et al. (1996) "Fluorometric Assay for DNA Polymerases and Reverse Transcriptase" Biotechniques 21: 664-672).

D. Protein Analysis.

Protein concentrations were determined using the Coomassie Plus Protein Assay (Pierce) and a bovine serum albumin standard. SDS-PAGE analysis of DnaA, DnaB, DnaC samples was performed using 4-12% acylamide gradient pre-cast gels (Novex NuPAGE®; Invitrogen) using MOPS running buffer (Invitrogen). Benchmark unstained protein molecular weight markers were used (Invitrogen). SDS-PAGE analysis of SSB samples was performed on 10-20% acrylamide Novex Tris-glycine pre-case gels (Invitrogen) using Tris-glycine running buffer (Invitrogen). Gels were stained with SimplyBlue SafeStain (Invitrogen) or with Coomassie Brilliant Blue. Comparable results were obtained with either staining method. Peptide sequencing for protein identification and mass determination was performed by Harvard Microchemistry Laboratory for DnaC.

E. Expression and Purification of DnaA.

Frozen cells were lysed by adding of Tris-sucrose buffer that had been pre-warmed to 45° C. to cell paste which had been stored at –20° C. To the stirred mixture, DTT and of lysis buffer (2M NaCl, 0.3M spermidine in Tris-sucrose, pH 7.5) were added. The mix was stirred for 1.5 hours. The cell paste is difficult to resuspend and dissolution should be fully confirmed prior to continuing with the purification steps. EDTA was then added. The pH of the slurry was tested and adjusted to pH 8 by the addition of Tris base. No lysozyme was added due to the use of a BL21 DE3 pLysS strain of cells. The slurry was incubated on ice for 30 minutes. The insoluble cellular components were removed by centrifugation. The recovered supernatant constituted Fraction I.

To Fraction I, 0.075% polyethyleneimine was added. Following 30 minutes of stirring at 4° C., the mix was centrifuged for 30 minutes. To the supernatant (Fraction II) ammonium sulfate was added to a 70% saturation level, over a 30 minute interval. The mixture was stirred for an additional 20 minutes at 4° C. and the precipitate collected by centrifugation. The pellet containing the DnaA was resuspended in Buffer $A_0$ (50 mM Tris-HCl, 0.1 mM EDTA, 20% glycerol, 2 mM DTT, 10 µM ATP, 10 mM MgOAc) to reach a conductivity below that measured for Buffer $A_{100}$ (Buffer $A_0$+100 mM NaCl) (Fraction III).

Figure 13:
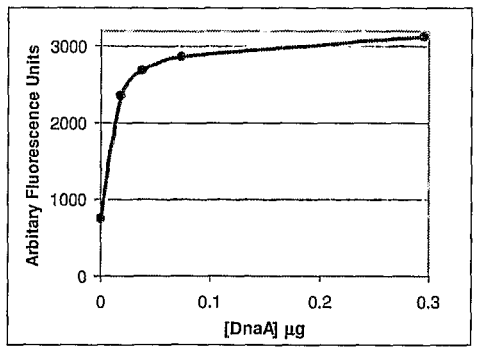
FIG. 13 shows a DnaA titration in the origin assay.

Diluted Fraction III was divided into two samples because of column capacity. Each aliquot was loaded onto a 20 mL SP-sepharose commercially pre-packed column (Amersham SP Hi-Prep 16/10_SP_XL) and eluted with a 100 mM to 1.2 M NaCl (Buffer B) gradient at a flow rate of 1 mL/min (Fraction IV). The eluate was collected and analyzed for protein concentration and by gel electrophoresis (as described above). The DnaA eluted in a single peak. Activity was evaluated by DnaA binding assays (gel shift and nitrocellulose filter binding) and origin reconstitution assay. Titration of the DnaA in the origin reconstitution assay was carried out in the presence of excess levels of polymerases, primase, DnaB and DnaC. The minimum amount of DnaA that allowed the reaction to reach a plateau was ~100 ng, which corresponds to a concentration of 76 nM DnaA. The results are shown in FIG. 13. A summary of the protein purification and activity analysis can be found in Table 19.

TABLE 19

E. coli DnaA Purification Summary

|  | Volume ml | [Protein] mg/ml | Total Protein mg | Specific Activity U/mg |
|---|---|---|---|---|
| Frac I | 216 | 21.88 | 4726.08 | ND |
| Frac II poly P ppt | 200 | 33.07 | 6614.00 | $2.76 \times 10^5$ |
| Frac III (AS 70%) | 2900 | 1.46 | 4234.00 | $2.51 \times 10^5$ |
| Frac VI (SP pool A)* | 43.2 | 1.852 | 80.01 | $2.57 \times 10^6$ |
| Frac VI (SP pool B)** | 43.2 | 3.2 | 138.24 | $2.64 \times 10^6$ |

*Fraction III divided due to column limitations
**Pools kept separate due to [protein] difference F. Expression and Purification of DnaB.

Frozen cells were resuspended by adding Tris-sucrose buffer that had been pre-warmed to 42° C. to cell popcorn which had been stored at –20° C. To the mixture, lysis buffer (10% w/v sucrose, 2 M NaCl, 0.3 M spermidine, pH 7.5), 174 µg/mL PMSF, and 5 mM EDTA) were added. The pH of the slurry was tested with pH paper and adjusted to pH 8.2 by the addition Tris base. The cells were lysed by adding ~3 mg/g cells of lysozyme (in Tris-sucrose buffer), stirring for 5 minutes, then placing the mix into centrifuge bottles and incubating on ice for 1 hour. After heat shocking the slurry at 37° C. for 6 minutes (inversion every 30 seconds to mix) the insoluble cellular components were removed by centrifugation. The recovered supernatant constituted Fraction I.

To Fraction I, ammonium sulfate was added slowly over 10 minutes to 50% saturation at 4° C. Following 30 minutes of stirring at 4° C., the mix was centrifuged for 45 minutes. The supernatant was discarded and the pellets stored at –80° C. until the next step of the purification.

The pellets containing the DnaB were resuspended in Buffer $B_{100}$ (50 mM Tris-HCl, pH 7.5, 1 mM EDTA, 20% glycerol, 5 mM DTT, 100 mM NaCl) and dialyzed overnight is 4 L of the same buffer with stirring at 4° C. Following dialysis, the sample was centrifuged to remove insoluble material. The sample was diluted with $B_0$ (50 mM Tris-HCl, pH 7.5, 1 mM EDTA, 20% glycerol) to reach a conductivity less than or equal to $B_{100}$ (Fraction II). The DnaB solution was loaded onto a Q Sepharose (Amersham, Fast Flow, 125 mL, 22 cm in height) column, pre-equilibrated with Buffer $B_{100}$, at a flow rate of ~3 mL/minute. The column was washed with ~0.5 L of Buffer $B_{100}$ and the DnaB was then eluted with a 1.5 L NaCl gradient (100 mM-700 mM) at a flow rate of ~3 mL/minute. The eluate was collected and analyzed for protein concentration, conductivity, and activity in the general priming assay. DnaB eluted as a single peak and fractions were pooled for the resulting Fraction III.

To Fraction III, ammonium sulfate was added slowly over 10 minutes to 50% saturation at 4° C. Following 30 minutes of stirring at 4° C., the mix was centrifuged for 45 minutes. The supernatant was discarded and the pellets stored at −80° C. until the next step of the purification.

The pellets containing the DnaB were resuspended in Buffer B-$Mg_0$ (50 mM Tris-HCl, pH 7.5, 1 mM EDTA, 20% glycerol, 10 mM Mg $Cl_2$) and dialyzed overnight is 4 L of the same buffer with stirring at 4° C. Following dialysis, the sample (Fraction IV) was centrifuged to remove insoluble material and loaded onto an ATP-agarose column (Sigma; 30 mL; 2.5 cm diameter) equilibrated in Buffer B-$Mg_0$ at a flow rate of ~2 mL/minute. The column was washed with Buffer B-$Mg_0$, 60 mL of Buffer B-$Mg_{50}$ (Buffer B-$Mg_0$+50 mM NaCl), and Buffer B-$Mg_{50}$+10 mM AMP at a flow rate of ~2 mL/minute. The protein was eluted by washing with Buffer B-$Mg_{50}$+10 mM ATP at a flow rate of ~2 mL/minute. The eluate was collected and analyzed by protein concentration determination and activity in the general priming assay. The DnaB eluted as a single peak and was pooled (Fraction V).

Fraction V was precipitated with ammonium sulfate added slowly over 10 minutes to 50% saturation at 4° C.). Following 30 minutes of stirring at 4° C., the mix was centrifuged for 45 minutes. The supernatant was discarded and the pellets stored at −80° C. until the final step of the purification.

The DnaB pellets were resuspended in Buffer B-$Mg_{50}$ and dialyzed overnight is 4 L of the same buffer with stirring at 4° C. Following dialysis, the final DnaB was centrifuged to remove insoluble material, aliquoted into cryogenic vials, snapfrozen in $N_2$(l), and stored at −80° C.

A summary of the protein purification and activity analysis can be found in the Table 20.

TABLE 20

DnaB Purification Summary

| Sample tested | Total Volume (mL) | [Protein] (mg/mL) | Total Protein (mg) | S.A. (U/mg) | Total Activity (U) |
| --- | --- | --- | --- | --- | --- |
| Frac I | 170 | 11.1 | 1892.4 | 2.77E+04 | 52458979 |
| Frac II (ammonium sulfate) | 48.9 | 16.8 | 820.7 | 6.94E+04 | 56991456 |
| Frac III (Q Sepharose) | 137.3 | 1.47 | 201.9 | 1.83E+05 | 36959395 |
| Frac IV (ammonium sulfate) | 22 | 8.6 | 189.6 | 1.82E+05 | 34468053 |
| Frac V (ATP-agarose) | 16.3 | 5.4 | 87.4 | 2.49E+05 | 21799067 |
| EP79 | 17.45 | 4.5 | 78.1 | 1.92E+05 | 15025520 |

Figure 14:
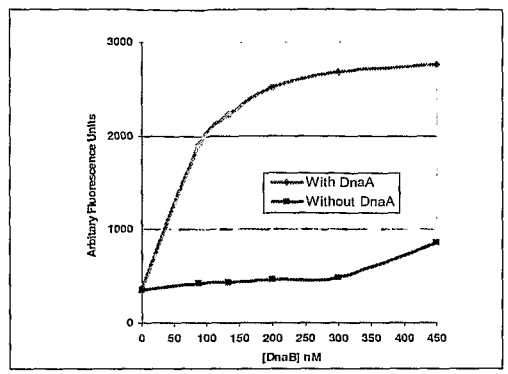
FIG. 14 shows a DnaB titration in the origin assay.
Figure 15:
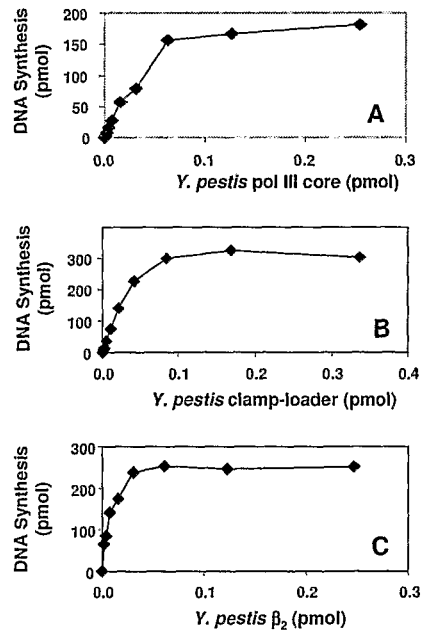
FIG. 15 shows the determination of *Y. pestis* DNA polymerase III holoenzyme component concentrations needed to obtain maximum activity in reconstitution assays.
Figure 16:
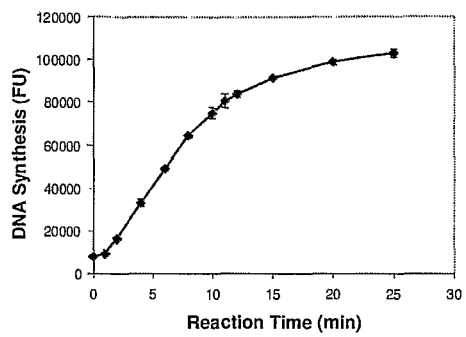
FIG. 16 shows reaction kinetics of the optimized *Y. pestis* DNA polymerase III HTS assay at 23° C.
Figure 17:
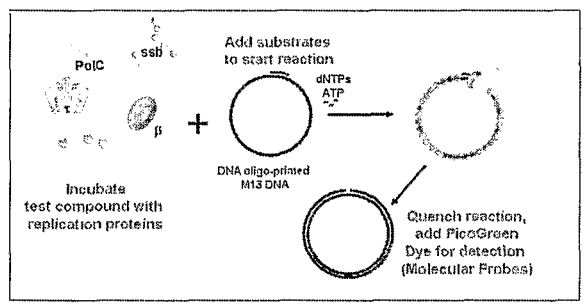
FIG. 17 shows a schematic of the *S. aureus* high-throughput screening assay.

Titration of the DnaB was carried out in the presence of 40 nM DnaG and excess levels of α, β, and τ complex for the General Priming assay and the excess of all proteins in the origin assay. The minimum amount of DnaB that allowed the reaction to reach a plateau was 0.125 μg, which corresponds to a concentration of 1.45 nM DnaB hexamer. More DnaB was required in the origin reconstitution assay to confirm the DnaA-dependent origin mechanism rather than General Priming (FIG. 14).

G. Expression and Purification of DnaC.

Frozen cells were lysed by adding Tris-sucrose buffer that had been pre-warmed to 45° C. to cell paste which had been stored at −20° C. to). To the mixture, DTT was added and the mix was stirred for 2 hours. The cell paste is more difficult to resuspend and dissolution should be fully confirmed prior to continuing with the purification steps. Lysis buffer (2M NaCl, 0.3M spermidine in Tris-sucrose, pH 7.5) was added. EDTA was then added. The pH of the slurry was tested with pH paper and adjusted to pH 8 by the addition of Tris base. Lysozyme in Tris-sucrose buffer was added. The slurry was placed into centrifuge bottles and incubated on ice for 1 hour. The insoluble cellular components were removed by centrifugation. The recovered supernatant constituted Fraction I.

To Fraction I, 0.075% polyethyleneimine was added. Following 30 minutes of stirring at 4° C., the mix was centrifuged for 30 minutes. To the supernatant (Fraction II), ammonium sulfate was added to a 48% saturation level over a 30-minute interval. The mixture was stirred for an additional 30 minutes at 4° C. and the precipitate collected by centrifugation.

The pellets containing the DnaC was resuspended in Buffer $B_{20}$ (50 mM Tris, pH, 7.5, 1 mM EDTA, 0.01% Brij, 10% glycerol, 5 mM DTT, 20 mM NaCl) and dialyzed overnight in the same buffer. Following dialysis, the sample was diluted with $B_0$ (no NaCl) to reach a conductivity less than or equal to $B_{20}$ and centrifuged to remove insoluble material. Sample was further diluted with $B_{20}$ to reach a protein concentration of ~10 mg/mL. The DnaC solution was loaded onto a DEAE column (Amersham, Fast Flow, 380 mL, 5 cm diameter) pre-equilibrated with Buffer $B_{20}$ at a flow rate of 1.25 mL/minute. The column flow through (Fraction IV) was collected. The flow through was loaded directly onto a heparin column (Amersham, 225 mL, 5 cm diameter). The column was washed with Buffer $B_{20}$ and DnaC was then eluted from the heparin column with a NaCl buffer gradient (20 mM-400 mM) at a flow rate of 3.5 mL/minute. The eluate was collected analyzed for protein concentration and by gel electrophoresis as described above. DnaC eluted as a single peak was pooled (Fraction V). Due to the level of purity and activity achieved, an amended purification scheme was adopted versus that utilized with previous preparations (which included hydroxylapetite and phosphocellulose chromatography).

The ECDA and ECRC Assays were used to analyze purification steps and final product following purification. Titration of the DnaC was carried out in the presence of excess levels of β, primosomal proteins, and Pol III*. The minimum amount of DnaC that allowed the ECRC reaction to reach a plateau was 0.15 μg, which corresponds to a concentration of 0.2 μM DnaC. Again, a higher concentration of DnaC was required in the origin reconstitution assay to suppress General Priming. A summary of the protein purification and activity analysis can be found in Table 21.

TABLE 21

DnaC Purification Summary

| | Total Volume mL | [Protein] mg/mL | Total Protein mg | S.A. U/mg | Total Activity U |
| --- | --- | --- | --- | --- | --- |
| Frac I | 890 | 26.83 | 23878.7 | — | — |
| Frac II (polyethylenimine) | 840 | 21.85 | 18354.0 | — | — |
| Frac III (48% AS cut) | 320 | 16.67 | 5334.4 | — | — |

TABLE 21-continued

DnaC Purification Summary

| | Total Volume mL | [Protein] mg/mL | Total Protein mg | S.A. U/mg | Total Activity U |
|---|---|---|---|---|---|
| Frac IV (DEAE FT)-Frac V (Heparin) | 250 | 0.64 | 161 | 2.95E+04 | 4.75E+06 |

Example 6

Conditions for *Y. pestis* High-Throughput Screening

A. Reconstitution of DNA Polymerase III Holoenzyme from *Y. pestis*.

With pol III core ($\alpha\epsilon\theta$), DnaX complex (DnaX complex; $\tau_3\delta\delta'\chi\psi$), beta ($\beta_2$), SSB and DnaG primase available in pure form, we reconstituted the *Y. pestis* replicative reaction by adapting the M13Gori assay used for the *E. coli* replication apparatus. This was enabled by our observation that the *Y. pestis* DnaG primase, like its *E. coli* counterpart, recognizes the bacteriophage G4 single-stranded origin and synthesizes an RNA primer. Reaction components, including *Y. pestis* pol III core, DnaX complex and β were diluted to the desired concentration in buffer and the reaction was initiated by adding 0.06 pmol M13Gori DNA (~500 pmol total nucleotide), DnaG primase, SSB, 10 mM magnesium acetate, 200 μM ATP, GTP, CTP and UTP, 48 μM dATP, dGTP, dCTP and 18 μM [$^3$H]dTTP (100 cpm/pmol). After a 5 min incubation 30° C., the reaction was terminated by acid precipitation of DNA onto glass microfiber filters. The amount of radiolabeled nucleotides incorporated into precipitated DNA was quantified by scintillation counting. One unit of activity is 1 pmol of total deoxyribonucleotide incorporated per minute at 30° C.

To achieve efficient DNA synthesis comparable to that observed with the *E. coli* holoenzyme, all three holoenzyme components (DnaX complex, $\beta_2$ and pol III) were required (FIG. 15) To determine the optimal concentration of the three components of the *Y. pestis* DNA pol III holoenzyme in reconstitution assays for screening of chemical compound libraries, each component was titrated individually in assays while holding the other two components at constant excess concentrations so only the component being titrated was limiting. The optimal concentrations for the three components in reconstitution assays are just above the linear response range (FIG. 15). Therefore, inhibition of any of the enzymes in the assay mix would be detected since they were at near-limiting concentrations.

B. Optimization of Conditions for Screening.

Using the purified components of the *Y. pestis* DNA replication system along with enzymatic activity data collected during purification, we have reconstituted a robust high-throughput screen in order to identify small molecule inhibitors of *Y. pestis* DNA replication. The assay readout is based on the fluorometric detection of dsDNA by the dsDNA-specific dye PicoGreen®. Optimal assay conditions have been determined by titration of essential buffer component including salt, pH, divalent cation ($Mg^{2+}$), reducing agents, detergents dNTPs, NTPs, template DNA and glycerol. Since compounds in our collection are dissolved in 100% dimethyl sulfoxide (DMSO), titrations of DMSO are necessary to determine the maximum volume fraction that can be added to the assay without impacting enzymatic activity. The susceptibility of the *Y. pestis* DNA replication system to DMSO also governs the maximum compound screening concentration. We have determined that the DMSO concentrations in our high-throughput screen can be as high as ~10% (v/v) without inhibiting the rate of the reaction.

All *Y. pestis* DNA polymerase subunits were titrated individually in the presence of an excess of the others in order to determine the linear activity ranges for each component in the HTS format. All assay substrates (ssDNA, dNTP's, rNTP's and buffer components) were also titrated to determine the concentrations that permitted optimal DNA replication without providing a large excess any of the essential assay components that could mask the action of inhibitors.

The HTS assays described in the following examples used similar methods as described herein for determining optimal assay conditions and proteins amounts.

Example 7

Conditions for *S. aureus* High-Throughput Screening

DNA replication activity is measured using the conversion of a primed, single-stranded DNA template (M13) to the duplex (ds) form. The assay readout is based on the fluorometric detection of dsDNA by the dsDNA-specific dye PicoGreen® (Molecular Probes) (Seville, et al. (1996). Fluorometric Assay for DNA Polymerases and Reverse Transcriptase. Biotechniques 21:664-672.) as shown in FIG. 17.

Optimal assay conditions were determined by titration of essential buffer components including NaCl, potassium acetate, potassium glutamate, divalent cation ($Mg^{2+}$), reducing agents (DTT and TCEP), detergents (NP-40), and glycerol, for example. Since screening is performed with compounds dissolved in 100% DMSO, titrations of DMSO were also performed in order to determine the maximum volume that can be added to the assay without impacting enzymatic activity. This data also governs the maximum compound screening concentration. All subunits were titrated individually in the presence of the others in order to determine the linear activity ranges for each component. PolC was titrated both in the presence and the absence of the beta subunit to determine the conditions for optimal beta dependence. Some assay substrates (dNTP's and ATP) were also titrated to identify optimal concentrations. The amount of primed single-stranded circular M13 DNA used as a substrate and PicoGreen® detection reagent added after completion of the reactions was taken from the amounts determined to yield the optimal signal-to-background in developing previous high-throughput screens (e.g. *E. coli* holoenzyme). Reactions kinetics were compared for singly and triply-primed single-stranded circular M13 DNA. Reaction kinetics at room temperature (~23° C.) in the presence of tolerable amounts of DMSO were also performed to determine the optimal reaction time for robotic automation of the screen. Since high throughput screening requires large batches of enzyme mix that will be used over several hours, enzyme stability studies were also conducted (inactivation kinetics at 23° C. and on ice). The enzyme mix was stable for at least five hours on ice.

The optimal conditions for measuring inhibition of the *S. aureus* DNA replication system were determined to occur in assay mixtures (25 μl) containing HEPES (pH 7.5), glycerol, Nonidet P-40, potassium glutamate, $MgCl_2$, TCEP (Tris(2-carboxyethyl)phoshine hydrochloride), DNA oligonucleotide triply-primed single-stranded circular M13 DNA, ATP, dGTP, dATP, dCTP, and dTTP. Reactions also contained *S. aureus* PolC protein, *S. aureus* Beta subunit, *S. aureus* Tau Complex and *S. aureus* SSB3 in amounts near-limiting according to titration of each component.

Example 8

Conditions for *S. pyogenes* High-Throughput Screening

Final *S. pyogenes* Holoezyme Priming and Elongation Assay Condition is for HTS.

The primed DNA substrate for this assay was prepared using M13Gori DNA, *E. coli* SSB and *E. coli* DnaG primase prior to performing the HTS since *S. pyogenes* DnaG primase was not included in this screen. Primed M13Gori DNA template (0.03 pmoles) was prepared in a buffer containing rNTPs, using *E. coli* SSB and *E. coli* DnaG primase in a reaction volume of 5 µL (Swart J R and Griep M A (1993) *J. Biol. Chem.* 268, 12970-12976).

The final HTS reactions were performed in a buffer containing 50 mM HEPES (pH 7.5), 7.5% glycerol, 0.02% NP40, 0-20 mM Mg(OAc)$_2$, 0-100 mM KAc, and 0.02 mM TCEP, 0-100 µM dNTPs, 0-100 µM rNTPs and primed template DNA. The final DMSO concentration was 0-20%. Reactions contained enzymes in amounts near-limiting according to titration of each component: *S. pyogenes* PolC polymerase, *S. pyogenes* tau-complex ($\tau_3\delta\delta'$), and *S. pyogenes* β.

Example 9

Conditions for *P. aeruginosa* High-Throughput Screening

DNA polymerase holoenzyme activity is measured by any using the conversion single-stranded circular DNA template (M13) to the duplex (ds) form. The assay readout is based on the fluorometric detection of dsDNA by the dsDNA-specific dye PicoGreen® (Molecular Probes, Seville, et al. (1996). Fluorometric Assay for DNA Polymerases and Reverse Transcriptase. Biotechniques 21:664-672.). Optimal assay conditions were determined by titration of essential buffer components including salt, pH, divalent cation (Mg$^{2+}$), reducing agents, detergents, and glycerol, for example. Since screening is performed with compounds dissolved in 100% DMSO, titrations of DMSO were also performed in order to determine the maximum volume that can be added to the assay without impacting enzymatic activity. This data also governs the maximum compound screening concentration. All subunits were titrated individually in the presence of an excess of the others in order to determine the linear activity ranges for each component. All assay substrates (ssDNA, dNTP's, ATP and rNTP's) were also be titrated to identify optimal concentrations.

Once the high-throughput assay was developed, it was assayed against at least part of a small molecule compound library, which contains about 250,000 discreet small molecules which have been purchased from a variety of suppliers and includes both combinatorial chemistry and historical compounds, as well as a natural product collection.

Minimal Holoenzyme Priming and Elongation Assay Conditions.

Reactions were performed in a buffer containing 50 mM HEPES (pH 7.5), 10% glycerol, 0.005% NP40, 0-100 mM Mg(OAc)$_2$, and 0.1 mM TCEP. The final DMSO concentration was usually 0-20%. The DNA substrate mix contained M13Gori ssDNA, 0-100 µM each dTTP, dATP, dCTP and dGTP, 0-100 µM each CTP, GTP, UTP, and ATP. Reactions contained enzymes in amounts near-limit according to the titration of each component: $\tau_3\delta\delta'$, DnaG, αε, β and SSB.

Holoenzyme Priming and Elongation Assay Conditions Including χψ.

Reactions were performed in a buffer containing 50 mM HEPES (pH 7.5), 10% glycerol, 0.005% NP40, 0-100 mM Mg(OAc)$_2$, and 0.1 mM TCEP. The final DMSO concentration was usually 0-20%. The DNA substrate mix contained M13Gori ssDNA, 0-100 µM each dTTP, dATP, dCTP and dGTP, 0-100 µM each CTP, GTP and UTP, and 0-100 µM ATP. Reactions contained enzymes in amounts near-limiting according to titration of each component: DnaG, $\tau_3\delta\delta'$, χψ, αε, β and SSB.

Example 10

Conditions for *B. subtilis* Replication Restart High-Throughput Screening

Figure 18:
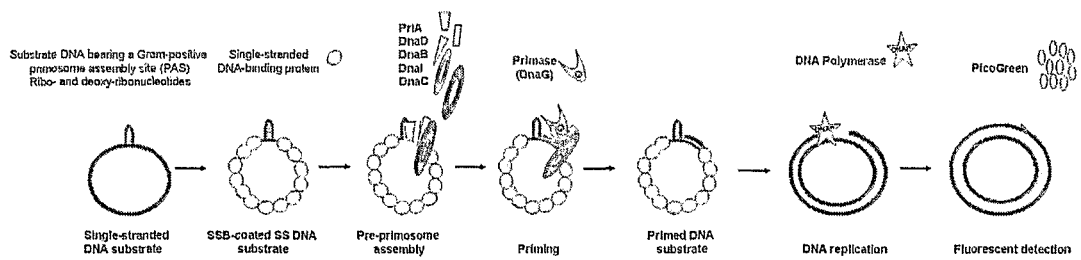
FIG. 18 shows a schematic of the *B. subtilis* replication restart high-throughput screening assay.

An enzyme mix containing *Bacillus subtilis* PriA, DnaD, DnaI, DnaC, DnaB, DnaG proteins and DNA polymerase was added to plates containing compound. A substrate mix containing template DNA, single-stranded DNA-binding protein, ribo- and deoxyribo-nucleotides was then added to initiate the reaction. After incubation at room temperature, reactions were stopped with EDTA PicoGreen® fluorescent dye was then added, and plates were read at an excitation wavelength of 485 nM and an emission wavelength of 538 nM. The assay is shown schematically in FIG. 18.

Buffer conditions: 40 mM potassium-Hepes, pH 7.6, 0-25 mM magnesium acetate, 0-500 mM potassium glutamate, 0-4% w/v polyethylene glycol MW 8000, 0-0.5% w/v Pluronic F68, 25 µM TCEP, 0-10% v/v dimethylsulfoxide. Substrate concentrations: 0-5 mM adenosine triphosphate; 0-100 µM cytosine triphosphate, uridine triphosphate, and guanosine triphosphate; 0-100 µM deoxyguanosine triphosphate, deoxyadenosine triphosphate, deoxythymidine triphosphate, and deoxycytidine triphosphate; 1.7 nM MP18-ssiA template DNA. Enzyme concentrations were used in amounts near-limiting according to titration of each compound: *Bacillus subtilis* SSB-1; *Bacillus subtilis* PriA monomer; *Bacillus subtilis* DnaD monomer; *Bacillus subtilis* DnaI monomer; *Bacillus subtilis* DnaC hexamer; *Bacillus subtilis* DnaB monomer; *Bacillus subtilis* DnaG monomer; *Bacillus subtilis* DnaE monomer.

Example 11

DNA Replication Initiation Activity for High-Throughput Screening

Figure 19:
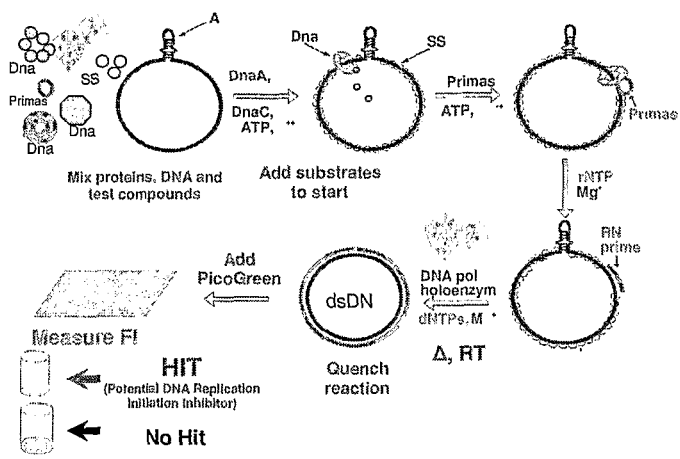
FIG. 19 shows a schematic of the DNA replication initiation activity for high-throughput screening.
Figure 20:
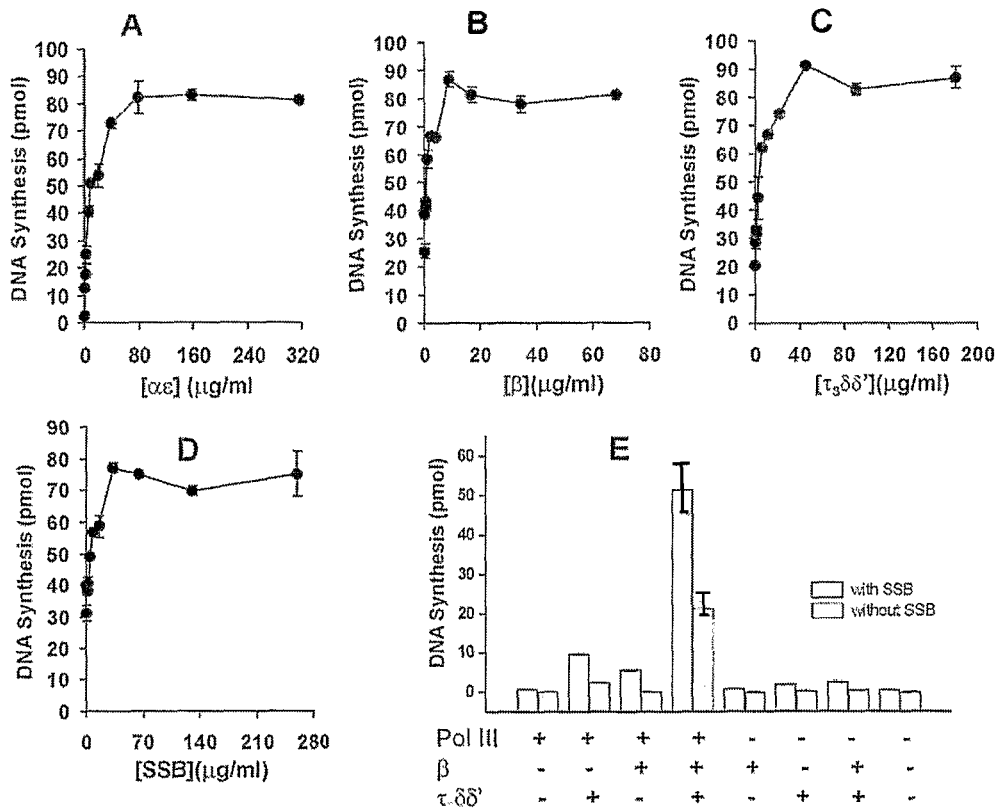
FIG. 20 shows reconstitution of *P. aeruginosa* Pol III holoenzyme. DNA synthesis was measured at 30° C. by the primer extension assay as described in Example 23. A, Titration of *P. aeruginosa* $\alpha\epsilon$ in the presence of saturating concentrations of *P. aeruginosa* $\beta$, $\tau_3\delta\delta'$ and SSB (17, 45, 26, µg/ml, respectively). B, Titration of *P. aeruginosa* $\beta$ in the presence of saturating concentrations of *P. aeruginosa* $\alpha\epsilon$, $\tau_3\delta\delta'$ and SSB (79, 45, 26, µg/ml, respectively). C, Titration of *P. aeruginosa* $\tau_3\delta\delta'$ in the presence of saturating concentrations of *P. aeruginosa* $\alpha\epsilon$, $\beta$ and SSB (79, 17, 26, µg/ml, respectively). D, Titration of *P. aeruginosa* SSB in the presence of saturating concentrations of *P. aeruginosa* $\alpha\epsilon$, $\beta$ and $\tau_3\delta\delta'$ (79, 9, 45, µg/ml, respectively). E, *P. aeruginosa* $\alpha\epsilon$, $\beta$, $\tau_3\delta\delta'$ and SSB were present at 20, 4, 22, 16, µg/ml, respectively, in combinations as indicated.

An enzyme mix containing *E. coli* SSB, DnaA, Beta, Primase, PolIII*, DnaC, and DnaB proteins was added to plates containing compound. A substrate nix containing template DNA, single-stranded DNA-binding protein, ribo- and deoxyribo-nucleotides was then added to initiate the reaction. After incubation at room temperature, reactions were stopped with EDTA PicoGreen® fluorescent dye was then added, and plates were read at an excitation wavelength of 485 nM and an emission wavelength of 538 nM. A schematic is shown in FIG. 19.

Buffer conditions: 40 mM potassium-Hepes, pH 7.5, 0-25 mM magnesium acetate, 0-100 mM potassium glutamate, 0-0.5% w/v Pluronic F68, 20 µM TCEP, 0.1 mg/ml BSA, 0-200 mM rNTPs. Substrate concentrations: 0-5 mM adenosine triphosphate; 0-100 µM cytosine triphosphate, uridine triphosphate, and guanosine triphosphate; 0-100 µM deoxyguanosine triphosphate, deoxyadenosine triphosphate, deoxythymidine triphosphate, and deoxycytidine triphosphate; 1.6 nM M13 A-site ss template DNA. Enzyme concentrations were used in amounts near-limiting according to titration of each component: DnaA; Beta; Primase; PolIII*; DnaB; and DnaC.

Example 12

Preparation of 5-Benzylidene-2-Thioxo-Thiazolidin-4-Ones

Knoevenagle condensation between rhodanine or thiazolidinedione was performed in a Personal Chemistry Emrys synthesizer:

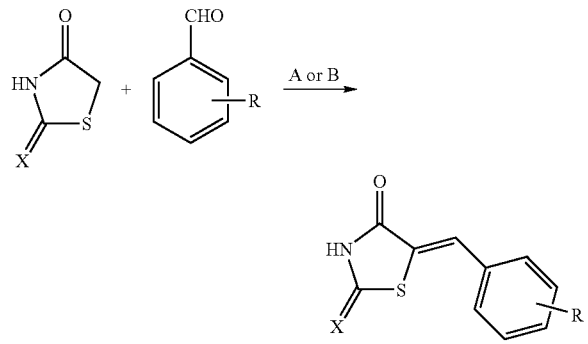

where X=S, O, or NH. In A, the reactant is rhodamine or thiazolidinedione, in the presence of KOAc ad AcOH/EtOH at 110° C., 30 min. μW. The yield was 30-80%. In B, the reactant is thiazolidindione, in the presence of EtOH, at 110° C., 30 min. μW. The yield was 30-80%.

Non-commercial aldehydes were prepared by nucleophilic aromatic substitution using a Personal Chemistry Emrys synthesizer:

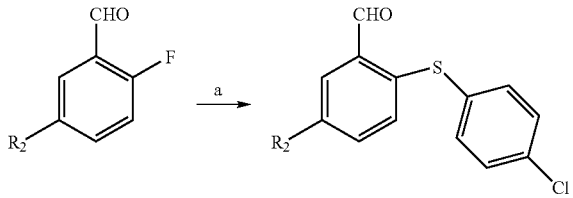

where R2 is $NO_2$, CH, or $CF_3$. The reaction conditions were 4-chlorothiophenol, KOH, DMF, 100° C., 25 min. μW. The yield was 25-50%.

Example 13

Construction of Overexpression Vectors Used in Example 18 to Example 22

The sequences of each gene were amplified by PCR from *P. aeruginosa* (PAO1) genomic DNA, and inserted in expression vectors. The PCR primers are shown in Table 24. With the exception of the SSB expression vector, all of the expression vectors utilized the semi-synthetic highly inducible and repressible pA1 promoter (Kim, D. R. and McHenry, C. S. (1996) "In Vivo Assembly of Overproduced DNA Polymerase III: Overproduction, Purification, and Characterization of the α, α-ε, and α-ε-θ Subunits" *J Biol Chem* 271: 20681-20689.). When necessary, *E. coli* low usage codons in the N-terminus of *P. aeruginosa* genes were altered to high usage codons, and non-AUG start codons were changed to AUG, to facilitate efficient translation in *E. coli*. A plasmid containing a pBR322 origin of replication, a gene expressing the lacIQ repressor protein, and the semi-synthetic promoter, pA1, which is repressed by lac, was used. The polylinker region was modified to introduce appropriate restriction sites to facilitate insertion of the desired *P. aeruginosa* genes. Details of each construct are included with the purification descriptions below. All purification steps were performed at 4° C. unless otherwise indicated.

TABLE 24

| Gene Amplified | Primer Direction | Sequence (5'-3') | Restriction Site(s) |
|---|---|---|---|
| dnaN | Sense | AGTCTTAATTAACATGCATTTCACCATTCAACGCGAA (SEQ ID NO: 2) | PacI |
| dnaN | Antisense | AGTCACTAGTTTATTAGAGGCGCATCGGCATGACGA (SEQ ID NO: 3) | SpeI |
| dnaE | Sense | AGTCTTAATTAAGCTTATGACCGTATCCTTCGTTCA (SEQ ID NO: 4) | PacI, HindIII |
| dnaE | Antisense | AGTCACTAGTTATTAACGATAATTGAGGAAGA (SEQ ID NO: 5) | SpeI |
| dnaQ | Sense | AGTCCATATGCGTAGCGTCGTACTGGATA (SEQ ID NO: 6) | NdeI |
| dnaQ | Antisense | AGTCGCTAGCAAGCTTATTCCTCCTCTACTATTCGCCGACCGGCGCCTCCA (SEQ ID NO: 7) | NheI, HindIII |

TABLE 24-continued

| Gene Amplified | Primer Direction | Sequence (5'-3') | Restriction Site(s) |
|---|---|---|---|
| dnaX | Sense | AGTCTTAATTAAGCTTATGAGCTATCAAGTTCTTGCGCGTAAAT (SEQ ID NO: 8) | PacI |
| dnaX | Antisense | AGTCACTAGTCTATCAGGCCTTGGCTTCCAAA (SEQ ID NO: 9) | SpeI |
| holA | Sense | AGTCTTAATTAAGCTAGCATGAAACTGACCCCGGCGCAACTCGCCAAGCACCT (SEQ ID NO: 10) | PacI |
| holA | Antisense | AGTCACTAGTATTAAGCTTTATCCTCCTCTATCAGGCTGCCGGCAGGCCGA (SEQ ID NO: 11) | SpeI |
| holB | Sense | AGTCCCATGGCTGATATCTATCCCT (SEQ ID NO: 12) | NcoI |
| holB | Antisense | AGTCACTAGTTATGCTAGCTTTCCTCCTCTACTAGCCCGGCCCGGGCAGGCTT (SEQ ID NO: 13) | SpeI |
| ssb | Sense | GATCCTGCAGGACGCGGTGCTGGTCCA (SEQ ID NO: 14) | PstI |
| ssb | Antisense | GTCAACTAGTCGCCTGAAAACGAAGA (SEQ ID NO: 15) | SpeI |

Example 14

Cell Growth and Lysis for Proteins Expressed in Example 18 to Example 22

Expression vectors were transfected into fermentation strains, AP1.L1 (F-, ompT hsdSB(rB-) (srl-recA)306::Tn10, T1 phage-resistant isolate) or MGC-1030 (mcrA mcrB λ-IN (rrnD-rrnE)1 lexA3 Δ(uvrD)::$T_{cr}$ Δ(o mpT)::Kmr). The time course of expression of recombinant proteins at 37° C. following IPTG induction was compared for the strains. The strain giving optimal protein expression was chosen for large scale growth. No deleterious effects on cell growth were observed with any of the clones following induction. Cells expressing P. aeruginosa recombinant proteins were grown in a 180 L fermentor at 37° C. (or 30° C. for αε expression) in F broth (yeast extract 14 g/L; tryptone 8 g/L; $K_2HPO_4$ 12 g/L; $KH_2PO_4$ 1.2 g/L; glucose 1%) plus 100 µg/ml ampicillin to an $OD_{600}$ of ~0.75. The pH was maintained at 7.2 by the addition of ammonium hydroxide. Additional ampicillin was added (200 µg/ml) and expression was induced (except SSB) by addition of IPTG to 1 mM. Cells were harvested at 3 hours post induction with simultaneous chilling to 14° C. in the harvest line. Cells were suspended in an equal volume of Tris-sucrose (50 mM Tris-HCl (pH 7.5), 10% sucrose) and frozen by liquid nitrogen. Cells constitutively expressing P. aeruginosa SSB were grown in the same conditions as described above, but without the IPTG induction step, and were harvested at stationary phase. Lysis was accomplished via creation of spheroplasts by treatment of cells with lysozyme in the presence of 10% sucrose (Cull, M. and McHenry, C. (1990) "Preparation of Extracts from Prokaryotes" Methods Enzymol. 12: 147-154). The presence of 18 mM spermidine kept the nucleoid condensed within partially disrupted cells and displaced DNA binding proteins. Centrifugation (16,000×g, 1 h, 4° C.) resulted in a DNA-free supernatant (Fraction I).

Example 15

Activity Assays for Example 18 to Example 22

Units are defined as pmol total nucleotide incorporated per minute at 30° C. DNA synthesis activity was monitored during purification of αε, β and $\tau_3\delta\delta'$ using a reconstituted E. coli DNA Pol III holoenzyme assay (Olson, et al., (1995) "DnaX-Complex of Escherichia coli DNA Polymerase III Holoenzyme: The χψ Complex Functions by Increasing the Affinity of τ and γ for δ-δ' to a Physiologically Relevant Range" J Biol Chem 270: 29570-29577). M13Gori singlestranded phage DNA was used as template DNA, and was purified as described (Johanson, et al. (1986) "Chemical Characterization and Purification of the β Subunit of the DNA Polymerase III Holoenzyme from an Overproducing Strain" J Biol Chem 261: 11460-11465). As purified P. aeruginosa subunits became available, these were substituted for their E. coli counterparts as indicated. Enzymes were diluted in EDB (50 mM HEPES (pH 7.5), 20% glycerol, 0.02% Nonidet P40, 0.2 mg/ml bovine serum albumin). Primase mix containing singlestranded DNA template, nucleotides, DnaG and SSB was prepared first by incubating the following components for 20 minutes at 30° C.: 50 mM HEPES, (pH 7.5), 20% glycerol, 0.02% Nonidet P40, 0.2 mg/ml bovine serum albumin, 13 mM Mg(OAc)$_2$, 5 mM DTT, 0.27 mM each of rGTP, rUTP, rATP and rCTP, 64 µM each of dATP, dCTP, dGTP, 24 µM dTTP, ~60 cpm/pmol [$^3$H]-dTTP, 2.4 nM M13 Gori ssDNA circles, 42 µg/ml E. coli SSB, and 1.0 µg/ml E. coli DnaG primase. Primase mix was then aliquoted and frozen for use in subsequent assays. Holoenzyme reactions were reconstituted by incubating primase mix with E. coli Pol III (αεθ), $\tau_3\delta\delta'\chi\psi$, and β in a 25 µL reaction volume for 5 min at 30° C. Buffer conditions were comparable to the priming reaction except that each of the components was 25% more dilute. Incorporation of [$^3$H]-dTTP was measured by TCA precipitation on GF-C filters (McHenry, C. S, and Crow, W. (1979) "DNA Polymerase III of Escherichia coli: Purification and Identification of Subunits" *J Biol Chem* 254: 1748-1753). For the component being assayed, the corresponding *E. coli* subunit was omitted and other components were used at saturating concentrations. Enzyme titrations were performed to determine the linear range of the assay, and specific activities were calculated using points in the linear range. In some cases where it was not necessary to determine absolute incorporation rates, formation of dsDNA was measured by fluorescent detection of dsDNA using PicoGreen® (Molecular Probes) (Seville, et al. (1996) "Fluorometric Assay for DNA Polymerases and Reverse Transcriptase" Biotechniques 21: 664-672). For these assays 100 RFU approximately equals 15 pmol nucleotide incorporated. In this case, 25 µL reactions were performed in opaque 96-well plates and stopped with 25 µL of 100 mM EDTA. PicoGreen® was diluted 1:150 in 10 mM TrisHCl (pH 7.5); 150 µL was added to each well. Fluorescence emission at 538 nm was measured in a GeminiEM platereader (Molecular Dynamics) exciting at 485 nm. DNA synthesis was measured as relative fluorescent units (RFU). Primer extension assays were performed on single-stranded DNA templates that had been primed with a synthetic DNA oligonucleotide, 5'-AGGCTGGCTGACCTTCATCAAGAGTAATCT-3' (SEQ ID NO: 16). The oligonucleotide primer was annealed to M13Gori single-stranded DNA circles by mixing a 1:1 molar ratio of primer to template in the presence of 0.1 M KCl and 50 nM HEPES (pH 7.5), heating to 95° C. for 4 minutes and slowly cooling to room temperature. Primer extension reactions were performed in a 25 µL reaction volume for 10 minutes in 50 mM HEPES (pH 7.5), 20% glycerol, 0.02% Nonidet P40, 0.2 mg/ml bovine serum albumin, 10 mM Mg(OAc)$_2$, 5 nM DTT, 0.2 mM rATP, 48 µM each of dATP, dCTP, dGTP, 24 µM dTTP, ~60 cpm/pmol [$^3$H]-dTTP, 2 nM primed template DNA and enzyme components as indicated. Acid precipitable $^3$H was measured to determine pmol of DNA incorporated. Reaction temperatures are indicated in the figure legends.

Example 16

Estimates of *Pseudomonas aeruginosa* Protein Complex Concentrations

We assumed that the stoichiometry of *P. aeruginosa* protein assemblies were the same as their *E. coli* counterparts: αε, β$_2$, τ$_3$δδ' and SSB$_4$. Protein concentrations were determined using the Coomassie Plus Protein Assay (Pierce) and a bovine serum albumin standard. Gel electrophoresis and Protein Analysis—SDS-PAGE analysis of αε, τ$_3$δδ' and β samples was performed using 4-12% acrylamide gradient pre-cast gels (Novex NuPAGE®; Invitrogen) using MOPS running buffer (Invitrogen). Benchmark unstained protein molecular weight markers were used (Invitrogen). SDS-PAGE analysis of SSB samples was performed on 10-20% acrylamide Novex Tris-glycine pre-case gels (Invitrogen) using Tris-glycine running buffer (Invitrogen). Gels were stained with SimplyBlue SafeStain (Invitrogen) or with Coomassie Brilliant Blue. Comparable results were obtained with either staining method. Densitometry was performed using a Kodak Image Station 440CF. Peptide mass fingerprinting for protein identification was performed by Amprox, Inc. (Carlsbad, Calif.). N-terminal sequencing was performed at the Molecular Resource Center (National Jewish Medical Center) using Edman degradation.

Example 17

Buffers Used in Purifications for Example 18 to Example 22

Subscripts indicate mM concentration of NaCl in each buffer (i.e., A$_{40}$ is A$_0$ and 40 mM NaCl). BW is 20% glycerol, 50 mM Tris-HCl (pH 8.0), 1 mM EDTA, 1 mM EGTA, 0.1 M KOAc (pH 8.0), 0.19 g/ml ammonium sulfate (i.e., 34% ammonium sulfate saturation). A$_0$ is 20 mM Tris-HCl, (pH 8.0), 10% glycerol, 0.1 mM EDTA, 0.1 mM EGTA, and 0.5 mM DTT. B$_0$ is 50 mM Tris-HCl, (pH 7.5), 10% glycerol, 0.5 mM EDTA, and 1 mM DTT. C is 50 mM imidazole, (pH 6.8), 10% glycerol, 50 mM NaCl, and 0.5 mM DTT. D is 25 mM HEPES (pH 7.5), 50 mM KCl, 10% glycerol, 0.1 mM EDTA, and 0.5 mM DTT. E$_0$ is 25 mM Tris-HCl (pH 7.5), 10% glycerol, 0.1 mM EDTA, and 0.5 mM DTT. F is 50 mM Tris-HCl (pH 7.5), 10% glycerol, 5 mM DTT, and 0.5 mM EDTA. G$_{100}$ is 25 mM Tris-HCl (pH 8.0), 10% glycerol, 0.2 mM EDTA, 1 mM DTT, and 100 mM NaCl.

Example 18

Expression and Purification of αε

The vector pA1-CB-NdeI and the dnaQ PCR fragment were cut with NdeI and NheI, and the dnaQ PCR fragment was inserted, resulting in the plasmid pA1-PA-dnaQ. The vector pA1-CB-NcoI and the dnaE PCR fragment were cut with SpeI and PacI, and the dnaE PCR fragment was inserted, resulting in the plasmid pA1-PA-dnaE. An operon expressing dnaQ and dnaE was constructed by digesting pA1-PA-dnaE1 with HindIII and SpeI. The fragment containing the dnaE gene (approximately 3.5 kb) was inserted into pA1-PA-dnaQ that had been digested with the same two restriction enzymes, resulting in the plasmid pA1-PA-core1, containing the dnaQ gene upstream of the dnaE gene. 2045 g of cells were grown, harvested and lysed as described above. Ammonium sulfate (0.21 g to each initial ml of Fraction I; 37% saturation) was added slowly to Fraction I. The precipitate was collected by centrifugation (16,000×g, 30 min, 4° C.). The pellet was resuspended using a dounce homogenizer in 0.125× Fraction I volume of BW buffer. The remaining precipitate was collected by centrifugation (16,000×g, 45 min, 4° C.). The pellet was resuspended in buffer A$_0$ and diluted to match the conductivity of buffer A$_{40}$, forming Fraction II. Fraction II was applied to a 5 cm×7 cm MacroPrep High S (Biorad) column connected in series with a 5 cm×35 cm DEAE Sepharose Fast Flow (Amersham) column equilibrated in A$_{20}$. The S column served to remove the endogenous *E. Coli* Pol III and RNA polymerase as well as a number of other major contaminating proteins, while allowing the majority of the *P. aeruginosa* αε to pass through. The columns were washed with 300 ml of buffer A$_{20}$. Then the S column was disconnected, and the DEAE column was washed with 3200 ml of buffer A$_{40}$ followed by a 6.4 liter linear gradient from 40 to 400 mM NaCl. The *P. aeruginosa* αε complex eluted at approximately 150 mM NaCl, and fractions with the highest specific activity were pooled to form Fraction III. Excess ε subunit eluted early in the gradient, while the αε complex eluted later. Fraction III was precipitated with 50% ammonium sulfate. Fraction III pellet was resuspended in buffer A$_0$, and was diluted to match the conductivity of buffer A$_{30}$ and applied to a 2.5 cm×41 cm Heparin Sepharose Fast Flow (Amersham) column equilibrated in buffer A$_{30}$. The column was washed with ~17 column volumes of buffer A$_{30}$, followed by a 2 liter linear gradient from 30-500 mM NaCl. αε eluted at approximately 100 mM NaCl, and fractions with the highest specific activity were pooled to form Fraction IV. SDS-PAGE analysis of the purification steps showed that Fraction IV was at least 95% pure. The purified polymerase complex exhibited an α:ε subunit stoichiometry of approximately 1:1 based on densitometric scans of gels of Fraction IV. Purified αε eluted as a single peak when subjected to high resolution gel filtration with Superdex-200 resin. A summary is shown in the following Table:

TABLE 25

Summary Data for Purification of DNA Polymerase III Holoenzyme Components

| Protein | Fraction | Total Activity U × $10^{-8}$ | Total Volume (ml) | Total Protein (mg) | Specific Activity U/mg × $10_{-5}$ |
|---|---|---|---|---|---|
| α/ε | Fr II (34% AS) | 10 | 2400 | 6240 | 1.7 |
|  | Fr III DEAE Pool | 3.3 | 820 | 656 | 5.0 |
|  | Fr IV Heparin Pool | 5.6 | 105 | 135 | 41 |
| β | Fr II (35-60% AS) | 130 | 1000 | 4430 | 29 |
|  | Fr III DEAE Pool | 170 | 228 | 2054 | 85 |
|  | Fr IV HAP Pool (dialyzed) | 100 | 253 | 1075 | 97 |
| τ3δδ' | Fr II (35% AS) | 13 | 1395 | 3125 | 4.1 |
|  | Fr III Heparin Pool* | 9.6 | 950 | 1074 | 9.0 |
|  | Fr IV DEAE Pool | 8.4 | 205 | 920 | 9.2 |
| SSB | Fr II (25% AS) |  | 1835 | 2881 |  |
|  | Fr III Q Pool |  | 385 | 2503 |  |

*FrIIIA, FrIIIB and FrIIIC from the three Heparin chromatography batches were pooled to form FrIII.

In initial trial purifications, a gap-filling assay was used to monitor non-processive polymerase activity. Both α and ε expressed well with this system, comprising greater than 25% of the total cell protein. When cells were grown and induced at 37° C., α was found largely in inclusion bodies. When growth and induction were performed at 30° C., the yield of soluble α increased approximately 3-fold. Preliminary studies indicated that ε had exonuclease activity as expected. The ε subunit from *E. coli* is insoluble when overproduced alone; upon co-expression with α it forms a 1:1 complex that is soluble, but excess ε is in inclusion bodies. By contrast, co-expression of the ε- and α-subunits from *P. aeruginosa* resulted in a large excess of soluble ε. Excess ε separated from the αε complex during purification. Initial purification attempts were complicated by the fact that αε exhibits a narrow pH tolerance, with optimal stability retained only at pH 7.5 or above. Exposure to pH 7.0 or below resulted in rapid loss of activity. In addition, we found that stability was markedly enhanced when EDTA or EGTA was included in the storage buffer. Therefore the purification protocol described here was performed entirely at pH 8.0 in the presence of EDTA and EGTA. As has been seen previously for *E. coli* Pol III. *P. aeruginosa* αε was relatively insoluble in ammonium sulfate.

Example 19

Expression and Purification of β

The vector pA1-CB-NdeI and the dnaN PCR fragment were cut with SpeI and PacI, and the dnaN PCR fragment was inserted, resulting in the plasmid pA1-PA-dnaN. 40 g of cells were grown, harvested and lysed as described above. Ammonium sulfate (0.197 g to each initial ml of Fraction I; 35% saturation) was added slowly to Fraction I, and the precipitate removed by centrifugation (16,000×g, 60 min, 4° C.). Ammonium sulfate was added to the resulting supernatant (0.153 g to each ml of 35% supernatant; 60% saturation) and the precipitate collected by centrifugation (16,000×g, 60 min, 4° C.). The pellet containing the 35-60% ammonium sulfate fi-action was resuspended in buffer $B_0$ diluted to match the conductivity of buffer $B_{50}$, forming Fraction II. Fraction II was applied a 2.5 cm×40 cm DEAE Sepharose Fast Flow column (Amersham) equilibrated in buffer $B_{50}$. The column was washed with 400 ml of buffer $B_{50}$, followed by a 2 liter linear gradient from 50 to 600 mM NaCl gradient. β subunit eluted at approximately 75 mM NaCl, and fractions with the highest specific activity were pooled to form Fraction III. Fraction III was applied to a 5×20 cm hydroxyapatite column (Hypatite C, Clarkson Chemical Company) equilibrated in buffer C. The column was washed with 800 ml buffer C, followed by a 4 liter linear gradient from 0-200 mM potassium phosphate. The β subunit eluted at approximately 100 mM phosphate, and fractions with the highest specific activity were pooled to form Fraction IV. Fraction IV was dialyzed into buffer D for storage. SDS-PAGE analysis of the purification steps showed that β was purified to near homogeneity.

Example 20

Expression and Purification of $\tau_3\delta\delta'$

The vector pA1-CB-NcoI and the holB PCR fragment were cut with SpeI and NcoI, and the holB PCR fragment was inserted, resulting in the plasmid pA1-PA-holB. The vector pA1-CB-NcoI and the holA PCR fragment were cut with SpeI and PacI, and the holA PCR fragment was inserted, resulting in the plasmid pA1-PA-holA. The vector pA1-CB-NcoI and the dnaX PCR fragment were cut with SpeI and PacI, and the dnaX PCR fragment was inserted, resulting in the plasmid pA1-PA-dnaX. An operon expressing holB, and holA was constructed by digesting both pA1-PA-holA and pA1-PA-holB with NheI and SpeI. The fragment from pA1-PA-holA containing holA (approximately 1 kb) was then inserted into the digested pA1-PA-holB, resulting in the plasmid pA1-PA-holBA. A three gene operon was then constructed by digesting both pA1-PA-dnaX and pA1-PA-holBA with HindIII and SpeI. The fragment of pA1-PA-dnaX containing the dnaX gene (approximately 2 kb) was then inserted into the digested pA1-PA-holBA plasmid, resulting in the plasmid pA1-PA-BAX, with the holB gene upstream, followed by holA and dnaX, respectively. 400 g of cells were grown, harvested and lysed as described above. We purified a complex of the essential components of the DnaX complex comprising τ, δ, and δ'. Unlike DnaX complex from *E. coli*, this complex lacks the χ and ψ subunits. Ammonium sulfate (0.197 g to each initial ml of Fraction I; 35% saturation) was added slowly to Fraction I, and the precipitate collected by centrifugation (16,000×g, 30 min, 4° C.). The ammonium sulfate pellet was resuspended in buffer $E_0$ and diluted to match the conductivity of buffer $E_{20}$, forming Fraction II. Fraction II was divided into three parts and one third was applied to 20 ml MacroPrep High S (Biorad; 4×5 ml S Econo-Pac cartridges) connected in series to a 5 cm×10.2 cm Heparin Sepharose 6 Fast Flow column (Amersham) equilibrated in buffer $E_{20}$. The columns were washed with 600 ml of buffer $E_{20}$. The High S cartridges were removed and the Heparin column was washed with another 200 ml of buffer $E_{20}$, followed by a 2 liter linear gradient from 20 to 1000 mM NaCl. $\tau_3\delta\delta'$ eluted at approximately 150 mM NaCl, and fractions with the highest specific activity were pooled to form Fraction IIIA. The columns were then regenerated as per manufacturer's recommendations, and additional Fraction II was purified, creating Fractions IIIB and IIIC. Ammonium sulfate (0.366 g/ml Fraction III; 60% saturation) was added slowly to each batch of Fraction III and the precipitate collected by centrifugation (16,000×g, 30 min, 4° C.). Fraction III pellets were resuspended in buffer Fo and diluted to match the conductivity of buffer $F_{20}$ and Fractions IIIA, IIIB and IIIC were pooled and applied to a 2.5×20 cm DEAE Fast Flow column (Amersham) equilibrated in buffer $F_{20}$. The column was washed with 300 ml of buffer $F_{20}$, followed by a 1000 ml linear gradient from 20-500 mM NaCl. $\tau_3\delta\delta'$ complex eluted at approximately 250 mM NaCl, and fractions with the highest specific activity were pooled to form Fraction IV. We were surprised to find that the $\tau$ subunit migrated with an apparent molecular weight that was almost 20 kD higher than the expected 73 kD. The identity of the protein was confirmed by N-terminal sequencing. Tryptic digest followed by mass spectrometry detected the expected C-terminus of the protein and no additional peptides besides those encoded by the dnaX gene. Therefore, the anomalous migration of the $\tau$ subunit does not appear to be the result of translational readthrough or frameshifting. The most likely explanation for the anomalous migration is that the protein has an unusually low isoelectric point (predicted pI≈4.6) resulting in reduced SDS binding under the pH conditions used in standard electrophoresis. The band migrated with a progressively lower apparent molecular mass as the pH of the gel running buffer was lowered. A protein of about 45 kD co-purified with $\tau_3\delta\delta'$ activity. N-terminal sequencing showed that this protein was an N-terminal fragment of $\tau$. Relative to the amount of full length DnaX, the amount of the N-terminal fragment was between 10-30% in different preparations. In *E. Coli*, the $\gamma$ subunit is formed by translational frameshifting, creating an N-terminal fragment of $\tau$ (Tsuchihashi, Z. and Kornberg, A. (1990) "Translational Frameshifting Generates the $\gamma$ Subunit of DNA Polymerase III Holoenzyme" Proc Natl Acad Sci USA 87: 2516-2520.). The *P. aeruginosa* dnaX gene lacks the consensus sequence thought to be responsible for the frameshift. The shorter protein is likely a proteolytic breakdown product of $\tau$.

Example 21

Expression and Purification of SSB

The vector pBlueScript II KS (Stratagene) and the ssb PCR fragment were digested with SpeI and PstI, and the ssb PCR fragment was inserted, resulting in the plasmid pBlue-lac-Pa-ssb. Unlike the vectors used for expression of the genes described above, this vector gave constitutive expression of the recombinant gene. 1000 g of cells were grown, harvested and lysed as described above. Ammonium sulfate (0.136 g to each initial ml of Fraction I; 25% saturation) was added slowly to Fraction I and the precipitate collected by centrifugation (16,000×g, 30 min, 4° C.). The ammonium sulfate pellets were resuspended in buffer $G_{100}$ and diluted in buffer $G_0$ to match the conductivity of buffer $G_{100}$, forming Fraction II. Insoluble material was removed by centrifugation and Fraction II was applied to a 5×10 cm column packed with Q Sepharose Fast Flow (Amersham) and equilibrated in buffer $G_{100}$. The column was washed with 1000 ml of buffer $G_{100}$, followed by a 2 liter linear gradient from 100 to 1000 mM NaCl. *P. aeruginosa* SSB eluted at approximately 320 mM NaCl, and fractions were pooled based on gel analysis of purity to form Fraction III. The identity of the purified protein was verified by peptide mass fingerprinting.

Initial attempts to express *P. aeruginosa* SSB using an inducible pA1 promoter resulted in very low expression levels. An excellent over-expression of *P. aeruginosa* SSB using a constitutive expression vector that included substantial upstream and downstream genomic sequence flanking the ssb gene has been reported. Reasoning that the genomic sequence context may enhance transcription or translation and/or stabilize the mRNA transcript, we expressed *P. aeruginosa* SSB using a construct that included 178 nucleotides of upstream genomic sequence and 97 nucleotides of downstream genomic sequence. This system produced *P. aeruginosa* SSB constitutively at a level of about 10% of total cellular protein.

Example 22

Other Proteins

*E. coli* holoenzyme components were purified as described: Pol III (Kim and McHenry, 1996), $\tau_3\delta\delta'\chi\psi$ (Pritchard, et al. (1996) "In Vivo Assembly of the $\tau$-Complex of the DNA Polymerase III Holoenzyme Expressed from a Five-Gene Artificial Operon: Cleavage of the $\tau$-Complex to Form a Mixed $\gamma$-$\tau$-Complex by the OmpT Protease" *J Biol Chem* 271: 10291-10298), $\tau$ (Dallmann et al. (1995) "DnaX Complex of *Escherichia coli* DNA Polymerase III Holoenzyme: Physical Characterization of the DnaX Subunits and Complexes" *J Biol Chem* 270: 29563-29569.), $\delta$ (Carter, et al. (1992) "Molecular Cloning Sequencing and Overexpression of the Structural Gene Encoding the $\delta$ Subunit of *Escherichia coli* DNA Polymerase III Holoenzyme" J Bacteriol 174: 7013-7025), $\delta'$ (Carter, et al. (1993) "Identification, Isolation, and Characterization of the Structural Gene Encoding the $\delta'$ Subunit of *Escherichia coli* DNA Polymerase III Holoenzyme" *J Bacteriol* 175: 3812-3822), $\beta$ (Johanson et al., (1986) "Chemical characterization and purification of the $\beta$ subunit of the DNA polymerase III holoenzyme from an overproducing strain" *J Biol Chem* 261:11460-11465), and $\chi\psi$ (Olson et al, (1995) "DnaX complex of *Escherichia coli* DNA polymerase III holoenzyme: The $\chi\psi$ complex functions by increasing the affinity of $\tau$ and $\gamma$ for $\delta$-$\delta'$ to a physiologically relevant range" *J Biol Chem* 270:29570-29577). $\tau_3\delta\delta'$ was reconstituted by mixing individual components at the specified molar ratio.

Example 23

Reconstitution of DNA Polymerase Holoenzyme Activity $\alpha\epsilon$, $\beta$, $\tau_3\delta\delta'$ and SSB were tested for their ability to reconstitute *P. aeruginosa* Pol III holoenzyme activity (FIG. 20A-D). The 8623-nt single-stranded circular DNA template was primed by a single DNA oligonucleotide primer. As expected, nucleotide incorporation was completely dependent on $\alpha\epsilon$; under the conditions shown there was a 2- to 5-fold stimulation by each of the other components. We found that decreasing the $\alpha\epsilon$ concentration gave a concomitant increase in the dependence on both $\beta$ and $\tau_3\delta\delta'$. Using a sub-saturating amount of $\alpha\epsilon$, the activity of each component was then measured alone and in combination with the other components (FIG. 20E). In the absence of SSB, only the combined presence of $\alpha\epsilon$, $\beta$, and $\tau_3\delta\delta$ was sufficient to produce a signal above background. In the presence of SSB, modest levels of synthesis by subassemblies was observed ($\alpha\epsilon+\beta$ or $\alpha\epsilon+\tau^3\delta\delta'$), but a synergistic increase in synthesis was evident when all components were combined. Addition of both $\tau_3\delta\delta'$ and $\beta$ to $\alpha\epsilon$ gave a 70-fold increase in activity over $\alpha\epsilon$ alone, consistent with the reconstitution of a highly processive holoenzyme. SSB only stimulated the reconstituted holoenzyme elongation reaction by about 2-fold. Changing the order of addition of SSB did not change the observed activity.

Example 24

$\alpha$, $\epsilon$, $\tau$, $\delta$ and $\delta'$ Form a Functional Complex that Co-Purifies on Gel Filtration We purified a subassembly of the *P. aeruginosa* Pol III holoenzyme that contained $\alpha$, $\epsilon$, $\tau$, $\delta$ and $\delta'$ by co-lysing cells expressing αε with cells expressing $\tau_3\delta\delta'$. Activity was assessed in the reconstitution assay using purified P. aeruginosa β. The activity was purified by ammonium sulfate fractionation followed by Q Sepharose chromatography and gel filtration. The complex had an apparent molecular mass of 500-600 kD based on gel filtration standards. The fact that these subunits formed a complex that was active in DNA synthesis and co-purified by gel filtration supports the functional relevance of the reconstituted system we have developed thus far. This complex was similar to the Pol III* complex that has been reported from E. coli except that it lacked χ and ψ.

Example 25

Figure 21:
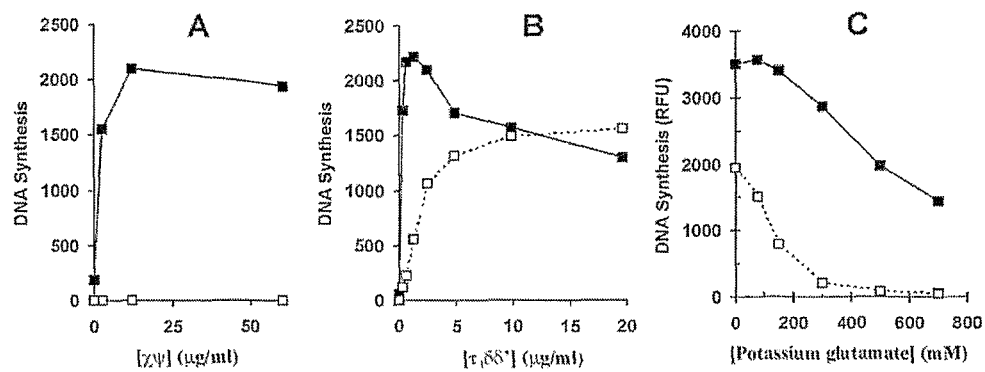
FIG. 21 shows stimulation of the *P. aeruginosa* reconstituted holoenzyme reaction by *E. coli* $\chi\psi$. DNA synthesis was measured by the holoenzyme reconstitution assay using PicoGreen® detection of dsDNA as described in Example 25. Reactions were performed for 5 minutes at 22° C. using templates pre-primed with *E. coli* DnaG primase and SSB. Since these reactions were performed using different priming conditions and reaction temperatures than used in the previous studies, the reaction components were re-titrated to determine the amounts needed to achieve saturation. Reaction buffers contained no added monovalent salt except as indicated in part C. A, (filled squares) Titration of *E. coli* $\chi\psi$ in the presence of saturating amounts of *P. aeruginosa* Pol $\alpha\epsilon$ and $\beta$ (14 and 9 µg/ml, respectively) and a limiting concentration of *P. aeruginosa* $\tau_3\delta\delta'$ (1 µg/ml). (hollow squares) Titration of *E. coli* $\chi\psi$ alone. B, Titration of *P. aeruginosa* $\tau_3\delta\delta'$ in the presence of saturating amounts of *P. aeruginosa* Pol $\alpha\epsilon$ and $\beta$ (14 and 9 µg/ml, respectively) with (filled squares) or without (hollow squares) a saturating amount of *E. coli* $\chi\psi$ (12 µg/ml). C, Titration of potassium glutamate in the presence of saturating amounts of *P. aeruginosa* Pol $\alpha\epsilon$ and $\beta$ (14 and 9 µg/ml, respectively) and a near-saturating level of $\tau_3\delta\delta'$ (3 µg/ml)

E. coli χψ Stimulates DNA Synthesis by Minimal Reconstituted P. aeruginosa Replicase In E. coli, the tightly associated χ and ψ subunits of the DnaX complex play a role into supporting DNA synthesis, especially at high salt and in increasing the affinity of the DnaX complex subunits for one another. In P. aeruginosa, ψ was not apparent by sequence comparison, and therefore these studies were performed with a subassembly of only the essential τ, δ and δ' subunits. In reconstituted P. aeruginosa Pol III holoenzyme elongation reactions in the presence of limiting $\tau_3\delta\delta'$ (~10% of the amount required for saturation) E. coli χψ was found to stimulate the reaction 10-fold (FIG. 21A). This suggested that E. coli χψ, though quite divergent, binds to P. aeruginosa $\tau_3\delta\delta'$ and stimulates the replicative reaction. A large molar excess of E. coli χψ was required to saturate the stimulatory response (ca. 100-fold), suggesting that the binding interaction was weak. Stimulation by E. coli χψ was most evident at sub-saturating concentrations of $\tau_3\delta\delta'$. With addition of high concentrations of $\tau_3\delta\delta'$, the same levels of DNA synthesis could be obtained as in the χψ-stimulated reactions (FIG. 21B). However, even when near saturating levels of $\tau_3\delta\delta'$ were used, the effect of E. coli χψ could be readily observed at elevated salt concentrations where χψ conferred an increase in salt tolerance (FIG. 21C).

Example 26

Interchange of E. coli and P. aeruginosa Pol III Holoenzyme Subunits

We had observed during purification that each of the P. aeruginosa subunits could substitute, at least to a degree, for its E. coli counterpart in an E. coli holoenzyme reconstitution assay. We wished to assess at a quantitative level the ability of each subunit to act as a surrogate in the non-cognate Pol III holoenzyme. In the E. coli holoenzyme assay, P. aeruginosa αε substituted on an equivalent molar basis for E. coli Pol III (FIG. 22A). In contrast, when β subunits were compared in the E. coli holoenzyme assay, 10-fold more P. aeruginosa β was required to achieve activity levels comparable to that exhibited by E. coli β, suggesting an impaired binding interaction between P. aeruginosa β and other E. coli holoenzyme components (FIG. 22B). Identical results were obtained for the P. aeruginosa αε and β titrations when χψ was omitted from the reaction. In the E. coli holoenzyme assay, 10-fold more P. aeruginosa $\tau_3\delta\delta'$ was required to achieve the same levels of synthesis relative to E. coli $\tau_3\delta\delta'$. However, P. aeruginosa $\tau_3\delta\delta'$ could be rescued by addition of E. coli χψ such that it functioned as well as the E. coli counterparts (FIG. 22C). In the P. aeruginosa holoenzyme assay, in the absence of additional components, we obtained the unexpected result that E. coli Pol III functions better than P. aeruginosa αε. Equivalent levels of synthesis are obtained at nearly 10-fold lower concentrations of E. coli Pol III (FIG. 23A). This difference is largely suppressed by addition of E. coli χψ that results in stimulation of P. aeruginosa αε about 5-fold with negligible affect on E. coli Pol III. Thus, as observed in the experiments reported in FIGS. 21 and 22, the P. aeruginosa proteins are stimulated by E. coli χψ more than the cognate system! This observation surprised us at first since it appeared to contradict the results reported in FIG. 21A where P. aeruginosa and E. coli polymerases were interchangeable in the E. coli system. We explored this observation further using various combinations of P. aeruginosa and E. coli components and found that the critical variable was DnaX complex. Replacement of P. aeruginosa $\tau_3\delta\delta'$ with E. coli DnaX complex in the P. aeruginosa holoenzyme reconstitution assay yielded a system where E. coli and P. aeruginosa polymerases gave equivalent synthesis (FIG. 23A). This and the results shown in FIG. 22A argue that the difference observed is not due to contamination of P. aeruginosa αε with inactive enzyme. When β subunits were compared in the P. aeruginosa holoenzyme assay, E. coli β substituted on an equimolar basis with P. aeruginosa β (FIG. 23B), with χψ giving a slight stimulation of both E. coli or P. aeruginosa β activity. Thus, the 10-fold deficit observed for P. aeruginosa β is eliminated by using it in a cognate system. This result indicates that the deficiency observed in the E. coli holoenzyme reconstituted assay was not due to part of the P. aeruginosa β being inactive. As observed in the E. coli holoenzyme reconstitution assay (FIG. 22C), P. aeruginosa $\tau_3\delta\delta'$ exhibited 10-fold lower activity than its E. coli counterpart (FIG. 23C), but this deficit could be overcome by addition of E. coli χψ.

Example 27

P. aeruginosa Cell Growth and Lysis

P. aeruginosa ΔrpoN cells were grown in a 180 L fermentor at 37° C. (or 30° C. for α/ε expression) in F broth (yeast extract 14 g/L; tryptone 8 g/L; $K_2HPO_4$ 12 g/L; $KH_2PO_4$ 1.2 g/L; glycerol 1%)+50 μg/ml gentamycin. The pH was maintained at 7.2 by the addition of ammonium hydroxide. Cells were harvested at mid log phase ($OD_{600}$ of ~2.5) with simultaneous chilling to 14° C. in the harvest line. Cells were suspended in an equal volume of Tris-sucrose (50 mM Tris-HCl (pH 7.5), 10% sucrose) and frozen by liquid nitrogen. Lysis was accomplished via creation of spheroplasts by treatment of cells with lysozyme in the presence of 10% sucrose (Cull and McHenry, 1990). The presence of 18 mM spermidine kept the nucleoid condensed within partially disrupted cells and displaced DNA binding proteins. Centrifugation (16,000×g, 1 h, 4° C.) resulted in a DNA-free supernatant (Fraction I).

Example 28

Buffers used in purifications for Example 29 to Example 32. Subscripts indicate mM concentration of NaCl in each buffer (i.e., $A_{40}=A_0+40$ mM NaCl). BW=20% glycerol, 50 nM Tris-HCl pH 8.0, 1 mM EDTA, 1 mM EGTA, 0.1 M KOAc pH 8.0, 0.20 g/ml ammonium sulfate (i.e., 35% ammonium sulfate saturation). $A_0$=25 mM Tris-HCl, pH 7.5, 10% glycerol, 0.1 mM EDTA and 0.1 mM EGTA. B=25 mM Na-Hepes, pH 8.0, 5% glycerol, 0.5 mM EDTA, and 0.1 mM EGTA. C=25 mM Na-Hepes, pH 8.0, 5% glycerol, 0.5 mM EDTA, 0.1 mM EGTA, 25% saturated ammonium sulfate. D=25 mM Na-Hepes, pH 8.0, 20% glycerol, 0.5 mM EDTA, and 0.1 mM EGTA. E=25 mM Tris-HCl, pH 7.5, 5% glycerol, 0.1 mM EDTA, 0.1 mM EGTA, and 50 mM NaCl. F=10% glycerol, 20 mM potassium phosphate, pH 8.0, 0.3 M NaCl, 0.01 mM EDTA, 0.01 mM DTT, 20 mM imidazole pH 8.0, 0.005% Tween-20. G=F except 50 mM imidazole. H=F except 250 mM imidazole.

Example 29

Purification of Native Tau Complex

Like the $\tau_3\delta\delta'$ complex, we found that the native DnaX complex was relatively insoluble in ammonium sulfate, providing a simple initial purification step to form Fraction II (Table 22). Approximately 2-fold loss in activity was observed between the isolation of Fraction II and the initiation of the subsequent chromatography step. This was observed in two subsequent purification steps, but not in the later stages of the purification. It may be attributable to the action of a protease that was eliminated during the latter stages of purification. All purification steps were performed at 4° C. To Fraction I, ammonium sulfate (0.226 g to each initial ml of Fraction I, i.e., 40% saturation) was added slowly. The precipitate collected by centrifugation (16,000×g, 30 min, 4° C.). The pellet was resuspended using a dounce homogenizer in 0.125×Fr I volume of BW. The remaining precipitate was collected by centrifugation (16,000×g, 45 min, 4° C.). The pellet was resuspended in 50 ml $A_0$, dialyzed for 4 hours versus $A_0$, and then diluted to 240 ml to match the conductivity of $A_{20}$ forming Fraction II. Fraction II was applied to a 2.5 cm×3 cm (15 ml) MacroPrep High S (Biorad) column connected in series with a 5 cm×12.7 cm (250 ml) Heparin Sepharose Fast Flow (Amersham) column equilibrated in $A_{20}$ at a flow rate of 6.4 ml/min. The columns were washed with 860 ml of $A_{20}$. Then the S column was disconnected and separately batch eluted with 48 ml $A_{1000}$ ("S eluate"). The Heparin column was developed with a 2.0 liter linear gradient from 20 to 300 mM NaCl at a flow rate of 2.8 ml/min. Tau complex activity eluted between fractions 35-45, which were pooled to form Fraction III (Table 22). Fraction III was applied without desalting to a 5 ml HiTrap Q Sepharose HP column (Amersham) equilibrated in buffer $A_{20}$ at a flow rate of 1.3 ml/min. The column was washed with 20 mls of buffer $A_{20}$, followed by a 50 ml linear gradient from 20-1000 mM NaCl. Tau complex activity eluted between fractions 45-53, which were pooled to form Fraction IV (Table 22). Fraction IV (4.3 ml) was adjusted to pH 8.0 by addition of 0.4 ml 1 M Hepes pH 8.0. 3.3 ml of a 40% slurry of methyl HIC resin (Biorad) that had been equilibrated in buffer B was then added to Fraction IV. The protein/resin slurry was then adjusted to 25% ammonium sulfate saturation by addition of 2.7 ml of saturated ammonium sulfate. This slurry was gently rocked for 30 minutes. Fresh methyl HIC resin was packed in a 1.5 cm×4.0 cm (7.0 ml) column and equilibrated in C. Following the 30 minute incubation, the protein/resin slurry was layered on the top of the methyl column bed at a flow rate of 1 ml/min. The column was then washed with 20 ml C, and developed with a 50 ml linear reverse salt gradient from C to D. Tau complex activity eluted between fractions 30-40, which were pooled to form Fraction V (Table 22). Fraction V was precipitated with 70% ammonium sulfate, divided into 6 aliquots. The precipitate was collected by centrifugation (16,000×g, 30 min) and flash frozen and stored at −80° C. A Superose-6 HR 10/30 column (Amersham) controlled by an AKTA FPLC (Amersham) was equilibrated in E. Half of the Fraction V pellets were resuspended in 0.55 ml E and applied to the Superose column at a flow rate of 0.3 ml/min. 0.25 ml fractions were collected, and fractions 22-26 were pooled to form Fraction VI (Table 22). The polypeptides present in Fraction VI were excised and identified by peptide mass fingerprinting. The results are shown in Table 23 along with the approximate abundance of each band estimated by densitometry. Fraction VI showed similar specific activity and salt tolerance to that observed with $\tau_3\delta\delta'$ assayed in the presence of E. coli $\chi\psi$ (FIG. 24).

TABLE 22

Purification Summary

| Fraction | Total Activity (Units) | Total Volume (ml) | Activity (Units/μl) | Total Protein (mg) | Protein Conc. (mg/ml) | Specific Activity (Units/mg) | Single Step Enrichment | Single Step Yield (%) |
|---|---|---|---|---|---|---|---|---|
| Fr I | | 1600 | | 28000 | 17.5 | | | |
| Fr II 35% AS | 2.0E+07 | 223 | 91 | 870 | 3.9 | 2.3E+04 | | |
| Fr II S-Heparin Load | 9.1E+06 | 240 | 38 | 864 | 3.6 | 1.1E+04 | | |
| Fr III Heparin Pool | 9.1E+06 | 260 | 35 | 130 | 0.5 | 7.0E+04 | 6.6 | 100 |
| Fr III Q Load | 4.2E+06 | 260 | 16 | 130 | 0.5 | 3.2E+04 | | |
| Fr IV Q Pool | 3.0E+06 | 4.5 | 660 | 45 | 10.1 | 6.5E+04 | 2.0 | 71 |
| Fr IV HIC Load | 2.6E+06 | 4.3 | 615 | 43 | 10.1 | 6.1E+04 | | |
| Fr V HIC Pool | 1.0E+06 | 9 | 113 | 9.9 | 1.1 | 1.0E+05 | 1.7 | 38 |
| Fr V Superose Load | 4.1E+05 | 0.55 | 745 | 4.2 | 7.6 | 9.8E+04 | | |
| Fr VI Superose Pool | 1.1E+05 | 1.5 | 73 | 0.18 | 0.1 | 6.1E+05 | 6.2 | 27 |

TABLE 23

Identification of Proteins in Native DnaX Complex

| Gel band | Approx. MW (kD) | Relative Abundance[1] | Assignment[2] | Sequence Annotation | Predicted MW (kD) |
|---|---|---|---|---|---|
| a | 110-140 | 2.0 | PA3640 | DNA polymerase III, alpha chain | 130.9 |
| b | 70-90 | 2.5 | PA1532 | DNA polymerase III, tau subunit | 73.3 |
| c | 48-50 | 0.6 | PA2991 | soluble pyridine nucleotide transhydrogenase | 51.1 |
| d | 43-47 | <0.4 | PA4408 | cell division protein FtsA | 44.6 |
| | | <0.4 | PA0002 | DNA polymerase III, beta chain | 40.7 |

TABLE 23-continued

Identification of Proteins in Native DnaX Complex

| Gel band | Approx. MW (kD) | Relative Abundance[1] | Assignment[2] | Sequence Annotation | Predicted MW (kD) |
|---|---|---|---|---|---|
| | | <0.4 | PA4760 | chaperone protein DnaJ | 40.3 |
| | | <0.4 | PA5004 | probable glycosyl transferase | 42.2 |
| e | 38-42 | <0.4 | PA3197 | hypothetical protein | 36.9 |
| f | 37 | 1.0 | PA3989 | DNA polymerase III, delta subunit | 37.4 |
| g | 35 | 0.9 | PA2961 | DNA polymerase III, delta prime subunit | 35.7 |
| h | 32 | 1.0 | PA4679 | hypothetical protein | 24.9 |
| i | 26 | 2.2 | PA1816 | DNA polymerase III, epsilon subunit | 26.8 |
| j | 18 | 0.8 | PA4232 | single-stranded DNA binding protein | 18.6 |
| k | 16.5 | 1.1 | PA3832 | DNA polymerase III, chi subunit | 16.1 |
| l | 16 | 0.4 | PA3126 | heat-shock protein IbpA | 16.6 |
| m | 15 | 0.6 | PA5406 | hypothetical protein | 12.4 |

[1]Relative to δ
[2]All of the identifed proteins derived from Pseudomonas aeruginosa Example 30

Cloning of Overexpression Vectors

The sequences of each gene were amplified by polymerase chain reaction (PCR) from *P. aeruginosa* genomic DNA, and inserted in expression vectors. When necessary, *E. coli* low usage codons in the N-terminus of *P. aeruginosa* genes were altered to high usage codons, and non-AUG start codons were altered to AUG, to facilitate efficient translation in *E. coli*. The PCR primers were as follows: holC forward 5'-GGATTCTA-GAAGGAGGAAGCTTTAGATGAC-CCGCGTCGATTTCTACG (SEQ ID NO:17), holC reverse 5'-GGATAGATCTCCTCCTGGATCCATCA-GATACGCGGCAGGC (SEQ ID NO: 18), PA4679 forward 5'-GGATTCTAGAAGGAGGAGATCTACGAT-GCCTGTGCGTGCGC (SEQ ID NO:19), PA4679 reverse 5'-GGATAAGCTTCCTCCTCGAGTCATCAT-TGAATCTCGCTCGACCAG (SEQ ID NO:62). *P. aeruginosa* chi DNA sequence is represented by SEQ ID NO: 104, and the protein sequence is represented by SEQ ID NO: 106. The vector pET14b was cut with XbaI and BamHI, the ho/C PCR fragment was cut with HindIII and BamHI, and the PA4679 PCR fragment was cut with XbaI and HindIII and the resulting fragments were ligated together, resulting in the plasmid pET14b-PA-4679holC. The vector pET14b and the PA4679 PCR fragment were cut with XbaI and XhoI and the resulting fragments were ligated together, resulting in the plasmid pET14b-PA-4679.

Vectors expressing 32 upstream amino acids at the N-terminus of PA4679 were constructed as follows. A 448 nucleotide fragment, PCR *P. aeruginosa* 4679-32, was PCR amplified from *P. aeruginosa* genomic DNA using the following primers: 5'-GGATTCTAGAAGGAGGTACCAAGCGATG-CAGATTACCAGTTGGC (SEQ ID NO:21) and 5'-CAG-CAGCAGGTAACCCGGA (SEQ ID NO:22). pET14b-PA-4679 and PCR *P. aeruginosa* 4679-32 were digested with XbaI and BstEII and the resulting fragments were ligated together, resulting in the plasmid pET14b-PA-N4679. pET14b-PA-4679HolC and PCR *P. aeruginosa* 4679-32 were digested with XbaI and BstEII and the resulting fragments were ligated together, resulting in the plasmid pET14b-PA-N4679HolC.

Vectors expressing 45 upstream amino acids at the N-terminus of PA4679 were constructed as follows. A 487 nucleotide fragment, PCR *P. aeruginosa* 4679-45, was PCR amplified from *P. aeruginosa* genomic DNA using the following primers: 5'-GGATTCTAGAAGGAGGTACCAACTAAT-GATCGAAGAACAGCGTCGC (SEQ ID NO:23) and 5'-CAGCAGCAGGTAACCCGGA (SEQ ID NO:24). pET14b-PA-4679 and PCR *P. aeruginosa* 4679-45 were digested with XbaI and BstEII and the resulting fragments were ligated together, resulting in the plasmid pET14b-PA-L4679. pET14b-PA-4679HolC and PCR *P. aeruginosa* 4679L were digested with XbaI and BstEII and the resulting fragments were ligated together, resulting in the plasmid pET14b-PA-L4679HolC.

Construction of a vector for expression of N-terminally His-tagged HolC: A 455 nucleotide fragment containing the ho/C gene, PCR *P. aeruginosa* holC, was PCR amplified from *P. aeruginosa* genomic DNA using the following primers: 5'-gatcATGCATACCCGCGTCGATTTC-TACGTGATCCCCA (SEQ ID NO:25) and 5'-GCATAC-TAGTGAGCTCTCATCAGATACGCGGCAGGCGAT (SEQ ID NO:26). The vector pA1-NB-KpnI was digested with PstI and SpeI and PCR *P. aeruginosa* holC was cut with NsiI and SpeI, and the resulting fragments were ligated together, resulting in the plasmid pA1-NB-PAholC.

Example 31

Affinity Purification of Tagged *P. aeruginosa* χ and PA4679 Variants

Cells transfected with pA1-NB-PAholC (expressing N-terminally hexa-His-tagged *P. aeruginosa* χ), pET14b-PA-4679 (expressing PA4679 protein), pET14b-PA-N4679 (expressing PA4679N32 protein) and pET14b-PA-L4679 (expressing PA4679N45 protein) were induced, lysed and Fraction I (crude lysates) were prepared as described above. Fraction I's were concentrated by precipitation with ammonium sulfate (80% saturation). Pellets were resuspended in 0.25× Fraction I volume of D, and desalted in F to remove residual ammonium sulfate and prepare for Ni-NTA affinity purification (Fraction II). To 0.5 ml *P. aeruginosa* tagged χ Fraction II were added 50 μl of Ni-NTA magnetic beads (Qiagen) and the mixture was rocked gently at 4° C. for 1 hour. The beads were immobilized on a magnet and the supernatant was removed and the beads were washed twice with 0.4 ml F. 1.0 ml of Fraction II from each PA4679 variant of interest was then added to the beads and the mixtures were rocked at 4° C. for 1 hour. The supernatant was removed and the beads were washed twice with 0.4 ml F, followed by one wash with 0.2 ml G. Proteins bound to Ni-NTA were then eluted from the beads with 75 μL of H. The eluted proteins would thus include tagged *P. aeruginosa* χ as well as any proteins bound to χ.

Example 32

Purification of χψ from an Overexpression Vector

Rosetta DE3 cells transfected with pET14b-PA-L4679HolC were grown to 1 $OD_{600}$ in a shake flask at 37° C. in F broth (yeast extract 14 g/L; tryptone 8 g/L; $K_2HPO_4$ 12 g/L; $KH_2PO_4$ 1.2 g/L; glucose 1%) with 100 μg/ml ampicillin and 10 μg/ml chloramphenicol. Expression was induced by addition of IPTG to 1 mM. Cells were harvested at 2 hours post induction. Cells were suspended in an equal volume of cold Tris-sucrose (50 mM Tris-HCl (pH 7.5), 10% sucrose) and frozen by liquid nitrogen. 9.7 g of frozen cells were lysed as described for *P. aeruginosa* above. The insoluble cellular components were removed by centrifugation (16,000×g, 60 min, 4° C.). The recovered supernatant (25 ml) constituted Fraction I. The complex was found to precipitate in low ammonium sulfate, forming a relatively high purity Fraction II (Table 25). To 25 ml of Fraction I, 10.7 ml saturated ammonium sulfate was added (30% saturation). The mixture was rocked for an additional 15 min at 4° C. and the precipitate collected by centrifugation (16,000×g, 30 min, 4° C.). The ammonium sulfate pellets were resuspended in 3.8 ml buffer $A_0$ to form Fraction II and adjusted in volume (using $A_0$) to match the conductivity of buffer $A_{30}$. Fraction II was loaded onto a 5 ml HiTrap Q Sepharose HP column (Amersham) equilibrated in Buffer $A_{30}$ at 1.5 ml/min. The column was washed with 35 ml of Buffer $A_{30}$ at a flow rate of 1 ml/min. The protein was eluted using a 75 ml linear gradient from 30 to 600 mM NaCl at a flow rate of 1 ml/min. Fractions showing peak *P. aeruginosa* χψ were pooled to form Fraction III (Table 25).

TABLE 25

*P. aeruginosa* χψ Purification Summary

| Fraction | Total Activity ($U \times 10^{-9}$) | Total Volume (ml) | Total Protein (mg) | Specific Activity ($U/mg \times 10^{-7}$) |
|---|---|---|---|---|
| Fr I | | 25 | 400 | |
| Fr II (30% AS) | 1.84 | 3.8 | 42 | 4.37 |
| Fr III (Q pool) | 2.25 | 20 | 48 | 4.69 |

Example 33

Expression and Purification of *P. aeruginosa* dnaG Primase

The sequence of dnaG was amplified by PCR from PA (PAO1) genomic DNA, and inserted in an expression vector that utilized the semi-synthetic highly inducible and repressible pA1 promoter as in Example 13. The PCR primers were 5'-GACTCATATGGCCGGCCTGATACCGCAAA (SEQ ID NO:27) (sense) and 5'-GACTACTAGTTCATCAGCTCTGGGAAGGCGATGAA (SEQ ID NO:28) (antisense). The vector pA1-CB-NdeI and the dnaG PCR fragment were cut with NdeI and SpeI, and the dnaG PCR fragment was inserted, resulting in the plasmid pA1-PA-dnaG. 800 g of cells were grown, harvested and lysed as described in Example 14. Ammonium sulfate (0.197 g to each initial ml of Fraction I; 35% saturation) was added slowly to Fraction I. The precipitate was collected by centrifugation (16,000×g, 30 min, 4° C.). The pellet was resuspended in 50 mM Tris-HCl, (pH 8.0), 20% glycerol, 0.4 mM EDTA, 2 mM DTT and 200 mM NaCl and allowed to rock 30 minutes. Insoluble material was removed by centrifugation (16,000×g, 30 min, 4° C.). The sample was diluted with water and saturated ammonium sulfate to a final concentration of 25 mM Tris-HCl, (pH 8.0), 10% glycerol, 0.2 mM EDTA, 1 mM DTT, 100 mM NaCl and 25% saturated ammonium sulfate (Fraction II). Fraction II was divided in two parts and one half was applied to a 5 cm×10 cm MacroPrep Methyl HIC (Biorad) column equilibrated in 25 mM Tris-HCl, (pH 8.0), 10% glycerol, 0.2 mM EDTA, 1 mM DTT, 100 mM NaCl and 25% saturated ammonium sulfate. The column was washed with 720 ml equilibration buffer and developed with a 2.0 liter reverse gradient from 25% to 0% saturated ammonium sulfate. DnaG eluted at approximately 15% ammonium sulfate saturation, and fractions with the highest specific activity were pooled to form Fraction IIIA. The Methyl HIC purification step was repeated with the second half of Fraction II to form Fraction IIIB. Fractions IIIA and IIIB were combined to form Fraction III, which was precipitated with 50% ammonium sulfate. Fraction III pellet was resuspended in 25 mM Tris-HCl, (pH 8.0), 10% glycerol, 0.2 mM EDTA and 1 mM DTT, and was diluted to match the conductivity of buffer 100 mM NaCl and applied to a 2.5 cm×14 cm MacroPrep High S (Amersham) column equilibrated in 25 mM Tris-HCl, (pH 8.0), 10% glycerol, 0.2 mM EDTA, 1 mM DTT and 100 mM NaCl. The column was washed with 440 ml of equilibration buffer, followed by a 700 ml linear gradient from 100-1000 mM NaCl. DnaG eluted at approximately 350 mM NaCl, and fractions with the highest specific activity were pooled to form Fraction IV (see Table 26).

TABLE 26

*P. aeruginosa* DnaG Purification Summary

| Fraction | Total Activity ($U \times 10^{-8}$) | Total Volume (ml) | Total Protein (mg) | Specific Activity ($U/mg \times 10^{-5}$) |
|---|---|---|---|---|
| Fr I | 9.1 | 1560 | 33743 | 0.27 |
| Fr II (35% AS) | 5.7 | 1450 | 3411 | 1.67 |
| Fr III (HIC pool) | 5.8 | 572 | 1441 | 4.00 |
| Fr IV (S pool) | 3.1 | 122 | 522 | 5.94 |

Example 34

Activity Assays for Products of Example 27 to Example 33

Units are defined as pmol nucleotide incorporated per minute at 22° C. DNA synthesis activity was measured in a reconstituted *P. aeruginosa* DNA polymerase III holoenzyme assay. M13Gori single-stranded phage DNA was used as template DNA, and was purified as described (Johanson, et al. (1986) "Chemical characterization and purification of the β subunit of the DNA polymerase III holoenzyme from an overproducing strain" *J Biol Chem* 261:11460-11465). Enzymes were diluted in EDB (50 mM Hepes, pH 7.5, 20% glycerol, 0.02% Nonidet P40, 0.2 mg/ml bovine serum albumin). Primase mix containing single-stranded DNA template, nucleotides and SSB was prepared first by incubating the following components for 20 minutes at 30° C.: 50 mM Hepes, pH 7.5, 20% glycerol, 0.02% Nonidet P40, 0.2 mg/ml bovine serum albumin, 13 mM Mg(OAc)$_2$, 5 mM DTT, 0.27 mM each of rGTP, rUTP, rATP and rCTP, 64 uM each of dATP, dCTP, dGTP, and dTTP, 1.4 nM M13 Gori ssDNA circles, 21 μg/ml *E. coli* SSB, and 1.0 μg/ml *E. coli* DnaG primase. Primase mix was then aliquoted and frozen for use in subsequent assays. Holoenzyme reactions were reconstituted by incubating primase mix with P. aeruginosa αε, τ₃δδ', and β in a 25 μL reaction volume for 5 minutes at 22° C. Buffer conditions were comparable to the priming reaction except that each of the components was 25% more dilute. Where indicated, some reactions were primed with P. aeruginosa DnaG primase and SSB in concurrent priming and elongation reactions (typically 30 minutes). In cases where it was not necessary to determine absolute incorporation rates, formation of dsDNA was measured by fluorescent detection of dsDNA using PicoGreen® (Molecular Probes). In this case, 25 μL reactions were performed in opaque 96-well plates and stopped with 25 μL of 100 mM EDTA. PicoGreen® was diluted 1:150 in 10 mM TrisHCl (pH 7.5); 150 μL was added to each well. Fluorescence emission at 538 nm was measured in a GeminiEM platereader (Molecular Dynamics) exciting at 485 nm. DNA synthesis was measured as relative fluorescent units (RFU). For these assays 100 RFU approximately equals 15 pmol nucleotide incorporated. Specific activities during purifications were determined in reactions containing 24 μM [$^3$H]-dTTP in place of cold dTTP. Incorporation of [$^3$H]-dTTP was measured by trichloroacetic acid (TCA) precipitation on GF-C filters (McHenry and Crow, (1979) "DNA polymerase III of *Escherichia coli*: purification and identification of subunits" *J Biol Chem* 254:1748-1753). Enzyme titrations were performed to determine the linear range of the assay, and specific activities were calculated using points in the linear range.

Example 35

Gel Electrophoresis and Protein Analysis for Example 29 to Example 32

SDS-PAGE analysis was performed using either 12% or 4-12% acrylamide pre-cast gels (Novex NuPAGE®; Invitrogen) with MOPS running buffer (Invitrogen). Benchmark unstained protein molecular weight markers were used (Invitrogen). SDS-PAGE analysis of SSB samples was performed on 10-20% acrylamide Novex Tris-glycine pre-case gels (Invitrogen) using Tris-glycine running buffer (Invitrogen). Gels were stained with SimplyBlue SafeStain (Invitrogen) or with Coomassie Brilliant Blue. Comparable results were obtained with either staining method. Densitometry was performed using a Kodak Image Station 440CF. Some N-terminal sequencing was performed using Edman degradation. Peptide mass fingerprinting for protein identification was performed by Amprox, Inc. (Carlsbad, Calif.).

Example 36

Cloning of S. Aureus DNA Replication Genes

A. Construction of pA1-SA-dnaN (Beta).

The S. aureus dnaN gene was identified in the NCBI database by a homology search using dnaN from S. pyogenes. Cloning of the S. aureus dnaN gene entailed PCR amplifying the dnaN gene (β) from the *Staphylococcus aureus* genomic DNA and inserting it into the vector pA1-CB-NdeI. The *Staphylococcus aureus* genomic DNA was derived from *Staphylococcus aureus* subspecies *aureus* Mu50. The construction of the vector pA1-CB-NdeI is described in U.S. Pat. No. 6,677,146. The β subunit is composed of 377 amino acids (SEQ ID NO:40). The gene encoding β is dnaN, and is composed of 1134 nucleotides including the stop codon (SEQ ID NO:38). The codon at position #8 is a low usage codon in *E. coli* and is changed to a high usage codon by the forward/sense primer. This change is from aga>cgc.

The forward/sense primer (SEQ ID NO:41) contains a 4 nucleotide 5' clamp to allow efficient digestion by the restriction enzyme. An NdeI restriction site follows the clamp, which is used for insertion into pA1-CB-NdeI. The ATG of the NdeI restriction site also serves as the start codon. The next 21 nucleotides make up the next seven codons that do not completely correspond to the 5' end of the gene because codon #8 is changed from a low usage codon to a high usage codon by the forward/sense primer. The next 25 nucleotides correspond to nucleotides 25-49 of the dnaN gene.

The reverse/antisense primer (SEQ ID NO:42) contains a 4 nucleotide 5' clamp to allow efficient digestion by the restriction enzyme. A SpeI restriction site follows the clamp, which is used for insertion into pA1-CB-NdeI. Next, there is a second non-complementary stop codon that will be in tandem with the native stop codon. This is followed by 20 nucleotides complementary to the 3' end of the dnaN gene.

Both the S. aureus dnaN PCR product and the plasmid pA1-CB-NdeI are digested with NdeI/SpeI restriction enzymes. The fragment of the PCR product containing the dnaN gene (1.1 kb) is inserted into the NdeI/SpeI digested pA1-CB-NdeI. This places the dnaN gene optimally spaced from the upstream ribosome binding site (RBS) and results in the plasmid pA1-SA-dnaN.

B. Construction of pA1-SA-polC (Alpha).

In Gram(+) organisms there tends to be two different possible alpha (α) subunits. One is thought of as a prototypic Gram(+) polIII and is designated as PolC, which is encoded by the polC gene. This protein contains the 3'-5' exonuclease (proofreading function) within the catalytic subunit. The second possible α subunit is similar to the Gram(−) α subunit (DnaE) and is designated DnaE and is coded by the dnaE gene. In Gram(−) organisms, the DnaE subunit is complexed with the epsilon (ε) and theta (θ) subunits to form the core complex. We have not identified the θ subunit in S. aureus and it has no known function in E. coli. We have identified a putative ε subunit (in Gram(−) organisms this subunit is encoded by the dnaQ gene and is the 3'-5' proofreading exonuclease) in the S. aureus genome, which is cloned and constructed with the dnaE gene to form a core operon described below.

The S. aureus polC gene was identified in the NCBI database by a homology search using polC from S. pyogenes. The PolC subunit is composed of 1438 amino acids (SEQ ID NO:45). The gene encoding PolC is composed of 4311 nucleotides including the stop codon (SEQ ID NO:43). The forward/sense primer (SEQ ID NO:46) contains a 4 nt 5' clamp to allow efficient digestion by the restriction enzyme. An NdeI restriction site follows the clamp, which is used for insertion into pA1-CB-NdeI. The ATG of the NdeI restriction site also selves as the start codon. The next 22 nucleotides correspond to nucleotides 4-25 of the polC gene.

The reverse/antisense primer (SEQ ID NO:47) contains a 4 nt 5' clamp to allow efficient digestion by the restriction enzyme. A SpeI restriction site follows the clamp, which is used for insertion into pA1-CB-NdeI. The restriction site is followed by a second stop codon that is adjacent to the native stop codon. The next 21 nucleotides are complementary to the 3' end of the polC gene.

Both the S. aureus polC PCR product and the plasmid pA1-CB-NdeI are digested with NdeI/SpeI restriction enzymes. The fragment of the PCR product containing the polC gene (4.3 kb) is inserted into the NdeI/SpeI digested pA1-CB-NdeI. This places the polC gene optimally spaced from the upstream RBS and results in the plasmid pA1-SA-PolC.

The pA1-SA-PolC plasmid was created with only one PCR step to obtain the entire gene, but since the polC gene is 4311 nucleotides in length, this cloning procedure could be done in a two-step process to reduce PCR mistakes. There is a unique KpnI restriction site approximately two-thirds of the way into the gene. In step one using the forward/sense primer described above and a $2^{nd}$ reverse primer selected from the sequence just downstream of the unique KpnI restriction site in the polC gene, a PCR reaction is performed. The resulting PCR product is digested with NdeI/KpnI restriction and the resulting fragment containing the 5' two-thirds (3 kb) of the polC gene is inserted into pA1-CB-NdeI that is digested with the same two restriction enzymes. This intermediate plasmid is named pA1-SA-PolC5'. In step two, the reverse primer described above and a $2^{nd}$ forward primer selected from the sequence just upstream of the unique KpnI restriction site in the polC gene are use in a PCR reaction. This PCR product is digested with KpnI/SpeI. The fragment (1.3 kb) from the digested PCR product containing the 3' one-third of the polC gene is inserted into the intermediate pA1-SA-PolC5' plasmid digested with the same two restriction enzymes, KpnI/SpeI. This results in the plasmid pA1-SA-PolC, which contains the full length *S. aureus* polC gene optimally spaced from the RBS.

C. Construction of pA1-SA-dnaQ (Epsilon).

The *S. aureus* dnaQ gene was identified in the NCBI database by a homology search using dnaQ from *S. pyogenes*. The ε subunit is composed of 184 amino acids (SEQ ID NO:50). The gene encoding ε is dnaQ (SEQ ID NO:48), and is composed of 552 nucleotides including the stop codon. The dnaQ gene contains NdeI, ClaI and NsiI restriction sites. This gene also has a low usage codon at position two and is changed to a high usage codon by the forward/sense primer (SEQ ID NO:51). This change will be ATA>ATC.

The forward/sense primer contains a 4 nt 5' clamp to allow efficient digestion by the restriction enzyme. A PacI restriction site follows the clamp, which is used for insertion into pA1-CB-NsiI. (The construction of the vector pA1-CB-NsiI is described in U.S. Pat. No. 6,677,146.) Next, there is a two nucleotide spacer to provide optimal spacing between the RBS and the start codon. The next six nucleotides represent the start codon and the modified codon #2. The next 20 nucleotides are underlined and correspond to nucleotides 7-26 of the dnaQ gene.

The reverse/antisense primer (SEQ ID NO:52) contains a 4 nucleotide 5' clamp to allow efficient digestion by the restriction enzyme. Overlapping KpnI and NcoI restriction sites follow the clamp. Next, there is a one nucleotide spacer to provide optimal spacing between the new RBS and the downstream gene during operon construction. The one nucleotide spacer is followed be a PstI restriction site. The PstI restriction site also provides spacing between the new RBS and the downstream gene during operon construction. The PstI gene could also be used to extract the downstream gene and place it in an N-terminal tagged vector, as it along with the one nucleotide spacer would maintain the same reading frame between the N-terminal tag sequence and the downstream gene. Following the PstI restriction site is a new RBS for use in expression of the downstream gene during operon construction. Next, there is a $2^{nd}$ stop codon that is adjacent to the native stop codon. The next 20 nucleotides are complementary to the 3' end of the dnaQ gene.

Both the *S. aureus* dnaQ PCR product and the plasmid pA1-CB-NsiI are digested with PacI/KpnI restriction enzymes. The fragment of the PCR product containing the dnaQ gene (0.6 kb) is inserted into the PacI/KpnI digested pA1-CB-NsiI. This places the dnaQ gene optimally spaced from the upstream RBS and results in the plasmid pA1-SA-dnaQ.

D. Construction of pA1-SA-dnaE (DnaE).

The *S. aureus* dnaE gene was identified in the NCBI database by a homology search using dnaE from *S. pyogenes*. The DnaE subunit is composed of 1065 amino acids (SEQ ID NO:55). The gene encoding DnaE is dnaE, and is composed of 3195 nucleotides including the stop codon (SEQ ID NO:53).

The forward/sense primer (SEQ ID NO:56) contains a 4 nucleotide 5' clamp to allow efficient digestion by the restriction enzyme. An NcoI restriction site follows the clamp, which is used for insertion into pA1-CB-NcoI. (The construction of the vector pA1-CB-NcoI is described in U.S. Pat. No. 6,677,146.) The NcoI restriction site overlaps the first four nucleotides of the 5' end of the dnaE gene. The next 18 nucleotides correspond to nucleotides 5-22 of the dnaE gene.

The reverse/antisense primer (SEQ ID NO:57) contains a 4 nucleotide 5' clamp to allow efficient digestion by the restriction enzyme. A SpeI restriction site follows the clamp, which is used for insertion into pA1-CB-NcoI. Next, is a second stop codon that is adjacent to the native stop codon. The next 20 nucleotides are complementary to the 3' end of the dnaE gene.

Both the dnaE PCR product and the pA1-CB-NcoI plasmid are digested with NcoI/SpeI restriction enzymes. The fragment of the digested PCR product containing the dnaE gene (3 kb) is inserted into the digested pA1-CB-NcoI plasmid. This places the dnaE gene optimally spaced downstream from the RBS in pA1-CB-NcoI. This plasmid is named pA1-SA-DnaE.

The pA1-SA-DnaE plasmid was created with only one PCR step to obtain the entire gene, but since the since the dnaE gene is 3198 nucleotides in length, this cloning procedure could be done in a two-step process. There is a unique ClaI restriction site approximately one-half of the way into the gene. In step one using the forward/sense primer described above and a 2nd reverse primer selected from the sequence just downstream of the unique ClaI restriction site in the dnaE gene, a PCR reaction is performed. The resulting PCR product is digested with NcoI/ClaI restriction and the resulting fragment containing the 5' one-half (1.5 kb) of the dnaE gene is inserted into pA1-CB-NcoI that is digested with the same two restriction enzymes. This intermediate plasmid is named pA1-SA-DnaE5'. In step two, the reverse/antisense primer described above and a $2^{nd}$ forward primer selected from the sequence just upstream of the unique ClaI restriction site in the dnaE gene are use in a PCR reaction. This PCR product is digested with ClaI/SpeI. The fragment (1.5 kb) from the digested PCR product containing the 3' one-half of the dnaE gene and is inserted into the intermediate pA1-SA-DnaE5' plasmid digested with the same two restriction enzymes, ClaI/SpeI. This results in the plasmid pA1-SA-DnaE (same as above), which contains the full length *S. aureus* dnaE gene optimally spaced from the RBS in the pA1-CB-NcoI plasmid.

E. Construction of pA1-SA-dnaQE (Epsilon and DnaE).

To construct an operon containing both the dnaQ and dnaE genes, both pA1-SA-dnaQ and pA1-SA-DnaE plasmids are digested with NcoI and SpeI restriction enzymes. The smaller fragment from the digestion of pA1-SA-DnaE (3.2 kb) contains the full length dnaE gene. This fragment is inserted into the digested pA1-SA-dnaQ plasmid. The new plasmid contains both dnaQ and dnaE and is named pA1-SA-dnaQE. This places the dnaE gene downstream of the dnaQ gene and downstream and optimally spaced from the new downstream RBS in pA1-SA-dnaQ.

F. Construction of pA1-SA-holB (Delta'-δ').

The *S. aureus* holB gene was identified in the NCBI database by a homology search using holB from *S. pyogenes*. The δ' subunit is composed of 308 amino acids (SEQ ID NO:60). The gene encoding δ' is holB, and is composed of 927 nucleotides including the stop codon (SEQ ID NO:58).

The forward/sense primer (SEQ ID NO:61) contains a 4 nucleotides 5' clamp to allow efficient digestion by the restriction enzyme. An NcoI restriction site follows the clamp, which is used for insertion into pA1-CB-NcoI. The NcoI restriction site overlaps the first four nucleotides of the 5' end of the holB gene. The next 17 nucleotides correspond to nucleotides 5-21 of the holB gene.

The reverse/antisense primer (SEQ ID NO:62) contains a 4 nucleotide 5' clamp to allow efficient digestion by the restriction enzyme. Next, there are adjacent KpnI, ClaI and PstI restriction sites, respectively. The KpnI restriction site is used for insertion into pA1-CB-NcoI. The ClaI restriction site will be used in operon construction, and the PstI restriction site is used as a spacer to provide optimal spacing between the RBS and the downstream gene in operon construction. Following the restriction sites is a new RBS for expression of the downstream gene. The RBS overlaps a second non-complementary stop codon that is adjacent to the native stop codon. Overlapping the $2^{nd}$ stop codon and the RBS may give more efficient expression of the downstream gene. The next 22 nucleotides are complementary to the 3' end of the holB gene. Additional sequences containing restriction sites and an RBS have been added downstream of the holB gene for use in operon construction.

Both the *S. aureus* holB PCR product and the plasmid pA1-CB-NcoI are digested with NcoI/KpnI restriction enzymes. The fragment of the PCR product containing the holB gene (0.9 kb) is inserted into the NcoI/KpnI digested pA1-CB-NcoI. This places the holB gene optimally spaced from the upstream RBS and results in the plasmid pA1-SA-holB. This also creates a new RBS site and restriction sites downstream of the holB gene that is used later in operon construction. This plasmid is named pA1-SA-holB.

G. Construction of pA1-SA-holA (Delta-δ).

The *S. aureus* holA gene was identified in the NCBI database by a homology search as described in Bullard et al. (Bullard, J. M., Pritchard, A. E., Song, M. S., Glover, B. P., Wieczorek, A., Chen, J., Janjic, N., McHenry, C. S. A Three-domain Structure for the delta Subunit of the DNA Polymerase III Holoenzyme; delta Domain III Binds delta' and Assembles into the DnaX Complex. *J. Biol Chem.* 277: 13246-13256 (2002)). The δ subunit is composed of 324 amino acids (SEQ ID NO:65). The gene encoding δ is holA, and is composed of 975 nucleotides including the stop codon (SEQ ID NO:63).

The forward/sense primer (SEQ ID NO:66) contains a 4 nucleotide 5' clamp to allow efficient digestion by the restriction enzyme. PacI and a ClaI restriction sites are overlapping, respectively, and follow the clamp. The PacI restriction site is use for insertion into pA1-CB-NcoI and the ClaI restriction site is used in operon construction. The ClaI restriction site overlaps the first two nucleotides of the start codon of the holA gene. The next 18 nucleotides correspond to nucleotides 2-20 of the holA gene.

The reverse/antisense primer (SEQ ID NO:67) contains a 4 nucleotide 5' clamp to allow efficient digestion by the restriction enzyme. Next, there are overlapping KpnI and NcoI restriction sites, respectively. The KpnI restriction site is used for insertion into pA1-CB-NcoI. The NcoI restriction site is used in operon construction. Following these two restriction sites is a one nucleotide spacer, which provides optimal spacing between the new RBS and a downstream gene in operon construction. This spacer is followed by a PstI restriction site, which also is used as a spacer to provide optimal spacing between the RBS and the downstream gene in operon construction. Following the restriction sites is a new RBS for expression of the downstream gene. The RBS overlaps a second non-complementary stop codon that is adjacent to the native stop codon. Overlapping the $2^{nd}$ stop codon and the RBS may give more efficient expression of the downstream gene. The next 24 nucleotides are complementary to the 3' end of the holA gene. A PCR reaction with these two primers and *S. aureus* genomic DNA as a substrate yields a PCR fragment containing the full-length holA gene. Additional sequences containing restriction sites and an RBS is added downstream of the holA gene for use in operon construction.

Both the *S. aureus* holA PCR product and the plasmid pA1-CB-NcoI are digested with PacI/KpnI restriction enzymes. The fragment of the PCR product containing the ho/A gene (1.0 kb) is inserted into the PacI/KpnI digested pA1-CB-NcoI. This places the holA gene optimally spaced from the upstream RBS and results in the plasmid pA1-SA-holA. This also creates a new RBS site and restriction sites downstream of the holA gene that is used later in operon construction.

H. Construction of pA1-SA-dnaX (Tau-τ).

The *S. aureus* dnaX gene was identified in the NCBI database by a homology search using dnaX from *S. pyogenes*. The τ subunit is composed of 565 amino acids (SEQ ID NO:70). The gene encoding τ is dnaX, and is composed of 1698 nucleotides including the stop codon (SEQ ID NO:68). The start codon in certain genes in *S. aureus* is TTG instead of ATG, this is the case with the dnaX gene. The start codon is changed from TTG>ATG by the forward/sense primer.

The forward/sense primer (SEQ ID NO:71) contains a 4 nucleotide 5' clamp to allow efficient digestion by the restriction enzyme. A PacI restriction site follows the clamp, which is used for insertion into pA1-CB-NcoI. Next, is a RcaI restriction site, which is used in operon construction. The RcaI restriction site overlaps the first four nucleotides of the dnaX gene. The next 18 nucleotides are underlined and correspond to nucleotides 5-22 of the dnaX gene.

The reverse/antisense primer (SEQ ID NO:72) contains a 4 nucleotide 5' clamp to allow efficient digestion by the restriction enzyme. A SpeI restriction site follows the clamp, which is used for insertion into pA1-CB-NcoI. Next, is a second non-complementary stop codon which is adjacent to the native codon. The next 21 nucleotides are complementary to the 3' end of the dnaX gene. A PCR reaction with these two primers and *S. aureus* genomic DNA as a substrate gives the PCR product containing full-length dnaX gene.

Both the *S. aureus* dnaX PCR product and the plasmid pA1-CB-NcoI are digested with PacI/SpeI restriction enzymes. The fragment of the PCR product containing the dnaX gene (1.7 kb) is inserted into the PacI/SpeI digested pA1-CB-NcoI. This places the dnaX gene optimally spaced from the upstream RBS and results in the plasmid pA1-SA-DnaX.

I. Construction of pA1-SA-BAX Containing an Operon Containing the Essential Clamp-Loader Subunits (δδ'τ).

The construction of an operon containing all three genes (ho/B, holA and dnaX) to constitute a minimal clamp-loading complex is accomplished in a two-step procedure.

First, the pA1-SA-holA plasmid is digested with NcoI and SpeI. The pA1-SA-DnaX plasmid is digested with RcaI and SpeI. The fragment from the RacI and SpeI digested pA1-SA-DnaX that contains the dnaX gene (1.7 kb) is inserted into the NcoI and SpeI digested pA1-SA-holA plasmid. The RacI and NcoI restriction sites anneal, but both sites are destroyed by the ligation. There are a number of isoschizomers of RacI, and there are five cleavage sites on the pA1-SA-DnaX plasmid. There is only one restriction site for SpeI. Therefore cleavage of pA1-SA-DnaX by RacI and SpeI will give six fragments. The fragment sizes are 178, 622, 1007, 3705, 105 and 1703 nucleotides in length. The fragment with 1703 nucleotides contains the dnaX gene. This fragment is digested on the 5' end with RacI and on the 3' end with SpeI. This fragment is isolated and inserted into the NcoI and SpeI digested pA1-SA-holA plasmid. This results in the plasmid pA1-SA-AX which contains the holA and dnaX genes. The dnaX gene is placed downstream and optimally spaced from the RBS created downstream of the holA gene in plasmid pA1-SA-holA.

In step two, both pA1-SA-AX and pA1-SA-holB are digested with ClaI and SpeI. The smaller fragment (2.7 kb) from the digested pA1-SA-AX which contains ho/A/dnaX is inserted into the digested pA1-SA-holB plasmid. This creates the plasmid pA1-SA-BAX, which contains holB, holA and dnaX. The dnaX gene is placed downstream and optimally spaced from the RBS created downstream of the holA gene in plasmid pA1-SA-holA, and the holA gene is placed downstream and optimally spaced from the RBS created downstream of the holB gene in plasmid pA1-SA-holB.

J. Construction of pA1-CB-SphI.

There is a need, in the construction of the next constructs, for a new expression vector. The vector pA1-CB-NcoI is modified to create the new vector pA1-CB-SphI. This is accomplished by synthesizing two oligonucleotides (SEQ ID NO:73 and SEQ ID NO:74) and annealing them so that there is a PacI sticky end on the 5' end and a KpnI sticky end on the 3' end.

The pA1-CB-NcoI plasmid is digested with PacI/KpnI restriction enzymes. The annealed oligonucleotides are inserted into the digested pA1-CB-NcoI thereby creating the new vector pA1-CB-SphI with a polyclonal region containing the restriction sites: PacI, SphI, NheI, KpnI, SpeI (SEQ ID NO:75). The only change between pA1-CB-NcoI and pA1-CB-SphI is the replacement of the NcoI restriction site by SphI. This allows a gene in which the start ATG is immediately followed by a "C" to be inserted into a vector and the spacing between the RBS and the start codon to be optimal.

K. Construction of pA1-SA-dnaG (Primase).

The S. aureus dnaG gene was identified in the NCBI database by a homology search using dnaG from S. pyogenes. The DnaG subunit is composed of 605 amino acids (SEQ ID NO:78). The gene encoding DnaG is dnaG, and is composed of 1719 nucleotides including the stop codon (SEQ ID NO:76). The start codon is TTG and is converted to ATG by the forward/sense primer in the PCR reaction. There are also two other low usage codons in the 5' end of the dnaG gene, which are converted to high usage codons by the forward primer. At position #2, the codon coding for Arg is changed from CGA>CGC and at position #3, the codon coding for Ile is changed from ATA>ATC.

The forward/sense primer (SEQ ID NO:79) contains a 4 nucleotide 5' clamp to allow efficient digestion by the restriction enzyme. A SphI restriction site follows the clamp, which is used for insertion into pA1-CB-SphI. The SphI restriction site overlaps the first four nucleotides of the gene. The first nine nucleotides of the gene do not correspond completely to the 5' end of the dnaG gene because of modification made by the forward primer to the first three codons. The next 20 nucleotides correspond to nucleotides 10-30 of the dnaG gene.

The reverse/antisense primer (SEQ ID NO:80) contains a 4 nucleotide 5' clamp to allow efficient digestion by the restriction enzyme. A SpeI restriction site follows the clamp, which is used for insertion into pA1-CB-SphI. The restriction site is followed by a second non-complementary stop codon that is adjacent to the native stop codon. The next 23 nucleotides are complementary to the 3' end of the dnaG gene. These two primers are used in a PCR reaction using S. aureus as a substrate and yield a PCR product containing the dnaG gene.

Both the S. aureus dnaG PCR product and the plasmid pA1-CB-SphI are digested with SphI/SpeI restriction enzymes. The fragment of the PCR product containing the dnaG gene (1.8 kb) is inserted into the SphI/SpeI digested pA1-CB-SphI. This places the dnaG gene optimally spaced from the upstream RBS and results in the plasmid pA1-SA-DnaG.

L. Construction of pA1-SA-ssb#1, #2, and #3 (SSB).

In the S. aureus genome we identified four ssb genes by a homology search using ssb from S. pyogenes. The first three SSB proteins and thus ssb genes are named SSB#1, #2 and #3. The three proteins encoded by these three genes are very similar, but different enough that their function or mode of function may vary. All three genes are cloned as individual constructs and then assembled into one operon in which all three genes can be expressed.

First, the S. aureus SSB#1 is composed of 141 amino acids (SEQ ID NO:83). The gene encoding SSB#1 is ssb#1, and is composed of 423 nucleotides including the stop codon (SEQ ID NO:81). The ssb#1 gene contains two low usage codons, one at position #2 and one at position #4. The codon at position #2 codes for Leu, and is changed by the forward/sense primer from TTA>CTG. The codon at position #4 codes for Arg, and is changed by the forward/sense primer from AGA>CGC.

The ssb#1 forward/sense primer (SEQ ID NO:84) contains a 4 nucleotide 5' clamp to allow efficient digestion by the restriction enzyme. An NdeI restriction site follows the clamp, which is used for insertion into pA1-CB-NdeI. The NdeI restriction site overlaps the first three nucleotides of the gene (start codon) but does not correspond completely to the 12 5' nucleotides of the ssb#1 gene because of modification made by the forward/sense primer to codons #2 and #4. The next 23 nucleotides correspond to nucleotides 13-36 of the ssb#1 gene.

The ssb#1 reverse/antisense primer (SEQ ID NO:85) contains a 4 nucleotide 5' clamp to allow efficient digestion by the restriction enzyme. Next, there are adjacent NheI and SphI restriction sites, respectively. The NheI restriction site is used for insertion into pA1-CB-NdeI. The SphI restriction site is used in operon construction. Following these two restriction sites is a one nucleotide spacer, which will provide optimal spacing between the new RBS and a downstream gene in operon construction. This spacer is followed by a PstI restriction site, which also is used as a spacer to provide optimal spacing between the RBS and the downstream gene in operon construction. Following the restriction sites is a new RBS for expression of the downstream gene. The RBS overlaps a second non-complementary stop codon that is adjacent to the native stop codon. The next 25 nucleotides are complementary to the 3' end of the ssb#1 gene. A PCR reaction with these two primers and S. aureus genomic DNA as a substrate gives the PCR product containing the S. Aureus ssb#1 gene.

Both the S. aureus ssb#1 PCR product and the plasmid pA1-CB-NdeI are digested with NdeI/NheI restriction enzymes. The fragment of the PCR product containing the ssb#1 gene (0.5 kb) is inserted into the NdeI/NheI digested pA1-CB-NdeI. This places the ssb#1 gene optimally spaced from the upstream RBS and results in the plasmid pA1-SA-ssb#1.

Second, the *S. aureus* SSB#2 is composed of 156 amino acids (SEQ ID NO:88). The gene encoding SSB#2 is ssb#2, and is composed of 468 nucleotides including the stop codon (SEQ ID NO:86). Codons #2, #4, #5 and #6 are low usage codons and are changed to high usage codons by the forward/sense primer. Codon #2 codes for Leu, and is changed from CTA>CTG. Codon #4 codes for Arg, and is changed from AGA>CGC. Codon #5 codes for Thr, and is changed from ACA>ACC. Codon #6 codes for Ile, and is changed from ATA>ATC.

The ssb#2 forward primer (SEQ ID NO:89) contains a 4 nucleotide 5' clamp to allow efficient digestion by the restriction enzyme. A SphI restriction site follows the clamp, which is used for insertion into pA1-CB-SphI. The SphI restriction site overlaps the first four nucleotides of the gene (start codon). The first 18 nucleotides do not correspond completely to the 5' end of the ssb#2 gene because of modification made by the forward/sense primer to codons #2, #4, #5 and #6. The next 20 nucleotides correspond to nucleotides 19-39 of the ssb#2 gene.

The ssb#2 reverse primer (SEQ ID NO:90) contains a 4 nucleotide 5' clamp to allow efficient digestion by the restriction enzyme. Next, there are adjacent KpnI, ClaI and PstI restriction sites, respectively. The KpnI restriction site is used for insertion into pA1-CB-SphI. The ClaI restriction site is used in operon construction. Next is a PstI restriction site, which is used as a spacer to provide optimal spacing between the RBS and the downstream gene in operon construction. Following the restriction sites is a new RBS for expression of the downstream gene. The RBS overlaps a second non-complementary stop codon that is adjacent to the native stop codon. The next 21 nucleotides are complementary to the 3' end of the ssb#2 gene. A PCR reaction with these two primers and *S. aureus* genomic DNA as a substrate gives the PCR product containing the ssb#2 gene.

Both the *S. aureus* ssb#2 PCR product and the plasmid pA1-CB-SphI are digested with SphI/KpnI restriction enzymes. The fragment of the PCR product containing the ssb#2 gene (0.5 kb) is inserted into the SphI/KpnI digested pA1-CB-SphI. This places the ssb#2 gene optimally spaced from the upstream RBS and results in the plasmid pA1-SA-ssb#2.

Third, the *S. aureus* SSB#3 is composed of 167 amino acids (SEQ ID NO:93). The gene encoding SSB#3 is ssb#3, and is composed of 501 nucleotides including the stop codon (SEQ ID NO:91). The ssb#3 gene contains low usage codons at positions #2, #3 and #4 which are changed to high usage codons by the forward/sense primer. Codon #2 codes for Leu, and is changed from CTA>CTG. Codon #3 codes for Asn, and is changed from AAT>AAC. Codon #4 codes for Arg, and is changed from AGA>CGC.

The ssb#3 forward/sense primer (SEQ ID NO:94) contains a 4 nucleotide 5' clamp to allow efficient digestion by the restriction enzyme. PacI and ClaI restriction sites are overlapping and follow the clamp. The PacI restriction site is used for insertion into pA1-CB-NdeI. The ClaI restriction site is used later for operon construction. The ClaI restriction site overlaps the first two nucleotides of the gene (start codon). The first four codons do not correspond completely to the 5' end of the ssb#3 gene because of modification made by the forward/sense primer to codons #2, #3 and #4. The next 23 nucleotides are underlined and correspond to nucleotides 13-36 of the ssb#3 gene.

The ssb#3 reverse/antisense primer (SEQ ID NO:95) contains a 4 nucleotide 5' clamp to allow efficient digestion by the restriction enzyme. Next, there is a SpeI restriction site for insertion into pA1-CB-NdeI. Following the restriction site is a second non-complementary stop codon that is adjacent to the native stop codon. The next 23 nucleotides are complementary to the 3' end of the ssb#3 gene. A PCR reaction with these two primers and *S. aureus* genomic DNA as a substrate gives the PCR product containing the *S. aureus* ssb#3 gene.

Both the *S. aureus* ssb#3 PCR product and the plasmid pA1-CB-NdeI are digested with PacI/SpeI restriction enzymes. The fragment of the PCR product containing the ssb#3 gene (0.5 kb) is inserted into the PacI/SpeI digested pA1-CB-NdeI. This places the ssb#3 gene optimally spaced from the upstream RBS and results in the plasmid pA1-SA-ssb#3.

M. Construction of pA1-SA-SSBoperon (SSB#, #2 and #3).

The construction of an operon containing all three genes (ssb#1, ssb#2 and ssb#3) is accomplished in a two-step procedure. Both steps are simple cut and paste (digest and ligate reactions). First, both pA1-SA-SSB#1 and pA1-SA-SSB#2 are digested with SphI/KpnI restriction enzymes. The smaller fragment from the digested pA1-SA-SSB#2 plasmid, which contains the full length ssb#2 gene is inserted into the digested pA1-SA-SSB#1 plasmid. This results in a plasmid containing both ssb#1 and ssb#2 genes. This plasmid is named pA1-SA-SSB#1/2.

The ssb#2 gene is placed downstream of the ssb#1 gene and is optimally spaced from the second downstream RBS constructed in plasmid pA1-SA-SSB#1.

Second, both the pA1-SA-SSB#1/2 plasmid and the pA1-SA-SSB#3 plasmid are digested with ClaI and SpeI restriction enzymes. The smaller fragment (0.5 kb) from the digested pA1-SA-SSB#3 plasmid containing the full length ssb#3 gene is inserted into the digested pA1-SA-SSB#1/2 plasmid. This results in a plasmid containing all three ssb genes, ssb#1, ssb#2 and ssb#3. This plasmid is named pA1-SA-SSBoperon.

N. Construction of pA1-SA-ssb#4.

In the *S. aureus* genome we also identified a fourth ssb gene. This protein (SSB#4) is very similar to the other three SSB proteins, but different enough that its function or mode of function may vary. Therefore we also cloned this gene and inserted it into the pA1-CB-SphI vector.

The *S. aureus* SSB#4 is composed of 131 amino acids (SEQ ID NO:98). The gene encoding SSB#4 is ssb#4, and is composed of 396 nucleotides including the stop codon (SEQ ID NO:96). The ssb#4 gene contains three low usage codons, one at position #2, one at position #9 and one at position #10. The codon at position #2 codes for Leu, and is changed by the forward/sense primer from CTA>CTG. The codon at position #9 codes for Gly, and is changed by the forward/sense primer from GGG>GGT. The codon at position #10 codes for Arg, and is changed by the forward/sense primer from AGA>CGC The ssb#4 forward primer (SEQ ID NO:99) contains a 4 nucleotide 5' clamp to allow efficient digestion by the restriction enzyme. A SphI restriction site follows the clamp, which is used for insertion into pA1-CB-SphI. The SphI restriction site overlaps the first four nucleotides of the gene (including the start codon). However the first 30 nucleotides does not correspond completely to the 5' end of the ssb#4 gene because of modification made by the forward/sense primer to codons

2, #9 and #10. The next 23 nucleotides correspond to nucleotides 31-53 of the ssb#4 gene.

The ssb#4 reverse primer (SEQ ID NO: 100) contains a 4 nucleotide 5' clamp to allow efficient digestion by the restriction enzyme. Next, there a SpeI site. The SpeI restriction site is used for insertion into pA1-CB-SphI. A second additional stop codon is added in tandem with the native stop codon. The next 21 nucleotides are complementary to the 3' end of the ssb#4 gene. A PCR reaction with these two primers and *S. aureus* genomic DNA as a substrate gives the PCR product containing the full-length *S. aureus* ssb#4 gene.

Both, the *S. aureus* ssb#4 PCR product and the plasmid pA1-CB-SphI are digested with SphI/SpeI restriction enzymes. The fragment of the PCR product containing the ssb#4 gene (0.4 kb) is inserted into the SphI/SpeI digested pA1-CB-SphI. This places the ssb#4 gene optimally spaced from the upstream RBS and results in the plasmid pA1-SA-ssb#4.

Example 37

Purification of the *S. aureus* Ssb3 and Ssb4 Proteins, and Identification of *S. aureus* Ssb3 as the Replicative Ssb A. Identification and Analysis of *S. aureus* Genes for ssb.

The NCBI database was searched for *S. aureus* genes that appeared to encode ssbs. At the time these searches were carried out, the NCBI database contained the chromosomal DNA sequences for three strains of *S. aureus*, designated N315, Mu50, and MW2. In addition, the database contained the sequence of the closely related *Staphylococcus* strain, *S. epidermidis*. The searches were initiated with the ssb sequence from *S. pyogenes*. Four ssb genes were identified and were designated ssb1, ssb2, ssb3, and ssb4 (Table 27).

TABLE 27

| | Ssb name | | | |
|---|---|---|---|---|
| | Ssb1 | Ssb2 | Ssb3 | Ssb4 |
| | | Ssb size (a.a.) | | |
| Strain | 141 | 156 | 167 | 131 |
| *S. aureus* N315 | — | SA1792 | SA0353 | SA1899 |
| *S. aureus* Mu50 | SAV0864 | SAV1983 | SAV0366 | SAV2096 |
| *S. aureus* MW2 | — | MW1921 | MW0342 | MW2021 |
| *S. epidermidis* | — | — | SE2371 | SE1695 |

While one or more of these genes may encode the replicative ssb, the ssb used by the *Staphylococcus* host cell to support DNA replication, these genes may also code for ssbs expressed by prophages or expressed by the host to support other processes, such as sporulation. There was a need to identify the specific ssb that *S. aureus* utilizes to support replication of the host chromosome.

It can be seen that the gene for Ssb1 was only encoded by one of the chromosomal sequences, that of *S. aureus* Mu50, but was absent from the other three strains (Table 27). Similarly, while the gene for Ssb2 was encoded by the three *S. aureus* genomes, it was absent from the *S. epidermidis* genome. In addition, SAV0864 as well as the genes located next to it in the *S. aureus* Mu50 genome were annotated, "Bacteriophage phi mu1", SA1792 as well as the genes located next to it in the *S. aureus* N315 genome were annotated, "[Bacteriophage phiN315]", SAV1983 as well as the genes located next to it in the *S. aureus* Mu50 genome were annotated, "Bacteriophage phi Sa 3mu", and MW1921 as well as the genes located next to it in the *S. aureus* MW2 genome were annotated, "Bacteriophage phi Sa 3 mw". For these reasons, the determination was made that neither of the genes ssb1 or ssb2 encode the *S. aureus* replicative ssb.

The gene for Ssb3 is present in all four of the *Staphylococcus* genomes (Table 27). It was noted that SA0353, the gene for Ssb3 in the *S. aureus* N315 genome, SAV0366 in the *S. aureus* Mu50 genome, and SE2371 in the *S. epidermidis* genome were all annotated "single-strand DNA-binding protein of phage phi PVL", and MW0342 in the *S. aureus* MW2 genome was annotated "single-strand DNA-binding protein of phage phi Sa 2 mw". Based on this information, it is possible that that the gene for Ssb3 actually does encode a phage protein. However, we noticed that in each case this gene was flanked by rpsF, the gene for 30S ribosomal protein S6, and rpsR, the gene for ribosomal protein S18. These two ribosomal proteins are essential host genes and it is therefore unlikely that the gene for Ssb3, which lies between them, would encode a phage protein. Therefore, despite the annotations described above, the determination was made that Ssb3 was a good candidate for the host-encoded replicative ssb.

The gene for Ssb4 is also present in all four of the *Staphylococcus* genomes (Table 27). It was noted that SA1899, the gene for Ssb4 in the *S. aureus* N315 genome, SAV2096, the gene for Ssb4 in the *S. aureus* Mu50 genome, and MW2021, the gene for Ssb4 in the *S. aureus* MW2 genome, were all annotated, "similar to single strand DNA binding protein", while SE1695, the gene for Ssb4 in the *S. epidermidis* genome, was simply annotated, "single strand DNA binding protein". In addition, none of these genes for Ssb4, nor the genes flanking them, were annotated as being phage encoded. The determination was made that Ssb4 was also a good candidate for the host-encoded replicative ssb.

B. Purification of *S. aureus* Ssb3.

Strain pA1-SA-ssb3(1)/DH5α was grown in a 250 L fermentor (Fermentation Run #03-25), to produce a large-scale growth of cells for purification of *S. aureus* Ssb3. F-medium (1.4% yeast extract, 0.8% tryptone, 1.2% $K_2HPO_4$, and 0.12% $KH_2PO_4$, pH 7.2) was sterilized, glucose was added to 1% from a 40% sterile solution and ampicillin (100 mg/L) was added. A large-scale inoculum (to 28 L), was initiated from a 1 ml glycerol stock culture (i.e., culture stored in 15% glycerol at −80° C.) and grown overnight at 37° C. with 40 LPM aeration. The inoculum was transferred (approximately 7.5 L) to the 250 L fermentor containing 160 L of F-medium with 1% glucose, and 100 mg/L ampicillin, starting $OD_{600}$ of 0.06. To calculate the amount of overnight culture to add to a fermentor run, enough should be added to bring the media present in the fermentor to an $OD_{600}$=0.06. This allows enough time for the cell density to double 3-4 times before induction. Quality control of the inoculum showed that 10 out of 10 colonies grown on LB media were also able to grow on ampicillin-containing medium. The culture was incubated at 37° C., with 40 LPM aeration, and stirred at 20 rpm. Expression of *S. aureus* ssb3 was induced by addition of IPTG to 1 mM when the culture reached an $OD_{600}$=0.925. The pH was maintained at 7.2 throughout the growth by addition of $NH_4OH$. Cell harvest was initiated 3 hours after induction and the cells were chilled to 10° C. during harvest. The harvest volume was 170 L, and the final harvest weight was approximately 2.09 kg of cell paste. An equal amount (w/w) of Tris-sucrose buffer (50 mM Tris (pH 7.5), 10% sucrose) was added to the cell paste. Cells were frozen by pouring the cells suspension into liquid nitrogen, and stored at −20° C., until processed.

Frozen cells were lysed by adding 150 g of a 1:1 suspension of frozen cells (75 g cells) in Tris-sucrose which had been stored at −20° C. to 206 ml Tris-sucrose buffer that had been pre-warmed to 45° C. (2.75 ml/g of cells). To inhibit proteases, 3.5 ml of 0.1 M phenylmethylsulfonylfluoride (PMSF, made fresh in isopropanol) and 7 dissolved protease inhibitor pellets ("Complete, EDTA-free", Roche) (I pellet/10 g of cells) were added. Dissolved protease inhibitor pellets were made by crushing and then dissolving in room-temperature Tris-Sucrose buffer (3 ml/pellet) with stirring. To the stirred mixture, 3.75 ml of 0.5 M 1,4-dithiothreitol (DTT) (0.05 ml/g of cells) and 18.75 ml of lysis buffer (2M NaCl, 0.3M spermidine in Tris-sucrose adjusted to pH 7.5) (0.25 ml/g of cells) were added. The pH of the slurry was tested with pH paper and adjusted to pH 8.0 by the addition of 2 M Tris base. Lysozyme (300 mg) was added in 15 ml of Tris-sucrose buffer (4 mg lysozyme/g of cells). After stirring 5 min the slurry was distributed into 350 ml centrifuge bottles and incubated at 4° C. for 1 hour. The 350 ml centrifuge bottles were then placed in a 37° C. swirling water bath and gently inverted every 30 seconds for 4 minutes. The insoluble cellular components were removed by centrifugation (23,000×g, 60 min, 4° C.). The recovered supernatant (334 ml) constituted Fraction I.

To 334 ml of Fraction I, ammonium sulfate (0.197 g for each initial ml of Fraction I; 35% saturation) was added over a 15 min interval. The mixture was stirred for an additional 30 min at 4° C. and the precipitate collected by centrifugation (23,000×g, 60 min, 4° C.). The pellet containing the 0-35% cut was resuspended in 50 ml of Buffer T (50 mM Tris-HCl, pH 7.5, 20% glycerol, 1.0 mM EDTA, and 5 mM DTT) containing no NaCl and frozen at −80° C. The resuspended pellets constituted Fraction II (50 ml, 1.956 mg/mil).

One half of Fraction II (48.9 mg) was loaded onto a Blue Dextran Sepharose 4B column (5.0 ml) equilibrated in Buffer T containing 100 mM NaCl at a flow rate of 0.14 ml/min. The column was washed with 40 ml of Buffer T containing 100 mM NaCl at a flow rate of 0.04 ml/min. The protein was eluted with 40 ml of Buffer T containing 0.5 M NaCl at a flow rate of 0.13 ml/min, followed by 30 ml of Buffer T containing 1.0 M NaCl at a flow rate of 0.13 ml/min. The eluate was collected in 2.0 fractions and analyzed for protein and by electrophoresis onto 10-20% SDS-PAGE gels (8×6.8×0.1 cm). The protein assay was carried out using BSA as a standard. Fractions 22-36 containing the S. aureus Ssb3 were pooled (Fraction III).

Fraction III (2.0 mg) was loaded onto a hydroxylapatite column (5.0 ml) equilibrated in Buffer T containing 400 mM NaCl at a flow rate of 0.1 ml/min. The column was washed with 15 ml of Buffer T containing 400 mM NaCl at a flow rate of 0.1 ml/min, followed by 25 ml of Buffer T containing 400 mM NaCl and 140 mM $KPO_4$ buffer at a flow rate of 0.1 ml/min. The eluate was collected in 2.2 ml fractions and analyzed by protein assays. The Ssb3 eluted as a peak between fractions 4-10, and fractions were frozen away individually.

C. Purification of S. aureus Ssb4.

Strain pA1-SA-ssb#4/DH5α was grown in a 250 L fermentor (Fermentation Run #03-29), to produce a large-scale growth of cells for purification of S. aureus Ssb4. F-medium (1.4% yeast extract, 0.8% tryptone, 1.2% $K_2HPO_4$, and 0.12% $KH_2PO_4$, pH 7.2) was sterilized, glucose was added to 1% from a 40% sterile solution and ampicillin (100 mg/L) was added. A large-scale inoculum (to 28 L), was initiated from a 1 ml glycerol stock culture (i.e., culture stored in 15% glycerol at −80° C.) and grown overnight at 37° C. with 40 LPM aeration. The inoculum was transferred (approximately 10.0 L) to the 250 L fermentor containing 160 L of F-medium with 1% glucose, and 100 mg/L ampicillin, starting $OD_{600}$ of 0.06. To calculate the amount of overnight culture to add to a fermentor run, enough should be added to bring the media present in the fermentor to an $OD_{600}$=0.06. This allows enough time for the cell density to double 3-4 times before induction. Quality control of the inoculum showed that 10 out of 10 colonies grown on LB media were also able to grow on ampicillin-containing medium. The culture was incubated at 37° C., with 40 LPM aeration, and stirred at 20 rpm. Expression of S. aureus ssb4 was induced by addition of IPTG to 1 mM when the culture reached an $OD_{600}$=1.17. The pH was maintained at 7.2 throughout the growth by addition of $NH_4OH$. Cell harvest was initiated 3 hours after induction at $OD_{600}$ equivalent of 5.88, and the cells were chilled to 10° C. during harvest. The harvest volume was 170 L, and the final harvest weight was approximately 2.22 kg of cell paste. An equal amount (w/w) of Tris-sucrose buffer (50 mM Tris (pH 7.5), 10% sucrose) was added to the cell paste. Cells were frozen by pouring the cells suspension into liquid nitrogen, and stored at −20° C., until processed.

Frozen cells were lysed by adding 236 g of a 1:1 suspension of frozen cells (118 g cells) in Tris-sucrose which had been stored at −20° C. to 325 ml Tris-sucrose buffer that had been pre-warmed to 45° C. (2.75 ml/g of cells). To inhibit proteases, 5.0 ml of 0.1 M phenylmethylsulfonylfluoride (PMSF, made fresh in isopropanol) and 10 dissolved protease inhibitor pellets ("Complete, EDTA-free", Roche) (1 pellet/10 g of cells) were added. Dissolved protease inhibitor pellets were made by crushing and then dissolving in room-temperature Tris-Sucrose buffer (3 ml/pellet) with stifling. To the stirred mixture, 5.9 ml of 0.5 M 1,4-dithiothreitol (DTT) (0.05 ml/g of cells) and 29.5 ml of lysis buffer (2M NaCl, 0.3M spermidine in Tris-sucrose adjusted to pH 7.5) (0.25 ml/g of cells) were added. The pH of the slurry was tested with pH paper and adjusted to pH 8.0 by the addition of 2 M Tris base. Lysozyme (472 mg) was added in 15 ml of Tris-sucrose buffer (4 mg lysozyme/g of cells). After stirring 5 min the slurry was distributed into 350 ml centrifuge bottles and incubated at 4° C. for 1 hour. The 350 ml centrifuge bottles were then placed in a 37° C. swirling water bath and gently inverted every 30 seconds for 4 minutes. The insoluble cellular components were removed by centrifugation (23,000×g, 60 min, 4° C.). The recovered supernatant (515 ml, 9.7 mg/ml) constituted Fraction I.

To 515 ml of Fraction I, ammonium sulfate (0.331 g for each initial ml of Fraction I; 55% saturation) was added over a 15 min interval. The mixture was stirred for an additional 30 min at 4° C. and the precipitate collected by centrifugation (23,000×g, 60 min, 4° C.). The pellet containing the 0-55% cut was resuspended in 225 ml of Buffer T (50 mM Tris-HCl, pH 7.5, 20% glycerol, 1.0 mM EDTA, and 5 mM DTT) containing no NaCl and frozen at −80° C. The resuspended pellets constituted Fraction II (225 ml, 12.2 mg/mil).

A portion of Fraction II (91.7 mg) was loaded onto a Blue Dextran Sepharose 4B column (5.0 ml) equilibrated in Buffer T containing 100 mM NaCl at a flow rate of 0.1 ml/min. The column was washed with 20 ml of Buffer T containing 100 mM NaCl at a flow rate of 0.1 ml/min. The protein was eluted with 20 ml of Buffer T containing 0.5 M NaCl at a flow rate of 0.1 ml/min, followed by 30 ml of Buffer T containing 1.0 M NaCl at a flow rate of 0.1 ml/min. The eluate was collected in 2.0 ml fractions and analyzed for protein and by electrophoresis onto 10-20% SDS-PAGE gels (8×6.8×0.1 cm). The protein assay was carried out using BSA as a standard. Fractions 5-15 containing the S. aureus Ssb4 were pooled (Fraction III).

Fraction III (13.3 mg) was loaded onto a hydroxylapatite column (5.0 ml) equilibrated in Buffer E (50 mM imidazole, pH 7.5, 20% glycerol, 1.0 mM NaCl, and 5 mM DTT) at a flow rate of 0.1 ml/min. The column was washed with 30 ml of Buffer E at a flow rate of 0.2 ml/min, followed by 22 ml of Buffer E containing 70 mM $KPO_4$ buffer at a flow rate of 0.2 ml/min. The eluate was analyzed by SDS-PAGE. The Ssb4 eluted in the 70 mM $KPO_4$ bump (Fraction IV).

Fraction IV (7.2 mg) was loaded directly onto a Q Sepharose High Performance column (5.0 ml) equilibrated in Buffer T containing 100 mM NaCl at a flow rate of 0.1 ml/min. The protein was eluted in 100 ml of Buffer T using a 100-500 mM NaCl gradient at a flow rate of 0.04 ml/min. The eluate was collected in 1.0 ml fractions and analyzed by protein assays and SDS-PAGE. The Ssb4 eluted as a single, concentrated peak of protein. Fractions 32-42 containing Ssb4 were frozen away individually.

D. Assay to Determine the Ability of S. aureus Ssb3 and Ssb4 to Support DNA Replication with S. aureus Proteins.

The replication of a DNA-primed single-stranded circular M13 DNA template using S. aureus replication proteins is dependent on the presence of a single-stranded DNA binding protein to coat the single-stranded DNA. DNA synthesis dependent on the presence of an ssb was measured in assay mixtures (25 µl) containing 35 mM HEPES (pH 7.5), 14% glycerol, 0.014% Nonidet P-40, 0.14 mg/mil BSA, 10 mM $MgCl_2$, 2.3 nM (as circles) of DNA oligonucleotide-primed single-stranded circular M13 DNA, 1 mM ATP, 48 µM each of dGTP, dATP, and dCTP, and 18 µM [$^3$H]TTP (approximately 60 cpm/pmol of total nucleotide). Reactions also contained S. aureus PolC protein (2.3 nM), S. aureus Beta subunit (15.4 nM), S. aureus Tau Complex (11.2 nM) and ssb, added as indicated in the experiment. The purifications of S. aureus PolC, Beta subunit, and Tau Complex are described below. The reactions were assembled on ice, initiated by starting incubation at 30° C., and incubated at 30° C. for 5 minutes. Reactions were terminated by placing the reaction tubes on ice, adding one drop of 0.2 M sodium pyrophosphate ($PP_i$), and 0.5 ml of 10% trichloroacetic acid. The amount of DNA synthesized was measured by filtering the mixture through GF/C filters (Whatman), trapping DNA products and removing unincorporated nucleoside triphosphates. Filters were washed with 12 ml 0.2M sodium $PP_i$/1M HCl followed by 4 ml of ethanol. The filters were dried and the incorporated [$^3$H]TMP was quantified by immersing the filters in 5 ml of liquid scintillation fluid (Ecoscint O, National Diagnostics) and counting with a Wallac 1450 MicroBeta TriLux scintillation counter (Perkin Elmer).

S. aureus Ssb3 and Ssb4 were tested for the ability to support DNA replication with S. aureus proteins as described above (FIG. 29). The S. aureus ssb preparations used were Ssb3, hydroxylapatite fraction 6, and Ssb4, Q Sepharose fraction 36 (see above). S. aureus Ssb3 and Ssb4 were added as indicated (9, 18, and 36 pmol of tetramer). As shown, S. aureus Ssb3 supported DNA replication in this system, but Ssb4 did not.

Since S. aureus Ssb3 was encoded by four out of four sequenced Staphylococcus genomes, and its gene is flanked on either side by the essential host genes rpsF and rpsR, and since it was active in supporting DNA replication using S. aureus proteins, Ssb3 was identified as the Staphylococcus replicative single-strand DNA-binding protein in vivo.

Example 38

Purification of the S. aureus PolC Protein after Modification of the Gene Encoding PolC to Abolish Expression of Truncated Forms of PolC A. Modification of the Gene Encoding S. aureus PolC.

An early purification of S. aureus PolC revealed that the preparation appeared to contain full-length PolC as well as two smaller proteins that appeared to be truncated forms of the full-length PolC. Cell cultures were grown from AP1.L1 and DH5α expressing S. aureus polC from plasmid pA1-SA-polC. Expression of PolC was induced by the addition of IPTG to 1 mM. Aliquots of the cultures were taken at 0, 1, 2, 3, 4, and 5 hours post-induction and the protein expression profile was analyzed by SDS-PAGE. The full-length form as well as the two smaller forms were all induced concurrently upon the addition of IPTG (FIG. 30).

An extract made from cells expressing PolC was partially purified using DEAE-Sepharose. The protein extract (770 mg) was loaded onto a DEAE Sepharose Fast Flow column (70 ml) equilibrated in Buffer B (20 mM Tris-HCl, pH 8.0, 30% glycerol, 0.025 mM EDTA, and 2 mM DTT) containing 20 mM NaCl. The protein was eluted in 700 ml of Buffer B using a 20-400 mM gradient of NaCl at a flow rate of 1.0 ml/min. The eluate was collected in 8 ml fractions and analyzed by protein assay and SDS-PAGE. The full-length form of S. aureus PolC as well as the two smaller forms all eluted from the column in a similar manner during chromatography (FIG. 31).

The amino-terminal amino acid sequence was determined for each of the three PolC peptides, using standard procedures (FIG. 32). The sequence of the upper band corresponded to the amino terminal sequence of the full-length protein as predicted from the translation of the nucleotide sequence. The sequences of the middle and lower bands corresponded to amino acid sequences beginning with amino acids 196 and 312, respectively, of the amino acid sequence as predicted from the translation of the nucleotide sequence. This confirmed that all three peptides were products of the S. aureus polC gene.

There was a need to express the S. aureus polC gene under conditions that resulted in production of only the full-length PolC polypeptide. The smaller forms of PolC appearing along with the full-length form may be produced as the result of proteolytic degradation of the full-length PolC by proteases in the E. coli extract. Surprisingly, each of the peptides contained a methionine residue as the first amino acid at its amino terminus (FIG. 32). We therefore considered the possibility that the smaller forms of PolC arose by separate translation initiation events at sites within the polC coding region.

We found a putative ribosome binding sequence in the polC gene that lies upstream of the methionine codon that initiates the first of the smaller PolC forms (corresponding to the middle PolC band on the gel; FIG. 33). The potential ribosome binding site, AGAGA (bolded in FIG. 33), lies sixteen nucleotides upstream of the methionine codon, also bolded in the figure. It was decided to express the polymerase from a polC gene with a nucleotide sequence that has been altered so that the predicted ribosome binding site has been obliterated, but the amino acid sequence is unchanged (bolded sequence TGAAA, FIG. 34). Similarly, another potential ribosome binding sequence (AGAGA, bolded in FIG. 35) lies twelve nucleotides upstream of the methionine codon that initiates the second of the smaller PolC forms (corresponding to the lower PolC band on the gel; FIG. 35). It was decided to express the polymerase from a polC gene with a nucleotide sequence that has been altered so that the second predicted ribosome binding site has also been obliterated, but the amino acid sequence is unchanged (CGCGA, bolded in FIG. 36).

A modified polC gene was created in which the nucleotide sequence was altered as described above but the translated amino acid sequence was unchanged. This work was carried out at ATG Laboratories, Inc., Eden Prairie, Minn. The resulting polC-expressing plasmid was designated pA1-SA-polCrevised. The modified polC coding sequence is represented as SEQ ID NO:101.

B. Purification of S. aureus PolC.

Strain pA1-SA-polCrevised/AP1.L1 was grown in a 250 L fermentor (Fermentation Run #03-14), to produce a large-scale growth of cells for purification of S. aureus PolC. F-medium (1.4% yeast extract, 0.8% tryptone, 1.2% $K_2HPO_4$, and 0.12% $KH_2PO_4$, pH 7.2) was sterilized, glucose was added to 1% from a 40% sterile solution and ampicillin (100 mg/L) was added. A large-scale inoculum (to 28 L), was initiated from a 1 ml glycerol stock culture (i.e., culture stored in 15% glycerol at –80° C.) and grown overnight at 37° C. with 40 LPM aeration. The inoculum was transferred (approximately 4.5 L) to the 250 L fermentor containing 160 L of F-medium with 1% glucose, and 100 mg/L ampicillin, starting $OD_{600}$ of 0.06. To calculate the amount of overnight culture to add to a fermentor run, enough should be added to bring the media present in the fermentor to an $OD_{600}$=0.06. This allows enough time for the cell density to double 3-4 times before induction. Quality control of the inoculum showed that 10 out of 10 colonies grown on LB media were also able to grow on ampicillin-containing medium. The culture was incubated at 37° C., with 40 LPM aeration, and stirred at 20 rpm. Expression of S. aureus polCrevised was induced by addition of IPTG to 1 mM when the culture reached an $OD_{600}$=0.612. The pH was maintained at 7.2 throughout the growth by addition of $NH_4OH$. Cell harvest was initiated 3 hours after induction at $OD_{600}$ equivalent of 5.60, and the cells were chilled to 10° C. during harvest. The harvest volume was 170 L, and the final harvest weight was approximately 1.81 kg of cell paste. An equal amount (w/w) of Tris-sucrose buffer (50 mM Tris (pH 7.5), 10% sucrose) was added to the cell paste. Cells were frozen by pouring the cells suspension into liquid nitrogen, and stored at –20° C., until processed.

Frozen cells were lysed by adding 1200 g of a 1:1 suspension of frozen cells (600 g cells) in Tris-sucrose which had been stored at –20° C. to 1650 ml Tris-sucrose buffer that had been pre-warmed to 45° C. (2.75 ml/g of cells). To inhibit proteases, 30.0 ml of 0.1 M phenylmethylsulfonylfluoride (PMSF, made fresh in isopropanol) (0.05 ml/g of cells) and dissolved protease inhibitor pellets ("Complete, EDTA-free", Roche) (1 pellet/12 g of cells) were added. Dissolved protease inhibitor pellets were made by crushing and then dissolving in room-temperature Tris-Sucrose buffer (3 ml/pellet) with stirring. To the stirred mixture, 30 ml of 0.5 M 1,4-dithiothreitol (DTT) (0.05 ml/g of cells) and 150 ml of lysis buffer (2M NaCl, 0.3M spermidine in Tris-sucrose adjusted to pH 7.5) (0.25 ml/g of cells) was added. The pH of the slurry was tested with pH paper and adjusted to pH 8.0 by the addition of 15 ml of 2 M Tris base. Lysozyme (2.4 g) was added in 50 ml of Tris-sucrose buffer (4 mg lysozyme/g of cells). After stirring 5 min the slurry was distributed into 350 ml centrifuge bottles and incubated at 4° C. for 1 hour. The 350 ml centrifuge bottles were then placed in a 37° C. swirling water bath and gently inverted every 30 seconds for 4 minutes. The insoluble cellular components were removed by centrifugation (23,000×g, 60 min, 4° C.). The recovered supernatant (2560 ml) constituted Fraction I (8.6 mg/ml). The above lysis was carried out twice, the second time on 750 g of cells. The resulting total Fraction I consisted of 5810 ml (7.9 mg/ml).

To 2560 ml of Fraction I, ammonium sulfate (0.166 g for each initial ml of Fraction I; 30% saturation) was added over a 15 min interval. The mixture was stirred for an additional 60 min at 4° C. and the precipitate collected by centrifugation (23,000×g, 60 min, 4° C.). Ammonium sulfate was added to the resulting supernatant (0.119 g to each ml of 30% supernatant, yielding 50% saturation) over a 15 min interval. The mixture was again stirred for 60 min at 4° C. and the precipitate collected by centrifugation (23,000×g, 60 min, 4° C.). The pellet containing the 30-50% cut was resuspended in 400 ml of Buffer A (50 mM Tris-HCl, pH 7.5, 10% glycerol, 0.5 mM EDTA, and 5 mM DTT) containing no NaCl and frozen at –80° C. The ammonium sulfate fractionation was carried out twice on a total of 5810 ml of Fraction I. The resuspended pellets constituted Fraction II (1000 ml, 15.1 mg/ml).

Fraction II (15233 mg) was diluted 2.2-fold with Buffer A without NaCl to a conductivity equivalent to Buffer A containing 200 mM NaCl and loaded onto a Heparin Sepharose 6 Fast Flow column (500 ml) equilibrated in Buffer A containing 200 mM NaCl at a flow rate of 2 ml/min. The column was washed with 1125 ml of Buffer A containing 200 mM NaCl at a flow rate of 3.7 ml/min. The protein was eluted in 4000 ml of Buffer A using a 200-800 mM NaCl gradient at a flow rate of 3.9 ml/min. The eluate was collected in 25 ml fractions and analyzed for protein, for ability to support DNA synthesis in the Recon assay, and by electrophoresis onto 4-12% SDS-PAGE gels (8×6.8×0.1 cm). The Recon assay was performed in EDB buffer for 5 minutes at 30 C in a 25 µl volume, using S. aureus beta and S. aureus tau complex at saturating concentrations, and using previously frozen primase mix made with E. coli primase and E. coli SSB. The EDB buffer and assay protocol are described in U.S. Pat. No. 6,677,146. Protein gels were stained with Coomassie Brilliant Blue. The S. aureus PolC eluted in a single peak (Fraction III; 500 ml).

Fraction III (784 mg) was diluted 4-fold with Buffer A without NaCl and loaded onto a DEAE Sepharose Fast Flow column (130 ml) equilibrated in Buffer A containing 100 mM NaCl at a flow rate of 1.5 ml/min. The protein was eluted in 600 ml of Buffer A using a 100-450 mM gradient of NaCl at a flow rate of 0.5 ml/min. The eluate was collected in 4 ml fractions and analyzed by protein and activity assays. The fractions were also analyzed using SDS-PAGE. The S. aureus PolC eluted as a peak in the middle of the gradient, and separated from most of the contaminating proteins. Fractions containing S. aureus PolC were pooled (Fraction IV; 44 ml).

Fraction IV (151.6 mg) was diluted 2.6-fold with Buffer A without NaCl and loaded onto a Q Sepharose High Performance column (45 ml) equilibrated in Buffer A plus 100 mM NaCl at a flow rate of 0.5 ml/min. The protein was eluted in 400 ml of Buffer A using a 100-500 mM gradient of NaCl at a flow rate of 0.4 ml/min. The eluted fractions (3.5 ml) were analyzed by protein and activity assays and by SDS-PAGE. There was no purification away from the few remaining contaminants at this stage. Neither the total units nor the specific activity were significantly changed by this step. Active fractions (45 ml, 158 mg) were not pooled but were purified individually by gel filtration in the following step.

A Superdex S-200 column (120 ml) was equilibrated in Buffer A containing 150 mM NaCl. Gel filtration was carried out on individual Q Sepharose fractions to remove the remaining minor contaminants. Because of the size limitations of the column, five separate runs were performed on roughly 10-15 mg of PolC per run. A 2.0 ml sample (6.6 mg/ml) was loaded onto the column at a flow rate of 0.2 ml/min. The sample was eluted from the column in 144 ml of Buffer A containing 150 mM NaCl at the same flow rate. The eluate was collected in 1.5 ml fractions. The protein concentrations were determined and the fractions were analyzed by SDS-PAGE. Fractions containing S. aureus PolC were included in the final pool (Fraction VI; 19 ml; 1.57 mg/mil). The gel filtration steps only resulted in a partial separation of PolC from other proteins, so only a 55% yield resulted after pooling the fractions containing pure polymerase. The final yield was 30 mg of PolC in the S-200 pool. The protein makeup from each step in the purification scheme was analyzed by SDS-polyacrylamide gel electrophoresis and is shown in a summary gel (FIG. 37). As can be seen, the full-length form of S. aureus PolC is expressed from the modified polC gene, polCrevised, but the two smaller forms of PolC are absent (FIG. 37).

Example 39

Purification of S. aureus Beta and S. aureus Tau Complex

A. Purification of S. aureus Beta.

Strain pA1-SA-dnaN/AP1.L1 was grown in a 250 L fermentor (Fermentation Run #03-03), to produce a large-scale growth of cells for purification of S. aureus beta. F-medium (1.4% yeast extract, 0.8% tryptone, 1.2% $K_2HPO_4$, and 0.12% $KH_2PO_4$, pH 7.2) was sterilized, glucose was added to 1% from a 40% sterile solution and ampicillin (100 mg/L) was added. A large-scale inoculum (to 28 L), was initiated from a 1 ml glycerol stock culture (i.e., culture stored in 15% glycerol at −80° C.) and grown overnight at 37° C. with 40 LPM aeration. The inoculum was transferred (approximately 4.0 L) to the 250 L fermentor containing 160 L of F-medium with 1% glucose, and 100 mg/L ampicillin, starting $OD_{600}$ of 0.06. To calculate the amount of overnight culture to add to a fermentor run, enough should be added to bring the media present in the fermentor to an $OD_{600}$=0.06. This allows enough time for the cell density to double 3-4 times before induction. Quality control of the inoculum showed that 10 out of 10 colonies grown on LB media were also able to grow on ampicillin-containing medium. The culture was incubated at 37° C., with 40 LPM aeration, and stirred at 20 rpm. Expression of S. aureus dnaN was induced by addition of IPTG to 1 mM when the culture reached an $OD_{600}$=0.740. The pH was maintained at 7.2 throughout the growth by addition of $NH_4OH$. Cell harvest was initiated 3 hours after induction at $OD_{600}$ equivalent of 5.52, and the cells were chilled to 10° C. during harvest. The harvest volume was 170 L, and the final harvest weight was approximately 1.93 kg of cell paste. An equal amount (w/w) of Tris-sucrose buffer (50 mM Tris (pH 7.5), 10% sucrose) was added to the cell paste. Cells were frozen by pouring the cells suspension into liquid nitrogen, and stored at −20° C., until processed.

Frozen cells were lysed by adding 300 g of a 1:1 suspension of frozen cells (150 g cells) in Tris-sucrose which had been stored at −20° C. to 412 ml Tris-sucrose buffer that had been pre-warmed to 45° C. (2.75 ml/g of cells). To inhibit proteases, 7.5 ml of 0.1 M phenylmethylsulfonylfluoride (PMSF, made fresh in isopropanol) (0.05 ml/g of cells) and dissolved protease inhibitor pellets ("Complete, EDTA-free", Roche) (1 pellet/12 g of cells) were added. Dissolved protease inhibitor pellets were made by crushing and then dissolving in room-temperature Tris-Sucrose buffer (3 ml/pellet) with stirring. To the stirred mixture, 7.5 ml of 0.5 M 1,4-dithiothreitol (DTT) (0.05 ml/g of cells) and 37.5 ml of lysis buffer (2M NaCl, 0.3M spermidine in Tris-sucrose adjusted to pH 7.5) (0.25 ml/g of cells) were added. The pH of the slurry was tested with pH paper and adjusted to pH 8.0 by the addition of 5 ml of 2 M Tris base. Lysozyme (600 mg) was added in 50 ml of Tris-sucrose buffer (4 mg lysozyme/g of cells). After stirring 5 min the slurry was distributed into 350 ml centrifuge bottles and incubated at 4° C. for 1 hour. The 350 ml centrifuge bottles were then placed in a 37° C. swirling water bath and gently inverted every 30 seconds for 4 minutes. The insoluble cellular components were removed by centrifugation (23,000×g, 60 min, 4° C.). The recovered supernatant (654 ml) constituted Fraction I (20.8 mg/ml).

To 654 ml of Fraction I, ammonium sulfate (0.442 g for each initial ml of Fraction I; 70% saturation) was added over a 15 min interval. The mixture was stirred for an additional 30 min at 4° C. and the precipitate collected by centrifugation (23,000×g, 60 min, 4° C.). Ammonium sulfate was added to the resulting supernatant (0.136 g to each ml of 70% supernatant, yielding 90% saturation) over a 15 min interval. The mixture was again stirred for 30 min at 4° C. and the precipitate collected by centrifugation (23,000×g, 60 min, 4° C.). The pellet containing the 70-90% cut was resuspended in Buffer A (50 mM Tris-HCl, pH 7.5, 10% glycerol, 0.5 mM EDTA, and 5 mM DTT) containing no NaCl and frozen at −80° C. The resuspended pellets constituted Fraction II (42 ml, 11.2 mg/ml).

Fraction II (470 mg) was diluted 13-fold with Buffer A without NaCl to a conductivity equivalent to Buffer A containing 25 mM NaCl and loaded onto a Q Sepharose High Performance column (450 ml) equilibrated in Buffer A containing 25 mM NaCl at a flow rate of 2 ml/min. The column was washed with 500 ml of Buffer A containing 25 mM NaCl at a flow rate of 5.1 ml/min. The protein was eluted in 4000 ml of Buffer A using a 25-525 mM NaCl gradient at a flow rate of 5.1 ml/min. The eluate was collected in 24 ml fractions and analyzed for protein, for ability to support DNA synthesis in the Recon assay, and by electrophoresis onto 4-12% SDS-PAGE gels (8×6.8×0.1 cm). The Recon assay was performed in EDB buffer for 5 minutes at 30 C in a 25 µl volume, using S. aureus PolC and S. aureus tau complex at saturating concentrations, and using previously frozen primase mix made with E. coli primase and E. Coli SSB. The EDB buffer and assay protocol are described in U.S. Pat. No. 6,677,146. Protein gels were stained with Simply Blue SafeStain (Invitrogen). The S. aureus beta eluted in a single peak (Fraction III; ~230 ml, 0.32 mg/ml). The final yield was 72.8 mg of beta in the Q Sepharose pool.

B. Purification of S. aureus Tau Complex.

Strain pA1-SA-BAX(1)/AP1.L1 was grown in a 250 L fermentor (Fermentation Run #03-02), to produce a large-scale growth of cells for purification of S. aureus Tau Complex. Note: For the purposes of the present document, 'Tau Complex' refers to the tau complex containing just 3 subunits with the stoichiometry (tau)$_3$: delta: delta prime. F-medium (1.4% yeast extract, 0.8% tryptone, 1.2% $K_2HPO_4$, and 0.12% $KH_2PO_4$, pH 7.2) was sterilized, glucose was added to 1% from a 40% sterile solution and ampicillin (100 mg/L) was added. A large-scale inoculum (to 28 L), was initiated from a 1 ml glycerol stock culture (i.e., culture stored in 15% glycerol at −80° C.) and grown overnight at 37° C. with 40 LPM aeration. The inoculum was transferred (approximately 4.5 L) to the 250 L fermentor containing 160 L of F-medium with 1% glucose, and 100 mg/L ampicillin, starting $OD_{600}$ of 0.06. To calculate the amount of overnight culture to add to a fermentor run, enough should be added to bring the media present in the fermentor to an $OD_{600}$=0.06. This allows enough time for the cell density to double 3-4 times before induction. Quality control of the inoculum showed that 10 out of 10 colonies grown on LB media were also able to grow on ampicillin-containing medium. The culture was incubated at 37° C., with 40 LPM aeration, and stirred at 20 rpm. Expression of S. aureus Tau Complex operon was induced by addition of IPTG to 1 mM when the culture reached an $OD_{600}$=0.900. The pH was maintained at 7.2 throughout the growth by addition of $NH_4OH$. Cell harvest was initiated 3 hours after induction at $OD_{600}$ equivalent of 6.52, and the cells were chilled to 10° C. during harvest. The harvest volume was 170 L, and the final harvest weight was approximately 2.06 kg of cell paste. An equal amount (w/w) of Tris-sucrose buffer (50 mM Tris (pH 7.5), 10% sucrose) was added to the cell paste. Cells were frozen by pouring the cells suspension into liquid nitrogen, and stored at −20° C., until processed.

Frozen cells were lysed by adding 1250 g of a 1:1 suspension of frozen cells (625 g cells) in Tris-sucrose which had been stored at −20° C. to 1725 ml Tris-sucrose buffer that had been pre-warmed to 45° C. (2.75 ml/g of cells). To the stirred mixture, 31.25 ml of 0.5 M 1,4-dithiothreitol (DTT) (0.05 ml/g of cells) and 156.25 ml of lysis buffer (2M NaCl, 0.3M spermidine in Tris-sucrose adjusted to pH 7.5) (0.25 ml/g of cells) was added. The pH of the slurry was tested with pH paper and adjusted to pH 7.5 by the addition of 17.5 ml of 2 M Tris base. Lysozyme (1.25 g) was added in 50 ml of Tris-sucrose buffer (2 mg lysozyme/g of cells). After stirring 5 min the slurry was distributed into 350 ml centrifuge bottles and incubated at 4° C. for 1 hour. The 350 ml centrifuge bottles were then placed in a 37° C. swirling water bath and gently inverted every 30 seconds for 4 minutes. The insoluble cellular components were removed by centrifugation (23,000×g, 60 min, 4° C.). The recovered supernatant (2600 ml) constituted Fraction I (16.5 mg/ml). The above lysis was carried out twice, and the resulting total Fraction I consisted of 5200 ml (16.3 mg/ml).

To 2600 ml of Fraction I, ammonium sulfate (0.213 g for each initial ml of Fraction I; 37% saturation) was added over a 15 min interval. The mixture was stirred for an additional 30 min at 4° C. and the precipitate collected by centrifugation (23,000×g, 60 min, 4° C.). Ammonium sulfate was added to the resulting supernatant (0.075 g to each ml of 37% supernatant, yielding 50% saturation) over a 15 min interval. The mixture was again stirred for 30 min at 4° C. and the precipitate collected by centrifugation (23,000×g, 60 min, 4° C.). The pellet containing the 37-50% cut was resuspended in 300 ml of Buffer A (50 mM Tris-HCl, pH 7.5, 10% glycerol, 0.5 mM EDTA, and 1 mM DTT) containing no NaCl and frozen at −80° C. The resuspended pellet constituted Fraction II (32.3 mg/ml). The ammonium sulfate fractionation was carried out twice on a total of 5200 ml of Fraction I.

One third of Fraction II (10594 mg, 328 ml) was diluted 6-fold with Buffer A without NaCl to a conductivity equivalent to Buffer A containing 135 mM NaCl and loaded onto a Heparin Sepharose column (450 ml) equilibrated in Buffer A containing 130 mM NaCl at a flow rate of 7 ml/min. The column was washed with 450 ml of Buffer A containing 130 mM NaCl at a flow rate of 7 ml/min. The protein was eluted in 4000 ml of Buffer A using a 135-500 mM NaCl gradient at a flow rate of 5.5 ml/min. The eluate was collected in 25 ml fractions and analyzed for protein, for ability to support DNA synthesis in the Recon assay, and by electrophoresis onto 4-12% SDS-PAGE gels (8×6.8×0.1 cm). The Recon assay was performed in EDB buffer for 5 minutes at 30 C in a 25 III volume, using *S. aureus* PolC and *S. aureus* beta at saturating concentrations, and using previously frozen primase mix made with *E. coli* primase and *E. coli* SSB. The EDB buffer and assay protocol are described in U.S. Pat. No. 6,677,146. Protein gels were stained with Coomassie Brilliant Blue. The *S. aureus* Tau Complex eluted in a single peak (Fraction III; 400 ml; 1.0 mg/ml). The above Heparin-Sepharose procedure was carried out two more times, yielding a total Fraction III of 1100 ml, 1.06 mg/ml. The Heparin column was washed with 1M NaCl between runs.

Fraction III (1166 mg) was loaded onto a hydroxylapatite column (450 ml; Hypatite C, Clarkson Chemical Company) equilibrated in Buffer B (50 mM imidazole, pH 6.8, 10% glycerol, 200 mM NaCl, 1 mM DTT, no EDTA) at a flow rate of 3.7 ml/min. The protein was eluted in 4000 ml of Buffer B using a 0-300 mM potassium phosphate buffer (KPB, pH 6.8) gradient at a flow rate of 3.7 ml/min. The eluate was collected in 25 ml fractions and analyzed by protein and activity assays. The fractions were also analyzed using SDS-PAGE. The *S. aureus* Tau Complex eluted as a peak in the middle of the gradient, and separated from most of the contaminating proteins. Fractions containing *S. aureus* Tau Complex were pooled (Fraction IV; 450 ml; 1.1 mg/ml).

An SP Sepharose High Performance column (450 ml) was equilibrated in Buffer A containing 100 mM NaCl. Fraction IV was diluted 4-fold with Buffer A containing no NaCl to a conductivity equivalent to Buffer A containing 100 mM NaCl (1780 ml final volume). The diluted sample was loaded onto the column at a flow rate of 420 ml/hr. The sample was eluted from the column in 4000 ml of a 100 to 400 mM NaCl gradient in Buffer A at a flow rate of 200 ml/l hr. The eluate was collected in 25 ml fractions. The protein concentrations and activity were determined and the fractions were analyzed using SDS-PAGE. The *S. aureus* Tau Complex eluted as a peak one third of the way through the gradient. Fractions containing *S. aureus* Tau Complex were pooled (Fraction V; 175 ml; 0.7 mg/ml).

What is claimed is:

1. A reconstituted bacterial replication assembly capable of functioning in a test for identifying compounds that modulate the ability of bacterial replication assembly to replicate DNA, where the reconstituted bacterial replication assembly comprises isolated *P. aeruginosa* DNA Polymerase III holoenzyme subunit proteins α, ε, τ, γ, δ, δ', χ, ψ, β; and SSB and primase, and wherein concentrations of the τ, δ, δ', χ and ψ are less than 1 nM.

* * * * *

UNITED STATES PATENT AND TRADEMARK OFFICE
CERTIFICATE OF CORRECTION

PATENT NO.       : 8,431,376 B2
APPLICATION NO.  : 11/568286
DATED            : April 30, 2013
INVENTOR(S)      : Jarvis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1811 days.

Signed and Sealed this
Eighth Day of September, 2015

Michelle K. Lee
*Director of the United States Patent and Trademark Office*

SEQUENCE LISTING

<160> NUMBER OF SEQ ID NOS: 106

<210> SEQ ID NO 1
<211> LENGTH: 9
<212> TYPE: DNA
<213> ORGANISM: Escherichia coli

<400> SEQUENCE: 1 ttatmcaca                                                          9

<210> SEQ ID NO 2
<211> LENGTH: 37
<212> TYPE: DNA
<213> ORGANISM: Artificial
<220> FEATURE:
<223> OTHER INFORMATION: primer

```
<400> SEQUENCE: 2
agtcttaatt aacatgcatt tcaccattca acgcgaa                              37

<210> SEQ ID NO 3
<211> LENGTH: 36
<212> TYPE: DNA
<213> ORGANISM: Artificial
<220> FEATURE:
<223> OTHER INFORMATION: primer

<400> SEQUENCE: 3
agtcactagt ttattagagg cgcatcggca tgacga                              36

<210> SEQ ID NO 4
<211> LENGTH: 36
<212> TYPE: DNA
<213> ORGANISM: Artificial
<220> FEATURE:
<223> OTHER INFORMATION: primer

<400> SEQUENCE: 4
agtcttaatt aagcttatga ccgtatcctt cgttca                              36

<210> SEQ ID NO 5
<211> LENGTH: 32
<212> TYPE: DNA
<213> ORGANISM: Artificial
<220> FEATURE:
<223> OTHER INFORMATION: primer

<400> SEQUENCE: 5
agtcactagt tattaacgat aattgaggaa ga                                  32

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
agtccatatg cgtagcgtcg tactggata                                      29

<210> SEQ ID NO 7
<211> LENGTH: 51
<212> TYPE: DNA
<213> ORGANISM: Artificial
<220> FEATURE:
<223> OTHER INFORMATION: primer

<400> SEQUENCE: 7
agtcgctagc aagcttattc ctcctctact attcgccgac cggcgcctcc a             51

<210> SEQ ID NO 8
<211> LENGTH: 44
<212> TYPE: DNA
<213> ORGANISM: Artificial
<220> FEATURE:
<223> OTHER INFORMATION: primer

<400> SEQUENCE: 8
agtcttaatt aagcttatga gctatcaagt tcttgcgcgt aaat                     44

<210> SEQ ID NO 9
<211> LENGTH: 32
<212> TYPE: DNA
```

```
<213> ORGANISM: Artificial
<220> FEATURE:
<223> OTHER INFORMATION: primer

<400> SEQUENCE: 9
agtcactagt ctatcaggcc ttggcttcca aa                                32

<210> SEQ ID NO 10
<211> LENGTH: 53
<212> TYPE: DNA
<213> ORGANISM: Artificial
<220> FEATURE:
<223> OTHER INFORMATION: primer

<400> SEQUENCE: 10
agtcttaatt aagctagcat gaaactgacc ccggcgcaac tcgccaagca cct          53

<210> SEQ ID NO 11
<211> LENGTH: 51
<212> TYPE: DNA
<213> ORGANISM: Artificial
<220> FEATURE:
<223> OTHER INFORMATION: primer

<400> SEQUENCE: 11
agtcactagt attaagcttt atcctcctct atcaggctgc ggcaggccg a             51

<210> SEQ ID NO 12
<211> LENGTH: 25
<212> TYPE: DNA
<213> ORGANISM: Artificial
<220> FEATURE:
<223> OTHER INFORMATION: primer

<400> SEQUENCE: 12
agtcccatgg ctgatatcta tccct                                         25

<210> SEQ ID NO 13
<211> LENGTH: 53
<212> TYPE: DNA
<213> ORGANISM: Artificial
<220> FEATURE:
<223> OTHER INFORMATION: primer

<400> SEQUENCE: 13
agtcactagt tatgctagct ttcctcctct actagcccgg cccgggcagg ctt          53

<210> SEQ ID NO 14
<211> LENGTH: 27
<212> TYPE: DNA
<213> ORGANISM: Artificial
<220> FEATURE:
<223> OTHER INFORMATION: primer

<400> SEQUENCE: 14
gatcctgcag gacgcggtgc tggtcca                                       27

<210> SEQ ID NO 15
<211> LENGTH: 26
<212> TYPE: DNA
<213> ORGANISM: Artificial
<220> FEATURE:
<223> OTHER INFORMATION: primer

<400> SEQUENCE: 15
gtcaactagt cgcctgaaaa cgaaga                                        26
```

```
<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
aggctggctg accttcatca agagtaatct                                      30

<210> SEQ ID NO 17
<211> LENGTH: 47
<212> TYPE: DNA
<213> ORGANISM: Artificial
<220> FEATURE:
<223> OTHER INFORMATION: primer

<400> SEQUENCE: 17
ggattctaga aggaggaagc tttagatgac ccgcgtcgat ttctacg                   47

<210> SEQ ID NO 18
<211> LENGTH: 40
<212> TYPE: DNA
<213> ORGANISM: Artificial
<220> FEATURE:
<223> OTHER INFORMATION: primer

<400> SEQUENCE: 18
ggatagatct cctcctggat ccatcagata cgcggcaggc                           40

<210> SEQ ID NO 19
<211> LENGTH: 41
<212> TYPE: DNA
<213> ORGANISM: Artificial
<220> FEATURE:
<223> OTHER INFORMATION: primer

<400> SEQUENCE: 19
ggattctaga aggaggagat ctacgatgcc tgtgcgtgcg c                         41

<210> SEQ ID NO 20
<211> LENGTH: 45
<212> TYPE: DNA
<213> ORGANISM: Artificial
<220> FEATURE:
<223> OTHER INFORMATION: primer

<400> SEQUENCE: 20
ggataagctt cctcctcgag tcatcattga atctcgctcg accag                     45

<210> SEQ ID NO 21
<211> LENGTH: 44
<212> TYPE: DNA
<213> ORGANISM: Artificial
<220> FEATURE:
<223> OTHER INFORMATION: primer

<400> SEQUENCE: 21
ggattctaga aggaggtacc aagcgatgca gattaccagt tggc                      44

<210> SEQ ID NO 22
<211> LENGTH: 19
<212> TYPE: DNA
<213> ORGANISM: Artificial
<220> FEATURE:
<223> OTHER INFORMATION: primer
```

<400> SEQUENCE: 22
cagcagcagg taacccgga                                                                                          19

<210> SEQ ID NO 23
<211> LENGTH: 46
<212> TYPE: DNA
<213> ORGANISM: Artificial
<220> FEATURE:
<223> OTHER INFORMATION: primer

<400> SEQUENCE: 23
ggattctaga aggaggtacc aactaatgat cgaagaacag cgtcgc                                    46

<210> SEQ ID NO 24
<211> LENGTH: 19
<212> TYPE: DNA
<213> ORGANISM: Artificial
<220> FEATURE:
<223> OTHER INFORMATION: primer

<400> SEQUENCE: 24
cagcagcagg taacccgga                                                                                          19

<210> SEQ ID NO 25
<211> LENGTH: 38
<212> TYPE: DNA
<213> ORGANISM: Artificial
<220> FEATURE:
<223> OTHER INFORMATION: primer

<400> SEQUENCE: 25
gatcatgcat acccgcgtcg atttctacgt gatcccca                                                    38

<210> SEQ ID NO 26
<211> LENGTH: 39
<212> TYPE: DNA
<213> ORGANISM: Artificial
<220> FEATURE:
<223> OTHER INFORMATION: primer

<400> SEQUENCE: 26
gcatactagt gagctctcat cagatacgcg gcaggcgat                                                 39

<210> SEQ ID NO 27
<211> LENGTH: 29
<212> TYPE: DNA
<213> ORGANISM: Artificial
<220> FEATURE:
<223> OTHER INFORMATION: primer

<400> SEQUENCE: 27
gactcatatg gccggcctga taccgcaaa                                                                    29

<210> SEQ ID NO 28
<211> LENGTH: 35
<212> TYPE: DNA
<213> ORGANISM: Artificial
<220> FEATURE:
<223> OTHER INFORMATION: primer

<400> SEQUENCE: 28
gactactagt tcatcagctc tgggaaggcg atgaa                                                        35

<210> SEQ ID NO 29
<211> LENGTH: 702
<212> TYPE: DNA

-continued

<213> ORGANISM: Pseudomonas aeruginosa

<400> SEQUENCE: 29

```
gtgcctgtgc gtgcgcgcgc cgcgatcgat gcgccgcagg cccgcgtccc gcaagccgag        60
gcgccggcca gcgcgccgag cgtggctccc gccgcgcccg tggaaggccg ggggatcccg       120
atcagcctgc cgaagccggg cgccccggcg gcgaagaaag ccgagccggt cgcgccggtc       180
gaagaggccc cggccgagtc gccggcggtc caggccccgc cgccgcgctt cgccttgcaa       240
ctgctgcagg cgggctcctg caccctgctg gtcgaactgc ccaccggcga acccttcgcc       300
agccgcgatc cgggttacct gctgctgcgc gacctgctgc gcgccgccgg cctgccggac       360
agcccgcggc tgatcggcga accggtacgc tggccgctgc tggcgcgcgg caacctcgac       420
cagggggccgc aggcggccct ggagttcgtc cagagcttcg tcgccgcgcg catggaggag       480
agcgagcgta gccgctgcct gtggttggtc ggcctgccgg cgatccgctt cgccggcgag       540
ggcgacgagg gcagcctgtt ccgcgagctg caggtggacg tctgggcgc aacctgggcc       600
gtgccaggcc tggaagccct catggaagaa cccgccctca agggcgagct gtggcgcgcc       660
atgcgccgtg tccgtcagcg ctggtcgagc gagattcaat ga                         702
```

<210> SEQ ID NO 30
<211> LENGTH: 702
<212> TYPE: DNA
<213> ORGANISM: Pseudomonas aeruginosa
<220> FEATURE:
<221> NAME/KEY: CDS
<222> LOCATION: (1)..(702)

<400> SEQUENCE: 30

```
atg cct gtg cgt gcg cgc gcc gcg atc gat gcg ccg cag gcc cgc gtc        48
Met Pro Val Arg Ala Arg Ala Ala Ile Asp Ala Pro Gln Ala Arg Val
1               5                   10                  15 ccg caa gcc gag gcg ccg gcc agc gcg ccg agc gtg gct ccc gcc gcg        96
Pro Gln Ala Glu Ala Pro Ala Ser Ala Pro Ser Val Ala Pro Ala Ala
                20                  25                  30 ccc gtg gaa ggc cgg ggg atc ccg atc agc ctg ccg aag ccg ggc gcc       144
Pro Val Glu Gly Arg Gly Ile Pro Ile Ser Leu Pro Lys Pro Gly Ala
            35                  40                  45 ccg gcg gcg aag aaa gcc gag ccg gtc gcg ccg gtc gaa gag gcc ccg       192
Pro Ala Ala Lys Lys Ala Glu Pro Val Ala Pro Val Glu Glu Ala Pro
        50                  55                  60 gcc gag tcg ccg gcg gtc cag gcc ccg ccg cgc ttc gcc ttg caa           240
Ala Glu Ser Pro Ala Val Gln Ala Pro Pro Arg Phe Ala Leu Gln
65                  70                  75                  80 ctg ctg cag gcg ggc tcc tgc acc ctg ctg gtc gaa ctg ccc acc ggc       288
Leu Leu Gln Ala Gly Ser Cys Thr Leu Leu Val Glu Leu Pro Thr Gly
                85                  90                  95 gaa ccc ttc gcc agc cgc gat ccg ggt tac ctg ctg ctg cgc gac ctg       336
Glu Pro Phe Ala Ser Arg Asp Pro Gly Tyr Leu Leu Leu Arg Asp Leu
                100                 105                 110 ctg cgc gcc gcc ggc ctg ccg gac agc ccg cgg ctg atc ggc gaa ccg       384
Leu Arg Ala Ala Gly Leu Pro Asp Ser Pro Arg Leu Ile Gly Glu Pro
            115                 120                 125 gta cgc tgg ccg ctg ctg gcg cgc ggc aac ctc gac cag ggg ccg cag       432
Val Arg Trp Pro Leu Leu Ala Arg Gly Asn Leu Asp Gln Gly Pro Gln
        130                 135                 140 gcg gcc ctg gag ttc gtc cag agc ttc gtc gcc gcg cgc atg gag gag       480
Ala Ala Leu Glu Phe Val Gln Ser Phe Val Ala Ala Arg Met Glu Glu
145                 150                 155                 160 agc gag cgt agc cgc tgc ctg tgg ttg gtc ggc ctg ccg gcg atc cgc       528
Ser Glu Arg Ser Arg Cys Leu Trp Leu Val Gly Leu Pro Ala Ile Arg
```

```
Ser Glu Arg Ser Arg Cys Leu Trp Leu Val Gly Leu Pro Ala Ile Arg
            165                 170                 175 ttc gcc ggc gag ggc gac gag ggc agc ctg ttc cgc gag ctg cag gtg      576
Phe Ala Gly Glu Gly Asp Glu Gly Ser Leu Phe Arg Glu Leu Gln Val
                180                 185                 190 gac ggt ctg ggc gca acc tgg gcc gtg cca ggc ctg gaa gcc ctc atg      624
Asp Gly Leu Gly Ala Thr Trp Ala Val Pro Gly Leu Glu Ala Leu Met
            195                 200                 205 gaa gaa ccc gcc ctc aag ggc gag ctg tgg cgc gcc atg cgc cgt gtc      672
Glu Glu Pro Ala Leu Lys Gly Glu Leu Trp Arg Ala Met Arg Arg Val
210                 215                 220 cgt cag cgc tgg tcg agc gag att caa tga                              702
Arg Gln Arg Trp Ser Ser Glu Ile Gln
225                 230

<210> SEQ ID NO 31
<211> LENGTH: 233
<212> TYPE: PRT
<213> ORGANISM: Pseudomonas aeruginosa

<400> SEQUENCE: 31

Met Pro Val Arg Ala Arg Ala Ile Asp Ala Pro Gln Ala Arg Val
1               5                   10                  15

Pro Gln Ala Glu Ala Pro Ala Ser Ala Pro Ser Val Ala Pro Ala Ala
                20                  25                  30

Pro Val Glu Gly Arg Gly Ile Pro Ile Ser Leu Pro Lys Pro Gly Ala
            35                  40                  45

Pro Ala Ala Lys Lys Ala Glu Pro Val Ala Pro Val Glu Glu Ala Pro
50                  55                  60

Ala Glu Ser Pro Ala Val Gln Ala Pro Pro Arg Phe Ala Leu Gln
65                  70                  75                  80

Leu Leu Gln Ala Gly Ser Cys Thr Leu Leu Val Glu Leu Pro Thr Gly
                85                  90                  95

Glu Pro Phe Ala Ser Arg Asp Pro Gly Tyr Leu Leu Leu Arg Asp Leu
            100                 105                 110

Leu Arg Ala Ala Gly Leu Pro Asp Ser Pro Arg Leu Ile Gly Glu Pro
        115                 120                 125

Val Arg Trp Pro Leu Leu Ala Arg Gly Asn Leu Asp Gln Gly Pro Gln
130                 135                 140

Ala Ala Leu Glu Phe Val Gln Ser Phe Val Ala Ala Arg Met Glu Glu
145                 150                 155                 160

Ser Glu Arg Ser Arg Cys Leu Trp Leu Val Gly Leu Pro Ala Ile Arg
                165                 170                 175

Phe Ala Gly Glu Gly Asp Glu Gly Ser Leu Phe Arg Glu Leu Gln Val
            180                 185                 190

Asp Gly Leu Gly Ala Thr Trp Ala Val Pro Gly Leu Glu Ala Leu Met
        195                 200                 205

Glu Glu Pro Ala Leu Lys Gly Glu Leu Trp Arg Ala Met Arg Arg Val
    210                 215                 220

Arg Gln Arg Trp Ser Ser Glu Ile Gln
225                 230

<210> SEQ ID NO 32
<211> LENGTH: 798
<212> TYPE: DNA
<213> ORGANISM: Pseudomonas aeruginosa

<400> SEQUENCE: 32
```

-continued

| | |
|---|---|
| atgcagataa ccagttggct gccccgccag ccgttgccgt tcgccgcacc ctcgcggccg | 60 |
| gagttgctgg agaccccgcc cgggaagag ccggcggtgc ctgtgcgtgc gcgcgccgcg | 120 |
| atcgatgcgc cgcaggcccg cgtcccgcaa gccgaggcgc cggccagcgc gccgagcgtg | 180 |
| gctcccgccg cgcccgtgga aggccggggg atcccgatca gcctgccgaa gccgggcgcc | 240 |
| ccggcggcga agaaagccga gccggtcgcg ccggtcgaag aggccccggc cgagtcgccg | 300 |
| gcggtccagg ccccgccgcc gcgcttcgcc ttgcaactgc tgcaggcggg ctcctgcacc | 360 |
| ctgctggtcg aactgcccac cggcgaaccc ttcgccagcc gcgatccggg ttacctgctg | 420 |
| ctgcgcgacc tgctgcgcgc cgccggcctg ccggacagcc cgcggctgat cggcgaaccg | 480 |
| gtacgctggc cgctgctggc gcgcggcaac ctcgaccagg ggccgcaggc ggccctggag | 540 |
| ttcgtccaga gcttcgtcgc cgcgcgcatg gaggagagcg agcgtagccg ctgcctgtgg | 600 |
| ttggtcggcc tgccggcgat ccgcttcgcc ggcgagggcg acgagggcag cctgttccgc | 660 |
| gagctgcagg tggacggtct gggcgcaacc tgggccgtgc caggcctgga agccctcatg | 720 |
| gaagaacccg ccctcaaggg cgagctgtgg cgcgccatgc gccgtgtccg tcagcgctgg | 780 |
| tcgagcgaga ttcaatga | 798 |

<210> SEQ ID NO 33
<211> LENGTH: 798
<212> TYPE: DNA
<213> ORGANISM: Pseudomonas aeruginosa
<220> FEATURE:
<221> NAME/KEY: CDS
<222> LOCATION: (1)..(798)

<400> SEQUENCE: 33

| | |
|---|---|
| atg cag ata acc agt tgg ctg ccc cgc cag ccg ttg ccg ttc gcc gca<br>Met Gln Ile Thr Ser Trp Leu Pro Arg Gln Pro Leu Pro Phe Ala Ala<br>1                  5                    10                 15 | 48 |
| ccc tcg cgg ccg gag ttg ctg gag acc ccg ccc cgg gaa gag ccg gcg<br>Pro Ser Arg Pro Glu Leu Leu Glu Thr Pro Pro Arg Glu Glu Pro Ala<br>            20                    25                    30 | 96 |
| gtg cct gtg cgt gcg cgc gcc gcg atc gat gcg ccg cag gcc cgc gtc<br>Val Pro Val Arg Ala Arg Ala Ala Ile Asp Ala Pro Gln Ala Arg Val<br>              35                   40                  45 | 144 |
| ccg caa gcc gag gcg ccg gcc agc gcg ccg agc gtg gct ccc gcc gcg<br>Pro Gln Ala Glu Ala Pro Ala Ser Ala Pro Ser Val Ala Pro Ala Ala<br>50                    55                    60 | 192 |
| ccc gtg gaa ggc cgg ggg atc ccg atc agc ctg ccg aag ccg ggc gcc<br>Pro Val Glu Gly Arg Gly Ile Pro Ile Ser Leu Pro Lys Pro Gly Ala<br>65                    70                    75                  80 | 240 |
| ccg gcg gcg aag aaa gcc gag ccg gtc gcg ccg gtc gaa gag gcc ccg<br>Pro Ala Ala Lys Lys Ala Glu Pro Val Ala Pro Val Glu Glu Ala Pro<br>                    85                    90                    95 | 288 |
| gcc gag tcg ccg gcg gtc cag gcc ccg ccg ccg cgc ttc gcc ttg caa<br>Ala Glu Ser Pro Ala Val Gln Ala Pro Pro Pro Arg Phe Ala Leu Gln<br>                        100                  105                  110 | 336 |
| ctg ctg cag gcg ggc tcc tgc acc ctg ctg gtc gaa ctg ccc acc ggc<br>Leu Leu Gln Ala Gly Ser Cys Thr Leu Leu Val Glu Leu Pro Thr Gly<br>              115                    120                  125 | 384 |
| gaa ccc ttc gcc agc cgc gat ccg ggt tac ctg ctg ctg cgc gac ctg<br>Glu Pro Phe Ala Ser Arg Asp Pro Gly Tyr Leu Leu Leu Arg Asp Leu<br>130                   135                   140 | 432 |
| ctg cgc gcc gcc ggc ctg ccg gac agc ccg cgg ctg atc ggc gaa ccg<br>Leu Arg Ala Ala Gly Leu Pro Asp Ser Pro Arg Leu Ile Gly Glu Pro<br>145                   150                   155                  160 | 480 |
| gta cgc tgg ccg ctg ctg gcg cgc ggc aac ctc gac cag ggg ccg cag | 528 |

-continued

```
Val Arg Trp Pro Leu Leu Ala Arg Gly Asn Leu Asp Gln Gly Pro Gln
                165                 170                 175 gcg gcc ctg gag ttc gtc cag agc ttc gtc gcc gcg cgc atg gag gag       576
Ala Ala Leu Glu Phe Val Gln Ser Phe Val Ala Ala Arg Met Glu Glu
                180                 185                 190 agc gag cgt agc cgc tgc ctg tgg ttg gtc ggc ctg ccg gcg atc cgc       624
Ser Glu Arg Ser Arg Cys Leu Trp Leu Val Gly Leu Pro Ala Ile Arg
                195                 200                 205 ttc gcc ggc gag ggc gac gag ggc agc ctg ttc cgc gag ctg cag gtg       672
Phe Ala Gly Glu Gly Asp Glu Gly Ser Leu Phe Arg Glu Leu Gln Val
        210                 215                 220 gac ggt ctg ggc gca acc tgg gcc gtg cca ggc ctg gaa gcc ctc atg       720
Asp Gly Leu Gly Ala Thr Trp Ala Val Pro Gly Leu Glu Ala Leu Met
225                 230                 235                 240 gaa gaa ccc gcc ctc aag ggc gag ctg tgg cgc gcc atg cgc cgt gtc       768
Glu Glu Pro Ala Leu Lys Gly Glu Leu Trp Arg Ala Met Arg Arg Val
                245                 250                 255 cgt cag cgc tgg tcg agc gag att caa tga                               798
Arg Gln Arg Trp Ser Ser Glu Ile Gln
                260                 265

<210> SEQ ID NO 34
<211> LENGTH: 265
<212> TYPE: PRT
<213> ORGANISM: Pseudomonas aeruginosa

<400> SEQUENCE: 34

Met Gln Ile Thr Ser Trp Leu Pro Arg Gln Pro Leu Pro Phe Ala Ala
1               5                   10                  15

Pro Ser Arg Pro Glu Leu Leu Glu Thr Pro Arg Glu Glu Pro Ala
                20                  25                  30

Val Pro Val Arg Ala Arg Ala Ala Ile Asp Ala Pro Gln Ala Arg Val
            35                  40                  45

Pro Gln Ala Glu Ala Pro Ala Ser Ala Pro Ser Val Ala Pro Ala Ala
        50                  55                  60

Pro Val Glu Gly Arg Gly Ile Pro Ile Ser Leu Pro Lys Pro Gly Ala
65                  70                  75                  80

Pro Ala Ala Lys Lys Ala Glu Pro Val Ala Pro Val Glu Glu Ala Pro
                85                  90                  95

Ala Glu Ser Pro Ala Val Gln Ala Pro Pro Arg Phe Ala Leu Gln
            100                 105                 110

Leu Leu Gln Ala Gly Ser Cys Thr Leu Leu Val Glu Leu Pro Thr Gly
        115                 120                 125

Glu Pro Phe Ala Ser Arg Asp Pro Gly Tyr Leu Leu Leu Arg Asp Leu
    130                 135                 140

Leu Arg Ala Ala Gly Leu Pro Asp Ser Pro Arg Leu Ile Gly Glu Pro
145                 150                 155                 160

Val Arg Trp Pro Leu Leu Ala Arg Gly Asn Leu Asp Gln Gly Pro Gln
                165                 170                 175

Ala Ala Leu Glu Phe Val Gln Ser Phe Val Ala Ala Arg Met Glu Glu
            180                 185                 190

Ser Glu Arg Ser Arg Cys Leu Trp Leu Val Gly Leu Pro Ala Ile Arg
        195                 200                 205

Phe Ala Gly Glu Gly Asp Glu Gly Ser Leu Phe Arg Glu Leu Gln Val
    210                 215                 220

Asp Gly Leu Gly Ala Thr Trp Ala Val Pro Gly Leu Glu Ala Leu Met
225                 230                 235                 240
```

-continued

```
Glu Glu Pro Ala Leu Lys Gly Glu Leu Trp Arg Ala Met Arg Arg Val
            245                 250                 255

Arg Gln Arg Trp Ser Ser Glu Ile Gln
        260                 265

<210> SEQ ID NO 35
<211> LENGTH: 837
<212> TYPE: DNA
<213> ORGANISM: Pseudomonas aeruginosa

<400> SEQUENCE: 35
ttgatcgaag aacagcgtcg ccgcgccttc ctgggcgcga tgcagataac cagttggctg      60
ccccgccagc cgttgccgtt cgccgcaccc tcgcggccgg agttgctgga gaccccgccc     120
cgggaagagc cggcggtgcc tgtgcgtgcg cgcgccgcga tcgatgcgcc gcaggcccgc     180
gtcccgcaag ccgaggcgcc ggccagcgcg ccgagcgtgg ctcccgccgc gcccgtggaa     240
ggccggggga tcccgatcag cctgccgaag ccgggcgccc cggcggcgaa gaaagccgag     300
ccggtcgcgc cggtcgaaga ggccccggcc gagtcgccgg cggtccaggc cccgccgccg     360
cgcttcgcct gcaactgct gcaggcgggc tcctgcaccc tgctggtcga actgccacc      420 ggcgaaccct tcgccagccg cgatccgggt tacctgctgc tgcgcgacct gctgcgcgcc     480
gccggcctgc cggacagccc gcggctgatc ggcgaaccgg tacgctggcc gctgctggcg     540
cgcggcaacc tcgaccaggg gccgcaggcg gccctggagt tcgtccagag cttcgtcgcc     600
gcgcgcatgg aggagagcga gcgtagccgc tgcctgtggt tggtcggcct gccggcgatc     660
cgcttcgccg gcgagggcga cgagggcagc ctgttccgcg agctgcaggt ggacggtctg     720
ggcgcaacct gggccgtgcc aggcctggaa gccctcatgg aagaaccggc cctcaagggc     780
gagctgtggc gcgccatgcg ccgtgtccgt cagcgctggt cgagcgagat tcaatga       837

<210> SEQ ID NO 36
<211> LENGTH: 837
<212> TYPE: DNA
<213> ORGANISM: Pseudomonas aeruginosa
<220> FEATURE:
<221> NAME/KEY: CDS
<222> LOCATION: (1)..(837)

<400> SEQUENCE: 36 ttg atc gaa gaa cag cgt cgc cgc gcc ttc ctg ggc gcg atg cag ata       48
Leu Ile Glu Glu Gln Arg Arg Arg Ala Phe Leu Gly Ala Met Gln Ile
1               5                   10                  15 acc agt tgg ctg ccc cgc cag ccg ttg ccg ttc gcc gca ccc tcg cgg       96
Thr Ser Trp Leu Pro Arg Gln Pro Leu Pro Phe Ala Ala Pro Ser Arg
            20                  25                  30 ccg gag ttg ctg gag acc ccg ccc cgg gaa gag ccg gcg gtg cct gtg      144
Pro Glu Leu Leu Glu Thr Pro Pro Arg Glu Glu Pro Ala Val Pro Val
        35                  40                  45 cgt gcg cgc gcc gcg atc gat gcg ccg cag gcc cgc gtc ccg caa gcc      192
Arg Ala Arg Ala Ala Ile Asp Ala Pro Gln Ala Arg Val Pro Gln Ala
    50                  55                  60 gag gcg ccg gcc agc gcg ccg agc gtg gct ccc gcc gcg ccc gtg gaa      240
Glu Ala Pro Ala Ser Ala Pro Ser Val Ala Pro Ala Ala Pro Val Glu
65                  70                  75                  80 ggc cgg ggg atc ccg atc agc ctg ccg aag ccg ggc gcc ccg gcg gcg      288
Gly Arg Gly Ile Pro Ile Ser Leu Pro Lys Pro Gly Ala Pro Ala Ala
                85                  90                  95 aag aaa gcc gag ccg gtc gcg ccg gtc gaa gag gcc ccg gcc gag tcg      336
Lys Lys Ala Glu Pro Val Ala Pro Val Glu Glu Ala Pro Ala Glu Ser
            100                 105                 110
```

| | | |
|---|---|---|
| ccg gcg gtc cag gcc ccg ccg cgc ttc gcc ttg caa ctg ctg cag<br>Pro Ala Val Gln Ala Pro Pro Arg Phe Ala Leu Gln Leu Leu Gln<br>115　　　　　　　　120　　　　　　　　125 | | 384 |
| gcg ggc tcc tgc acc ctg ctg gtc gaa ctg ccc acc ggc gaa ccc ttc<br>Ala Gly Ser Cys Thr Leu Leu Val Glu Leu Pro Thr Gly Glu Pro Phe<br>130　　　　　　　　135　　　　　　　　140 | | 432 |
| gcc agc cgc gat ccg ggt tac ctg ctg ctg cgc gac ctg ctg cgc gcc<br>Ala Ser Arg Asp Pro Gly Tyr Leu Leu Leu Arg Asp Leu Leu Arg Ala<br>145　　　　　　　　150　　　　　　　　155　　　　　　　　160 | | 480 |
| gcc ggc ctg ccg gac agc ccg cgg ctg atc ggc gaa ccg gta cgc tgg<br>Ala Gly Leu Pro Asp Ser Pro Arg Leu Ile Gly Glu Pro Val Arg Trp<br>165　　　　　　　　170　　　　　　　　175 | | 528 |
| ccg ctg ctg gcg cgc ggc aac ctc gac cag ggg ccg cag gcg gcc ctg<br>Pro Leu Leu Ala Arg Gly Asn Leu Asp Gln Gly Pro Gln Ala Ala Leu<br>180　　　　　　　　185　　　　　　　　190 | | 576 |
| gag ttc gtc cag agc ttc gtc gcc gcg cgc atg gag gag agc gag cgt<br>Glu Phe Val Gln Ser Phe Val Ala Ala Arg Met Glu Glu Ser Glu Arg<br>195　　　　　　　　200　　　　　　　　205 | | 624 |
| agc cgc tgc ctg tgg ttg gtc ggc ctg ccg gcg atc cgc ttc gcc ggc<br>Ser Arg Cys Leu Trp Leu Val Gly Leu Pro Ala Ile Arg Phe Ala Gly<br>210　　　　　　　　215　　　　　　　　220 | | 672 |
| gag ggc gac gag ggc agc ctg ttc cgc gag ctg cag gtg gac ggt ctg<br>Glu Gly Asp Glu Gly Ser Leu Phe Arg Glu Leu Gln Val Asp Gly Leu<br>225　　　　　　　　230　　　　　　　　235　　　　　　　　240 | | 720 |
| ggc gca acc tgg gcc gtg cca ggc ctg gaa gcc ctc atg gaa gaa ccc<br>Gly Ala Thr Trp Ala Val Pro Gly Leu Glu Ala Leu Met Glu Glu Pro<br>245　　　　　　　　250　　　　　　　　255 | | 768 |
| gcc ctc aag ggc gag ctg tgg cgc gcc atg cgc cgt gtc cgt cag cgc<br>Ala Leu Lys Gly Glu Leu Trp Arg Ala Met Arg Arg Val Arg Gln Arg<br>260　　　　　　　　265　　　　　　　　270 | | 816 |
| tgg tcg agc gag att caa tga<br>Trp Ser Ser Glu Ile Gln<br>275 | | 837 |

<210> SEQ ID NO 37
<211> LENGTH: 278
<212> TYPE: PRT
<213> ORGANISM: Pseudomonas aeruginosa

<400> SEQUENCE: 37

Leu Ile Glu Glu Gln Arg Arg Ala Phe Leu Gly Ala Met Gln Ile
1　　　　　　　　5　　　　　　　　10　　　　　　　　15

Thr Ser Trp Leu Pro Arg Gln Pro Leu Pro Phe Ala Ala Pro Ser Arg
　　　　　　20　　　　　　　　25　　　　　　　　30

Pro Glu Leu Leu Glu Thr Pro Arg Glu Glu Pro Ala Val Pro Val
　　35　　　　　　　　40　　　　　　　　45

Arg Ala Arg Ala Ala Ile Asp Ala Pro Gln Ala Arg Val Pro Gln Ala
50　　　　　　　　55　　　　　　　　60

Glu Ala Pro Ala Ser Ala Pro Ser Val Ala Pro Ala Ala Pro Val Glu
65　　　　　　　　70　　　　　　　　75　　　　　　　　80

Gly Arg Gly Ile Pro Ile Ser Leu Pro Lys Pro Gly Ala Pro Ala Ala
　　　　　　　　85　　　　　　　　90　　　　　　　　95

Lys Lys Ala Glu Pro Val Ala Pro Val Glu Glu Ala Pro Ala Glu Ser
　　　　　　100　　　　　　　　105　　　　　　　　110

Pro Ala Val Gln Ala Pro Pro Arg Phe Ala Leu Gln Leu Leu Gln
　　　115　　　　　　　　120　　　　　　　　125

Ala Gly Ser Cys Thr Leu Leu Val Glu Leu Pro Thr Gly Glu Pro Phe
130　　　　　　　　135　　　　　　　　140

```
Ala Ser Arg Asp Pro Gly Tyr Leu Leu Leu Arg Asp Leu Leu Arg Ala
145                 150                 155                 160

Ala Gly Leu Pro Asp Ser Pro Arg Leu Ile Gly Glu Pro Val Arg Trp
            165                 170                 175

Pro Leu Leu Ala Arg Gly Asn Leu Asp Gln Gly Pro Gln Ala Ala Leu
        180                 185                 190

Glu Phe Val Gln Ser Phe Val Ala Ala Arg Met Glu Glu Ser Glu Arg
    195                 200                 205

Ser Arg Cys Leu Trp Leu Val Gly Leu Pro Ala Ile Arg Phe Ala Gly
210                 215                 220

Glu Gly Asp Glu Gly Ser Leu Phe Arg Glu Leu Gln Val Asp Gly Leu
225                 230                 235                 240

Gly Ala Thr Trp Ala Val Pro Gly Leu Glu Ala Leu Met Glu Glu Pro
                245                 250                 255

Ala Leu Lys Gly Glu Leu Trp Arg Ala Met Arg Arg Val Arg Gln Arg
        260                 265                 270

Trp Ser Ser Glu Ile Gln
        275
```

<210> SEQ ID NO 38
<211> LENGTH: 1134
<212> TYPE: DNA
<213> ORGANISM: Staphylococcus aureus

<400> SEQUENCE: 38

```
atgatggaat tcactattaa aagagattat tttattacac aattaaatga cacattaaaa      60
gctatttcac caagaacaac attacctata ttaactggta tcaaaatcga tgcgaaagaa     120
catgaagtta tactaactgg ttcagactct gaaatttcaa tagaaatcac tattcctaaa     180
actgtagatg gcgaagatat tgtcaatatt tcagaaacag gctcagtagt acttcctgga     240
cgattctttg ttgatattat aaaaaaatta cctggtaaag atgttaaatt atctacaaat     300
gaacaattcc agacattaat tacatcaggt cattctgaat ttaatttaag tggcttagat     360
ccagatcaat atcctttatt acctcaagtt tctagagatg acgcaattca attgtcggta     420
aaagtgctta aaaacgtgat tgcacaaacg aattttgcag tgtccacctc agaaacacgc     480
ccagtactaa ctggtgtgaa ctggcttata caagaaaatg aattaatatg cacagcgact     540
gactcacacc gcttggctgt aagaaagttg cagttagaag atgtttctga aaacaaaaat     600
gtcatcattc aggtaaggc tttagctgaa ttaaataaaa ttatgtctga caatgaagaa     660
gacattgata tcttctttgc ttcaaaccaa gttttattta agttggaaa tgtgaacttt     720
atttctcgat tattagaagg acattatcct gatacaacac gtttattccc tgaaaactat     780
gaaattaaat taagtataga caatggggag ttttatcatg cgattgatcg tgcctcttta     840
ttagcacgtg aaggtggtaa taacgttatt aaattaagta caggtgatga cgttgttgaa     900
ttatcttcta catcaccaga aattggtact gtaaaagaag aagttgatgc aaacgatgtt     960
gaaggtggta gcctgaaaat ttcattcaac tctaaatata tgatggatgc tttaaaagca    1020
atcgataatg atgaggttga agttgaattc ttcggtacaa tgaaaccatt tattctaaaa    1080
ccaaaaggtg acgactcggt aacgcaatta attttaccaa tcagaactta ctaa          1134
```

<210> SEQ ID NO 39
<211> LENGTH: 1134
<212> TYPE: DNA
<213> ORGANISM: Staphylococcus aureus
<220> FEATURE:
<221> NAME/KEY: CDS

<222> LOCATION: (1)..(1134)

<400> SEQUENCE: 39

```
atg atg gaa ttc act att aaa aga gat tat ttt att aca caa tta aat      48
Met Met Glu Phe Thr Ile Lys Arg Asp Tyr Phe Ile Thr Gln Leu Asn
 1               5                  10                  15 gac aca tta aaa gct att tca cca aga aca aca tta cct ata tta act      96
Asp Thr Leu Lys Ala Ile Ser Pro Arg Thr Thr Leu Pro Ile Leu Thr
             20                  25                  30 ggt atc aaa atc gat gcg aaa gaa cat gaa gtt ata cta act ggt tca     144
Gly Ile Lys Ile Asp Ala Lys Glu His Glu Val Ile Leu Thr Gly Ser
         35                  40                  45 gac tct gaa att tca ata gaa atc act att cct aaa act gta gat ggc     192
Asp Ser Glu Ile Ser Ile Glu Ile Thr Ile Pro Lys Thr Val Asp Gly
 50                  55                  60 gaa gat att gtc aat att tca gaa aca ggc tca gta gta ctt cct gga     240
Glu Asp Ile Val Asn Ile Ser Glu Thr Gly Ser Val Val Leu Pro Gly
 65                  70                  75                  80 cga ttc ttt gtt gat att ata aaa aaa tta cct ggt aaa gat gtt aaa     288
Arg Phe Phe Val Asp Ile Ile Lys Lys Leu Pro Gly Lys Asp Val Lys
                 85                  90                  95 tta tct aca aat gaa caa ttc cag aca tta att aca tca ggt cat tct     336
Leu Ser Thr Asn Glu Gln Phe Gln Thr Leu Ile Thr Ser Gly His Ser
            100                 105                 110 gaa ttt aat tta agt ggc tta gat cca gat caa tat cct tta tta cct     384
Glu Phe Asn Leu Ser Gly Leu Asp Pro Asp Gln Tyr Pro Leu Leu Pro
        115                 120                 125 caa gtt tct aga gat gac gca att caa ttg tcg gta aaa gtg ctt aaa     432
Gln Val Ser Arg Asp Asp Ala Ile Gln Leu Ser Val Lys Val Leu Lys
    130                 135                 140 aac gtg att gca caa acg aat ttt gca gtg tcc acc tca gaa aca cgc     480
Asn Val Ile Ala Gln Thr Asn Phe Ala Val Ser Thr Ser Glu Thr Arg
145                 150                 155                 160 cca gta cta act ggt gtg aac tgg ctt ata caa gaa aat gaa tta ata     528
Pro Val Leu Thr Gly Val Asn Trp Leu Ile Gln Glu Asn Glu Leu Ile
                165                 170                 175 tgc aca gcg act gac tca cac cgc ttg gct gta aga aag ttg cag tta     576
Cys Thr Ala Thr Asp Ser His Arg Leu Ala Val Arg Lys Leu Gln Leu
            180                 185                 190 gaa gat gtt tct gaa aac aaa aat gtc atc att cca ggt aag gct tta     624
Glu Asp Val Ser Glu Asn Lys Asn Val Ile Ile Pro Gly Lys Ala Leu
        195                 200                 205 gct gaa tta aat aaa att atg tct gac aat gaa gaa gac att gat atc     672
Ala Glu Leu Asn Lys Ile Met Ser Asp Asn Glu Glu Asp Ile Asp Ile
    210                 215                 220 ttc ttt gct tca aac caa gtt tta ttt aaa gtt gga aat gtg aac ttt     720
Phe Phe Ala Ser Asn Gln Val Leu Phe Lys Val Gly Asn Val Asn Phe
225                 230                 235                 240 att tct cga tta tta gaa gga cat tat cct gat aca aca cgt tta ttc     768
Ile Ser Arg Leu Leu Glu Gly His Tyr Pro Asp Thr Thr Arg Leu Phe
                245                 250                 255 cct gaa aac tat gaa att aaa tta agt ata gac aat ggg gag ttt tat     816
Pro Glu Asn Tyr Glu Ile Lys Leu Ser Ile Asp Asn Gly Glu Phe Tyr
            260                 265                 270 cat gcg att gat cgt gcc tct tta tta gca cgt gaa ggt ggt aat aac     864
His Ala Ile Asp Arg Ala Ser Leu Leu Ala Arg Glu Gly Gly Asn Asn
        275                 280                 285 gtt att aaa tta agt aca ggt gat gac gtt gtt gaa tta tct tct aca     912
Val Ile Lys Leu Ser Thr Gly Asp Asp Val Val Glu Leu Ser Ser Thr
    290                 295                 300
```

```
tca cca gaa att ggt act gta aaa gaa gaa gtt gat gca aac gat gtt    960
Ser Pro Glu Ile Gly Thr Val Lys Glu Glu Val Asp Ala Asn Asp Val
305             310                 315                 320 gaa ggt ggt agc ctg aaa att tca ttc aac tct aaa tat atg atg gat   1008
Glu Gly Gly Ser Leu Lys Ile Ser Phe Asn Ser Lys Tyr Met Met Asp
            325                 330                 335 gct tta aaa gca atc gat aat gat gag gtt gaa gtt gaa ttc ttc ggt   1056
Ala Leu Lys Ala Ile Asp Asn Asp Glu Val Glu Val Glu Phe Phe Gly
        340                 345                 350 aca atg aaa cca ttt att cta aaa cca aaa ggt gac gac tcg gta acg   1104
Thr Met Lys Pro Phe Ile Leu Lys Pro Lys Gly Asp Asp Ser Val Thr
    355                 360                 365 caa tta att tta cca atc aga act tac taa                           1134
Gln Leu Ile Leu Pro Ile Arg Thr Tyr
    370                 375

<210> SEQ ID NO 40
<211> LENGTH: 377
<212> TYPE: PRT
<213> ORGANISM: Staphylococcus aureus

<400> SEQUENCE: 40

Met Met Glu Phe Thr Ile Lys Arg Asp Tyr Phe Ile Thr Gln Leu Asn
1               5                   10                  15

Asp Thr Leu Lys Ala Ile Ser Pro Arg Thr Thr Leu Pro Ile Leu Thr
            20                  25                  30

Gly Ile Lys Ile Asp Ala Lys Glu His Glu Val Ile Leu Thr Gly Ser
        35                  40                  45

Asp Ser Glu Ile Ser Ile Glu Ile Thr Ile Pro Lys Thr Val Asp Gly
    50                  55                  60

Glu Asp Ile Val Asn Ile Ser Gly Thr Gly Ser Val Val Leu Pro Gly
65                  70                  75                  80

Arg Phe Phe Val Asp Ile Ile Lys Lys Leu Pro Gly Lys Asp Val Lys
                85                  90                  95

Leu Ser Thr Asn Glu Gln Phe Gln Thr Leu Ile Thr Ser Gly His Ser
            100                 105                 110

Glu Phe Asn Leu Ser Gly Leu Asp Pro Asp Gln Tyr Pro Leu Leu Pro
        115                 120                 125

Gln Val Ser Arg Asp Asp Ala Ile Gln Leu Ser Val Lys Val Leu Lys
    130                 135                 140

Asn Val Ile Ala Gln Thr Asn Phe Ala Val Ser Thr Ser Glu Thr Arg
145                 150                 155                 160

Pro Val Leu Thr Gly Val Asn Trp Leu Ile Gln Glu Asn Glu Leu Ile
                165                 170                 175

Cys Thr Ala Thr Asp Ser His Arg Leu Ala Val Arg Lys Leu Gln Leu
            180                 185                 190

Glu Asp Val Ser Glu Asn Lys Asn Val Ile Ile Pro Gly Lys Ala Leu
        195                 200                 205

Ala Glu Leu Asn Lys Ile Met Ser Asp Asn Glu Glu Asp Ile Asp Ile
    210                 215                 220

Phe Phe Ala Ser Asn Gln Val Leu Phe Lys Val Gly Asn Val Asn Phe
225                 230                 235                 240

Ile Ser Arg Leu Leu Glu Gly His Tyr Pro Asp Thr Thr Arg Leu Phe
                245                 250                 255

Pro Glu Asn Tyr Glu Ile Lys Leu Ser Ile Asp Asn Gly Glu Phe Tyr
            260                 265                 270

His Ala Ile Asp Arg Ala Ser Leu Leu Ala Arg Glu Gly Gly Asn Asn
```

|  |  | 275 |  |  | 280 |  |  | 285 |  |
|---|---|---|---|---|---|---|---|---|---|

Val Ile Lys Leu Ser Thr Gly Asp Asp Val Val Glu Leu Ser Ser Thr
    290                          295                        300

Ser Pro Glu Ile Gly Thr Val Lys Glu Val Asp Ala Asn Asp Val
305                        310                        315                    320

Glu Gly Gly Ser Leu Lys Ile Ser Phe Asn Ser Lys Tyr Met Met Asp
                      325                        330                        335

Ala Leu Lys Ala Ile Asp Asn Asp Glu Val Glu Val Glu Phe Phe Gly
                      340                        345                        350

Thr Met Lys Pro Phe Ile Leu Lys Pro Lys Gly Asp Asp Ser Val Thr
                355                        360                        365

Gln Leu Ile Leu Pro Ile Arg Thr Tyr
    370                      375

<210> SEQ ID NO 41
<211> LENGTH: 56
<212> TYPE: DNA
<213> ORGANISM: Artificial
<220> FEATURE:
<223> OTHER INFORMATION: primer

<400> SEQUENCE: 41
gatccatatg atggaattca ctattaaacg cgattatttt attacacaat aaatg      56

<210> SEQ ID NO 42
<211> LENGTH: 33
<212> TYPE: DNA
<213> ORGANISM: Artificial
<220> FEATURE:
<223> OTHER INFORMATION: primer

<400> SEQUENCE: 42
agctactagt ctattagtaa gttctgattg gta      33

<210> SEQ ID NO 43
<211> LENGTH: 4311
<212> TYPE: DNA
<213> ORGANISM: Staphylococcus aureus

<400> SEQUENCE: 43
atgacagagc aacaaaaatt taaagtgctt gctgatcaaa ttaaaatttc aaatcaatta      60
gatgctgaaa ttttaaattc aggtgaactg acacgtatag atgtttctaa caaaaacaga     120
acatgggaat tcatattac attaccacaa ttcttagctc atgaagatta tttattattt     180
ataaatgcaa tagagcaaga gtttaaagat atcgccaacg ttacatgtcg ttttacggta     240
acaaatggca cgaatcaaga tgaacatgca ttaaatact tgggcactg tattgaccaa     300 acagctttat ctccaaaagt taaggtcaa ttgaaacaga aaaagcttat tatgtctgga     360
aaagtattaa agtaatggt atcaaatgac attgaacgta tcatttga taaggcatgt     420 aatggaagtc ttatcaaagc gtttagaaat tgtggttttg atatcgataa aatcatattc    480
gaaacaaatg ataatgatca agaacaaaac ttagcttctt tagaagcaca tattcaagaa    540
gaagacgaac aaagtgcacg attggcaaca gagaaacttg aaaaaatgaa agctgaaaaa    600
gcgaaacaac aagataacaa cgaaagtgct gtcgataagt gtcaaattgg taagccgatt    660
caaattgaaa atattaaacc aattgaatct attattgagg aagagtttaa agttgcaata    720
gagggtgtca ttttttgatat aaacttaaaa gaacttaaaa gtggtcgtca tatcgtagaa    780
attaaagtga ctgactatac ggactcatta gtttaaaaa tgtttactcg taaaaacaaa    840

```
gatgatttag aacattttaa agcgctaagt gtaggtaaat gggttagggc tcaaggtcgt    900
attgaagaag atacatttat tagagattta gttatgatga tgtctgatat tgaagagatt    960
aaaaaagcga caaaaaaaga taaggctgaa gaaaagcgtg tagaattcca cttgcatact   1020
gcaatgagcc aaatgatgg tatacccaat attggtgcgt atgttaaaca ggcagcagac   1080
tggggacatc cagccattgc ggttacagac cataatgttg tgcaagcatt tccagatgct   1140
cacgcagcag cggaaaaaca tggcattaaa atgatatacg gtatggaagg tatgttagtt   1200
gatgatggtg ttccgattgc atacaaacca caagatgtcg tattaaaaga tgctacttat   1260
gttgtgttcg acgttgagac aactggttta tcaaatcagt atgataaaat catcgagctt   1320
gcagctgtga aagttcataa cggtgaaatc atcgataagt ttgaaaggtt tagtaatccg   1380
catgaacgat tatcggaaac gattatcaat ttgacgcata ttactgatga tatgttagta   1440
gatgcccctg agattgaaga agtacttaca gagtttaaag aatgggttgg cgatgcgata   1500
ttcgtagcgc ataatgcttc gtttgatatg ggctttatcg atacgggata tgaacgtctt   1560
gggtttggac catcaacgaa tggtgttatc gatactttag aattatctcg tacgattaat   1620
actgaatatg gtaaacatgg tttgaatttc ttagctaaaa aatatggcgt agaattaacg   1680
caacatcacc gtgccattta tgatacagaa gcaacagctt acattttcat aaaaatggtt   1740
caacaaatga agaattagg tgtattaaat cataacgaaa tcaacaaaaa actcagtaat   1800
gaagatgcat ataaacgtgc aagacctagc catgtcacat taattgtaca aaaccaacaa   1860
ggtcttaaaa atctatttaa aattgtaagt gcatcattgg tgaagtattt ctaccgtaca   1920
cctcgaattc cacgttcatt gttagatgaa tatcgtgagg gattattggt aggtacagcg   1980
tgtgatgaag gtgaattatt tacggcagtt atgcagaagg accagagcca agttgaaaaa   2040
attgccaaat attatgattt tattgaaatt caaccaccgg cactttatca agatttaatt   2100
gatagagagc ttattagaga tactgaaaca ttacatgaaa tttatcaacg tttaatacat   2160
gcaggtgaca cagcgggtat acctgttatt gcgacaggaa atgcacacta tttgtttgaa   2220
catgatggta tcgcacgtaa aattttaata gcatcacaac ccggcaatcc acttaatcgc   2280
tcaactttac cggaagcaca ttttagaact acagatgaaa tgttaaacga gtttcatttt   2340
ttaggtgaag aaaaagcgca tgaaattgtt gtgaaaaata caaacgaatt agcagatcga   2400
attgaacgtg ttgttcctat taaagatgaa ttatacacac gcgtatgga aggtgctaac   2460 gaagaaatta gagaactaag ttatacaaat gcgcgtaaac tgtatggtga agacctgcct   2520
caaatcgtaa ttgatcgatt agaaaagaa ttaaaagta ttatcggtaa tggatttgcg   2580
gtaatttact taatttcgca acgtttagtt aaaaaatcat tagatgatgg atacttagtt   2640
ggttcccgtg gttcagtagg ttctagtttt gtagcgacaa tgactgagat tactgaagta   2700
aacccgttac cgccacacta tatttgtccg aactgtaaaa cgagtgaatt tttcaatgat   2760
ggttcagtag gatcaggatt cgatttacct gataagacgt gtgaaacttg tggagcgcca   2820
cttattaaag aaggacaaga tattccgttt gaaacatttt taggatttaa gggagataaa   2880
gttcctgata tcgacttaaa ctttagtggt gaatatcaac cgaatgccca taactacaca   2940
aaagtattat ttggtgagga taaagtattc cgtgcaggta caattggtac cgttgctgaa   3000
aagactgctt ttggttatgt taaaggttat ttgaatgatc aaggcatcca caaaagaggc   3060
gctgaaatag atcgactcgt taaaggatgt acaggtgtta aacgtacaac tggacagcat   3120
ccaggaggta ttattgtagt acctgattac atggatattt atgattttac gccgatacaa   3180
tatcctgccg atgatcaaaa ttcagcatgg atgacgacac attttgattt ccattctatt   3240
```

```
catgataatg tattaaaact tgatatactt ggacacgatg atccaacaat gattcgtatg    3300
cttcaagatt tatcgggcat tgatccaaaa acgatacctg tagatgacaa agaagtcatg    3360
caaatattta gtacacctga agtttaggt gttactgaag atgaaatttt atgtaaaaca     3420
ggtacgtttg gggttccaga attcggtaca gggttcgtgc gtcaaatgtt agaagataca    3480
aagccaacaa cattttctga attagttcaa atctcaggat tatctcatgg tacagatgtg    3540
tggttaggca atgctcaaga attaattaaa accggtatat gtgatttatc aagtgtaatt    3600
ggttgtcgtg atgatatcat ggtttattta atgtatgctg gtttagaacc atcaatggct    3660
tttaaaataa tggagtcagt acgtaaaggt aaaggtttaa ctgaagaaat gattgaaacg    3720
atgaaagaaa atgaagtgcc ggattggtat ttagattcat gtcttaaaat taagtacatg    3780
ttccctaaag cccatgcagc agcatacgtt ttaatggcag tacgtatcgc atatttcaaa    3840
gtacatcatc cactttatta ctatgcatct tactttacaa ttcgtgcgtc agattttgat    3900
ttaatcacga tgattaaaga taaacaagc attcgaaata ctgtaaaaga catgtattct    3960
cgctatatgg atctaggtaa aaaagaaaaa gacgtattaa cagtcttgga aattatgaat    4020
gaaatggcgc atcgaggtta tcgaatgcaa ccgattagtt tagaaaagag tcaggcgttc    4080
gaatttatca ttgaaggcga tacacttatt ccgccgttca tatcagtgcc tgggcttggc    4140
gaaaacgttg cgaaacgaat tgttgaagct cgtgacgatg cccattttt atcaaaagaa     4200 gatttaaaca aaaaagctgg attatctcag aaaattattg agtatttaga tgagttaggc    4260
tcattaccga atttaccaga taaagctcaa ctttcgatat ttgatatgta a             4311

<210> SEQ ID NO 44
<211> LENGTH: 4311
<212> TYPE: DNA
<213> ORGANISM: Staphylococcus aureus
<220> FEATURE:
<221> NAME/KEY: CDS
<222> LOCATION: (1)..(4311)

<400> SEQUENCE: 44 atg aca gag caa caa aaa ttt aaa gtg ctt gct gat caa att aaa att       48
Met Thr Glu Gln Gln Lys Phe Lys Val Leu Ala Asp Gln Ile Lys Ile
1               5                   10                  15 tca aat caa tta gat gct gaa att tta aat tca ggt gaa ctg aca cgt       96
Ser Asn Gln Leu Asp Ala Glu Ile Leu Asn Ser Gly Glu Leu Thr Arg
                20                  25                  30 ata gat gtt tct aac aaa aac aga aca tgg gaa ttt cat att aca tta      144
Ile Asp Val Ser Asn Lys Asn Arg Thr Trp Glu Phe His Ile Thr Leu
            35                  40                  45 cca caa ttc tta gct cat gaa gat tat tta tta ttt ata aat gca ata      192
Pro Gln Phe Leu Ala His Glu Asp Tyr Leu Leu Phe Ile Asn Ala Ile
        50                  55                  60 gag caa gag ttt aaa gat atc gcc aac gtt aca tgt cgt ttt acg gta      240
Glu Gln Glu Phe Lys Asp Ile Ala Asn Val Thr Cys Arg Phe Thr Val
65                  70                  75                  80 aca aat ggc acg aat caa gat gaa cat gca att aaa tac ttt ggg cac      288
Thr Asn Gly Thr Asn Gln Asp Glu His Ala Ile Lys Tyr Phe Gly His
                85                  90                  95 tgt att gac caa aca gct tta tct cca aaa gtt aaa ggt caa ttg aaa      336
Cys Ile Asp Gln Thr Ala Leu Ser Pro Lys Val Lys Gly Gln Leu Lys
            100                 105                 110 cag aaa aag ctt att atg tct gga aaa gta tta aaa gta atg gta tca      384
Gln Lys Lys Leu Ile Met Ser Gly Lys Val Leu Lys Val Met Val Ser
        115                 120                 125 aat gac att gaa cgt aat cat ttt gat aag gca tgt aat gga agt ctt      432
```

```
                                                                -continued

Asn Asp Ile Glu Arg Asn His Phe Asp Lys Ala Cys Asn Gly Ser Leu
        130                 135                 140 atc aaa gcg ttt aga aat tgt ggt ttt gat atc gat aaa atc ata ttc       480
Ile Lys Ala Phe Arg Asn Cys Gly Phe Asp Ile Asp Lys Ile Ile Phe
145                 150                 155                 160 gaa aca aat gat aat gat caa gaa caa aac tta gct tct tta gaa gca       528
Glu Thr Asn Asp Asn Asp Gln Glu Gln Asn Leu Ala Ser Leu Glu Ala
                165                 170                 175 cat att caa gaa gaa gac gaa caa agt gca cga ttg gca aca gag aaa       576
His Ile Gln Glu Glu Asp Glu Gln Ser Ala Arg Leu Ala Thr Glu Lys
            180                 185                 190 ctt gaa aaa atg aaa gct gaa aaa gcg aaa caa caa gat aac aac gaa       624
Leu Glu Lys Met Lys Ala Glu Lys Ala Lys Gln Gln Asp Asn Asn Glu
        195                 200                 205 agt gct gtc gat aag tgt caa att ggt aag ccg att caa att gaa aat       672
Ser Ala Val Asp Lys Cys Gln Ile Gly Lys Pro Ile Gln Ile Glu Asn
210                 215                 220 att aaa cca att gaa tct att att gag gaa gag ttt aaa gtt gca ata       720
Ile Lys Pro Ile Glu Ser Ile Ile Glu Glu Glu Phe Lys Val Ala Ile
225                 230                 235                 240 gag ggt gtc att ttt gat ata aac tta aaa gaa ctt aaa agt ggt cgt       768
Glu Gly Val Ile Phe Asp Ile Asn Leu Lys Glu Leu Lys Ser Gly Arg
                245                 250                 255 cat atc gta gaa att aaa gtg act gac tat acg gac tca tta gtt tta       816
His Ile Val Glu Ile Lys Val Thr Asp Tyr Thr Asp Ser Leu Val Leu
            260                 265                 270 aaa atg ttt act cgt aaa aac aaa gat gat tta gaa cat ttt aaa gcg       864
Lys Met Phe Thr Arg Lys Asn Lys Asp Asp Leu Glu His Phe Lys Ala
        275                 280                 285 cta agt gta ggt aaa tgg gtt agg gct caa ggt cgt att gaa gaa gat       912
Leu Ser Val Gly Lys Trp Val Arg Ala Gln Gly Arg Ile Glu Glu Asp
290                 295                 300 aca ttt att aga gat tta gtt atg atg atg tct gat att gaa gag att       960
Thr Phe Ile Arg Asp Leu Val Met Met Met Ser Asp Ile Glu Glu Ile
305                 310                 315                 320 aaa aaa gcg aca aaa aaa gat aag gct gaa gaa aag cgt gta gaa ttc      1008
Lys Lys Ala Thr Lys Lys Asp Lys Ala Glu Glu Lys Arg Val Glu Phe
                325                 330                 335 cac ttg cat act gca atg agc caa atg gat ggt ata ccc aat att ggt      1056
His Leu His Thr Ala Met Ser Gln Met Asp Gly Ile Pro Asn Ile Gly
            340                 345                 350 gcg tat gtt aaa cag gca gca gac tgg gga cat cca gcc att gcg gtt      1104
Ala Tyr Val Lys Gln Ala Ala Asp Trp Gly His Pro Ala Ile Ala Val
        355                 360                 365 aca gac cat aat gtt gtg caa gca ttt cca gat gct cac gca gca gcg      1152
Thr Asp His Asn Val Val Gln Ala Phe Pro Asp Ala His Ala Ala Ala
370                 375                 380 gaa aaa cat ggc att aaa atg ata tac ggt atg gaa ggt atg tta gtt      1200
Glu Lys His Gly Ile Lys Met Ile Tyr Gly Met Glu Gly Met Leu Val
385                 390                 395                 400 gat gat ggt gtt ccg att gca tac aaa cca caa gat gtc gta tta aaa      1248
Asp Asp Gly Val Pro Ile Ala Tyr Lys Pro Gln Asp Val Val Leu Lys
                405                 410                 415 gat gct act tat gtt gtg ttc gac gtt gag aca act ggt tta tca aat      1296
Asp Ala Thr Tyr Val Val Phe Asp Val Glu Thr Thr Gly Leu Ser Asn
            420                 425                 430 cag tat gat aaa atc atc gag ctt gca gct gtg aaa gtt cat aac ggt      1344
Gln Tyr Asp Lys Ile Ile Glu Leu Ala Ala Val Lys Val His Asn Gly
        435                 440                 445 gaa atc atc gat aag ttt gaa agg ttt agt aat ccg cat gaa cga tta      1392
```

-continued

```
                Glu Ile Ile Asp Lys Phe Glu Arg Phe Ser Asn Pro His Glu Arg Leu
                    450                 455                 460 tcg gaa acg att atc aat ttg acg cat att act gat gat atg tta gta    1440
Ser Glu Thr Ile Ile Asn Leu Thr His Ile Thr Asp Asp Met Leu Val
465                 470                 475                 480 gat gcc cct gag att gaa gaa gta ctt aca gag ttt aaa gaa tgg gtt    1488
Asp Ala Pro Glu Ile Glu Glu Val Leu Thr Glu Phe Lys Glu Trp Val
                485                 490                 495 ggc gat gcg ata ttc gta gcg cat aat gct tcg ttt gat atg ggc ttt    1536
Gly Asp Ala Ile Phe Val Ala His Asn Ala Ser Phe Asp Met Gly Phe
            500                 505                 510 atc gat acg gga tat gaa cgt ctt ggg ttt gga cca tca acg aat ggt    1584
Ile Asp Thr Gly Tyr Glu Arg Leu Gly Phe Gly Pro Ser Thr Asn Gly
        515                 520                 525 gtt atc gat act tta gaa tta tct cgt acg att aat act gaa tat ggt    1632
Val Ile Asp Thr Leu Glu Leu Ser Arg Thr Ile Asn Thr Glu Tyr Gly
    530                 535                 540 aaa cat ggt ttg aat ttc tta gct aaa aaa tat ggc gta gaa tta acg    1680
Lys His Gly Leu Asn Phe Leu Ala Lys Lys Tyr Gly Val Glu Leu Thr
545                 550                 555                 560 caa cat cac cgt gcc att tat gat aca gaa gca aca gct tac att ttc    1728
Gln His His Arg Ala Ile Tyr Asp Thr Glu Ala Thr Ala Tyr Ile Phe
                565                 570                 575 ata aaa atg gtt caa caa atg aaa gaa tta ggt gta tta aat cat aac    1776
Ile Lys Met Val Gln Gln Met Lys Glu Leu Gly Val Leu Asn His Asn
                580                 585                 590 gaa atc aac aaa aaa ctc agt aat gaa gat gca tat aaa cgt gca aga    1824
Glu Ile Asn Lys Lys Leu Ser Asn Glu Asp Ala Tyr Lys Arg Ala Arg
            595                 600                 605 cct agc cat gtc aca tta att gta caa aac caa caa ggt ctt aaa aat    1872
Pro Ser His Val Thr Leu Ile Val Gln Asn Gln Gln Gly Leu Lys Asn
        610                 615                 620 cta ttt aaa att gta agt gca tca ttg gtg aag tat ttc tac cgt aca    1920
Leu Phe Lys Ile Val Ser Ala Ser Leu Val Lys Tyr Phe Tyr Arg Thr
625                 630                 635                 640 cct cga att cca cgt tca ttg tta gat gaa tat cgt gag gga tta ttg    1968
Pro Arg Ile Pro Arg Ser Leu Leu Asp Glu Tyr Arg Glu Gly Leu Leu
                645                 650                 655 gta ggt aca gcg tgt gat gaa ggt gaa tta ttt acg gca gtt atg cag    2016
Val Gly Thr Ala Cys Asp Glu Gly Glu Leu Phe Thr Ala Val Met Gln
                660                 665                 670 aag gac cag agc caa gtt gaa aaa att gcc aaa tat tat gat ttt att    2064
Lys Asp Gln Ser Gln Val Glu Lys Ile Ala Lys Tyr Tyr Asp Phe Ile
            675                 680                 685 gaa att caa cca ccg gca ctt tat caa gat tta att gat aga gag ctt    2112
Glu Ile Gln Pro Pro Ala Leu Tyr Gln Asp Leu Ile Asp Arg Glu Leu
        690                 695                 700 att aga gat act gaa aca tta cat gaa att tat caa cgt tta ata cat    2160
Ile Arg Asp Thr Glu Thr Leu His Glu Ile Tyr Gln Arg Leu Ile His
705                 710                 715                 720 gca ggt gac aca gcg ggt ata cct gtt att gcg aca gga aat gca cac    2208
Ala Gly Asp Thr Ala Gly Ile Pro Val Ile Ala Thr Gly Asn Ala His
                725                 730                 735 tat ttg ttt gaa cat gat ggt atc gca cgt aaa att tta ata gca tca    2256
Tyr Leu Phe Glu His Asp Gly Ile Ala Arg Lys Ile Leu Ile Ala Ser
                740                 745                 750 caa ccc ggc aat cca ctt aat cgc tca act tta ccg gaa gca cat ttt    2304
Gln Pro Gly Asn Pro Leu Asn Arg Ser Thr Leu Pro Glu Ala His Phe
            755                 760                 765 aga act aca gat gaa atg tta aac gag ttt cat ttt tta ggt gaa gaa    2352
```

```
                                              -continued

Arg Thr Thr Asp Glu Met Leu Asn Glu Phe His Phe Leu Gly Glu Glu
    770             775             780 aaa gcg cat gaa att gtt gtg aaa aat aca aac gaa tta gca gat cga    2400
Lys Ala His Glu Ile Val Val Lys Asn Thr Asn Glu Leu Ala Asp Arg
785             790             795             800 att gaa cgt gtt gtt cct att aaa gat gaa tta tac aca ccg cgt atg    2448
Ile Glu Arg Val Val Pro Ile Lys Asp Glu Leu Tyr Thr Pro Arg Met
            805             810             815 gaa ggt gct aac gaa gaa att aga gaa cta agt tat aca aat gcg cgt    2496
Glu Gly Ala Asn Glu Glu Ile Arg Glu Leu Ser Tyr Thr Asn Ala Arg
        820             825             830 aaa ctg tat ggt gaa gac ctg cct caa atc gta att gat cga tta gaa    2544
Lys Leu Tyr Gly Glu Asp Leu Pro Gln Ile Val Ile Asp Arg Leu Glu
    835             840             845 aaa gaa tta aaa agt att atc ggt aat gga ttt gcg gta att tac tta    2592
Lys Glu Leu Lys Ser Ile Ile Gly Asn Gly Phe Ala Val Ile Tyr Leu
850             855             860 att tcg caa cgt tta gtt aaa aaa tca tta gat gat gga tac tta gtt    2640
Ile Ser Gln Arg Leu Val Lys Lys Ser Leu Asp Asp Gly Tyr Leu Val
865             870             875             880 ggt tcc cgt ggt tca gta ggt tct agt ttt gta gcg aca atg act gag    2688
Gly Ser Arg Gly Ser Val Gly Ser Ser Phe Val Ala Thr Met Thr Glu
            885             890             895 att act gaa gta aac ccg tta ccg cca cac tat att tgt ccg aac tgt    2736
Ile Thr Glu Val Asn Pro Leu Pro Pro His Tyr Ile Cys Pro Asn Cys
        900             905             910 aaa acg agt gaa ttt ttc aat gat ggt tca gta gga tca gga ttc gat    2784
Lys Thr Ser Glu Phe Phe Asn Asp Gly Ser Val Gly Ser Gly Phe Asp
    915             920             925 tta cct gat aag acg tgt gaa act tgt gga gcg cca ctt att aaa gaa    2832
Leu Pro Asp Lys Thr Cys Glu Thr Cys Gly Ala Pro Leu Ile Lys Glu
930             935             940 gga caa gat att ccg ttt gaa aca ttt tta gga ttt aag gga gat aaa    2880
Gly Gln Asp Ile Pro Phe Glu Thr Phe Leu Gly Phe Lys Gly Asp Lys
945             950             955             960 gtt cct gat atc gac tta aac ttt agt ggt gaa tat caa ccg aat gcc    2928
Val Pro Asp Ile Asp Leu Asn Phe Ser Gly Glu Tyr Gln Pro Asn Ala
            965             970             975 cat aac tac aca aaa gta tta ttt ggt gag gat aaa gta ttc cgt gca    2976
His Asn Tyr Thr Lys Val Leu Phe Gly Glu Asp Lys Val Phe Arg Ala
        980             985             990 ggt aca att ggt acc gtt gct gaa aag act gct ttt ggt tat gtt aaa    3024
Gly Thr Ile Gly Thr Val Ala Glu Lys Thr Ala Phe Gly Tyr Val Lys
    995            1000            1005 ggt tat ttg aat gat caa ggc atc cac aaa aga ggc gct gaa ata        3069
Gly Tyr Leu Asn Asp Gln Gly Ile His Lys Arg Gly Ala Glu Ile
1010            1015            1020 gat cga ctc gtt aaa gga tgt aca ggt gtt aaa cgt aca act gga        3114
Asp Arg Leu Val Lys Gly Cys Thr Gly Val Lys Arg Thr Thr Gly
    1025            1030            1035 cag cat cca gga ggt att att gta gta cct gat tac atg gat att       3159
Gln His Pro Gly Gly Ile Ile Val Val Pro Asp Tyr Met Asp Ile
        1040            1045            1050 tat gat ttt acg ccg ata caa tat cct gcc gat gat caa aat tca       3204
Tyr Asp Phe Thr Pro Ile Gln Tyr Pro Ala Asp Asp Gln Asn Ser
    1055            1060            1065 gca tgg atg acg aca cat ttt gat ttc cat tct att cat gat aat       3249
Ala Trp Met Thr Thr His Phe Asp Phe His Ser Ile His Asp Asn
1070            1075            1080 gta tta aaa ctt gat ata ctt gga cac gat gat cca aca atg att       3294
```

```
Val Leu Lys Leu Asp Ile Leu Gly His Asp Asp Pro Thr Met Ile
    1085                1090                1095 cgt atg ctt caa gat tta tcg ggc att gat cca aaa acg ata cct    3339
Arg Met Leu Gln Asp Leu Ser Gly Ile Asp Pro Lys Thr Ile Pro
1100                1105                1110 gta gat gac aaa gaa gtc atg caa ata ttt agt aca cct gaa agt    3384
Val Asp Asp Lys Glu Val Met Gln Ile Phe Ser Thr Pro Glu Ser
    1115                1120                1125 tta ggt gtt act gaa gat gaa att tta tgt aaa aca ggt acg ttt    3429
Leu Gly Val Thr Glu Asp Glu Ile Leu Cys Lys Thr Gly Thr Phe
1130                1135                1140 ggg gtt cca gaa ttc ggt aca ggg ttc gtg cgt caa atg tta gaa    3474
Gly Val Pro Glu Phe Gly Thr Gly Phe Val Arg Gln Met Leu Glu
    1145                1150                1155 gat aca aag cca aca aca ttt tct gaa tta gtt caa atc tca gga    3519
Asp Thr Lys Pro Thr Thr Phe Ser Glu Leu Val Gln Ile Ser Gly
1160                1165                1170 tta tct cat ggt aca gat gtg tgg tta ggc aat gct caa gaa tta    3564
Leu Ser His Gly Thr Asp Val Trp Leu Gly Asn Ala Gln Glu Leu
    1175                1180                1185 att aaa acc ggt ata tgt gat tta tca agt gta att ggt tgt cgt    3609
Ile Lys Thr Gly Ile Cys Asp Leu Ser Ser Val Ile Gly Cys Arg
1190                1195                1200 gat gat atc atg gtt tat tta atg tat gct ggt tta gaa cca tca    3654
Asp Asp Ile Met Val Tyr Leu Met Tyr Ala Gly Leu Glu Pro Ser
    1205                1210                1215 atg gct ttt aaa ata atg gag tca gta cgt aaa ggt aaa ggt tta    3699
Met Ala Phe Lys Ile Met Glu Ser Val Arg Lys Gly Lys Gly Leu
1220                1225                1230 act gaa gaa atg att gaa acg atg aaa gaa aat gaa gtg ccg gat    3744
Thr Glu Glu Met Ile Glu Thr Met Lys Glu Asn Glu Val Pro Asp
    1235                1240                1245 tgg tat tta gat tca tgt ctt aaa att aag tac atg ttc cct aaa    3789
Trp Tyr Leu Asp Ser Cys Leu Lys Ile Lys Tyr Met Phe Pro Lys
1250                1255                1260 gcc cat gca gca gca tac gtt tta atg gca gta cgt atc gca tat    3834
Ala His Ala Ala Ala Tyr Val Leu Met Ala Val Arg Ile Ala Tyr
    1265                1270                1275 ttc aaa gta cat cat cca ctt tat tac tat gca tct tac ttt aca    3879
Phe Lys Val His His Pro Leu Tyr Tyr Tyr Ala Ser Tyr Phe Thr
1280                1285                1290 att cgt gcg tca gat ttt gat tta atc acg atg att aaa gat aaa    3924
Ile Arg Ala Ser Asp Phe Asp Leu Ile Thr Met Ile Lys Asp Lys
    1295                1300                1305 aca agc att cga aat act gta aaa gac atg tat tct cgc tat atg    3969
Thr Ser Ile Arg Asn Thr Val Lys Asp Met Tyr Ser Arg Tyr Met
1310                1315                1320 gat cta ggt aaa aaa gaa aaa gac gta tta aca gtc ttg gaa att    4014
Asp Leu Gly Lys Lys Glu Lys Asp Val Leu Thr Val Leu Glu Ile
    1325                1330                1335 atg aat gaa atg gcg cat cga ggt tat cga atg caa ccg att agt    4059
Met Asn Glu Met Ala His Arg Gly Tyr Arg Met Gln Pro Ile Ser
1340                1345                1350 tta gaa aag agt cag gcg ttc gaa ttt atc att gaa ggc gat aca    4104
Leu Glu Lys Ser Gln Ala Phe Glu Phe Ile Ile Glu Gly Asp Thr
    1355                1360                1365 ctt att ccg ccg ttc ata tca gtg cct ggg ctt ggc gaa aac gtt    4149
Leu Ile Pro Pro Phe Ile Ser Val Pro Gly Leu Gly Glu Asn Val
1370                1375                1380 gcg aaa cga att gtt gaa gct cgt gac gat ggc cca ttt tta tca    4194
```

```
Ala Lys Arg Ile Val Glu Ala Arg Asp Asp Gly Pro Phe Leu Ser
    1385                1390                1395 aaa gaa gat tta aac aaa aaa gct gga tta tct cag aaa att att    4239
Lys Glu Asp Leu Asn Lys Lys Ala Gly Leu Ser Gln Lys Ile Ile
    1400                1405                1410 gag tat tta gat gag tta ggc tca tta ccg aat tta cca gat aaa    4284
Glu Tyr Leu Asp Glu Leu Gly Ser Leu Pro Asn Leu Pro Asp Lys
    1415                1420                1425 gct caa ctt tcg ata ttt gat atg taa                            4311
Ala Gln Leu Ser Ile Phe Asp Met
    1430                1435

<210> SEQ ID NO 45
<211> LENGTH: 1436
<212> TYPE: PRT
<213> ORGANISM: Staphylococcus aureus

<400> SEQUENCE: 45

Met Thr Glu Gln Gln Lys Phe Lys Val Leu Ala Asp Gln Ile Lys Ile
1               5                   10                  15

Ser Asn Gln Leu Asp Ala Glu Ile Leu Asn Ser Gly Glu Leu Thr Arg
            20                  25                  30

Ile Asp Val Ser Asn Lys Asn Arg Thr Trp Glu Phe His Ile Thr Leu
        35                  40                  45

Pro Gln Phe Leu Ala His Glu Asp Tyr Leu Leu Phe Ile Asn Ala Ile
    50                  55                  60

Glu Gln Glu Phe Lys Asp Ile Ala Asn Val Thr Cys Arg Phe Thr Val
65                  70                  75                  80

Thr Asn Gly Thr Asn Gln Asp Glu His Ala Ile Lys Tyr Phe Gly His
                85                  90                  95

Cys Ile Asp Gln Thr Ala Leu Ser Pro Lys Val Lys Gly Gln Leu Lys
            100                 105                 110

Gln Lys Lys Leu Ile Met Ser Gly Lys Val Leu Lys Val Met Val Ser
        115                 120                 125

Asn Asp Ile Glu Arg Asn His Phe Asp Lys Ala Cys Asn Gly Ser Leu
    130                 135                 140

Ile Lys Ala Phe Arg Asn Cys Gly Phe Asp Ile Asp Lys Ile Ile Phe
145                 150                 155                 160

Glu Thr Asn Asp Asn Asp Gln Glu Gln Asn Leu Ala Ser Leu Glu Ala
                165                 170                 175

His Ile Gln Glu Glu Asp Glu Gln Ser Ala Arg Leu Ala Thr Glu Lys
            180                 185                 190

Leu Glu Lys Met Lys Ala Glu Lys Ala Lys Gln Gln Asp Asn Asn Glu
        195                 200                 205

Ser Ala Val Asp Lys Cys Gln Ile Gly Lys Pro Ile Gln Ile Glu Asn
    210                 215                 220

Ile Lys Pro Ile Glu Ser Ile Ile Glu Glu Phe Lys Val Ala Ile
225                 230                 235                 240

Glu Gly Val Ile Phe Asp Ile Asn Leu Lys Glu Leu Lys Ser Gly Arg
                245                 250                 255

His Ile Val Glu Ile Lys Val Thr Asp Tyr Thr Asp Ser Leu Val Leu
            260                 265                 270

Lys Met Phe Thr Arg Lys Asn Lys Asp Asp Leu Glu His Phe Lys Ala
        275                 280                 285

Leu Ser Val Gly Lys Trp Val Arg Ala Gln Gly Arg Ile Glu Glu Asp
    290                 295                 300
```

```
Thr Phe Ile Arg Asp Leu Val Met Met Met Ser Asp Ile Glu Glu Ile
305                 310                 315                 320

Lys Lys Ala Thr Lys Asp Lys Ala Glu Lys Arg Val Glu Phe
            325                 330                 335

His Leu His Thr Ala Met Ser Gln Met Asp Gly Ile Pro Asn Ile Gly
            340                 345                 350

Ala Tyr Val Lys Gln Ala Ala Asp Trp Gly His Pro Ala Ile Ala Val
                355                 360                 365

Thr Asp His Asn Val Val Gln Ala Phe Pro Asp Ala His Ala Ala
370                 375                 380

Glu Lys His Gly Ile Lys Met Ile Tyr Gly Met Glu Gly Met Leu Val
385                 390                 395                 400

Asp Asp Gly Val Pro Ile Ala Tyr Lys Pro Gln Asp Val Val Leu Lys
                405                 410                 415

Asp Ala Thr Tyr Val Val Phe Asp Val Glu Thr Thr Gly Leu Ser Asn
            420                 425                 430

Gln Tyr Asp Lys Ile Ile Glu Leu Ala Ala Val Lys Val His Asn Gly
        435                 440                 445

Glu Ile Ile Asp Lys Phe Glu Arg Phe Ser Asn Pro His Glu Arg Leu
450                 455                 460

Ser Glu Thr Ile Ile Asn Leu Thr His Ile Thr Asp Asp Met Leu Val
465                 470                 475                 480

Asp Ala Pro Glu Ile Glu Val Leu Thr Glu Phe Lys Glu Trp Val
            485                 490                 495

Gly Asp Ala Ile Phe Val Ala His Asn Ala Ser Phe Asp Met Gly Phe
                500                 505                 510

Ile Asp Thr Gly Tyr Glu Arg Leu Gly Phe Gly Pro Ser Thr Asn Gly
            515                 520                 525

Val Ile Asp Thr Leu Glu Leu Ser Arg Thr Ile Asn Thr Glu Tyr Gly
530                 535                 540

Lys His Gly Leu Asn Phe Leu Ala Lys Lys Tyr Gly Val Glu Leu Thr
545                 550                 555                 560

Gln His His Arg Ala Ile Tyr Asp Thr Glu Ala Thr Ala Tyr Ile Phe
                565                 570                 575

Ile Lys Met Val Gln Gln Met Lys Glu Leu Gly Val Leu Asn His Asn
            580                 585                 590

Glu Ile Asn Lys Lys Leu Ser Asn Glu Asp Ala Tyr Lys Arg Ala Arg
        595                 600                 605

Pro Ser His Val Thr Leu Ile Val Gln Asn Gln Gly Leu Lys Asn
            610                 615                 620

Leu Phe Lys Ile Val Ser Ala Ser Leu Val Lys Tyr Phe Tyr Arg Thr
625                 630                 635                 640

Pro Arg Ile Pro Arg Ser Leu Leu Asp Glu Tyr Arg Glu Gly Leu Leu
                645                 650                 655

Val Gly Thr Ala Cys Asp Glu Gly Glu Leu Phe Thr Ala Val Met Gln
            660                 665                 670

Lys Asp Gln Ser Gln Val Glu Lys Ile Ala Lys Tyr Tyr Asp Phe Ile
        675                 680                 685

Glu Ile Gln Pro Pro Ala Leu Tyr Gln Asp Leu Ile Asp Arg Glu Leu
690                 695                 700

Ile Arg Asp Thr Glu Thr Leu His Glu Ile Tyr Gln Arg Leu Ile His
705                 710                 715                 720

Ala Gly Asp Thr Ala Gly Ile Pro Val Ile Ala Thr Gly Asn Ala His
                725                 730                 735
```

```
Tyr Leu Phe Glu His Asp Gly Ile Ala Arg Lys Ile Leu Ile Ala Ser
            740                 745                 750

Gln Pro Gly Asn Pro Leu Asn Arg Ser Thr Leu Pro Glu Ala His Phe
            755                 760             765

Arg Thr Thr Asp Glu Met Leu Asn Glu Phe His Phe Leu Gly Glu Glu
            770                 775             780

Lys Ala His Glu Ile Val Val Lys Asn Thr Asn Glu Leu Ala Asp Arg
785                 790                 795                 800

Ile Glu Arg Val Val Pro Ile Lys Asp Glu Leu Tyr Thr Pro Arg Met
                805                 810                 815

Glu Gly Ala Asn Glu Glu Ile Arg Glu Leu Ser Tyr Thr Asn Ala Arg
            820                 825                 830

Lys Leu Tyr Gly Glu Asp Leu Pro Gln Ile Val Ile Asp Arg Leu Glu
            835                 840                 845

Lys Glu Leu Lys Ser Ile Ile Gly Asn Gly Phe Ala Val Ile Tyr Leu
850                 855                 860

Ile Ser Gln Arg Leu Val Lys Lys Ser Leu Asp Asp Gly Tyr Leu Val
865                 870                 875                 880

Gly Ser Arg Gly Ser Val Gly Ser Ser Phe Val Ala Thr Met Thr Glu
            885                 890                 895

Ile Thr Glu Val Asn Pro Leu Pro Pro His Tyr Ile Cys Pro Asn Cys
            900                 905                 910

Lys Thr Ser Glu Phe Phe Asn Asp Gly Ser Val Gly Ser Gly Phe Asp
            915                 920             925

Leu Pro Asp Lys Thr Cys Glu Thr Cys Gly Ala Pro Leu Ile Lys Glu
            930                 935             940

Gly Gln Asp Ile Pro Phe Glu Thr Phe Leu Gly Phe Lys Gly Asp Lys
945                 950                 955             960

Val Pro Asp Ile Asp Leu Asn Phe Ser Gly Glu Tyr Gln Pro Asn Ala
                965                 970             975

His Asn Tyr Thr Lys Val Leu Phe Gly Glu Asp Lys Val Phe Arg Ala
            980                 985                 990

Gly Thr Ile Gly Thr Val Ala Glu Lys Thr Ala Phe Gly Tyr Val Lys
            995                 1000                1005

Gly Tyr Leu Asn Asp Gln Gly Ile His Lys Arg Gly Ala Glu Ile
            1010            1015                1020

Asp Arg Leu Val Lys Gly Cys Thr Gly Val Lys Arg Thr Thr Gly
            1025            1030            1035

Gln His Pro Gly Gly Ile Ile Val Val Pro Asp Tyr Met Asp Ile
            1040            1045            1050

Tyr Asp Phe Thr Pro Ile Gln Tyr Pro Ala Asp Asp Gln Asn Ser
            1055            1060            1065

Ala Trp Met Thr Thr His Phe Asp Phe His Ser Ile His Asp Asn
            1070            1075            1080

Val Leu Lys Leu Asp Ile Leu Gly His Asp Asp Pro Thr Met Ile
            1085            1090            1095

Arg Met Leu Gln Asp Leu Ser Gly Ile Asp Pro Lys Thr Ile Pro
            1100            1105            1110

Val Asp Asp Lys Glu Val Met Gln Ile Phe Ser Thr Pro Glu Ser
            1115            1120            1125

Leu Gly Val Thr Glu Asp Glu Ile Leu Cys Lys Thr Gly Thr Phe
            1130            1135            1140

Gly Val Pro Glu Phe Gly Thr Gly Phe Val Arg Gln Met Leu Glu
```

-continued

```
        1145                1150                1155

Asp Thr Lys Pro Thr Thr Phe Ser Glu Leu Val Gln Ile Ser Gly
    1160                1165                1170

Leu Ser His Gly Thr Asp Val Trp Leu Gly Asn Ala Gln Glu Leu
    1175                1180                1185

Ile Lys Thr Gly Ile Cys Asp Leu Ser Ser Val Ile Gly Cys Arg
    1190                1195                1200

Asp Asp Ile Met Val Tyr Leu Met Tyr Ala Gly Leu Glu Pro Ser
    1205                1210                1215

Met Ala Phe Lys Ile Met Glu Ser Val Arg Lys Gly Lys Gly Leu
    1220                1225                1230

Thr Glu Glu Met Ile Glu Thr Met Lys Glu Asn Glu Val Pro Asp
    1235                1240                1245

Trp Tyr Leu Asp Ser Cys Leu Lys Ile Lys Tyr Met Phe Pro Lys
    1250                1255                1260

Ala His Ala Ala Ala Tyr Val Leu Met Ala Val Arg Ile Ala Tyr
    1265                1270                1275

Phe Lys Val His His Pro Leu Tyr Tyr Tyr Ala Ser Tyr Phe Thr
    1280                1285                1290

Ile Arg Ala Ser Asp Phe Asp Leu Ile Thr Met Ile Lys Asp Lys
    1295                1300                1305

Thr Ser Ile Arg Asn Thr Val Lys Asp Met Tyr Ser Arg Tyr Met
    1310                1315                1320

Asp Leu Gly Lys Lys Glu Lys Asp Val Leu Thr Val Leu Glu Ile
    1325                1330                1335

Met Asn Glu Met Ala His Arg Gly Tyr Arg Met Gln Pro Ile Ser
    1340                1345                1350

Leu Glu Lys Ser Gln Ala Phe Glu Phe Ile Ile Glu Gly Asp Thr
    1355                1360                1365

Leu Ile Pro Pro Phe Ile Ser Val Pro Gly Leu Gly Glu Asn Val
    1370                1375                1380

Ala Lys Arg Ile Val Glu Ala Arg Asp Asp Gly Pro Phe Leu Ser
    1385                1390                1395

Lys Glu Asp Leu Asn Lys Lys Ala Gly Leu Ser Gln Lys Ile Ile
    1400                1405                1410

Glu Tyr Leu Asp Glu Leu Gly Ser Leu Pro Asn Leu Pro Asp Lys
    1415                1420                1425

Ala Gln Leu Ser Ile Phe Asp Met
    1430                1435

<210> SEQ ID NO 46
<211> LENGTH: 32
<212> TYPE: DNA
<213> ORGANISM: Artificial
<220> FEATURE:
<223> OTHER INFORMATION: primer

<400> SEQUENCE: 46
gtaccatatg acagagcaac aaaaatttaa ag                                  32

<210> SEQ ID NO 47
<211> LENGTH: 34
<212> TYPE: DNA
<213> ORGANISM: Artificial
<220> FEATURE:
<223> OTHER INFORMATION: primer

<400> SEQUENCE: 47
```

```
gttcactagt ctattacata tcaaatatcg aaag                                34
```

<210> SEQ ID NO 48
<211> LENGTH: 555
<212> TYPE: DNA
<213> ORGANISM: Staphylococcus aureus

<400> SEQUENCE: 48

```
atgatacaag atgcgtttgt tgcacttgat tttgaaacag caaatggtaa acgtacaagt      60
atttgttctg tcggaatggt taaagtcatt gatagtcaaa taacagaaac atttcatact     120
cttgtgaatc cgcaagacta tttttcacaa caaaatatta agttcatgg catacaacca     180 gaagatgttg aaaatgcacc tacgtttgac tacgtatttc catatatgat gcaatttatt     240
gcagatttac ctgttgtcgc acataacgcg gcatttgata tgaacgtctt acatcaaagc     300
attcaaaata ttggtttacc aactccaaat ttaacttact tttgtagtta caacttgct     360 aaaagaaccg ttgattcgta tcgatacggt ttaaaacata tgatggagtt ttatcaatta     420
gattttcatg gtcatcatga tgcattgaat gatgccaaag catgcgcaat gattactttt     480
aggctactga aaaattatga aaatttaaca tatgtaacta atatttatgg taaaaatcta     540
aaagataaag gctag                                                     555
```

<210> SEQ ID NO 49
<211> LENGTH: 555
<212> TYPE: DNA
<213> ORGANISM: Staphylococcus aureus
<220> FEATURE:
<221> NAME/KEY: CDS
<222> LOCATION: (1)..(555)

<400> SEQUENCE: 49

```
atg ata caa gat gcg ttt gtt gca ctt gat ttt gaa aca gca aat ggt       48
Met Ile Gln Asp Ala Phe Val Ala Leu Asp Phe Glu Thr Ala Asn Gly
1               5                   10                  15 aaa cgt aca agt att tgt tct gtc gga atg gtt aaa gtc att gat agt       96
Lys Arg Thr Ser Ile Cys Ser Val Gly Met Val Lys Val Ile Asp Ser
            20                  25                  30 caa ata aca gaa aca ttt cat act ctt gtg aat ccg caa gac tat ttt      144
Gln Ile Thr Glu Thr Phe His Thr Leu Val Asn Pro Gln Asp Tyr Phe
        35                  40                  45 tca caa caa aat att aaa gtt cat ggc ata caa cca gaa gat gtt gaa      192
Ser Gln Gln Asn Ile Lys Val His Gly Ile Gln Pro Glu Asp Val Glu
    50                  55                  60 aat gca cct acg ttt gac tac gta ttt cca tat atg atg caa ttt att      240
Asn Ala Pro Thr Phe Asp Tyr Val Phe Pro Tyr Met Met Gln Phe Ile
65                  70                  75                  80 gca gat tta cct gtt gtc gca cat aac gcg gca ttt gat atg aac gtc      288
Ala Asp Leu Pro Val Val Ala His Asn Ala Ala Phe Asp Met Asn Val
                85                  90                  95 tta cat caa agc att caa aat att ggt tta cca act cca aat tta act      336
Leu His Gln Ser Ile Gln Asn Ile Gly Leu Pro Thr Pro Asn Leu Thr
            100                 105                 110 tac ttt tgt agt tat caa ctt gct aaa aga acc gtt gat tcg tat cga      384
Tyr Phe Cys Ser Tyr Gln Leu Ala Lys Arg Thr Val Asp Ser Tyr Arg
        115                 120                 125 tac ggt tta aaa cat atg atg gag ttt tat caa tta gat ttt cat ggt      432
Tyr Gly Leu Lys His Met Met Glu Phe Tyr Gln Leu Asp Phe His Gly
    130                 135                 140 cat cat gat gca ttg aat gat gcc aaa gca tgc gca atg att act ttt      480
His His Asp Ala Leu Asn Asp Ala Lys Ala Cys Ala Met Ile Thr Phe
```

```
                 145                 150                 155                 160
agg cta ctg aaa aat tat gaa aat tta aca tat gta act aat att tat        528
Arg Leu Leu Lys Asn Tyr Glu Asn Leu Thr Tyr Val Thr Asn Ile Tyr
                165                 170                 175 ggt aaa aat cta aaa gat aaa ggc tag                                    555
Gly Lys Asn Leu Lys Asp Lys Gly
            180
```

<210> SEQ ID NO 50
<211> LENGTH: 184
<212> TYPE: PRT
<213> ORGANISM: Staphylococcus aureus

<400> SEQUENCE: 50

```
Met Ile Gln Asp Ala Phe Val Ala Leu Asp Phe Glu Thr Ala Asn Gly
1               5                   10                  15

Lys Arg Thr Ser Ile Cys Ser Val Gly Met Val Lys Val Ile Asp Ser
                20                  25                  30

Gln Ile Thr Glu Thr Phe His Thr Leu Val Asn Pro Gln Asp Tyr Phe
            35                  40                  45

Ser Gln Gln Asn Ile Lys Val His Gly Ile Gln Pro Glu Asp Val Glu
        50                  55                  60

Asn Ala Pro Thr Phe Asp Tyr Val Phe Pro Tyr Met Met Gln Phe Ile
65                  70                  75                  80

Ala Asp Leu Pro Val Val Ala His Asn Ala Ala Phe Asp Met Asn Val
                85                  90                  95

Leu His Gln Ser Ile Gln Asn Ile Gly Leu Pro Thr Pro Asn Leu Thr
            100                 105                 110

Tyr Phe Cys Ser Tyr Gln Leu Ala Lys Arg Thr Val Asp Ser Tyr Arg
        115                 120                 125

Tyr Gly Leu Lys His Met Met Glu Phe Tyr Gln Leu Asp Phe His Gly
130                 135                 140

His His Asp Ala Leu Asn Asp Ala Lys Ala Cys Ala Met Ile Thr Phe
145                 150                 155                 160

Arg Leu Leu Lys Asn Tyr Glu Asn Leu Thr Tyr Val Thr Asn Ile Tyr
                165                 170                 175

Gly Lys Asn Leu Lys Asp Lys Gly
            180
```

<210> SEQ ID NO 51
<211> LENGTH: 40
<212> TYPE: DNA
<213> ORGANISM: Artificial
<220> FEATURE:
<223> OTHER INFORMATION: primer

<400> SEQUENCE: 51
gatcttaatt aaagatgatc caagatgcgt ttgttgcact          40

<210> SEQ ID NO 52
<211> LENGTH: 50
<212> TYPE: DNA
<213> ORGANISM: Artificial
<220> FEATURE:
<223> OTHER INFORMATION: primer

<400> SEQUENCE: 52
tagcggtacc atggactgca gcctccttca ctagccttta tcttttagat          50

<210> SEQ ID NO 53

<211> LENGTH: 3198
<212> TYPE: DNA
<213> ORGANISM: Staphylococcus aureus

<400> SEQUENCE: 53

```
atggtggcat atttaaatat tcatacggct tatgatttgt taaattcaag cttaaaaata    60
gaagatgccg taagacttgc tgtgtctgaa aatgttgatg cacttgccat aactgacacc   120
aatgtattgt atggttttcc taaattttat gatgcatgta tagcaaataa cattaaaccg   180
attttggta tgacaatata tgtgacaaat ggattaaata cagtcgaaac agttgttcta   240
gctaaaaata atgatggatt aaaagatttg tatcaactat catcggaaat aaaaatgaat   300
tcaatggaaa atgtttcatt tgaactattg caacaatttt catcgaattt gattatcatt   360
tttaaaaatg ttgcagacga acatcgtgac attgttcaag tttttgattc gcatgaagat   420
acgtatttag atcatcaaag tgttttagtt cagggtataa agcacgtatg gattcaaaat   480
gtttgttacc aaacacgtca agatgccgat acgatttctg cattagcagc tattagagac   540
aatgcaaaat tagacttaat tcatgatcaa gaagattttg gtgcacattt tttaactgaa   600
aaggaaatta acaattaga tattaaccaa gaatatttaa cgcaggttga tgttatagct   660
caaaagtgta atgcagaatt aaaatatcat caatctctac ttcctcaata tcagacacct   720
aacgatgaat cagctaaaaa atatttgtgg cgtgtcttag ttacacaatt gaaaaaatta   780
gaacttaatt atgacgtcta tttagagcga ttgaaatatg agtataaagt tattactaat   840
atgggttttg aagattattt cttaatagta agtgatttaa tccattatgc gaaaacgaat   900
gatgtgatgg taggtccagg tcgtggttct tcagctggct cactggtcag ttatttacta   960
ggtattacaa cgattgatcc tattaaattc aatctattat ttgaacgtttt tttaaaccca  1020
gaacgtgtaa caatgcctga tatagatatt gactttgaag atacacgccg agaaagggtt  1080
attcagtacg tccaagaaaa atatggcgag ctacatgtat ctggaattgt gactttcggt  1140
catctgcttg caagagcggt tgctagggat gttggacgaa ttatgggtt tgatgaagtt  1200
acattaaatg aaatttcaag tttaatccca cataaattag gaattacact tgatgaagca  1260
tatcaaattg acgattttaa aaaatttgta catcgaaacc atcgacatga acgctggttc  1320
agtatttgta aaagttaga aggtttacca agacatacat ctacacatgc ggcaggaatt  1380
attattaatg accatccatt atatgaatat gcccctttaa cgaaagggga tacaggatta  1440
ttaacgcaat ggacaatgac tgaagccgaa cgaattgggt tattaaaaat agattttcta  1500
gggttgagaa acttatcgat tattcatcaa atcttaatac aagtcaaaaa agatttaggt  1560
attaatattg atatcgaaaa gattccgttc gatgatcaaa agtgtttga attgttgtcg  1620
caaggagata cgactggcat attccaatta gagtcagacg tgtaagaag tgtattaaaa  1680
aaattaaagc cggaacactt tgaagatatt gttgctgtaa cttctttgta tagaccaggt  1740
ccaatggaag aaattccaac ttacattaca agaagacatg atccaagcaa agttcaatat  1800
ttacatccac atttagaacc tatattaaaa aatacttacg gtgttattat ttatcaagag  1860
caaattatgc aaatagcgag cacatttgca aacttcagtt atggtgaagc ggatattta  1920
agaagagcaa tgagtaaaaa aaatagagct gttcttgaaa gtgagcgtca acattttata  1980
gaaggtgcaa agcaaaatgg ttatcacgaa gacattagta agcaaatatt tgatttgatt  2040
ctgaaatttg ctgattatgg ttttcctaga gcacatgctg tcagctattc taaaattgca  2100
tacattatga gcttttttaaa agtccattat ccaaattatt tttacgcaaa tattttaagt  2160
aatgttattg gaagtgagaa gaaaactgct caaatgatag aagaagcaaa aaacaaggt   2220
```

-continued

```
atcactatat tgccaccgaa cattaacgaa agtcattggt tttataaacc ttcccaagaa      2280
ggcatttatt tatcaattgg tacaattaaa ggtgttggtt atcaaagtgt gaaagtgatt      2340
gttgatgaac gttatcagaa cggcaaattt aaagatttct ttgattttgc tagacgtata      2400
ccgaagagag tcaaaacgag aaagttactt gaagcactga ttttagtggg agcgtttgat      2460
gcttttggta aaacacgttc aacgttgttg caagctattg atcaagtgtt ggatggcgat      2520
ttaaacattg aacaagatgg tttttttattt gatatttttaa cgccaaaaca gatgtatgaa     2580
gataaagaag aattgcctga tgcacttatt agtcagtacg aaaaagaata tttaggattt      2640
tatgtttcgc aacacccagt agataaaaag tttgttgcca acaatatttt aacgatattt      2700
aaattgagta acgcgcagaa ttataaacct atattagtac agtttgataa agttaaacaa      2760
attcgaacta aaaatggtca aaatatggca ttcgtcacat aaatgatgg cattgaaact       2820 ttagatggtg tgattttccc taatcagttt aaaaagtacg aagagttgtt atcacataat      2880
gacttgttta tagttagcgg gaaatttgac catagaaagc aacaacgtca actaattata      2940
aatgagattc agacattagc cactttttgaa gaacaaaaat tagcatttgc caaacaaatt     3000
ataattagaa ataaatcaca aatagatatg tttgaagaga tgattaaagc tacgaaagag     3060
aatgctaatg atgttgtgtt atcctttttat gatgaaacga ttaaacaaat gactacttta    3120
ggctatatta atcaaaaaga tagtatgttt aataattttta tacaatccctt taaccctagt  3180 gatattaggc ttatataa                                                 3198

<210> SEQ ID NO 54
<211> LENGTH: 3198
<212> TYPE: DNA
<213> ORGANISM: Staphylococcus aureus
<220> FEATURE:
<221> NAME/KEY: CDS
<222> LOCATION: (1)..(3198)

<400> SEQUENCE: 54 atg gtg gca tat tta aat att cat acg gct tat gat ttg tta aat tca       48
Met Val Ala Tyr Leu Asn Ile His Thr Ala Tyr Asp Leu Leu Asn Ser
1               5                   10                  15 agc tta aaa ata gaa gat gcc gta aga ctt gct gtg tct gaa aat gtt       96
Ser Leu Lys Ile Glu Asp Ala Val Arg Leu Ala Val Ser Glu Asn Val
            20                  25                  30 gat gca ctt gcc ata act gac acc aat gta ttg tat ggt ttt cct aaa      144
Asp Ala Leu Ala Ile Thr Asp Thr Asn Val Leu Tyr Gly Phe Pro Lys
        35                  40                  45 ttt tat gat gca tgt ata gca aat aac att aaa ccg att ttt ggt atg      192
Phe Tyr Asp Ala Cys Ile Ala Asn Asn Ile Lys Pro Ile Phe Gly Met
    50                  55                  60 aca ata tat gtg aca aat gga tta aat aca gtc gaa aca gtt gtt cta      240
Thr Ile Tyr Val Thr Asn Gly Leu Asn Thr Val Glu Thr Val Val Leu
65                  70                  75                  80 gct aaa aat aat gat gga tta aaa gat ttg tat caa cta tca tcg gaa      288
Ala Lys Asn Asn Asp Gly Leu Lys Asp Leu Tyr Gln Leu Ser Ser Glu
                85                  90                  95 ata aaa atg aat tca atg gaa aat gtt tca ttt gaa cta ttg caa caa      336
Ile Lys Met Asn Ser Met Glu Asn Val Ser Phe Glu Leu Leu Gln Gln
            100                 105                 110 ttt tca tcg aat ttg att atc att ttt aaa aat gtt gca gac gaa cat      384
Phe Ser Ser Asn Leu Ile Ile Ile Phe Lys Asn Val Ala Asp Glu His
        115                 120                 125 cgt gac att gtt caa gtt ttt gat tcg cat gaa gat acg tat tta gat      432
Arg Asp Ile Val Gln Val Phe Asp Ser His Glu Asp Thr Tyr Leu Asp
    130                 135                 140
```

-continued

| | | | | | | | | | | | | | | | | |
|---|---|---|---|---|---|---|---|---|---|---|---|---|---|---|---|---|
| cat | caa | agt | gtt | tta | gtt | cag | ggt | ata | aag | cac | gta | tgg | att | caa | aat | 480 |
| His | Gln | Ser | Val | Leu | Val | Gln | Gly | Ile | Lys | His | Val | Trp | Ile | Gln | Asn | |
| 145 | | | | 150 | | | | | 155 | | | | | 160 | | |
| gtt | tgt | tac | caa | aca | cgt | caa | gat | gcc | gat | acg | att | tct | gca | tta | gca | 528 |
| Val | Cys | Tyr | Gln | Thr | Arg | Gln | Asp | Ala | Asp | Thr | Ile | Ser | Ala | Leu | Ala | |
| | | | | 165 | | | | | 170 | | | | | 175 | | |
| gct | att | aga | gac | aat | gca | aaa | tta | gac | tta | att | cat | gat | caa | gaa | gat | 576 |
| Ala | Ile | Arg | Asp | Asn | Ala | Lys | Leu | Asp | Leu | Ile | His | Asp | Gln | Glu | Asp | |
| | | | 180 | | | | | 185 | | | | | 190 | | | |
| ttt | ggt | gca | cat | ttt | tta | act | gaa | aag | gaa | att | aaa | caa | tta | gat | att | 624 |
| Phe | Gly | Ala | His | Phe | Leu | Thr | Glu | Lys | Glu | Ile | Lys | Gln | Leu | Asp | Ile | |
| | | | | 195 | | | | | 200 | | | | | 205 | | |
| aac | caa | gaa | tat | tta | acg | cag | gtt | gat | gtt | ata | gct | caa | aag | tgt | aat | 672 |
| Asn | Gln | Glu | Tyr | Leu | Thr | Gln | Val | Asp | Val | Ile | Ala | Gln | Lys | Cys | Asn | |
| | 210 | | | | | 215 | | | | | 220 | | | | | |
| gca | gaa | tta | aaa | tat | cat | caa | tct | cta | ctt | cct | caa | tat | cag | aca | cct | 720 |
| Ala | Glu | Leu | Lys | Tyr | His | Gln | Ser | Leu | Leu | Pro | Gln | Tyr | Gln | Thr | Pro | |
| 225 | | | | | 230 | | | | | 235 | | | | | 240 | |
| aac | gat | gaa | tca | gct | aaa | aaa | tat | ttg | tgg | cgt | gtc | tta | gtt | aca | caa | 768 |
| Asn | Asp | Glu | Ser | Ala | Lys | Lys | Tyr | Leu | Trp | Arg | Val | Leu | Val | Thr | Gln | |
| | | | | 245 | | | | | 250 | | | | | 255 | | |
| ttg | aaa | aaa | tta | gaa | ctt | aat | tat | gac | gtc | tat | tta | gag | cga | ttg | aaa | 816 |
| Leu | Lys | Lys | Leu | Glu | Leu | Asn | Tyr | Asp | Val | Tyr | Leu | Glu | Arg | Leu | Lys | |
| | | | 260 | | | | | 265 | | | | | 270 | | | |
| tat | gag | tat | aaa | gtt | att | act | aat | atg | ggt | ttt | gaa | gat | tat | ttc | tta | 864 |
| Tyr | Glu | Tyr | Lys | Val | Ile | Thr | Asn | Met | Gly | Phe | Glu | Asp | Tyr | Phe | Leu | |
| | | | | 275 | | | | | 280 | | | | | 285 | | |
| ata | gta | agt | gat | tta | atc | cat | tat | gcg | aaa | acg | aat | gat | gtg | atg | gta | 912 |
| Ile | Val | Ser | Asp | Leu | Ile | His | Tyr | Ala | Lys | Thr | Asn | Asp | Val | Met | Val | |
| | 290 | | | | | 295 | | | | | 300 | | | | | |
| ggt | cca | ggt | cgt | ggt | tct | tca | gct | ggc | tca | ctg | gtc | agt | tat | tta | cta | 960 |
| Gly | Pro | Gly | Arg | Gly | Ser | Ser | Ala | Gly | Ser | Leu | Val | Ser | Tyr | Leu | Leu | |
| 305 | | | | | 310 | | | | | 315 | | | | | 320 | |
| ggt | att | aca | acg | att | gat | cct | att | aaa | ttc | aat | cta | tta | ttt | gaa | cgt | 1008 |
| Gly | Ile | Thr | Thr | Ile | Asp | Pro | Ile | Lys | Phe | Asn | Leu | Leu | Phe | Glu | Arg | |
| | | | | 325 | | | | | 330 | | | | | 335 | | |
| ttt | tta | aac | cca | gaa | cgt | gta | aca | atg | cct | gat | ata | gat | att | gac | ttt | 1056 |
| Phe | Leu | Asn | Pro | Glu | Arg | Val | Thr | Met | Pro | Asp | Ile | Asp | Ile | Asp | Phe | |
| | | | 340 | | | | | 345 | | | | | 350 | | | |
| gaa | gat | aca | cgc | cga | gaa | agg | gtt | att | cag | tac | gtc | caa | gaa | aaa | tat | 1104 |
| Glu | Asp | Thr | Arg | Arg | Glu | Arg | Val | Ile | Gln | Tyr | Val | Gln | Glu | Lys | Tyr | |
| | | | | 355 | | | | | 360 | | | | | 365 | | |
| ggc | gag | cta | cat | gta | tct | gga | att | gtg | act | ttc | ggt | cat | ctg | ctt | gca | 1152 |
| Gly | Glu | Leu | His | Val | Ser | Gly | Ile | Val | Thr | Phe | Gly | His | Leu | Leu | Ala | |
| | 370 | | | | | 375 | | | | | 380 | | | | | |
| aga | gcg | gtt | gct | agg | gat | gtt | gga | cga | att | atg | ggg | ttt | gat | gaa | gtt | 1200 |
| Arg | Ala | Val | Ala | Arg | Asp | Val | Gly | Arg | Ile | Met | Gly | Phe | Asp | Glu | Val | |
| 385 | | | | | 390 | | | | | 395 | | | | | 400 | |
| aca | tta | aat | gaa | att | tca | agt | tta | atc | cca | cat | aaa | tta | gga | att | aca | 1248 |
| Thr | Leu | Asn | Glu | Ile | Ser | Ser | Leu | Ile | Pro | His | Lys | Leu | Gly | Ile | Thr | |
| | | | | 405 | | | | | 410 | | | | | 415 | | |
| ctt | gat | gaa | gca | tat | caa | att | gac | gat | ttt | aaa | aaa | ttt | gta | cat | cga | 1296 |
| Leu | Asp | Glu | Ala | Tyr | Gln | Ile | Asp | Asp | Phe | Lys | Lys | Phe | Val | His | Arg | |
| | | | 420 | | | | | 425 | | | | | 430 | | | |
| aac | cat | cga | cat | gaa | cgc | tgg | ttc | agt | att | tgt | aaa | aag | tta | gaa | ggt | 1344 |
| Asn | His | Arg | His | Glu | Arg | Trp | Phe | Ser | Ile | Cys | Lys | Lys | Leu | Glu | Gly | |
| | 435 | | | | | 440 | | | | | 445 | | | | | |
| tta | cca | aga | cat | aca | tct | aca | cat | gcg | gca | gga | att | att | att | aat | gac | 1392 |
| Leu | Pro | Arg | His | Thr | Ser | Thr | His | Ala | Ala | Gly | Ile | Ile | Ile | Asn | Asp | |
| 450 | | | | | 455 | | | | | 460 | | | | | | |

```
cat cca tta tat gaa tat gcc cct tta acg aaa ggg gat aca gga tta      1440
His Pro Leu Tyr Glu Tyr Ala Pro Leu Thr Lys Gly Asp Thr Gly Leu
465                 470                 475                 480 tta acg caa tgg aca atg act gaa gcc gaa cga att ggg tta tta aaa      1488
Leu Thr Gln Trp Thr Met Thr Glu Ala Glu Arg Ile Gly Leu Leu Lys
            485                 490                 495 ata gat ttt cta ggg ttg aga aac tta tcg att att cat caa atc tta      1536
Ile Asp Phe Leu Gly Leu Arg Asn Leu Ser Ile Ile His Gln Ile Leu
        500                 505                 510 ata caa gtc aaa aaa gat tta ggt att aat att gat atc gaa aag att      1584
Ile Gln Val Lys Lys Asp Leu Gly Ile Asn Ile Asp Ile Glu Lys Ile
    515                 520                 525 ccg ttc gat gat caa aaa gtg ttt gaa ttg ttg tcg caa gga gat acg      1632
Pro Phe Asp Asp Gln Lys Val Phe Glu Leu Leu Ser Gln Gly Asp Thr
530                 535                 540 act ggc ata ttc caa tta gag tca gac ggt gta aga agt gta tta aaa      1680
Thr Gly Ile Phe Gln Leu Glu Ser Asp Gly Val Arg Ser Val Leu Lys
545                 550                 555                 560 aaa tta aag ccg gaa cac ttt gaa gat att gtt gct gta act tct ttg      1728
Lys Leu Lys Pro Glu His Phe Glu Asp Ile Val Ala Val Thr Ser Leu
            565                 570                 575 tat aga cca ggt cca atg gaa gaa att cca act tac att aca aga aga      1776
Tyr Arg Pro Gly Pro Met Glu Glu Ile Pro Thr Tyr Ile Thr Arg Arg
        580                 585                 590 cat gat cca agc aaa gtt caa tat tta cat cca cat tta gaa cct ata      1824
His Asp Pro Ser Lys Val Gln Tyr Leu His Pro His Leu Glu Pro Ile
    595                 600                 605 tta aaa aat act tac ggt gtt att att tat caa gag caa att atg caa      1872
Leu Lys Asn Thr Tyr Gly Val Ile Ile Tyr Gln Glu Gln Ile Met Gln
610                 615                 620 ata gcg agc aca ttt gca aac ttc agt tat ggt gaa gcg gat att tta      1920
Ile Ala Ser Thr Phe Ala Asn Phe Ser Tyr Gly Glu Ala Asp Ile Leu
625                 630                 635                 640 aga aga gca atg agt aaa aaa aat aga gct gtt ctt gaa agt gag cgt      1968
Arg Arg Ala Met Ser Lys Lys Asn Arg Ala Val Leu Glu Ser Glu Arg
            645                 650                 655 caa cat ttt ata gaa ggt gca aag caa aat ggt tat cac gaa gac att      2016
Gln His Phe Ile Glu Gly Ala Lys Gln Asn Gly Tyr His Glu Asp Ile
        660                 665                 670 agt aag caa ata ttt gat ttg att ctg aaa ttt gct gat tat ggt ttt      2064
Ser Lys Gln Ile Phe Asp Leu Ile Leu Lys Phe Ala Asp Tyr Gly Phe
    675                 680                 685 cct aga gca cat gct gtc agc tat tct aaa att gca tac att atg agc      2112
Pro Arg Ala His Ala Val Ser Tyr Ser Lys Ile Ala Tyr Ile Met Ser
690                 695                 700 ttt tta aaa gtc cat tat cca aat tat ttt tac gca aat att tta agt      2160
Phe Leu Lys Val His Tyr Pro Asn Tyr Phe Tyr Ala Asn Ile Leu Ser
705                 710                 715                 720 aat gtt att gga agt gag aag aaa act gct caa atg ata gaa gaa gca      2208
Asn Val Ile Gly Ser Glu Lys Lys Thr Ala Gln Met Ile Glu Glu Ala
            725                 730                 735 aaa aaa caa ggt atc act ata ttg cca ccg aac att aac gaa agt cat      2256
Lys Lys Gln Gly Ile Thr Ile Leu Pro Pro Asn Ile Asn Glu Ser His
        740                 745                 750 tgg ttt tat aaa cct tcc caa gaa ggc att tat tta tca att ggt aca      2304
Trp Phe Tyr Lys Pro Ser Gln Glu Gly Ile Tyr Leu Ser Ile Gly Thr
    755                 760                 765 att aaa ggt gtt ggt tat caa agt gtg aaa gtg att gtt gat gaa cgt      2352
Ile Lys Gly Val Gly Tyr Gln Ser Val Lys Val Ile Val Asp Glu Arg
770                 775                 780
```

| | | | | | | | | | | | | | | |
|---|---|---|---|---|---|---|---|---|---|---|---|---|---|---|
| tat | cag | aac | ggc | aaa | ttt | aaa | gat | ttc | ttt | gat | ttt | gct | aga | cgt | ata | 2400 |
| Tyr | Gln | Asn | Gly | Lys | Phe | Lys | Asp | Phe | Phe | Asp | Phe | Ala | Arg | Arg | Ile |
| 785 | | | | 790 | | | | | 795 | | | | | 800 |

```
tat cag aac ggc aaa ttt aaa gat ttc ttt gat ttt gct aga cgt ata         2400
Tyr Gln Asn Gly Lys Phe Lys Asp Phe Phe Asp Phe Ala Arg Arg Ile
785                 790                 795                 800 ccg aag aga gtc aaa acg aga aag tta ctt gaa gca ctg att tta gtg         2448
Pro Lys Arg Val Lys Thr Arg Lys Leu Leu Glu Ala Leu Ile Leu Val
                805                 810                 815 gga gcg ttt gat gct ttt ggt aaa aca cgt tca acg ttg ttg caa gct         2496
Gly Ala Phe Asp Ala Phe Gly Lys Thr Arg Ser Thr Leu Leu Gln Ala
            820                 825                 830 att gat caa gtg ttg gat ggc gat tta aac att gaa caa gat ggt ttt         2544
Ile Asp Gln Val Leu Asp Gly Asp Leu Asn Ile Glu Gln Asp Gly Phe
        835                 840                 845 tta ttt gat att tta acg cca aaa cag atg tat gaa gat aaa gaa gaa         2592
Leu Phe Asp Ile Leu Thr Pro Lys Gln Met Tyr Glu Asp Lys Glu Glu
850                 855                 860 ttg cct gat gca ctt att agt cag tac gaa aaa gaa tat tta gga ttt         2640
Leu Pro Asp Ala Leu Ile Ser Gln Tyr Glu Lys Glu Tyr Leu Gly Phe
865                 870                 875                 880 tat gtt tcg caa cac cca gta gat aaa aag ttt gtt gcc aaa caa tat         2688
Tyr Val Ser Gln His Pro Val Asp Lys Lys Phe Val Ala Lys Gln Tyr
                885                 890                 895 tta acg ata ttt aaa ttg agt aac gcg cag aat tat aaa cct ata tta         2736
Leu Thr Ile Phe Lys Leu Ser Asn Ala Gln Asn Tyr Lys Pro Ile Leu
            900                 905                 910 gta cag ttt gat aaa gtt aaa caa att cga act aaa aat ggt caa aat         2784
Val Gln Phe Asp Lys Val Lys Gln Ile Arg Thr Lys Asn Gly Gln Asn
        915                 920                 925 atg gca ttc gtc aca tta aat gat ggc att gaa act tta gat ggt gtg         2832
Met Ala Phe Val Thr Leu Asn Asp Gly Ile Glu Thr Leu Asp Gly Val
930                 935                 940 att ttc cct aat cag ttt aaa aag tac gaa gag ttg tta tca cat aat         2880
Ile Phe Pro Asn Gln Phe Lys Lys Tyr Glu Glu Leu Leu Ser His Asn
945                 950                 955                 960 gac ttg ttt ata gtt agc ggg aaa ttt gac cat aga aag caa caa cgt         2928
Asp Leu Phe Ile Val Ser Gly Lys Phe Asp His Arg Lys Gln Gln Arg
                965                 970                 975 caa cta att ata aat gag att cag aca tta gcc act ttt gaa gaa caa         2976
Gln Leu Ile Ile Asn Glu Ile Gln Thr Leu Ala Thr Phe Glu Glu Gln
            980                 985                 990 aaa tta gca ttt gcc aaa caa att  ata att aga aat aaa  tca caa ata       3024
Lys Leu Ala Phe Ala Lys Gln Ile  Ile Ile Arg Asn Lys  Ser Gln Ile
        995                 1000                 1005 gat atg  ttt gaa gag atg att  aaa gct acg aaa gag  aat gct aat          3069
Asp Met  Phe Glu Glu Met Ile  Lys Ala Thr Lys Glu  Asn Ala Asn
    1010                1015                 1020 gat gtt  gtg tta tcc ttt tat  gat gaa acg att aaa  caa atg act          3114
Asp Val  Val Leu Ser Phe Tyr  Asp Glu Thr Ile Lys  Gln Met Thr
    1025                1030                 1035 act tta  ggc tat att aat caa  aaa gat agt atg ttt  aat aat ttt          3159
Thr Leu  Gly Tyr Ile Asn Gln  Lys Asp Ser Met Phe  Asn Asn Phe
    1040                1045                 1050 ata caa  tcc ttt aac cct agt  gat att agg ctt ata  taa                  3198
Ile Gln  Ser Phe Asn Pro Ser  Asp Ile Arg Leu Ile
    1055                1060                 1065
```

<210> SEQ ID NO 55
<211> LENGTH: 1065
<212> TYPE: PRT
<213> ORGANISM: Staphylococcus aureus

<400> SEQUENCE: 55

```
Met Val Ala Tyr Leu Asn Ile His Thr Ala Tyr Asp Leu Leu Asn Ser
1               5                   10                  15

Ser Leu Lys Ile Glu Asp Ala Val Arg Leu Ala Val Ser Glu Asn Val
            20                  25                  30

Asp Ala Leu Ala Ile Thr Asp Thr Asn Val Leu Tyr Gly Phe Pro Lys
                35                  40                  45

Phe Tyr Asp Ala Cys Ile Ala Asn Asn Ile Lys Pro Ile Phe Gly Met
        50                  55                  60

Thr Ile Tyr Val Thr Asn Gly Leu Asn Thr Val Glu Thr Val Val Leu
65                  70                  75                  80

Ala Lys Asn Asn Asp Gly Leu Lys Asp Leu Tyr Gln Leu Ser Ser Glu
                85                  90                  95

Ile Lys Met Asn Ser Met Glu Asn Val Ser Phe Glu Leu Leu Gln Gln
                100                 105                 110

Phe Ser Ser Asn Leu Ile Ile Ile Phe Lys Asn Val Ala Asp Glu His
            115                 120                 125

Arg Asp Ile Val Gln Val Phe Asp Ser His Glu Asp Thr Tyr Leu Asp
        130                 135                 140

His Gln Ser Val Leu Val Gln Gly Ile Lys His Val Trp Ile Gln Asn
145                 150                 155                 160

Val Cys Tyr Gln Thr Arg Gln Asp Ala Asp Thr Ile Ser Ala Leu Ala
                165                 170                 175

Ala Ile Arg Asp Asn Ala Lys Leu Asp Leu Ile His Asp Gln Glu Asp
                180                 185                 190

Phe Gly Ala His Phe Leu Thr Glu Lys Glu Ile Lys Gln Leu Asp Ile
        195                 200                 205

Asn Gln Glu Tyr Leu Thr Gln Val Asp Val Ile Ala Gln Lys Cys Asn
    210                 215                 220

Ala Glu Leu Lys Tyr His Gln Ser Leu Leu Pro Gln Tyr Gln Thr Pro
225                 230                 235                 240

Asn Asp Glu Ser Ala Lys Lys Tyr Leu Trp Arg Val Leu Val Thr Gln
                245                 250                 255

Leu Lys Lys Leu Glu Leu Asn Tyr Asp Val Tyr Leu Glu Arg Leu Lys
            260                 265                 270

Tyr Glu Tyr Lys Val Ile Thr Asn Met Gly Phe Glu Asp Tyr Phe Leu
        275                 280                 285

Ile Val Ser Asp Leu Ile His Tyr Ala Lys Thr Asn Asp Val Met Val
    290                 295                 300

Gly Pro Gly Arg Gly Ser Ser Ala Gly Ser Leu Val Ser Tyr Leu Leu
305                 310                 315                 320

Gly Ile Thr Thr Ile Asp Pro Ile Lys Phe Asn Leu Leu Phe Glu Arg
                325                 330                 335

Phe Leu Asn Pro Glu Arg Val Thr Met Pro Asp Ile Asp Ile Asp Phe
            340                 345                 350

Glu Asp Thr Arg Arg Glu Arg Val Ile Gln Tyr Val Gln Glu Lys Tyr
        355                 360                 365

Gly Glu Leu His Val Ser Gly Ile Val Thr Phe Gly His Leu Leu Ala
    370                 375                 380

Arg Ala Val Ala Arg Asp Val Gly Arg Ile Met Gly Phe Asp Glu Val
385                 390                 395                 400

Thr Leu Asn Glu Ile Ser Ser Leu Ile Pro His Lys Leu Gly Ile Thr
                405                 410                 415

Leu Asp Glu Ala Tyr Gln Ile Asp Asp Phe Lys Lys Phe Val His Arg
```

```
                420             425             430
Asn His Arg His Glu Arg Trp Phe Ser Ile Cys Lys Lys Leu Glu Gly
            435             440             445

Leu Pro Arg His Thr Ser Thr His Ala Ala Gly Ile Ile Ile Asn Asp
450             455             460

His Pro Leu Tyr Glu Tyr Ala Pro Leu Thr Lys Gly Asp Thr Gly Leu
465             470             475             480

Leu Thr Gln Trp Thr Met Thr Glu Ala Glu Arg Ile Gly Leu Leu Lys
            485             490             495

Ile Asp Phe Leu Gly Leu Arg Asn Leu Ser Ile Ile His Gln Ile Leu
            500             505             510

Ile Gln Val Lys Lys Asp Leu Gly Ile Asn Ile Asp Ile Glu Lys Ile
            515             520             525

Pro Phe Asp Asp Gln Lys Val Phe Glu Leu Leu Ser Gln Gly Asp Thr
            530             535             540

Thr Gly Ile Phe Gln Leu Glu Ser Asp Gly Val Arg Ser Val Leu Lys
545             550             555             560

Lys Leu Lys Pro Glu His Phe Glu Asp Ile Val Ala Val Thr Ser Leu
                565             570             575

Tyr Arg Pro Gly Pro Met Glu Glu Ile Pro Thr Tyr Ile Thr Arg Arg
            580             585             590

His Asp Pro Ser Lys Val Gln Tyr Leu His Pro His Leu Glu Pro Ile
            595             600             605

Leu Lys Asn Thr Tyr Gly Val Ile Ile Tyr Gln Glu Gln Ile Met Gln
            610             615             620

Ile Ala Ser Thr Phe Ala Asn Phe Ser Tyr Gly Glu Ala Asp Ile Leu
625             630             635             640

Arg Arg Ala Met Ser Lys Lys Asn Arg Ala Val Leu Glu Ser Glu Arg
                645             650             655

Gln His Phe Ile Glu Gly Ala Lys Gln Asn Gly Tyr His Glu Asp Ile
            660             665             670

Ser Lys Gln Ile Phe Asp Leu Ile Leu Lys Phe Ala Asp Tyr Gly Phe
            675             680             685

Pro Arg Ala His Ala Val Ser Tyr Ser Lys Ile Ala Tyr Ile Met Ser
            690             695             700

Phe Leu Lys Val His Tyr Pro Asn Tyr Phe Tyr Ala Asn Ile Leu Ser
705             710             715             720

Asn Val Ile Gly Ser Glu Lys Lys Thr Ala Gln Met Ile Glu Glu Ala
                725             730             735

Lys Lys Gln Gly Ile Thr Ile Leu Pro Pro Asn Ile Asn Glu Ser His
            740             745             750

Trp Phe Tyr Lys Pro Ser Gln Glu Gly Ile Tyr Leu Ser Ile Gly Thr
            755             760             765

Ile Lys Gly Val Gly Tyr Gln Ser Val Lys Val Ile Val Asp Glu Arg
            770             775             780

Tyr Gln Asn Gly Lys Phe Lys Asp Phe Phe Asp Phe Ala Arg Arg Ile
785             790             795             800

Pro Lys Arg Val Lys Thr Arg Lys Leu Leu Glu Ala Leu Ile Leu Val
            805             810             815

Gly Ala Phe Asp Ala Phe Gly Lys Thr Arg Ser Thr Leu Leu Gln Ala
            820             825             830

Ile Asp Gln Val Leu Asp Gly Asp Leu Asn Ile Glu Gln Asp Gly Phe
            835             840             845
```

Leu Phe Asp Ile Leu Thr Pro Lys Gln Met Tyr Glu Asp Lys Glu Glu
            850                 855                 860

Leu Pro Asp Ala Leu Ile Ser Gln Tyr Glu Lys Glu Tyr Leu Gly Phe
865                 870                 875                 880

Tyr Val Ser Gln His Pro Val Asp Lys Lys Phe Val Ala Lys Gln Tyr
                885                 890                 895

Leu Thr Ile Phe Lys Leu Ser Asn Ala Gln Asn Tyr Lys Pro Ile Leu
                900                 905                 910

Val Gln Phe Asp Lys Val Lys Gln Ile Arg Thr Lys Asn Gly Gln Asn
            915                 920                 925

Met Ala Phe Val Thr Leu Asn Asp Gly Ile Glu Thr Leu Asp Gly Val
    930                 935                 940

Ile Phe Pro Asn Gln Phe Lys Lys Tyr Glu Glu Leu Leu Ser His Asn
945                 950                 955                 960

Asp Leu Phe Ile Val Ser Gly Lys Phe Asp His Arg Lys Gln Gln Arg
                965                 970                 975

Gln Leu Ile Ile Asn Glu Ile Gln Thr Leu Ala Thr Phe Glu Glu Gln
                980                 985                 990

Lys Leu Ala Phe Ala Lys Gln Ile  Ile Ile Arg Asn Lys  Ser Gln Ile
            995                 1000                1005

Asp Met  Phe Glu Glu Met Ile  Lys Ala Thr Lys Glu  Asn Ala Asn
    1010                1015                1020

Asp Val  Val Leu Ser Phe Tyr  Asp Glu Thr Ile Lys  Gln Met Thr
    1025                1030                1035

Thr Leu  Gly Tyr Ile Asn Gln  Lys Asp Ser Met Phe  Asn Asn Phe
    1040                1045                1050

Ile Gln  Ser Phe Asn Pro Ser  Asp Ile Arg Leu Ile
    1055                1060                1065

<210> SEQ ID NO 56
<211> LENGTH: 28
<212> TYPE: DNA
<213> ORGANISM: Artificial
<220> FEATURE:
<223> OTHER INFORMATION: primer

<400> SEQUENCE: 56
gactccatgg tggcatattt aaatattc                                      28

<210> SEQ ID NO 57
<211> LENGTH: 33
<212> TYPE: DNA
<213> ORGANISM: Artificial
<220> FEATURE:
<223> OTHER INFORMATION: primer

<400> SEQUENCE: 57
gactactagt ctattatata agcctaatat cac                                33

<210> SEQ ID NO 58
<211> LENGTH: 927
<212> TYPE: DNA
<213> ORGANISM: Staphylococcus aureus

<400> SEQUENCE: 58
atggatgaac agcaacaatt gacgaatgca tatcattcaa ataaattatc gcatgcctat      60
ttatttgaag gtgatgatgc acaaacgatg aaacaagttg cgattaattt tgcaaagctt     120
attttatgtc aaacagatag tcaatgtgaa acaaaggtta gtacatataa tcatccagac     180

-continued

```
tttatgtata tatcaacaac tgagaatgca attaagaaag aacaagttga acaacttgtg      240
cgtcatatga atcaacttcc tatagaaagc acaaataaag tgtacatcat tgaagacttt      300
gaaaagttaa ctgttcaagg ggaaaacagt atcttgaaat tcttgaaga accaccggac       360 aatacgattg ctattttatt gtctacaaaa cctgagcaaa ttttagacac aatccattca      420
aggtgtcagc atgtgtattt caagcctatt gataaagaaa agtttataaa tagattagtt      480
gaacaaaaca tgtctaagcc agtagctgaa atgattagta cttatactac gcaaatagat      540
aatgcaatag cttttaaatga agaatttgat ttattagcat taaggaaatc agttatacgt      600
tggtgtgaat tgttgcttac taacaagcca atggcactta taggtattat tgatttattg      660
aaacaggcta aaataaaaa actgcaatct ttaactattg cagctgtgaa tggtttcttc       720
gaagatatca tacatacaaa ggtaaatgta gaggataaac aaatatatag tgatttaaaa      780
aatgatattg atcaatatgc gcaaaagttg tcgtttaatc aattattttt gatgtttgat      840
caactgacgg aagcacataa gaaattgaat caaaatgtaa atccaacgct tgtatttgaa      900
caaatcgtaa ttaagggtgt gagttag                                         927
```

<210> SEQ ID NO 59
<211> LENGTH: 927
<212> TYPE: DNA
<213> ORGANISM: Staphylococcus aureus
<220> FEATURE:
<221> NAME/KEY: CDS
<222> LOCATION: (1)..(927)

<400> SEQUENCE: 59

```
atg gat gaa cag caa caa ttg acg aat gca tat cat tca aat aaa tta       48
Met Asp Glu Gln Gln Gln Leu Thr Asn Ala Tyr His Ser Asn Lys Leu
1               5                   10                  15 tcg cat gcc tat tta ttt gaa ggt gat gat gca caa acg atg aaa caa       96
Ser His Ala Tyr Leu Phe Glu Gly Asp Asp Ala Gln Thr Met Lys Gln
            20                  25                  30 gtt gcg att aat ttt gca aag ctt att tta tgt caa aca gat agt caa      144
Val Ala Ile Asn Phe Ala Lys Leu Ile Leu Cys Gln Thr Asp Ser Gln
        35                  40                  45 tgt gaa aca aag gtt agt aca tat aat cat cca gac ttt atg tat ata      192
Cys Glu Thr Lys Val Ser Thr Tyr Asn His Pro Asp Phe Met Tyr Ile
    50                  55                  60 tca aca act gag aat gca att aag aaa gaa caa gtt gaa caa ctt gtg      240
Ser Thr Thr Glu Asn Ala Ile Lys Lys Glu Gln Val Glu Gln Leu Val
65                  70                  75                  80 cgt cat atg aat caa ctt cct ata gaa agc aca aat aaa gtg tac atc      288
Arg His Met Asn Gln Leu Pro Ile Glu Ser Thr Asn Lys Val Tyr Ile
                85                  90                  95 att gaa gac ttt gaa aag tta act gtt caa ggg gaa aac agt atc ttg      336
Ile Glu Asp Phe Glu Lys Leu Thr Val Gln Gly Glu Asn Ser Ile Leu
            100                 105                 110 aaa ttt ctt gaa gaa cca ccg gac aat acg att gct att tta ttg tct      384
Lys Phe Leu Glu Glu Pro Pro Asp Asn Thr Ile Ala Ile Leu Leu Ser
        115                 120                 125 aca aaa cct gag caa att tta gac aca atc cat tca agg tgt cag cat      432
Thr Lys Pro Glu Gln Ile Leu Asp Thr Ile His Ser Arg Cys Gln His
    130                 135                 140 gtg tat ttc aag cct att gat aaa gaa aag ttt ata aat aga tta gtt      480
Val Tyr Phe Lys Pro Ile Asp Lys Glu Lys Phe Ile Asn Arg Leu Val
145                 150                 155                 160 gaa caa aac atg tct aag cca gta gct gaa atg att agt act tat act      528
Glu Gln Asn Met Ser Lys Pro Val Ala Glu Met Ile Ser Thr Tyr Thr
                165                 170                 175
```

```
acg caa ata gat aat gca ata gct tta aat gaa gaa ttt gat tta tta      576
Thr Gln Ile Asp Asn Ala Ile Ala Leu Asn Glu Glu Phe Asp Leu Leu
        180                 185                 190 gca tta agg aaa tca gtt ata cgt tgg tgt gaa ttg ttg ctt act aac      624
Ala Leu Arg Lys Ser Val Ile Arg Trp Cys Glu Leu Leu Leu Thr Asn
            195                 200                 205 aag cca atg gca ctt ata ggt att att gat tta ttg aaa cag gct aaa      672
Lys Pro Met Ala Leu Ile Gly Ile Ile Asp Leu Leu Lys Gln Ala Lys
210                 215                 220 aat aaa aaa ctg caa tct tta act att gca gct gtg aat ggt tcc ttc      720
Asn Lys Lys Leu Gln Ser Leu Thr Ile Ala Ala Val Asn Gly Phe Phe
225                 230                 235                 240 gaa gat atc ata cat aca aag gta aat gta gag gat aaa caa ata tat      768
Glu Asp Ile Ile His Thr Lys Val Asn Val Glu Asp Lys Gln Ile Tyr
                245                 250                 255 agt gat tta aaa aat gat att gat caa tat gcg caa aag ttg tcg ttt      816
Ser Asp Leu Lys Asn Asp Ile Asp Gln Tyr Ala Gln Lys Leu Ser Phe
            260                 265                 270 aat caa tta ttt ttg atg ttt gat caa ctg acg gaa gca cat aag aaa      864
Asn Gln Leu Phe Leu Met Phe Asp Gln Leu Thr Glu Ala His Lys Lys
        275                 280                 285 ttg aat caa aat gta aat cca acg ctt gta ttt gaa caa atc gta att      912
Leu Asn Gln Asn Val Asn Pro Thr Leu Val Phe Glu Gln Ile Val Ile
290                 295                 300 aag ggt gtg agt tag                                                   927
Lys Gly Val Ser
305

<210> SEQ ID NO 60
<211> LENGTH: 308
<212> TYPE: PRT
<213> ORGANISM: Staphylococcus aureus

<400> SEQUENCE: 60

Met Asp Glu Gln Gln Gln Leu Thr Asn Ala Tyr His Ser Asn Lys Leu
1               5                   10                  15

Ser His Ala Tyr Leu Phe Glu Gly Asp Asp Ala Gln Thr Met Lys Gln
            20                  25                  30

Val Ala Ile Asn Phe Ala Lys Leu Ile Leu Cys Gln Thr Asp Ser Gln
        35                  40                  45

Cys Glu Thr Lys Val Ser Thr Tyr Asn His Pro Asp Phe Met Tyr Ile
    50                  55                  60

Ser Thr Thr Glu Asn Ala Ile Lys Lys Glu Gln Val Glu Gln Leu Val
65                  70                  75                  80

Arg His Met Asn Gln Leu Pro Ile Glu Ser Thr Asn Lys Val Tyr Ile
                85                  90                  95

Ile Glu Asp Phe Glu Lys Leu Thr Val Gln Gly Glu Asn Ser Ile Leu
            100                 105                 110

Lys Phe Leu Glu Glu Pro Pro Asp Asn Thr Ile Ala Ile Leu Leu Ser
        115                 120                 125

Thr Lys Pro Glu Gln Ile Leu Asp Thr Ile His Ser Arg Cys Gln His
    130                 135                 140

Val Tyr Phe Lys Pro Ile Asp Lys Glu Lys Phe Ile Asn Arg Leu Val
145                 150                 155                 160

Glu Gln Asn Met Ser Lys Pro Val Ala Glu Met Ile Ser Thr Tyr Thr
                165                 170                 175

Thr Gln Ile Asp Asn Ala Ile Ala Leu Asn Glu Glu Phe Asp Leu Leu
            180                 185                 190
```

```
Ala Leu Arg Lys Ser Val Ile Arg Trp Cys Glu Leu Leu Thr Asn
            195                 200                 205

Lys Pro Met Ala Leu Ile Gly Ile Ile Asp Leu Leu Lys Gln Ala Lys
210                 215                 220

Asn Lys Lys Leu Gln Ser Leu Thr Ile Ala Ala Val Asn Gly Phe Phe
225                 230                 235                 240

Glu Asp Ile Ile His Thr Lys Val Asn Val Glu Asp Lys Gln Ile Tyr
            245                 250                 255

Ser Asp Leu Lys Asn Asp Ile Asp Gln Tyr Ala Gln Lys Leu Ser Phe
            260                 265                 270

Asn Gln Leu Phe Leu Met Phe Asp Gln Leu Thr Glu Ala His Lys Lys
            275                 280                 285

Leu Asn Gln Asn Val Asn Pro Thr Leu Val Phe Glu Gln Ile Val Ile
            290                 295                 300

Lys Gly Val Ser
305

<210> SEQ ID NO 61
<211> LENGTH: 27
<212> TYPE: DNA
<213> ORGANISM: Artificial
<220> FEATURE:
<223> OTHER INFORMATION: primer

<400> SEQUENCE: 61
actgccatgg atgaacagca acaattg                                          27

<210> SEQ ID NO 62
<211> LENGTH: 51
<212> TYPE: DNA
<213> ORGANISM: Artificial
<220> FEATURE:
<223> OTHER INFORMATION: primer

<400> SEQUENCE: 62
tagcggtacc atcgatctgc agcctcctac taactcacac ccttaattac g               51

<210> SEQ ID NO 63
<211> LENGTH: 975
<212> TYPE: DNA
<213> ORGANISM: Staphylococcus aureus

<400> SEQUENCE: 63
atgagcgaca atattgtagc tatttatgga gatgtgcctg aattggttga aaaacaaagt      60
gcagaaatca tatcacaatt tttgaaaagt gatagagatg actttaactt tgtgaaatat    120
aatttatacg aaacagagat tgcaccaatt gttgaagaaa cattaacatt gcctttcttt    180
tcagataaaa aagcaatttt ggttaaaaat gcatatatat ttacaggtga aaaagcgcca    240
aaagatatgg ctcataatgt agatcaatta atagaattta ttgaaaaata tgatggcgaa    300
aatttgattg tctttgagat atatcaaaat aaacttgatg aaagaaaaaa gttaactaaa    360
actctaaaaa agcatgcaag gcttaaaaaa atagagcaaa tgtctgaaga agaaataaaa    420
aaatggattc aaagtaaatt aaatgagaat tcaaagata tcaaaagaga tgcattagat    480
ttatttattg agttgacagg tattaacttt aatattgtct cacaagagat agaaaagttg    540
attttatttt taggcgatag accaacaatt aataagcagg atgttaacca aattattaat    600
agaagtttag agcaaatgt attttttactg actgaataca ttcagaaaag aaagaaagaa    660
caagcaattc atttagtaaa agatttaata actatgaaag aagaaccaat taaattactt    720
```

-continued

```
gcactaatta caagtaatta ccgattattt tatcaatgta agattctgag tcaaaaagga    780
tatagtggac agcaaattgc taaaacaata ggagtgcatc catacagagt aaaattagcg    840
ttaggacaag taagacatta tcaacttgat gaattattga atattgtaga tgcttgtgcg    900
gaaactgatt ataaacttaa atcatcatat atggataaac agttaatact ggaattattc    960
attctatctt tataa                                                    975
```

```
<210> SEQ ID NO 64
<211> LENGTH: 975
<212> TYPE: DNA
<213> ORGANISM: Staphylococcus aureus
<220> FEATURE:
<221> NAME/KEY: CDS
<222> LOCATION: (1)..(975)

<400> SEQUENCE: 64
```

```
atg agc gac aat att gta gct att tat gga gat gtg cct gaa ttg gtt     48
Met Ser Asp Asn Ile Val Ala Ile Tyr Gly Asp Val Pro Glu Leu Val
1               5                   10                  15 gaa aaa caa agt gca gaa atc ata tca caa ttt ttg aaa agt gat aga     96
Glu Lys Gln Ser Ala Glu Ile Ile Ser Gln Phe Leu Lys Ser Asp Arg
            20                  25                  30 gat gac ttt aac ttt gtg aaa tat aat tta tac gaa aca gag att gca    144
Asp Asp Phe Asn Phe Val Lys Tyr Asn Leu Tyr Glu Thr Glu Ile Ala
        35                  40                  45 cca att gtt gaa gaa aca tta aca ttg cct ttc ttt tca gat aaa aaa    192
Pro Ile Val Glu Glu Thr Leu Thr Leu Pro Phe Phe Ser Asp Lys Lys
    50                  55                  60 gca att ttg gtt aaa aat gca tat ata ttt aca ggt gaa aaa gcg cca    240
Ala Ile Leu Val Lys Asn Ala Tyr Ile Phe Thr Gly Glu Lys Ala Pro
65                  70                  75                  80 aaa gat atg gct cat aat gta gat caa tta ata gaa ttt att gaa aaa    288
Lys Asp Met Ala His Asn Val Asp Gln Leu Ile Glu Phe Ile Glu Lys
                85                  90                  95 tat gat ggc gaa aat ttg att gtc ttt gag ata tat caa aat aaa ctt    336
Tyr Asp Gly Glu Asn Leu Ile Val Phe Glu Ile Tyr Gln Asn Lys Leu
            100                 105                 110 gat gaa aga aaa aag tta act aaa act cta aaa aag cat gca agg ctt    384
Asp Glu Arg Lys Lys Leu Thr Lys Thr Leu Lys Lys His Ala Arg Leu
        115                 120                 125 aaa aaa ata gag caa atg tct gaa gaa gaa ata aaa aaa tgg att caa    432
Lys Lys Ile Glu Gln Met Ser Glu Glu Glu Ile Lys Lys Trp Ile Gln
    130                 135                 140 agt aaa tta aat gag aat ttc aaa gat atc aaa aga gat gca tta gat    480
Ser Lys Leu Asn Glu Asn Phe Lys Asp Ile Lys Arg Asp Ala Leu Asp
145                 150                 155                 160 tta ttt att gag ttg aca ggt att aac ttt aat att gtc tca caa gag    528
Leu Phe Ile Glu Leu Thr Gly Ile Asn Phe Asn Ile Val Ser Gln Glu
                165                 170                 175 ata gaa aag ttg att tta ttt tta ggc gat aga cca aca att aat aag    576
Ile Glu Lys Leu Ile Leu Phe Leu Gly Asp Arg Pro Thr Ile Asn Lys
            180                 185                 190 cag gat gtt aac caa att att aat aga agt tta gag caa aat gta ttt    624
Gln Asp Val Asn Gln Ile Ile Asn Arg Ser Leu Glu Gln Asn Val Phe
        195                 200                 205 tta ctg act gaa tac att cag aaa aga aag aaa gaa caa gca att cat    672
Leu Leu Thr Glu Tyr Ile Gln Lys Arg Lys Lys Glu Gln Ala Ile His
    210                 215                 220 tta gta aaa gat tta ata act atg aaa gaa gaa cca att aaa tta ctt    720
Leu Val Lys Asp Leu Ile Thr Met Lys Glu Glu Pro Ile Lys Leu Leu
```

```
                       225                 230                 235                 240 gca cta att aca agt aat tac cga tta ttt tat caa tgt aag att ctg         768
Ala Leu Ile Thr Ser Asn Tyr Arg Leu Phe Tyr Gln Cys Lys Ile Leu
                245                 250                 255 agt caa aaa gga tat agt gga cag caa att gct aaa aca ata gga gtg         816
Ser Gln Lys Gly Tyr Ser Gly Gln Gln Ile Ala Lys Thr Ile Gly Val
            260                 265                 270 cat cca tac aga gta aaa tta gcg tta gga caa gta aga cat tat caa         864
His Pro Tyr Arg Val Lys Leu Ala Leu Gly Gln Val Arg His Tyr Gln
        275                 280                 285 ctt gat gaa tta ttg aat att gta gat gct tgt gcg gaa act gat tat         912
Leu Asp Glu Leu Leu Asn Ile Val Asp Ala Cys Ala Glu Thr Asp Tyr
    290                 295                 300 aaa ctt aaa tca tca tat atg gat aaa cag tta ata ctg gaa tta ttc         960
Lys Leu Lys Ser Ser Tyr Met Asp Lys Gln Leu Ile Leu Glu Leu Phe
305                 310                 315                 320 att cta tct tta taa                                                     975
Ile Leu Ser Leu <210> SEQ ID NO 65
<211> LENGTH: 324
<212> TYPE: PRT
<213> ORGANISM: Staphylococcus aureus

<400> SEQUENCE: 65

Met Ser Asp Asn Ile Val Ala Ile Tyr Gly Asp Val Pro Glu Leu Val
1               5                   10                  15

Glu Lys Gln Ser Ala Glu Ile Ile Ser Gln Phe Leu Lys Ser Asp Arg
            20                  25                  30

Asp Asp Phe Asn Phe Val Lys Tyr Asn Leu Tyr Glu Thr Glu Ile Ala
        35                  40                  45

Pro Ile Val Glu Glu Thr Leu Thr Leu Pro Phe Phe Ser Asp Lys Lys
    50                  55                  60

Ala Ile Leu Val Lys Asn Ala Tyr Ile Phe Thr Gly Glu Lys Ala Pro
65                  70                  75                  80

Lys Asp Met Ala His Asn Val Asp Gln Leu Ile Glu Phe Ile Glu Lys
                85                  90                  95

Tyr Asp Gly Glu Asn Leu Ile Val Phe Glu Ile Tyr Gln Asn Lys Leu
            100                 105                 110

Asp Glu Arg Lys Lys Leu Thr Lys Thr Leu Lys Lys His Ala Arg Leu
        115                 120                 125

Lys Lys Ile Glu Gln Met Ser Glu Glu Ile Lys Lys Trp Ile Gln
    130                 135                 140

Ser Lys Leu Asn Glu Asn Phe Lys Asp Ile Lys Arg Asp Ala Leu Asp
145                 150                 155                 160

Leu Phe Ile Glu Leu Thr Gly Ile Asn Phe Asn Ile Val Ser Gln Glu
                165                 170                 175

Ile Glu Lys Leu Ile Leu Phe Leu Gly Asp Arg Pro Thr Ile Asn Lys
            180                 185                 190

Gln Asp Val Asn Gln Ile Ile Asn Arg Ser Leu Glu Gln Asn Val Phe
        195                 200                 205

Leu Leu Thr Glu Tyr Ile Gln Lys Arg Lys Glu Gln Ala Ile His
    210                 215                 220

Leu Val Lys Asp Leu Ile Thr Met Lys Glu Glu Pro Ile Lys Leu Leu
225                 230                 235                 240

Ala Leu Ile Thr Ser Asn Tyr Arg Leu Phe Tyr Gln Cys Lys Ile Leu
                245                 250                 255
```

```
Ser Gln Lys Gly Tyr Ser Gly Gln Gln Ile Ala Lys Thr Ile Gly Val
            260                 265                 270

His Pro Tyr Arg Val Lys Leu Ala Leu Gly Gln Val Arg His Tyr Gln
        275                 280                 285

Leu Asp Glu Leu Leu Asn Ile Val Asp Ala Cys Ala Glu Thr Asp Tyr
    290                 295                 300

Lys Leu Lys Ser Ser Tyr Met Asp Lys Gln Leu Ile Leu Glu Leu Phe
305                 310                 315                 320

Ile Leu Ser Leu

<210> SEQ ID NO 66
<211> LENGTH: 35
<212> TYPE: DNA
<213> ORGANISM: Artificial
<220> FEATURE:
<223> OTHER INFORMATION: primer

<400> SEQUENCE: 66
gatcttaatt aatcgatgag cgacaatatt gtagc                              35

<210> SEQ ID NO 67
<211> LENGTH: 52
<212> TYPE: DNA
<213> ORGANISM: Artificial
<220> FEATURE:
<223> OTHER INFORMATION: primer

<400> SEQUENCE: 67
tagcggtacc atggactgca gcctcctatt ataaagatag aatgaataat tc            52

<210> SEQ ID NO 68
<211> LENGTH: 1698
<212> TYPE: DNA
<213> ORGANISM: Staphylococcus aureus

<400> SEQUENCE: 68
ttgaattatc aagccttata tcgtatgtac agaccccaaa gtttcgagga tgtcgtcgga     60
caagaacatg tcacgaagac attgcgcaat gcgatttcga agaaaaaaca gtcgcatgct    120 tatatttta gtggtccgag aggtacgggg aaaacgagta ttgccaaagt gtttgctaaa    180
gcaatcaact gtctaaatag cactgatgga gaaccttgta atgaatgtca tatttgtaaa    240
ggcattacgc aggggactaa ttcagatgtg atagaaattg atgctgctag taataatggc    300
gttgatgaaa taagaaatat tagagacaaa gttaaatatg caccaagtga atcgaaatat    360 aaagttttata ttatagatga ggtgcacatg ctaacaacag gtgcttttaa tgcccttttta    420 aagacgttag aagaacctcc agcacacgct atttttatat tggcaacgac agaaccacat    480
aaaatccctc caacaatcat ttctagggca caacgttttg attttaaagc aattagccta    540
gatcaaattg ttgaacgttt aaaatttgta gcagatgcac aacaaattga atgtgaagat    600
gaagccttgg catttatcgc taaagcgtct gaaggggggta tgcgtgatgc attaagtatt    660
atggatcagg ctattgcatt tggtgatggt acgttaacat gcaagatgc gttgaatgtc    720 acaggtagcg tacatgatga agcgttggat cacttgtttg atgatattgt acaaggtgac    780
gtacaagcat cttttaaaaa ataccatcag tttataacag agggtaaaga agtgaatcgc    840
ctaataaatg atatgattta ttttgtcaga gatacgatta tgaataaaac atctgagaaa    900
gatactgagt atcgagcact gatgaactta gaattagata tgttatatca aatgattgat    960
cttattaatg atacattagt gtcgattcgt tttagtgtga atcaaaacgt tcatttgaa   1020
```

| | | |
|---|---|---|
| gtgttgttag taaaattagc tgagcagatt aagggtcaac cacaagtgat tgcgaatgta | 1080 | |
| gctgaaccag cacaaattgc ttcatcgcca acacagatg tattgttgca acgtatggaa | 1140 | |
| cagttagagc aagaattaaa aacactaaaa gcacaaggag tgagtgtcgc tcctgctcaa | 1200 | |
| aaatcttcga aaaagcctgc gagaggcata caaaaatcta aaatgcatt ttcaatgcaa | 1260 | |
| caaattgcaa aagtgctaga taaagcgaat aaggcagata tcaaattgtt gaaagatcat | 1320 | |
| tggcaagaag tgattgatca tgccaaaaac aatgataaaa aatcactcgt tagtttattg | 1380 | |
| caaaattcgg aacctgtggc ggcaagtgaa gatcacgtac ttgtgaaatt tgaggaagag | 1440 | |
| atccattgtg aaatcgtcaa taaagacgac gagaaacgta gtagtataga aagtgttgta | 1500 | |
| tgtaatatcg ttaataaaaa cgttaaagtt gttggtgtac catcagatca atggcaaaga | 1560 | |
| gttcgaacgg agtatttaca aaatcgtaaa acgaaggcg atgatatgcc aaagcaacaa | 1620 | |
| gcacaacaaa cagatattgc tcaaaaagca aaagatcttt tcggtgaaga aactgtacat | 1680 | |
| gtgatagatg aagagtga | 1698 | |

<210> SEQ ID NO 69
<211> LENGTH: 1698
<212> TYPE: DNA
<213> ORGANISM: Staphylococcus aureus
<220> FEATURE:
<221> NAME/KEY: CDS
<222> LOCATION: (1)..(1698)

<400> SEQUENCE: 69

| | | |
|---|---|---|
| ttg aat tat caa gcc tta tat cgt atg tac aga ccc caa agt ttc gag<br>Leu Asn Tyr Gln Ala Leu Tyr Arg Met Tyr Arg Pro Gln Ser Phe Glu<br>1               5                   10                  15 | 48 | |
| gat gtc gtc gga caa gaa cat gtc acg aag aca ttg cgc aat gcg att<br>Asp Val Val Gly Gln Glu His Val Thr Lys Thr Leu Arg Asn Ala Ile<br>            20                  25                  30 | 96 | |
| tcg aaa gaa aaa cag tcg cat gct tat att ttt agt ggt ccg aga ggt<br>Ser Lys Glu Lys Gln Ser His Ala Tyr Ile Phe Ser Gly Pro Arg Gly<br>        35                  40                  45 | 144 | |
| acg ggg aaa acg agt att gcc aaa gtg ttt gct aaa gca atc aac tgt<br>Thr Gly Lys Thr Ser Ile Ala Lys Val Phe Ala Lys Ala Ile Asn Cys<br>    50                  55                  60 | 192 | |
| cta aat agc act gat gga gaa cct tgt aat gaa tgt cat att tgt aaa<br>Leu Asn Ser Thr Asp Gly Glu Pro Cys Asn Glu Cys His Ile Cys Lys<br>65                  70                  75                  80 | 240 | |
| ggc att acg cag ggg act aat tca gat gtg ata gaa att gat gct gct<br>Gly Ile Thr Gln Gly Thr Asn Ser Asp Val Ile Glu Ile Asp Ala Ala<br>                85                  90                  95 | 288 | |
| agt aat aat ggc gtt gat gaa ata aga aat att aga gac aaa gtt aaa<br>Ser Asn Asn Gly Val Asp Glu Ile Arg Asn Ile Arg Asp Lys Val Lys<br>            100                 105                 110 | 336 | |
| tat gca cca agt gaa tcg aaa tat aaa gtt tat att ata gat gag gtg<br>Tyr Ala Pro Ser Glu Ser Lys Tyr Lys Val Tyr Ile Ile Asp Glu Val<br>        115                 120                 125 | 384 | |
| cac atg cta aca aca ggt gct ttt aat gcc ctt tta aag acg tta gaa<br>His Met Leu Thr Thr Gly Ala Phe Asn Ala Leu Leu Lys Thr Leu Glu<br>    130                 135                 140 | 432 | |
| gaa cct cca gca cac gct att ttt ata ttg gca acg aca gaa cca cat<br>Glu Pro Pro Ala His Ala Ile Phe Ile Leu Ala Thr Thr Glu Pro His<br>145                 150                 155                 160 | 480 | |
| aaa atc cct cca aca atc att tct agg gca caa cgt ttt gat ttt aaa<br>Lys Ile Pro Pro Thr Ile Ile Ser Arg Ala Gln Arg Phe Asp Phe Lys<br>                165                 170                 175 | 528 | |

-continued

```
gca att agc cta gat caa att gtt gaa cgt tta aaa ttt gta gca gat          576
Ala Ile Ser Leu Asp Gln Ile Val Glu Arg Leu Lys Phe Val Ala Asp
        180                 185                 190 gca caa caa att gaa tgt gaa gat gaa gcc ttg gca ttt atc gct aaa          624
Ala Gln Gln Ile Glu Cys Glu Asp Glu Ala Leu Ala Phe Ile Ala Lys
    195                 200                 205 gcg tct gaa ggg ggt atg cgt gat gca tta agt att atg gat cag gct          672
Ala Ser Glu Gly Gly Met Arg Asp Ala Leu Ser Ile Met Asp Gln Ala
210                 215                 220 att gca ttt ggt gat ggt acg tta aca ttg caa gat gcg ttg aat gtc          720
Ile Ala Phe Gly Asp Gly Thr Leu Thr Leu Gln Asp Ala Leu Asn Val
225                 230                 235                 240 aca ggt agc gta cat gat gaa gcg ttg gat cac ttg ttt gat gat att          768
Thr Gly Ser Val His Asp Glu Ala Leu Asp His Leu Phe Asp Asp Ile
            245                 250                 255 gta caa ggt gac gta caa gca tct ttt aaa aaa tac cat cag ttt ata          816
Val Gln Gly Asp Val Gln Ala Ser Phe Lys Lys Tyr His Gln Phe Ile
        260                 265                 270 aca gag ggt aaa gaa gtg aat cgc cta ata aat gat atg att tat ttt          864
Thr Glu Gly Lys Glu Val Asn Arg Leu Ile Asn Asp Met Ile Tyr Phe
    275                 280                 285 gtc aga gat acg att atg aat aaa aca tct gag aaa gat act gag tat          912
Val Arg Asp Thr Ile Met Asn Lys Thr Ser Glu Lys Asp Thr Glu Tyr
290                 295                 300 cga gca ctg atg aac tta gaa tta gat atg tta tat caa atg att gat          960
Arg Ala Leu Met Asn Leu Glu Leu Asp Met Leu Tyr Gln Met Ile Asp
305                 310                 315                 320 ctt att aat gat aca tta gtg tcg att cgt ttt agt gtg aat caa aac         1008
Leu Ile Asn Asp Thr Leu Val Ser Ile Arg Phe Ser Val Asn Gln Asn
            325                 330                 335 gtt cat ttt gaa gtg tta tta gta aaa tta gct gag cag att aag ggt         1056
Val His Phe Glu Val Leu Leu Val Lys Leu Ala Glu Gln Ile Lys Gly
        340                 345                 350 caa cca caa gtg att gcg aat gta gct gaa cca gca caa att gct tca         1104
Gln Pro Gln Val Ile Ala Asn Val Ala Glu Pro Ala Gln Ile Ala Ser
    355                 360                 365 tcg cca aac aca gat gta ttg ttg caa cgt atg gaa cag tta gag caa         1152
Ser Pro Asn Thr Asp Val Leu Leu Gln Arg Met Glu Gln Leu Glu Gln
370                 375                 380 gaa tta aaa aca cta aaa gca caa gga gtg agt gtc gct cct gct caa         1200
Glu Leu Lys Thr Leu Lys Ala Gln Gly Val Ser Val Ala Pro Ala Gln
385                 390                 395                 400 aaa tct tcg aaa aag cct gcg aga ggc ata caa aaa tct aaa aat gca         1248
Lys Ser Ser Lys Lys Pro Ala Arg Gly Ile Gln Lys Ser Lys Asn Ala
            405                 410                 415 ttt tca atg caa caa att gca aaa gtg cta gat aaa gcg aat aag gca         1296
Phe Ser Met Gln Gln Ile Ala Lys Val Leu Asp Lys Ala Asn Lys Ala
        420                 425                 430 gat atc aaa ttg ttg aaa gat cat tgg caa gaa gtg att gat cat gcc         1344
Asp Ile Lys Leu Leu Lys Asp His Trp Gln Glu Val Ile Asp His Ala
    435                 440                 445 aaa aac aat gat aaa aaa tca ctc gtt agt tta ttg caa aat tcg gaa         1392
Lys Asn Asn Asp Lys Lys Ser Leu Val Ser Leu Leu Gln Asn Ser Glu
450                 455                 460 cct gtg gcg gca agt gaa gat cac gta ctt gtg aaa ttt gag gaa gag         1440
Pro Val Ala Ala Ser Glu Asp His Val Leu Val Lys Phe Glu Glu Glu
465                 470                 475                 480 atc cat tgt gaa atc gtc aat aaa gac gac gag aaa cgt agt agt ata         1488
Ile His Cys Glu Ile Val Asn Lys Asp Asp Glu Lys Arg Ser Ser Ile
            485                 490                 495
```

-continued

```
gaa agt gtt gta tgt aat atc gtt aat aaa aac gtt aaa gtt gtt ggt     1536
Glu Ser Val Val Cys Asn Ile Val Asn Lys Asn Val Lys Val Val Gly
        500                 505                 510 gta cca tca gat caa tgg caa aga gtt cga acg gag tat tta caa aat     1584
Val Pro Ser Asp Gln Trp Gln Arg Val Arg Thr Glu Tyr Leu Gln Asn
        515                 520                 525 cgt aaa aac gaa ggc gat gat atg cca aag caa caa gca caa caa aca     1632
Arg Lys Asn Glu Gly Asp Asp Met Pro Lys Gln Gln Ala Gln Gln Thr
    530                 535                 540 gat att gct caa aaa gca aaa gat ctt ttc ggt gaa gaa act gta cat     1680
Asp Ile Ala Gln Lys Ala Lys Asp Leu Phe Gly Glu Glu Thr Val His
545                 550                 555                 560 gtg ata gat gaa gag tga                                             1698
Val Ile Asp Glu Glu
                565
```

<210> SEQ ID NO 70
<211> LENGTH: 565
<212> TYPE: PRT
<213> ORGANISM: Staphylococcus aureus

<400> SEQUENCE: 70

```
Leu Asn Tyr Gln Ala Leu Tyr Arg Met Tyr Arg Pro Gln Ser Phe Glu
1               5                   10                  15

Asp Val Val Gly Gln Glu His Val Thr Lys Thr Leu Arg Asn Ala Ile
            20                  25                  30

Ser Lys Glu Lys Gln Ser His Ala Tyr Ile Phe Ser Gly Pro Arg Gly
        35                  40                  45

Thr Gly Lys Thr Ser Ile Ala Lys Val Phe Ala Lys Ala Ile Asn Cys
    50                  55                  60

Leu Asn Ser Thr Asp Gly Glu Pro Cys Asn Glu Cys His Ile Cys Lys
65                  70                  75                  80

Gly Ile Thr Gln Gly Thr Asn Ser Asp Val Ile Glu Ile Asp Ala Ala
                85                  90                  95

Ser Asn Asn Gly Val Asp Glu Ile Arg Asn Ile Arg Asp Lys Val Lys
            100                 105                 110

Tyr Ala Pro Ser Glu Ser Lys Tyr Lys Val Tyr Ile Asp Glu Val
        115                 120                 125

His Met Leu Thr Thr Gly Ala Phe Asn Ala Leu Leu Lys Thr Leu Glu
    130                 135                 140

Glu Pro Pro Ala His Ala Ile Phe Ile Leu Ala Thr Thr Glu Pro His
145                 150                 155                 160

Lys Ile Pro Pro Thr Ile Ile Ser Arg Ala Gln Arg Phe Asp Phe Lys
                165                 170                 175

Ala Ile Ser Leu Asp Gln Ile Val Glu Arg Leu Lys Phe Val Ala Asp
            180                 185                 190

Ala Gln Gln Ile Glu Cys Glu Asp Glu Ala Leu Ala Phe Ile Ala Lys
        195                 200                 205

Ala Ser Glu Gly Gly Met Arg Asp Ala Leu Ser Ile Met Asp Gln Ala
    210                 215                 220

Ile Ala Phe Gly Asp Gly Thr Leu Thr Leu Gln Asp Ala Leu Asn Val
225                 230                 235                 240

Thr Gly Ser Val His Asp Glu Ala Leu Asp His Leu Phe Asp Asp Ile
                245                 250                 255

Val Gln Gly Asp Val Gln Ala Ser Phe Lys Lys Tyr His Gln Phe Ile
            260                 265                 270

Thr Glu Gly Lys Glu Val Asn Arg Leu Ile Asn Asp Met Ile Tyr Phe
```

```
                275                 280                 285
Val Arg Asp Thr Ile Met Asn Lys Thr Ser Glu Lys Asp Thr Glu Tyr
290                 295                 300

Arg Ala Leu Met Asn Leu Glu Leu Asp Met Leu Tyr Gln Met Ile Asp
305                 310                 315                 320

Leu Ile Asn Asp Thr Leu Val Ser Ile Arg Phe Ser Val Asn Gln Asn
                325                 330                 335

Val His Phe Glu Val Leu Leu Val Lys Leu Ala Glu Gln Ile Lys Gly
            340                 345                 350

Gln Pro Gln Val Ile Ala Asn Val Ala Glu Pro Ala Gln Ile Ala Ser
        355                 360                 365

Ser Pro Asn Thr Asp Val Leu Leu Gln Arg Met Glu Gln Leu Glu Gln
370                 375                 380

Glu Leu Lys Thr Leu Lys Ala Gln Gly Val Ser Val Ala Pro Ala Gln
385                 390                 395                 400

Lys Ser Ser Lys Lys Pro Ala Arg Gly Ile Gln Lys Ser Lys Asn Ala
                405                 410                 415

Phe Ser Met Gln Gln Ile Ala Lys Val Leu Asp Lys Ala Asn Lys Ala
            420                 425                 430

Asp Ile Lys Leu Leu Lys Asp His Trp Gln Glu Val Ile Asp His Ala
        435                 440                 445

Lys Asn Asn Asp Lys Lys Ser Leu Val Ser Leu Leu Gln Asn Ser Glu
    450                 455                 460

Pro Val Ala Ala Ser Glu Asp His Val Leu Val Lys Phe Glu Glu Glu
465                 470                 475                 480

Ile His Cys Glu Ile Val Asn Lys Asp Glu Lys Arg Ser Ser Ile
                485                 490                 495

Glu Ser Val Val Cys Asn Ile Val Asn Lys Asn Val Lys Val Val Gly
                500                 505                 510

Val Pro Ser Asp Gln Trp Gln Arg Val Arg Thr Glu Tyr Leu Gln Asn
            515                 520                 525

Arg Lys Asn Glu Gly Asp Asp Met Pro Lys Gln Gln Ala Gln Gln Thr
    530                 535                 540

Asp Ile Ala Gln Lys Ala Lys Asp Leu Phe Gly Glu Glu Thr Val His
545                 550                 555                 560

Val Ile Asp Glu Glu
            565

<210> SEQ ID NO 71
<211> LENGTH: 36
<212> TYPE: DNA
<213> ORGANISM: Artificial
<220> FEATURE:
<223> OTHER INFORMATION: primer

<400> SEQUENCE: 71
gatcttaatt aatcatgaat tatcaagcct tatatc                            36

<210> SEQ ID NO 72
<211> LENGTH: 34
<212> TYPE: DNA
<213> ORGANISM: Artificial
<220> FEATURE:
<223> OTHER INFORMATION: primer

<400> SEQUENCE: 72
gcatactagt tcatcactct tcatctatca catg                              34
```

```
<210> SEQ ID NO 73
<211> LENGTH: 23
<212> TYPE: DNA
<213> ORGANISM: Artificial
<220> FEATURE:
<223> OTHER INFORMATION: primer

<400> SEQUENCE: 73
taagcatgca aaaaaaaagg tac                                              23

<210> SEQ ID NO 74
<211> LENGTH: 21
<212> TYPE: DNA
<213> ORGANISM: Artificial
<220> FEATURE:
<223> OTHER INFORMATION: primer

<400> SEQUENCE: 74
cttttttttt gcatgcttaa t                                                21

<210> SEQ ID NO 75
<211> LENGTH: 70
<212> TYPE: DNA
<213> ORGANISM: Artificial
<220> FEATURE:
<223> OTHER INFORMATION: primer

<400> SEQUENCE: 75
gaattcggat cccgggtcta gaggaggtta attaagcatg caaaaaaaaa gctagcggta       60
ccactagtgg                                                             70

<210> SEQ ID NO 76
<211> LENGTH: 1818
<212> TYPE: DNA
<213> ORGANISM: Staphylococcus aureus

<400> SEQUENCE: 76
ttgcgaatag atcaatcgat cattaatgaa ataaagata  aaaccgacat tttagacttg       60
gtaagtgaat atgtaaaact agaaaagaga ggacgcaatt atataggttt gtgtccttt       120 catgatgaaa agacaccttc atttacagtt tctgaagata acaaatctg tcattgtttt       180 ggttgtaaaa aaggtggcaa tgttttcaa tttactcaag aaattaaaga catatcattt       240
gttgaagcgg ttaaagaatt aggtgataga gttaatgttg ctgtagatat tgaggcaaca      300
caatctaact caaatgttca aattgcttct gatgatttac aaatgattga atgcatgag       360 ttaatacaag aatttttatta ttacgcttta acaagacag tcgaaggcga caagcatta       420 acatacttac aagaacgtgg ttttacagat gcgcttatta agagcgagg cattggcttt       480 gcacccgata gctcacattt tgtcatgat tttcttcaaa aaagggtta cgatattgaa       540 ttagcatatg aagccggatt attatcacgt aacgaagaaa atttcagtta ttacgataga      600
tttcgaaatc gtattatgtt tcctttgaaa aatgcgcaag gaagaattgt tggatattca     660
ggtcgaacat ataccggtca agaaccaaaa taccttaaata gtcctgaaac gcctatcttt      720 caaaaagaa agttgttata aacttagat aaagcacgta atcaattag aaaattagat        780 gaaattgtat tactagaagg ttttatggat gttataaaat ctgatactgc tggcttgaaa      840
aacgttgttg caacaatggg tacacagttg tcagatgaac atattacctt tatacgaaag      900
ttaacatcaa atataacatt aatgtttgat ggggattttg cgggtagtga agcaacactt      960
aaaacaggtc aacatttgtt acagcaaggg ctaaatgtat tgttataca attgccatct      1020
```

```
ggcatggatc cggatgaata cattggtaag tatggcaacg acgcatttac tactttgta     1080 aaaaatgaca aaaagtcatt tgcacattat aaagtaagta tattaaaaga tgaaattgca     1140
cataatgacc tttcatatga acgttatttg aaagaactga gtcatgacat ttcacttatg     1200
aagtcatcaa ttctgcaaca aaaggctata atgatgttg cgccatttt caatgttagt       1260 cctgagcagt tagctaacga aatacaattc aatcaagcac cagccaatta ttatccagaa     1320
gatgagtatg gcggttatga tgagtatggc ggttatattg aacctgagcc aattggtatg     1380
gcacaatttg acaatttgag ccgtcaagaa aaagcggagc gagcatttt aaaacattta      1440 atgagagata agatacatt tttaaattat tatgaaagtg ttgataagga taacttcaca      1500
aatcagcatt ttaaatatgt attcgaagtc ttacatgatt tttatgcgga aaatgatcaa     1560
tataatatca gtgatgctgt gcagtatgtt aattcaaatg agttgagaga aacactaatt     1620
agcttagaac aatataattt gaatgacgaa ccatatgaaa atgaaattga tgattatgtc     1680
aatgttatta tgaaaaagg acaagaaaca attgagtcat tgaatcataa attaagggaa     1740
gctacaagga ttggcgatgt agaattacaa aaatactatt tacagcaaat tgttgctaag    1800
aataaagaac gcatgtag                                                   1818

<210> SEQ ID NO 77
<211> LENGTH: 1818
<212> TYPE: DNA
<213> ORGANISM: Staphylococcus aureus
<220> FEATURE:
<221> NAME/KEY: CDS
<222> LOCATION: (1)..(1818)

<400> SEQUENCE: 77 ttg cga ata gat caa tcg atc att aat gaa ata aaa gat aaa acc gac      48
Leu Arg Ile Asp Gln Ser Ile Ile Asn Glu Ile Lys Asp Lys Thr Asp
1               5                   10                  15 att tta gac ttg gta agt gaa tat gta aaa cta gaa aag aga gga cgc      96
Ile Leu Asp Leu Val Ser Glu Tyr Val Lys Leu Glu Lys Arg Gly Arg
            20                  25                  30 aat tat ata ggt ttg tgt cct ttt cat gat gaa aag aca cct tca ttt     144
Asn Tyr Ile Gly Leu Cys Pro Phe His Asp Glu Lys Thr Pro Ser Phe
        35                  40                  45 aca gtt tct gaa gat aaa caa atc tgt cat tgt ttt ggt tgt aaa aaa     192
Thr Val Ser Glu Asp Lys Gln Ile Cys His Cys Phe Gly Cys Lys Lys
    50                  55                  60 ggt ggc aat gtt ttt caa ttt act caa gaa att aaa gac ata tca ttt     240
Gly Gly Asn Val Phe Gln Phe Thr Gln Glu Ile Lys Asp Ile Ser Phe
65                  70                  75                  80 gtt gaa gcg gtt aaa gaa tta ggt gat aga gtt aat gtt gct gta gat     288
Val Glu Ala Val Lys Glu Leu Gly Asp Arg Val Asn Val Ala Val Asp
                85                  90                  95 att gag gca aca caa tct aac tca aat gtt caa att gct tct gat gat     336
Ile Glu Ala Thr Gln Ser Asn Ser Asn Val Gln Ile Ala Ser Asp Asp
            100                 105                 110 tta caa atg att gaa atg cat gag tta ata caa gaa ttt tat tat tac     384
Leu Gln Met Ile Glu Met His Glu Leu Ile Gln Glu Phe Tyr Tyr Tyr
        115                 120                 125 gct tta aca aag aca gtc gaa ggc gaa caa gca tta aca tac tta caa     432
Ala Leu Thr Lys Thr Val Glu Gly Glu Gln Ala Leu Thr Tyr Leu Gln
    130                 135                 140 gaa cgt ggt ttt aca gat gcg ctt att aaa gag cga ggc att ggc ttt     480
Glu Arg Gly Phe Thr Asp Ala Leu Ile Lys Glu Arg Gly Ile Gly Phe
145                 150                 155                 160 gca ccc gat agc tca cat ttt tgt cat gat ttt ctt caa aaa aag ggt     528
```

-continued

| | | | | | | | | | | | | | | | |
|---|---|---|---|---|---|---|---|---|---|---|---|---|---|---|---|
| Ala | Pro | Asp | Ser | Ser | His | Phe | Cys | His | Asp | Phe | Leu | Gln | Lys | Lys | Gly |
| | | | 165 | | | | 170 | | | | | 175 | | | |

```
tac gat att gaa tta gca tat gaa gcc gga tta tta tca cgt aac gaa    576
Tyr Asp Ile Glu Leu Ala Tyr Glu Ala Gly Leu Leu Ser Arg Asn Glu
            180                 185                 190 gaa aat ttc agt tat tac gat aga ttt cga aat cgt att atg ttt cct    624
Glu Asn Phe Ser Tyr Tyr Asp Arg Phe Arg Asn Arg Ile Met Phe Pro
            195                 200                 205 ttg aaa aat gcg caa gga aga att gtt gga tat tca ggt cga aca tat    672
Leu Lys Asn Ala Gln Gly Arg Ile Val Gly Tyr Ser Gly Arg Thr Tyr
    210                 215                 220 acc ggt caa gaa cca aaa tac cta aat agt cct gaa acg cct atc ttt    720
Thr Gly Gln Glu Pro Lys Tyr Leu Asn Ser Pro Glu Thr Pro Ile Phe
225                 230                 235                 240 caa aaa aga aag ttg tta tat aac tta gat aaa gca cgt aaa tca att    768
Gln Lys Arg Lys Leu Leu Tyr Asn Leu Asp Lys Ala Arg Lys Ser Ile
                245                 250                 255 aga aaa tta gat gaa att gta tta cta gaa ggt ttt atg gat gtt ata    816
Arg Lys Leu Asp Glu Ile Val Leu Leu Glu Gly Phe Met Asp Val Ile
            260                 265                 270 aaa tct gat act gct ggc ttg aaa aac gtt gtt gca aca atg ggt aca    864
Lys Ser Asp Thr Ala Gly Leu Lys Asn Val Val Ala Thr Met Gly Thr
            275                 280                 285 cag ttg tca gat gaa cat att acc ttt ata cga aag tta aca tca aat    912
Gln Leu Ser Asp Glu His Ile Thr Phe Ile Arg Lys Leu Thr Ser Asn
            290                 295                 300 ata aca tta atg ttt gat ggg gat ttt gcg ggt agt gaa gca aca ctt    960
Ile Thr Leu Met Phe Asp Gly Asp Phe Ala Gly Ser Glu Ala Thr Leu
305                 310                 315                 320 aaa aca ggt caa cat ttg tta cag caa ggg cta aat gta ttt gtt ata    1008
Lys Thr Gly Gln His Leu Leu Gln Gln Gly Leu Asn Val Phe Val Ile
                325                 330                 335 caa ttg cca tct ggc atg gat ccg gat gaa tac att ggt aag tat ggc    1056
Gln Leu Pro Ser Gly Met Asp Pro Asp Glu Tyr Ile Gly Lys Tyr Gly
            340                 345                 350 aac gac gca ttt act act ttt gta aaa aat gac aaa aag tca ttt gca    1104
Asn Asp Ala Phe Thr Thr Phe Val Lys Asn Asp Lys Lys Ser Phe Ala
            355                 360                 365 cat tat aaa gta agt ata tta aaa gat gaa att gca cat aat gac ctt    1152
His Tyr Lys Val Ser Ile Leu Lys Asp Glu Ile Ala His Asn Asp Leu
    370                 375                 380 tca tat gaa cgt tat ttg aaa gaa ctg agt cat gac att tca ctt atg    1200
Ser Tyr Glu Arg Tyr Leu Lys Glu Leu Ser His Asp Ile Ser Leu Met
385                 390                 395                 400 aag tca tca att ctg caa caa aag gct ata aat gat gtt gcg cca ttt    1248
Lys Ser Ser Ile Leu Gln Gln Lys Ala Ile Asn Asp Val Ala Pro Phe
                405                 410                 415 ttc aat gtt agt cct gag cag tta gct aac gaa ata caa ttc aat caa    1296
Phe Asn Val Ser Pro Glu Gln Leu Ala Asn Glu Ile Gln Phe Asn Gln
            420                 425                 430 gca cca gcc aat tat tat cca gaa gat gag tat ggt ggt tat gat gag    1344
Ala Pro Ala Asn Tyr Tyr Pro Glu Asp Glu Tyr Gly Gly Tyr Asp Glu
            435                 440                 445 tat ggc ggt tat att gaa cct gag cca att ggt atg gca caa ttt gac    1392
Tyr Gly Gly Tyr Ile Glu Pro Glu Pro Ile Gly Met Ala Gln Phe Asp
    450                 455                 460 aat ttg agc cgt caa gaa aaa gcg gag cga gca ttt tta aaa cat tta    1440
Asn Leu Ser Arg Gln Glu Lys Ala Glu Arg Ala Phe Leu Lys His Leu
465                 470                 475                 480 atg aga gat aaa gat aca ttt tta aat tat tat gaa agt gtt gat aag    1488
Met Arg Asp Lys Asp Thr Phe Leu Asn Tyr Tyr Glu Ser Val Asp Lys
```

```
                Met Arg Asp Lys Asp Thr Phe Leu Asn Tyr Tyr Glu Ser Val Asp Lys
                                485                 490                 495 gat aac ttc aca aat cag cat ttt aaa tat gta ttc gaa gtc tta cat         1536
Asp Asn Phe Thr Asn Gln His Phe Lys Tyr Val Phe Glu Val Leu His
            500                 505                 510 gat ttt tat gcg gaa aat gat caa tat aat atc agt gat gct gtg cag         1584
Asp Phe Tyr Ala Glu Asn Asp Gln Tyr Asn Ile Ser Asp Ala Val Gln
            515                 520                 525 tat gtt aat tca aat gag ttg aga gaa aca cta att agc tta gaa caa         1632
Tyr Val Asn Ser Asn Glu Leu Arg Glu Thr Leu Ile Ser Leu Glu Gln
530                 535                 540 tat aat ttg aat gac gaa cca tat gaa aat gaa att gat gat tat gtc         1680
Tyr Asn Leu Asn Asp Glu Pro Tyr Glu Asn Glu Ile Asp Asp Tyr Val
545                 550                 555                 560 aat gtt att aat gaa aaa gga caa gaa aca att gag tca ttg aat cat         1728
Asn Val Ile Asn Glu Lys Gly Gln Glu Thr Ile Glu Ser Leu Asn His
                565                 570                 575 aaa tta agg gaa gct aca agg att ggc gat gta gaa tta caa aaa tac         1776
Lys Leu Arg Glu Ala Thr Arg Ile Gly Asp Val Glu Leu Gln Lys Tyr
                580                 585                 590 tat tta cag caa att gtt gct aag aat aaa gaa cgc atg tag                 1818
Tyr Leu Gln Gln Ile Val Ala Lys Asn Lys Glu Arg Met
            595                 600                 605

<210> SEQ ID NO 78
<211> LENGTH: 605
<212> TYPE: PRT
<213> ORGANISM: Staphylococcus aureus

<400> SEQUENCE: 78

Leu Arg Ile Asp Gln Ser Ile Ile Asn Glu Ile Lys Asp Lys Thr Asp
1               5                   10                  15

Ile Leu Asp Leu Val Ser Glu Tyr Val Lys Leu Glu Lys Arg Gly Arg
            20                  25                  30

Asn Tyr Ile Gly Leu Cys Pro Phe His Asp Glu Lys Thr Pro Ser Phe
        35                  40                  45

Thr Val Ser Glu Asp Lys Gln Ile Cys His Cys Phe Gly Cys Lys Lys
    50                  55                  60

Gly Gly Asn Val Phe Gln Phe Thr Gln Glu Ile Lys Asp Ile Ser Phe
65                  70                  75                  80

Val Glu Ala Val Lys Glu Leu Gly Asp Arg Val Asn Val Ala Val Asp
                85                  90                  95

Ile Glu Ala Thr Gln Ser Asn Ser Asn Val Gln Ile Ala Ser Asp Asp
            100                 105                 110

Leu Gln Met Ile Glu Met His Glu Leu Ile Gln Glu Phe Tyr Tyr Tyr
        115                 120                 125

Ala Leu Thr Lys Thr Val Glu Gly Glu Gln Ala Leu Thr Tyr Leu Gln
    130                 135                 140

Glu Arg Gly Phe Thr Asp Ala Leu Ile Lys Glu Arg Gly Ile Gly Phe
145                 150                 155                 160

Ala Pro Asp Ser Ser His Phe Cys His Asp Phe Leu Gln Lys Lys Gly
                165                 170                 175

Tyr Asp Ile Glu Leu Ala Tyr Glu Ala Gly Leu Leu Ser Arg Asn Glu
            180                 185                 190

Glu Asn Phe Ser Tyr Tyr Asp Arg Phe Arg Asn Arg Ile Met Phe Pro
        195                 200                 205

Leu Lys Asn Ala Gln Gly Arg Ile Val Gly Tyr Ser Gly Arg Thr Tyr
    210                 215                 220
```

Thr Gly Gln Glu Pro Lys Tyr Leu Asn Ser Pro Glu Thr Pro Ile Phe
225                 230                 235                 240

Gln Lys Arg Lys Leu Leu Tyr Asn Leu Asp Lys Ala Arg Lys Ser Ile
            245                 250                 255

Arg Lys Leu Asp Glu Ile Val Leu Leu Glu Gly Phe Met Asp Val Ile
        260                 265                 270

Lys Ser Asp Thr Ala Gly Leu Lys Asn Val Val Ala Thr Met Gly Thr
    275                 280                 285

Gln Leu Ser Asp Glu His Ile Thr Phe Ile Arg Lys Leu Thr Ser Asn
290                 295                 300

Ile Thr Leu Met Phe Asp Gly Asp Phe Ala Gly Ser Glu Ala Thr Leu
305                 310                 315                 320

Lys Thr Gly Gln His Leu Leu Gln Gln Gly Leu Asn Val Phe Val Ile
            325                 330                 335

Gln Leu Pro Ser Gly Met Asp Pro Asp Glu Tyr Ile Gly Lys Tyr Gly
        340                 345                 350

Asn Asp Ala Phe Thr Thr Phe Val Lys Asn Asp Lys Lys Ser Phe Ala
    355                 360                 365

His Tyr Lys Val Ser Ile Leu Lys Asp Glu Ile Ala His Asn Asp Leu
370                 375                 380

Ser Tyr Glu Arg Tyr Leu Lys Glu Leu Ser His Asp Ile Ser Leu Met
385                 390                 395                 400

Lys Ser Ser Ile Leu Gln Gln Lys Ala Ile Asn Asp Val Ala Pro Phe
            405                 410                 415

Phe Asn Val Ser Pro Glu Gln Leu Ala Asn Glu Ile Gln Phe Asn Gln
        420                 425                 430

Ala Pro Ala Asn Tyr Tyr Pro Glu Asp Glu Tyr Gly Tyr Asp Glu
    435                 440                 445

Tyr Gly Gly Tyr Ile Glu Pro Glu Pro Ile Gly Met Ala Gln Phe Asp
450                 455                 460

Asn Leu Ser Arg Gln Glu Lys Ala Glu Arg Ala Phe Leu Lys His Leu
465                 470                 475                 480

Met Arg Asp Lys Asp Thr Phe Leu Asn Tyr Tyr Glu Ser Val Asp Lys
            485                 490                 495

Asp Asn Phe Thr Asn Gln His Phe Lys Tyr Val Phe Glu Val Leu His
        500                 505                 510

Asp Phe Tyr Ala Glu Asn Asp Gln Tyr Asn Ile Ser Asp Ala Val Gln
    515                 520                 525

Tyr Val Asn Ser Asn Glu Leu Arg Glu Thr Leu Ile Ser Leu Glu Gln
530                 535                 540

Tyr Asn Leu Asn Asp Glu Pro Tyr Glu Asn Ile Asp Asp Tyr Val
545                 550                 555                 560

Asn Val Ile Asn Glu Lys Gly Gln Glu Thr Ile Glu Ser Leu Asn His
            565                 570                 575

Lys Leu Arg Glu Ala Thr Arg Ile Gly Asp Val Glu Leu Gln Lys Tyr
        580                 585                 590

Tyr Leu Gln Gln Ile Val Ala Lys Asn Lys Glu Arg Met
595                 600                 605

<210> SEQ ID NO 79
<211> LENGTH: 35
<212> TYPE: DNA
<213> ORGANISM: Artificial
<220> FEATURE:
<223> OTHER INFORMATION: primer

<400> SEQUENCE: 79
gactgcatgc gcatcgatca atcgatcatt aatga                                   35

<210> SEQ ID NO 80
<211> LENGTH: 36
<212> TYPE: DNA
<213> ORGANISM: Artificial
<220> FEATURE:
<223> OTHER INFORMATION: primer

<400> SEQUENCE: 80
gctaactagt ctactacatg cgttctttat tcttag                                  36

<210> SEQ ID NO 81
<211> LENGTH: 426
<212> TYPE: DNA
<213> ORGANISM: Staphylococcus aureus

<400> SEQUENCE: 81
atgttaaaca gaacagtatt agtaggacga ttaacaaaag acccagaatt aagaagcacg        60
ccaaatggtg taaatgtagg gacattcaca ttagcagtaa acagaacatt cacgaatgct       120
caaggcgagc gtgaagcaga ttttataaac gtagtagtgt tcaaaaaaca agctgaaaac       180
gttaaaaact acctttctaa aggatcgttg gcaggtgtag acggacgact acaaacacgt       240
aactatgaaa acaaagacgg gcaacgtgta tttgttacag aagtagtagc ggacagtgtt       300
caattcttag aaccgaagaa taacaaccaa caacaaaaca caattatca acaacaaga        360 caaactcaaa ctggtaataa tccttttgat aacaacgcag actctataga ggatcttcct       420
ttttag                                                                  426

<210> SEQ ID NO 82
<211> LENGTH: 426
<212> TYPE: DNA
<213> ORGANISM: Staphylococcus aureus
<220> FEATURE:
<221> NAME/KEY: CDS
<222> LOCATION: (1)..(426)

<400> SEQUENCE: 82 atg tta aac aga aca gta tta gta gga cga tta aca aaa gac cca gaa          48
Met Leu Asn Arg Thr Val Leu Val Gly Arg Leu Thr Lys Asp Pro Glu
1               5                   10                  15 tta aga agc acg cca aat ggt gta aat gta ggg aca ttc aca tta gca          96
Leu Arg Ser Thr Pro Asn Gly Val Asn Val Gly Thr Phe Thr Leu Ala
            20                  25                  30 gta aac aga aca ttc acg aat gct caa ggc gag cgt gaa gca gat ttt         144
Val Asn Arg Thr Phe Thr Asn Ala Gln Gly Glu Arg Glu Ala Asp Phe
        35                  40                  45 ata aac gta gta gtg ttc aaa aaa caa gct gaa aac gtt aaa aac tac         192
Ile Asn Val Val Val Phe Lys Lys Gln Ala Glu Asn Val Lys Asn Tyr
    50                  55                  60 ctt tct aaa gga tcg ttg gca ggt gta gac gga cga cta caa aca cgt         240
Leu Ser Lys Gly Ser Leu Ala Gly Val Asp Gly Arg Leu Gln Thr Arg
65                  70                  75                  80 aac tat gaa aac aaa gac ggg caa cgt gta ttt gtt aca gaa gta gta         288
Asn Tyr Glu Asn Lys Asp Gly Gln Arg Val Phe Val Thr Glu Val Val
                85                  90                  95 gcg gac agt gtt caa ttc tta gaa ccg aag aat aac aac caa caa caa         336
Ala Asp Ser Val Gln Phe Leu Glu Pro Lys Asn Asn Asn Gln Gln Gln
            100                 105                 110

```
aac aac aat tat caa caa caa aga caa act caa act ggt aat aat cct    384
Asn Asn Asn Tyr Gln Gln Gln Arg Gln Thr Gln Thr Gly Asn Asn Pro
            115                 120                 125 ttt gat aac aac gca gac tct ata gag gat ctt cct ttt tag            426
Phe Asp Asn Asn Ala Asp Ser Ile Glu Asp Leu Pro Phe
130                 135                 140

<210> SEQ ID NO 83
<211> LENGTH: 141
<212> TYPE: PRT
<213> ORGANISM: Staphylococcus aureus

<400> SEQUENCE: 83

Met Leu Asn Arg Thr Val Leu Val Gly Arg Leu Thr Lys Asp Pro Glu
1               5                   10                  15

Leu Arg Ser Thr Pro Asn Gly Val Asn Val Gly Thr Phe Thr Leu Ala
            20                  25                  30

Val Asn Arg Thr Phe Thr Asn Ala Gln Gly Glu Arg Glu Ala Asp Phe
        35                  40                  45

Ile Asn Val Val Val Phe Lys Lys Gln Ala Glu Asn Val Lys Asn Tyr
    50                  55                  60

Leu Ser Lys Gly Ser Leu Ala Gly Val Asp Gly Arg Leu Gln Thr Arg
65                  70                  75                  80

Asn Tyr Glu Asn Lys Asp Gly Gln Arg Val Phe Val Thr Glu Val Val
                85                  90                  95

Ala Asp Ser Val Gln Phe Leu Glu Pro Lys Asn Asn Asn Gln Gln Gln
            100                 105                 110

Asn Asn Asn Tyr Gln Gln Gln Arg Gln Thr Gln Thr Gly Asn Asn Pro
        115                 120                 125

Phe Asp Asn Asn Ala Asp Ser Ile Glu Asp Leu Pro Phe
    130                 135                 140

<210> SEQ ID NO 84
<211> LENGTH: 42
<212> TYPE: DNA
<213> ORGANISM: Artificial
<220> FEATURE:
<223> OTHER INFORMATION: primer

<400> SEQUENCE: 84
gtcacatatg ctgaaccgca cagtattagt aggacgatta ac                     42

<210> SEQ ID NO 85
<211> LENGTH: 55
<212> TYPE: DNA
<213> ORGANISM: Artificial
<220> FEATURE:
<223> OTHER INFORMATION: primer

<400> SEQUENCE: 85
atcggctagc gcatgcactg cagcctccta ctaaaaagga agatcctcta tagag        55

<210> SEQ ID NO 86
<211> LENGTH: 471
<212> TYPE: DNA
<213> ORGANISM: Staphylococcus aureus

<400> SEQUENCE: 86
atgctaaaca gaacaatatt agttggtcgt ttaactagag acccagaatt aagaaccact    60
caaagtggtg taaatgtagc atcattcaca ttagcagtta accgcacatt tacgaatgca   120
caaggagagc gcgaggcaga ctttattaat atcatcgtat ttaaaaaaca agcagagaac   180
```

```
gttaataaat acctatctaa aggatcgttg gcgggcgtag atggtaggtt acaaacgcgg      240
aactatgaaa ataaggaagg tcaacgtgta tacgttacgg aagttattgc tgatagtatt      300
caatttttag aaccgaaaaa ctcaaatgac actcaacaag atttatatca acaacaagta      360
caacaaacac gtggacaatc gcaatattca ataacaaac cagtaaaaga taatccgttt       420
gcgaatgcaa atggtccgat tgaactaaat gatgatgatt taccattctg a              471
```

<210> SEQ ID NO 87
<211> LENGTH: 471
<212> TYPE: DNA
<213> ORGANISM: Staphylococcus aureus
<220> FEATURE:
<221> NAME/KEY: CDS
<222> LOCATION: (1)..(471)

<400> SEQUENCE: 87

```
atg cta aac aga aca ata tta gtt ggt cgt tta act aga gac cca gaa       48
Met Leu Asn Arg Thr Ile Leu Val Gly Arg Leu Thr Arg Asp Pro Glu
1               5                   10                  15 tta aga acc act caa agt ggt gta aat gta gca tca ttc aca tta gca       96
Leu Arg Thr Thr Gln Ser Gly Val Asn Val Ala Ser Phe Thr Leu Ala
                20                  25                  30 gtt aac cgc aca ttt acg aat gca caa gga gag cgc gag gca gac ttt      144
Val Asn Arg Thr Phe Thr Asn Ala Gln Gly Glu Arg Glu Ala Asp Phe
            35                  40                  45 att aat atc atc gta ttt aaa aaa caa gca gag aac gtt aat aaa tac      192
Ile Asn Ile Ile Val Phe Lys Lys Gln Ala Glu Asn Val Asn Lys Tyr
        50                  55                  60 cta tct aaa gga tcg ttg gcg ggc gta gat ggt agg tta caa acg cgg      240
Leu Ser Lys Gly Ser Leu Ala Gly Val Asp Gly Arg Leu Gln Thr Arg
65                  70                  75                  80 aac tat gaa aat aag gaa ggt caa cgt gta tac gtt acg gaa gtt att      288
Asn Tyr Glu Asn Lys Glu Gly Gln Arg Val Tyr Val Thr Glu Val Ile
                85                  90                  95 gct gat agt att caa ttt tta gaa ccg aaa aac tca aat gac act caa      336
Ala Asp Ser Ile Gln Phe Leu Glu Pro Lys Asn Ser Asn Asp Thr Gln
            100                 105                 110 caa gat tta tat caa caa caa gta caa caa aca cgt gga caa tcg caa      384
Gln Asp Leu Tyr Gln Gln Gln Val Gln Gln Thr Arg Gly Gln Ser Gln
        115                 120                 125 tat tca aat aac aaa cca gta aaa gat aat ccg ttt gcg aat gca aat      432
Tyr Ser Asn Asn Lys Pro Val Lys Asp Asn Pro Phe Ala Asn Ala Asn
130                 135                 140 ggt ccg att gaa cta aat gat gat gat tta cca ttc tga              471
Gly Pro Ile Glu Leu Asn Asp Asp Asp Leu Pro Phe
145                 150                 155
```

<210> SEQ ID NO 88
<211> LENGTH: 156
<212> TYPE: PRT
<213> ORGANISM: Staphylococcus aureus

<400> SEQUENCE: 88

```
Met Leu Asn Arg Thr Ile Leu Val Gly Arg Leu Thr Arg Asp Pro Glu
1               5                   10                  15

Leu Arg Thr Thr Gln Ser Gly Val Asn Val Ala Ser Phe Thr Leu Ala
                20                  25                  30

Val Asn Arg Thr Phe Thr Asn Ala Gln Gly Glu Arg Glu Ala Asp Phe
            35                  40                  45

Ile Asn Ile Ile Val Phe Lys Lys Gln Ala Glu Asn Val Asn Lys Tyr
```

```
                50                  55                  60
Leu Ser Lys Gly Ser Leu Ala Gly Val Asp Gly Arg Leu Gln Thr Arg
 65                  70                  75                  80

Asn Tyr Glu Asn Lys Glu Gly Gln Arg Val Tyr Val Thr Glu Val Ile
                 85                  90                  95

Ala Asp Ser Ile Gln Phe Leu Glu Pro Lys Asn Ser Asn Asp Thr Gln
            100                 105                 110

Gln Asp Leu Tyr Gln Gln Val Gln Gln Thr Arg Gly Gln Ser Gln
        115                 120                 125

Tyr Ser Asn Asn Lys Pro Val Lys Asp Asn Pro Phe Ala Asn Ala Asn
    130                 135                 140

Gly Pro Ile Glu Leu Asn Asp Asp Leu Pro Phe
145                 150                 155
```

<210> SEQ ID NO 89
<211> LENGTH: 44
<212> TYPE: DNA
<213> ORGANISM: Artificial
<220> FEATURE:
<223> OTHER INFORMATION: primer

<400> SEQUENCE: 89
gatcgcatgc tgaaccgcac catcttagtt ggtcgtttaa ctag                44

<210> SEQ ID NO 90
<211> LENGTH: 50
<212> TYPE: DNA
<213> ORGANISM: Artificial
<220> FEATURE:
<223> OTHER INFORMATION: primer

<400> SEQUENCE: 90
gtcaggtacc atcgatctgc agcctcctat cagaatggta aatcatcatc          50

<210> SEQ ID NO 91
<211> LENGTH: 504
<212> TYPE: DNA
<213> ORGANISM: Staphylococcus aureus

<400> SEQUENCE: 91
atgctaaata gagttgtatt agtaggtcgt ttaacgaaag atccggaata cagaaccact     60
ccctcaggtg tgagtgtagc gacattcact cttgcagtaa atcgtacgtt cacgaatgct    120 caagggagc gcgaagcaga ttttattaac tgtgttgttt ttagaagaca agcagataat    180
gtaaataact atttatctaa aggtagttta gctggtgtag atggtcgctt acaatcccgt    240
aattatgaaa atcaagaagg tcgtcgtgtg tttgttactg aagttgtgtg tgatagcgtt    300
caattccttg aacctaaaaa tgcgcaacaa atggtggcc aacgtcaaca aaatgaattc    360
caagattacg gtcaaggatt cggtggtcaa caatcaggac aaaacaattc gtacaataat    420
tcatcaaaca cgaaacaatc tgataatcca tttgcaaatg caaacggacc gattgatata    480
agtgatgatg acttaccatt ctaa                                          504

<210> SEQ ID NO 92
<211> LENGTH: 504
<212> TYPE: DNA
<213> ORGANISM: Staphylococcus aureus
<220> FEATURE:
<221> NAME/KEY: CDS
<222> LOCATION: (1)..(504)

<400> SEQUENCE: 92

```
atg cta aat aga gtt gta tta gta ggt cgt tta acg aaa gat ccg gaa      48
Met Leu Asn Arg Val Val Leu Val Gly Arg Leu Thr Lys Asp Pro Glu
1               5                   10                  15 tac aga acc act ccc tca ggt gtg agt gta gcg aca ttc act ctt gca      96
Tyr Arg Thr Thr Pro Ser Gly Val Ser Val Ala Thr Phe Thr Leu Ala
                20                  25                  30 gta aat cgt acg ttc acg aat gct caa ggg gag cgc gaa gca gat ttt     144
Val Asn Arg Thr Phe Thr Asn Ala Gln Gly Glu Arg Glu Ala Asp Phe
            35                  40                  45 att aac tgt gtt gtt ttt aga aga caa gca gat aat gta aat aac tat     192
Ile Asn Cys Val Val Phe Arg Arg Gln Ala Asp Asn Val Asn Asn Tyr
        50                  55                  60 tta tct aaa ggt agt tta gct ggt gta gat ggt cgc tta caa tcc cgt     240
Leu Ser Lys Gly Ser Leu Ala Gly Val Asp Gly Arg Leu Gln Ser Arg
65                  70                  75                  80 aat tat gaa aat caa gaa ggt cgt cgt gtg ttt gtt act gaa gtt gtg     288
Asn Tyr Glu Asn Gln Glu Gly Arg Arg Val Phe Val Thr Glu Val Val
                85                  90                  95 tgt gat agc gtt caa ttc ctt gaa cct aaa aat gcg caa caa aat ggt     336
Cys Asp Ser Val Gln Phe Leu Glu Pro Lys Asn Ala Gln Gln Asn Gly
                100                 105                 110 ggc caa cgt caa caa aat gaa ttc caa gat tac ggt caa gga ttc ggt     384
Gly Gln Arg Gln Gln Asn Glu Phe Gln Asp Tyr Gly Gln Gly Phe Gly
            115                 120                 125 ggt caa caa tca gga caa aac aat tcg tac aat aat tca tca aac acg     432
Gly Gln Gln Ser Gly Gln Asn Asn Ser Tyr Asn Asn Ser Ser Asn Thr
        130                 135                 140 aaa caa tct gat aat cca ttt gca aat gca aac gga ccg att gat ata     480
Lys Gln Ser Asp Asn Pro Phe Ala Asn Ala Asn Gly Pro Ile Asp Ile
145                 150                 155                 160 agt gat gat gac tta cca ttc taa                                     504
Ser Asp Asp Asp Leu Pro Phe
                165

<210> SEQ ID NO 93
<211> LENGTH: 167
<212> TYPE: PRT
<213> ORGANISM: Staphylococcus aureus

<400> SEQUENCE: 93

Met Leu Asn Arg Val Val Leu Val Gly Arg Leu Thr Lys Asp Pro Glu
1               5                   10                  15

Tyr Arg Thr Thr Pro Ser Gly Val Ser Val Ala Thr Phe Thr Leu Ala
                20                  25                  30

Val Asn Arg Thr Phe Thr Asn Ala Gln Gly Glu Arg Glu Ala Asp Phe
            35                  40                  45

Ile Asn Cys Val Val Phe Arg Arg Gln Ala Asp Asn Val Asn Asn Tyr
        50                  55                  60

Leu Ser Lys Gly Ser Leu Ala Gly Val Asp Gly Arg Leu Gln Ser Arg
65                  70                  75                  80

Asn Tyr Glu Asn Gln Glu Gly Arg Arg Val Phe Val Thr Glu Val Val
                85                  90                  95

Cys Asp Ser Val Gln Phe Leu Glu Pro Lys Asn Ala Gln Gln Asn Gly
                100                 105                 110

Gly Gln Arg Gln Gln Asn Glu Phe Gln Asp Tyr Gly Gln Gly Phe Gly
            115                 120                 125

Gly Gln Gln Ser Gly Gln Asn Asn Ser Tyr Asn Asn Ser Ser Asn Thr
        130                 135                 140
```

-continued

```
Lys Gln Ser Asp Asn Pro Phe Ala Asn Ala Asn Gly Pro Ile Asp Ile
145                 150                 155                 160

Ser Asp Asp Asp Leu Pro Phe
                165

<210> SEQ ID NO 94
<211> LENGTH: 50
<212> TYPE: DNA
<213> ORGANISM: Artificial
<220> FEATURE:
<223> OTHER INFORMATION: primer

<400> SEQUENCE: 94
gactttaatt aatcgatgct gaaccgcgtt gtattagtag gtcgtttaac            50

<210> SEQ ID NO 95
<211> LENGTH: 36
<212> TYPE: DNA
<213> ORGANISM: Artificial
<220> FEATURE:
<223> OTHER INFORMATION: primer

<400> SEQUENCE: 95
gtcaactagt ctattagaat ggtaagtcat catcac                           36

<210> SEQ ID NO 96
<211> LENGTH: 396
<212> TYPE: DNA
<213> ORGANISM: Staphylococcus aureus

<400> SEQUENCE: 96
atgctaaata aaatcgtaat tgtcgggaga ctgacgaaag acgcacaaat atttgaaaag   60
gaggatagaa aaattgcaac gttttgtgtt gcaacgcacc gaaattataa agatgaaaat  120
ggagaaatcg tctgtgatta ccttattctgt aaagcatttg gcaagttagc ttctaatata  180
gaaaaatata ctaatcaagg tacattggtt ggtataactg gtcaaatgag atcaagaaag  240
tatgataaag acggacaaac acactttgtc actgaattat atgttgaaac aataaaattt  300
atgtccccta atcccaaaa taatgaaatt ctctcagata gtattttaga tattgactct   360
caaaatatag ataatcatga cttattagaa atttaa                           396

<210> SEQ ID NO 97
<211> LENGTH: 396
<212> TYPE: DNA
<213> ORGANISM: Staphylococcus aureus
<220> FEATURE:
<221> NAME/KEY: CDS
<222> LOCATION: (1)..(396)

<400> SEQUENCE: 97 atg cta aat aaa atc gta att gtc ggg aga ctg acg aaa gac gca caa    48
Met Leu Asn Lys Ile Val Ile Val Gly Arg Leu Thr Lys Asp Ala Gln
1               5                   10                  15 ata ttt gaa aag gag gat aga aaa att gca acg ttt tgt gtt gca acg    96
Ile Phe Glu Lys Glu Asp Arg Lys Ile Ala Thr Phe Cys Val Ala Thr
            20                  25                  30 cac cga aat tat aaa gat gaa aat gga gaa atc gtc tgt gat tac tta   144
His Arg Asn Tyr Lys Asp Glu Asn Gly Glu Ile Val Cys Asp Tyr Leu
        35                  40                  45 ttc tgt aaa gca ttt ggc aag tta gct tct aat ata gaa aaa tat act   192
Phe Cys Lys Ala Phe Gly Lys Leu Ala Ser Asn Ile Glu Lys Tyr Thr
    50                  55                  60 aat caa ggt aca ttg gtt ggt ata act ggt caa atg aga tca aga aag   240
```

```
Asn Gln Gly Thr Leu Val Gly Ile Thr Gly Gln Met Arg Ser Arg Lys
 65                  70                  75                  80 tat gat aaa gac gga caa aca cac ttt gtc act gaa tta tat gtt gaa      288
Tyr Asp Lys Asp Gly Gln Thr His Phe Val Thr Glu Leu Tyr Val Glu
                 85                  90                  95 aca ata aaa ttt atg tcc cct aaa tcc caa aat aat gaa att ctc tca      336
Thr Ile Lys Phe Met Ser Pro Lys Ser Gln Asn Asn Glu Ile Leu Ser
            100                 105                 110 gat agt att tta gat att gac tct caa aat ata gat aat cat gac tta      384
Asp Ser Ile Leu Asp Ile Asp Ser Gln Asn Ile Asp Asn His Asp Leu
        115                 120                 125 tta gaa att taa                                                       396
Leu Glu Ile
    130
```

```
<210> SEQ ID NO 98
<211> LENGTH: 131
<212> TYPE: PRT
<213> ORGANISM: Staphylococcus aureus

<400> SEQUENCE: 98

Met Leu Asn Lys Ile Val Ile Val Gly Arg Leu Thr Lys Asp Ala Gln
1               5                   10                  15

Ile Phe Glu Lys Glu Asp Arg Lys Ile Ala Thr Phe Cys Val Ala Thr
            20                  25                  30

His Arg Asn Tyr Lys Asp Glu Asn Gly Glu Ile Val Cys Asp Tyr Leu
        35                  40                  45

Phe Cys Lys Ala Phe Gly Lys Leu Ala Ser Asn Ile Glu Lys Tyr Thr
    50                  55                  60

Asn Gln Gly Thr Leu Val Gly Ile Thr Gly Gln Met Arg Ser Arg Lys
65                  70                  75                  80

Tyr Asp Lys Asp Gly Gln Thr His Phe Val Thr Glu Leu Tyr Val Glu
                85                  90                  95

Thr Ile Lys Phe Met Ser Pro Lys Ser Gln Asn Asn Glu Ile Leu Ser
            100                 105                 110

Asp Ser Ile Leu Asp Ile Asp Ser Gln Asn Ile Asp Asn His Asp Leu
        115                 120                 125

Leu Glu Ile
    130
```

```
<210> SEQ ID NO 99
<211> LENGTH: 59
<212> TYPE: DNA
<213> ORGANISM: Artificial
<220> FEATURE:
<223> OTHER INFORMATION: primer

<400> SEQUENCE: 99
gatcgcatgc tgaataaaat cgtaattgtc ggtcgcctga cgaaagacgc aaaatattt      59
```

```
<210> SEQ ID NO 100
<211> LENGTH: 34
<212> TYPE: DNA
<213> ORGANISM: Artificial
<220> FEATURE:
<223> OTHER INFORMATION: primer

<400> SEQUENCE: 100
gatcactagt ctattaaatt tctaataagt catg                                 34
```

```
<210> SEQ ID NO 101
```

<211> LENGTH: 4311
<212> TYPE: DNA
<213> ORGANISM: Staphylococcus aureus

<400> SEQUENCE: 101

```
atgacagagc aacaaaaatt taaagtgctt gctgatcaaa ttaaaatttc aaatcaatta      60
gatgctgaaa ttttaaattc aggtgaactg acacgtatag atgtttctaa caaaaacaga     120
acatgggaat tcatattac attaccacaa ttcttagctc atgaagatta tttattattt     180
ataaatgcaa tagagcaaga gtttaaagat atcgccaacg ttacatgtcg ttttacggta     240
acaaatggca cgaatcaaga tgaacatgca attaaatact tgggcactg tattgaccaa      300
acagctttat ctccaaaagt taaaggtcaa ttgaaacaga aaagcttat tatgtctgga      360
aaagtattaa agtaatggt atcaaatgac attgaacgta atcattttga taaggcatgt     420
aatggaagtc ttatcaaagc gtttagaaat tgtggttttg atatcgataa aatcatattc     480
gaaacaaatg ataatgatca gaacaaaac ttagcttctt tagaagcaca tattcaagaa      540
gaagacgaac aaagtgcacg attggcaact gaaaaacttg aaaaaatgaa agctgaaaaa     600
gcgaaacaac aagataacaa cgaaagtgct gtcgataagt gtcaaattgg taagccgatt     660
caaattgaaa atattaaacc aattgaatct attattgagg aagagtttaa agttgcaata     720
gagggtgtca tttttgatat aaacttaaaa gaacttaaaa gtggtcgtca tatcgtagaa     780
attaaagtga ctgactatac ggactcatta gttttaaaaa tgtttactcg taaaaacaaa     840
gatgatttag aacattttaa agcgctaagt gtaggtaaat gggttagggc tcaaggtcgt     900
attgaagaag atacatttat tcgcgattta gttatgatga tgtctgatat tgaagagatt     960
aaaaaagcga caaaaaaaga taaggctgaa gaaaagcgtg tagaattcca cttgcatact    1020
gcaatgagcc aaatggatgg tatacccaat attggtgcgt atgttaaaca ggcagcagac    1080
tgggacatc cagccattgc ggttacagac cataatgttg tgcaagcatt tccagatgct    1140
cacgcagcag cggaaaaaca tggcattaaa atgatatacg gtatggaagg tatgttagtt    1200
gatgatggtg ttccgattgc atacaaacca caagatgtcg tattaaaaga tgctacttat    1260
gttgtgttcg acgttgagac aactggttta tcaaatcagt atgataaaat catcgagctt    1320
gcagctgtga agttcataa cggtgaaatc atcgataagt ttgaaaggtt tagtaatccg    1380
catgaacgat tatcggaaac gattatcaat ttgacgcata ttactgatga tatgttagta    1440
gatgcccctg agattgaaga agtacttaca gagtttaaag aatgggttgg cgatgcgata    1500
ttcgtagcgc ataatgcttc gtttgatatg ggctttatcg atacgggata tgaacgtctt    1560
gggtttggac catcaacgaa tggtgttatc gatactttag aattatctcg tacgattaat    1620
actgaatatg gtaaacatgg tttgaatttc ttagctaaaa aatatggcgt agaattaacg    1680
caacatcacc gtgccattta tgatacagaa gcaacagctt acattttcat aaaaatggtt    1740
caacaaatga agaattagg tgtattaaat cataacgaaa tcaacaaaaa actcagtaat    1800
gaagatgcat ataaacgtgc aagacctagc catgtcacat taattgtaca aaaccaacaa    1860
ggtcttaaaa atctatttaa aattgtaagt gcatcattgg tgaagtattt ctaccgtaca    1920
cctcgaattc cacgttcatt gttagatgaa tatcgtgagg gattattggt aggtacagcg    1980
tgtgatgaag gtgaattatt tacggcagtt atgcagaagg accagagcca agttgaaaaa    2040
attgccaaat attatgattt tattgaaatt caaccaccgg cactttatca agatttaatt    2100
gatagagagc ttattagaga tactgaaaca ttacatgaaa tttatcaacg tttaatacat    2160
gcaggtgaca cagcgggtat acctgttatt gcgacaggaa atgcacacta tttgtttgaa    2220
```

```
catgatggta tcgcacgtaa aattttaata gcatcacaac ccggcaatcc acttaatcgc      2280
tcaactttac cggaagcaca ttttagaact acagatgaaa tgttaaacga gtttcatttt      2340
ttaggtgaag aaaaagcgca tgaaattgtt gtgaaaaata caaacgaatt agcagatcga      2400
attgaacgtg ttgttcctat taagatgaa ttatacacac cgcgtatgga aggtgctaac      2460
gaagaaatta gagaactaag ttatacaaat gcgcgtaaac tgtatggtga agacctgcct      2520
caaatcgtaa ttgatcgatt agaaaaagaa ttaaaagta ttatcggtaa tggatttgcg       2580
gtaatttact taatttcgca acgtttagtt aaaaaatcat tagatgatgg atacttagtt      2640
ggttcccgtg gttcagtagg ttctagtttt gtagcgacaa tgactgagat tactgaagta      2700
aacccgttac cgccacacta tatttgtccg aactgtaaaa cgagtgaatt tttcaatgat      2760
ggttcagtag gatcaggatt cgatttacct gataagacgt gtgaaacttg tggagcgcca      2820
cttattaaag aaggacaaga tattccgttt gaaacatttt taggatttaa gggagataaa      2880
gttcctgata tcgacttaaa ctttagtggt gaatatcaac cgaatgccca taactacaca      2940
aaagtattat ttggtgagga taaagtattc cgtgcaggta caattggtac cgttgctgaa      3000
aagactgctt ttggttatgt taaaggttat ttgaatgatc aaggcatcca caaaagaggc      3060
gctgaaatag atcgactcgt taaggatgt acaggtgtta aacgtacaac tggacagcat       3120
ccaggaggta ttattgtagt acctgattac atggatattt tgattttac gccgatacaa       3180 tatcctgccg atgatcaaaa ttcagcatgg atgacgacac attttgattt ccattctatt      3240
catgataatg tattaaaact tgatatactt ggacacgatg atccaacaat gattcgtatg      3300
cttcaagatt tatcgggcat tgatccaaaa acgatacctg tagatgacaa agaagtcatg      3360
caaatattta gtacacctga agtttaggt gttactgaag atgaaatttt atgtaaaaca       3420
ggtacgtttg gggttccaga attcggtaca gggttcgtgc gtcaaatgtt agaagataca      3480
aagccaacaa catttctga attagttcaa atctcaggat tatctcatgg tacagatgtg       3540
tggttaggca atgctcaaga attaattaaa accggtatat gtgatttatc aagtgtaatt      3600
ggttgtcgtg atgatatcat ggtttattta atgtatgctg gtttagaacc atcaatggct      3660
tttaaaataa tggagtcagt acgtaaaggt aaaggtttaa ctgaagaaat gattgaaacg      3720
atgaaagaaa atgaagtgcc ggattggtat ttagattcat gtcttaaaat taagtacatg      3780
ttccctaaag cccatgcagc agcatacgtt ttaatggcag tacgtatcgc atatttcaaa      3840
gtacatcatc cactttatta ctatgcatct tactttacaa ttcgtgcgtc agattttgat      3900
ttaatcacga tgattaaaga taaacaagc attcgaaata ctgtaaaaga catgtattct       3960
cgctatatgg atctaggtaa aaaagaaaaa gacgtattaa cagtcttgga aattatgaat      4020
gaaatggcgc atcgaggtta tcgaatgcaa ccgattagtt tagaaaagag tcaggcgttc      4080
gaatttatca ttgaaggcga tacacttatt ccgccgttca tatcagtgcc tgggcttggc      4140
gaaaacgttg cgaaacgaat tgttgaagct cgtgacgatg gcccattttt atcaaaagaa      4200
gatttaaaca aaaagctgg attatctcag aaaattattg agtatttaga tgagttaggc       4260
tcattaccga atttaccaga taaagctcaa ctttcgatat ttgatatgta a               4311
```

<210> SEQ ID NO 102
<211> LENGTH: 4311
<212> TYPE: DNA
<213> ORGANISM: Staphylococcus aureus
<220> FEATURE:
<221> NAME/KEY: CDS
<222> LOCATION: (1)..(4311)

<400> SEQUENCE: 102

```
atg aca gag caa caa aaa ttt aaa gtg ctt gct gat caa att aaa att        48
Met Thr Glu Gln Gln Lys Phe Lys Val Leu Ala Asp Gln Ile Lys Ile
1               5                   10                  15 tca aat caa tta gat gct gaa att tta aat tca ggt gaa ctg aca cgt        96
Ser Asn Gln Leu Asp Ala Glu Ile Leu Asn Ser Gly Glu Leu Thr Arg
            20                  25                  30 ata gat gtt tct aac aaa aac aga aca tgg gaa ttt cat att aca tta      144
Ile Asp Val Ser Asn Lys Asn Arg Thr Trp Glu Phe His Ile Thr Leu
        35                  40                  45 cca caa ttc tta gct cat gaa gat tat tta tta ttt ata aat gca ata      192
Pro Gln Phe Leu Ala His Glu Asp Tyr Leu Leu Phe Ile Asn Ala Ile
50                  55                  60 gag caa gag ttt aaa gat atc gcc aac gtt aca tgt cgt ttt acg gta      240
Glu Gln Glu Phe Lys Asp Ile Ala Asn Val Thr Cys Arg Phe Thr Val
65                  70                  75                  80 aca aat ggc acg aat caa gat gaa cat gca att aaa tac ttt ggg cac      288
Thr Asn Gly Thr Asn Gln Asp Glu His Ala Ile Lys Tyr Phe Gly His
                85                  90                  95 tgt att gac caa aca gct tta tct cca aaa gtt aaa ggt caa ttg aaa      336
Cys Ile Asp Gln Thr Ala Leu Ser Pro Lys Val Lys Gly Gln Leu Lys
            100                 105                 110 cag aaa aag ctt att atg tct gga aaa gta tta aaa gta atg gta tca      384
Gln Lys Lys Leu Ile Met Ser Gly Lys Val Leu Lys Val Met Val Ser
        115                 120                 125 aat gac att gaa cgt aat cat ttt gat aag gca tgt aat gga agt ctt      432
Asn Asp Ile Glu Arg Asn His Phe Asp Lys Ala Cys Asn Gly Ser Leu
130                 135                 140 atc aaa gcg ttt aga aat tgt ggt ttt gat atc gat aaa atc ata ttc      480
Ile Lys Ala Phe Arg Asn Cys Gly Phe Asp Ile Asp Lys Ile Ile Phe
145                 150                 155                 160 gaa aca aat gat aat gat caa gaa caa aac tta gct tct tta gaa gca      528
Glu Thr Asn Asp Asn Asp Gln Glu Gln Asn Leu Ala Ser Leu Glu Ala
                165                 170                 175 cat att caa gaa gaa gac gaa caa agt gca cga ttg gca act gaa aaa      576
His Ile Gln Glu Glu Asp Glu Gln Ser Ala Arg Leu Ala Thr Glu Lys
            180                 185                 190 ctt gaa aaa atg aaa gct gaa aaa gcg aaa caa caa gat aac aac gaa      624
Leu Glu Lys Met Lys Ala Glu Lys Ala Lys Gln Gln Asp Asn Asn Glu
        195                 200                 205 agt gct gtc gat aag tgt caa att ggt aag ccg att caa att gaa aat      672
Ser Ala Val Asp Lys Cys Gln Ile Gly Lys Pro Ile Gln Ile Glu Asn
210                 215                 220 att aaa cca att gaa tct att att gag gaa gag ttt aaa gtt gca ata      720
Ile Lys Pro Ile Glu Ser Ile Ile Glu Glu Glu Phe Lys Val Ala Ile
225                 230                 235                 240 gag ggt gtc att ttt gat ata aac tta aaa gaa ctt aaa agt ggt cgt      768
Glu Gly Val Ile Phe Asp Ile Asn Leu Lys Glu Leu Lys Ser Gly Arg
                245                 250                 255 cat atc gta gaa att aaa gtg act gac tat acg gac tca tta gtt tta      816
His Ile Val Glu Ile Lys Val Thr Asp Tyr Thr Asp Ser Leu Val Leu
            260                 265                 270 aaa atg ttt act cgt aaa aac aaa gat gat tta gaa cat ttt aaa gcg      864
Lys Met Phe Thr Arg Lys Asn Lys Asp Asp Leu Glu His Phe Lys Ala
        275                 280                 285 cta agt gta ggt aaa tgg gtt agg gct caa ggt cgt att gaa gaa gat      912
Leu Ser Val Gly Lys Trp Val Arg Ala Gln Gly Arg Ile Glu Glu Asp
290                 295                 300 aca ttt att cgc gat tta gtt atg atg atg tct gat att gaa gag att      960
Thr Phe Ile Arg Asp Leu Val Met Met Met Ser Asp Ile Glu Glu Ile
305                 310                 315                 320
```

```
aaa aaa gcg aca aaa aaa gat aag gct gaa gaa aag cgt gta gaa ttc      1008
Lys Lys Ala Thr Lys Lys Asp Lys Ala Glu Glu Lys Arg Val Glu Phe
            325             330             335 cac ttg cat act gca atg agc caa atg gat ggt ata ccc aat att ggt      1056
His Leu His Thr Ala Met Ser Gln Met Asp Gly Ile Pro Asn Ile Gly
        340             345             350 gcg tat gtt aaa cag gca gca gac tgg gga cat cca gcc att gcg gtt      1104
Ala Tyr Val Lys Gln Ala Ala Asp Trp Gly His Pro Ala Ile Ala Val
            355             360             365 aca gac cat aat gtt gtg caa gca ttt cca gat gct cac gca gca gcg      1152
Thr Asp His Asn Val Val Gln Ala Phe Pro Asp Ala His Ala Ala Ala
370             375             380 gaa aaa cat ggc att aaa atg ata tac ggt atg gaa ggt atg tta gtt      1200
Glu Lys His Gly Ile Lys Met Ile Tyr Gly Met Glu Gly Met Leu Val
385             390             395             400 gat gat ggt gtt ccg att gca tac aaa cca caa gat gtc gta tta aaa      1248
Asp Asp Gly Val Pro Ile Ala Tyr Lys Pro Gln Asp Val Val Leu Lys
            405             410             415 gat gct act tat gtt gtg ttc gac gtt gag aca act ggt tta tca aat      1296
Asp Ala Thr Tyr Val Val Phe Asp Val Glu Thr Thr Gly Leu Ser Asn
            420             425             430 cag tat gat aaa atc atc gag ctt gca gct gtg aaa gtt cat aac ggt      1344
Gln Tyr Asp Lys Ile Ile Glu Leu Ala Ala Val Lys Val His Asn Gly
            435             440             445 gaa atc atc gat aag ttt gaa agg ttt agt aat ccg cat gaa cga tta      1392
Glu Ile Ile Asp Lys Phe Glu Arg Phe Ser Asn Pro His Glu Arg Leu
450             455             460 tcg gaa acg att atc aat ttg acg cat att act gat gat atg tta gta      1440
Ser Glu Thr Ile Ile Asn Leu Thr His Ile Thr Asp Asp Met Leu Val
465             470             475             480 gat gcc cct gag att gaa gaa gta ctt aca gag ttt aaa gaa tgg gtt      1488
Asp Ala Pro Glu Ile Glu Glu Val Leu Thr Glu Phe Lys Glu Trp Val
            485             490             495 ggc gat gcg ata ttc gta gcg cat aat gct tcg ttt gat atg ggc ttt      1536
Gly Asp Ala Ile Phe Val Ala His Asn Ala Ser Phe Asp Met Gly Phe
            500             505             510 atc gat acg gga tat gaa cgt ctt ggg ttt gga cca tca acg aat ggt      1584
Ile Asp Thr Gly Tyr Glu Arg Leu Gly Phe Gly Pro Ser Thr Asn Gly
            515             520             525 gtt atc gat act tta gaa tta tct cgt acg att aat act gaa tat ggt      1632
Val Ile Asp Thr Leu Glu Leu Ser Arg Thr Ile Asn Thr Glu Tyr Gly
530             535             540 aaa cat ggt ttg aat ttc tta gct aaa aaa tat ggc gta gaa tta acg      1680
Lys His Gly Leu Asn Phe Leu Ala Lys Lys Tyr Gly Val Glu Leu Thr
545             550             555             560 caa cat cac cgt gcc att tat gat aca gaa aca gct tac att ttc          1728
Gln His His Arg Ala Ile Tyr Asp Thr Glu Thr Ala Tyr Ile Phe
            565             570             575 ata aaa atg gtt caa caa atg aaa gaa tta ggt gta tta aat cat aac      1776
Ile Lys Met Val Gln Gln Met Lys Glu Leu Gly Val Leu Asn His Asn
            580             585             590 gaa atc aac aaa aaa ctc agt aat gaa gat gca tat aaa cgt gca aga      1824
Glu Ile Asn Lys Lys Leu Ser Asn Glu Asp Ala Tyr Lys Arg Ala Arg
            595             600             605 cct agc cat gtc aca tta att gta caa aac caa caa ggt ctt aaa aat      1872
Pro Ser His Val Thr Leu Ile Val Gln Asn Gln Gln Gly Leu Lys Asn
            610             615             620 cta ttt aaa att gta agt gca tca ttg gtg aag tat ttc tac cgt aca      1920
Leu Phe Lys Ile Val Ser Ala Ser Leu Val Lys Tyr Phe Tyr Arg Thr
625             630             635             640
```

```
cct cga att cca cgt tca ttg tta gat gaa tat cgt gag gga tta ttg      1968
Pro Arg Ile Pro Arg Ser Leu Leu Asp Glu Tyr Arg Glu Gly Leu Leu
                645                 650                 655 gta ggt aca gcg tgt gat gaa ggt gaa tta ttt acg gca gtt atg cag      2016
Val Gly Thr Ala Cys Asp Glu Gly Glu Leu Phe Thr Ala Val Met Gln
            660                 665                 670 aag gac cag agc caa gtt gaa aaa att gcc aaa tat tat gat ttt att      2064
Lys Asp Gln Ser Gln Val Glu Lys Ile Ala Lys Tyr Tyr Asp Phe Ile
        675                 680                 685 gaa att caa cca ccg gca ctt tat caa gat tta att gat aga gag ctt      2112
Glu Ile Gln Pro Pro Ala Leu Tyr Gln Asp Leu Ile Asp Arg Glu Leu
    690                 695                 700 att aga gat act gaa aca tta cat gaa att tat caa cgt tta ata cat      2160
Ile Arg Asp Thr Glu Thr Leu His Glu Ile Tyr Gln Arg Leu Ile His
705                 710                 715                 720 gca ggt gac aca gcg ggt ata cct gtt att gcg aca gga aat gca cac      2208
Ala Gly Asp Thr Ala Gly Ile Pro Val Ile Ala Thr Gly Asn Ala His
                725                 730                 735 tat ttg ttt gaa cat gat ggt atc gca cgt aaa att tta ata gca tca      2256
Tyr Leu Phe Glu His Asp Gly Ile Ala Arg Lys Ile Leu Ile Ala Ser
            740                 745                 750 caa ccc ggc aat cca ctt aat cgc tca act tta ccg gaa gca cat ttt      2304
Gln Pro Gly Asn Pro Leu Asn Arg Ser Thr Leu Pro Glu Ala His Phe
        755                 760                 765 aga act aca gat gaa atg tta aac gag ttt cat ttt tta ggt gaa gaa      2352
Arg Thr Thr Asp Glu Met Leu Asn Glu Phe His Phe Leu Gly Glu Glu
    770                 775                 780 aaa gcg cat gaa att gtt gtg aaa aat aca aac gaa tta gca gat cga      2400
Lys Ala His Glu Ile Val Val Lys Asn Thr Asn Glu Leu Ala Asp Arg
785                 790                 795                 800 att gaa cgt gtt gtt cct att aaa gat gaa tta tac aca ccg cgt atg      2448
Ile Glu Arg Val Val Pro Ile Lys Asp Glu Leu Tyr Thr Pro Arg Met
                805                 810                 815 gaa ggt gct aac gaa gaa att aga gaa cta agt tat aca aat gcg cgt      2496
Glu Gly Ala Asn Glu Glu Ile Arg Glu Leu Ser Tyr Thr Asn Ala Arg
            820                 825                 830 aaa ctg tat ggt gaa gac ctg cct caa atc gta att gat cga tta gaa      2544
Lys Leu Tyr Gly Glu Asp Leu Pro Gln Ile Val Ile Asp Arg Leu Glu
        835                 840                 845 aaa gaa tta aaa agt att atc ggt aat gga ttt gcg gta att tac tta      2592
Lys Glu Leu Lys Ser Ile Ile Gly Asn Gly Phe Ala Val Ile Tyr Leu
    850                 855                 860 att tcg caa cgt tta gtt aaa aaa tca tta gat gat gga tac tta gtt      2640
Ile Ser Gln Arg Leu Val Lys Lys Ser Leu Asp Asp Gly Tyr Leu Val
865                 870                 875                 880 ggt tcc cgt ggt tca gta ggt tct agt ttt gta gcg aca atg act gag      2688
Gly Ser Arg Gly Ser Val Gly Ser Ser Phe Val Ala Thr Met Thr Glu
                885                 890                 895 att act gaa gta aac ccg tta ccg cca cac tat att tgt ccg aac tgt      2736
Ile Thr Glu Val Asn Pro Leu Pro Pro His Tyr Ile Cys Pro Asn Cys
            900                 905                 910 aaa acg agt gaa ttt ttc aat gat ggt tca gta gga tca gga ttc gat      2784
Lys Thr Ser Glu Phe Phe Asn Asp Gly Ser Val Gly Ser Gly Phe Asp
        915                 920                 925 tta cct gat aag acg tgt gaa act tgt gga gcg cca ctt att aaa gaa      2832
Leu Pro Asp Lys Thr Cys Glu Thr Cys Gly Ala Pro Leu Ile Lys Glu
    930                 935                 940 gga caa gat att ccg ttt gaa aca ttt tta gga ttt aag gga gat aaa      2880
Gly Gln Asp Ile Pro Phe Glu Thr Phe Leu Gly Phe Lys Gly Asp Lys
945                 950                 955                 960
```

```
gtt cct gat atc gac tta aac ttt agt ggt gaa tat caa ccg aat gcc      2928
Val Pro Asp Ile Asp Leu Asn Phe Ser Gly Glu Tyr Gln Pro Asn Ala
                965                 970                 975 cat aac tac aca aaa gta tta ttt ggt gag gat aaa gta ttc cgt gca      2976
His Asn Tyr Thr Lys Val Leu Phe Gly Glu Asp Lys Val Phe Arg Ala
            980                 985                 990 ggt aca att ggt acc gtt gct gaa     aag act gct ttt ggt tat gtt aaa  3024
Gly Thr Ile Gly Thr Val Ala Glu     Lys Thr Ala Phe Gly Tyr Val Lys
                995                 1000                1005 ggt tat ttg aat gat caa ggc atc cac aaa aga ggc gct gaa ata          3069
Gly Tyr Leu Asn Asp Gln Gly Ile His Lys Arg Gly Ala Glu Ile
        1010                1015                1020 gat cga ctc gtt aaa gga tgt aca ggt gtt aaa cgt aca act gga          3114
Asp Arg Leu Val Lys Gly Cys Thr Gly Val Lys Arg Thr Thr Gly
1025                1030                1035 cag cat cca gga ggt att att gta gta cct gat tac atg gat att          3159
Gln His Pro Gly Gly Ile Ile Val Val Pro Asp Tyr Met Asp Ile
        1040                1045                1050 tat gat ttt acg ccg ata caa tat cct gcc gat gat caa aat tca          3204
Tyr Asp Phe Thr Pro Ile Gln Tyr Pro Ala Asp Asp Gln Asn Ser
1055                1060                1065 gca tgg atg acg aca cat ttt gat ttc cat tct att cat gat aat          3249
Ala Trp Met Thr Thr His Phe Asp Phe His Ser Ile His Asp Asn
        1070                1075                1080 gta tta aaa ctt gat ata ctt gga cac gat gat cca aca atg att          3294
Val Leu Lys Leu Asp Ile Leu Gly His Asp Asp Pro Thr Met Ile
1085                1090                1095 cgt atg ctt caa gat tta tcg ggc att gat cca aaa acg ata cct          3339
Arg Met Leu Gln Asp Leu Ser Gly Ile Asp Pro Lys Thr Ile Pro
        1100                1105                1110 gta gat gac aaa gaa gtc atg caa ata ttt agt aca cct gaa agt          3384
Val Asp Asp Lys Glu Val Met Gln Ile Phe Ser Thr Pro Glu Ser
1115                1120                1125 tta ggt gtt act gaa gat gaa att tta tgt aaa aca ggt acg ttt          3429
Leu Gly Val Thr Glu Asp Glu Ile Leu Cys Lys Thr Gly Thr Phe
        1130                1135                1140 ggg gtt cca gaa ttc ggt aca ggg ttc gtg cgt caa atg tta gaa          3474
Gly Val Pro Glu Phe Gly Thr Gly Phe Val Arg Gln Met Leu Glu
1145                1150                1155 gat aca aag cca aca aca ttt tct gaa tta gtt caa atc tca gga          3519
Asp Thr Lys Pro Thr Thr Phe Ser Glu Leu Val Gln Ile Ser Gly
        1160                1165                1170 tta tct cat ggt aca gat gtg tgg tta ggc aat gct caa gaa tta          3564
Leu Ser His Gly Thr Asp Val Trp Leu Gly Asn Ala Gln Glu Leu
1175                1180                1185 att aaa acc ggt ata tgt gat tta tca agt gta att ggt tgt cgt          3609
Ile Lys Thr Gly Ile Cys Asp Leu Ser Ser Val Ile Gly Cys Arg
        1190                1195                1200 gat gat atc atg gtt tat tta atg tat gct ggt tta gaa cca tca          3654
Asp Asp Ile Met Val Tyr Leu Met Tyr Ala Gly Leu Glu Pro Ser
1205                1210                1215 atg gct ttt aaa ata atg gag tca gta cgt aaa ggt aaa ggt tta          3699
Met Ala Phe Lys Ile Met Glu Ser Val Arg Lys Gly Lys Gly Leu
        1220                1225                1230 act gaa gaa atg att gaa acg atg aaa gaa aat gaa gtg ccg gat          3744
Thr Glu Glu Met Ile Glu Thr Met Lys Glu Asn Glu Val Pro Asp
1235                1240                1245 tgg tat tta gat tca tgt ctt aaa att aag tac atg ttc cct aaa          3789
Trp Tyr Leu Asp Ser Cys Leu Lys Ile Lys Tyr Met Phe Pro Lys
        1250                1255                1260
```

```
gcc cat gca gca gca tac gtt tta atg gca gta cgt atc gca tat      3834
Ala His Ala Ala Ala Tyr Val Leu Met Ala Val Arg Ile Ala Tyr
    1265             1270                 1275 ttc aaa gta cat cat cca ctt tat tac tat gca tct tac ttt aca      3879
Phe Lys Val His His Pro Leu Tyr Tyr Tyr Ala Ser Tyr Phe Thr
1280             1285                 1290 att cgt gcg tca gat ttt gat tta atc acg atg att aaa gat aaa      3924
Ile Arg Ala Ser Asp Phe Asp Leu Ile Thr Met Ile Lys Asp Lys
        1295             1300                 1305 aca agc att cga aat act gta aaa gac atg tat tct cgc tat atg      3969
Thr Ser Ile Arg Asn Thr Val Lys Asp Met Tyr Ser Arg Tyr Met
    1310             1315                 1320 gat cta ggt aaa aaa gaa aaa gac gta tta aca gtc ttg gaa att      4014
Asp Leu Gly Lys Lys Glu Lys Asp Val Leu Thr Val Leu Glu Ile
1325             1330                 1335 atg aat gaa atg gcg cat cga ggt tat cga atg caa ccg att agt      4059
Met Asn Glu Met Ala His Arg Gly Tyr Arg Met Gln Pro Ile Ser
        1340             1345                 1350 tta gaa aag agt cag gcg ttc gaa ttt atc att gaa ggc gat aca      4104
Leu Glu Lys Ser Gln Ala Phe Glu Phe Ile Ile Glu Gly Asp Thr
    1355             1360                 1365 ctt att ccg ccg ttc ata tca gtg cct ggg ctt ggc gaa aac gtt      4149
Leu Ile Pro Pro Phe Ile Ser Val Pro Gly Leu Gly Glu Asn Val
1370             1375                 1380 gcg aaa cga att gtt gaa gct cgt gac gat ggc cca ttt tta tca      4194
Ala Lys Arg Ile Val Glu Ala Arg Asp Asp Gly Pro Phe Leu Ser
        1385             1390                 1395 aaa gaa gat tta aac aaa aaa gct gga tta tct cag aaa att att      4239
Lys Glu Asp Leu Asn Lys Lys Ala Gly Leu Ser Gln Lys Ile Ile
    1400             1405                 1410 gag tat tta gat gag tta ggc tca tta ccg aat tta cca gat aaa      4284
Glu Tyr Leu Asp Glu Leu Gly Ser Leu Pro Asn Leu Pro Asp Lys
1415             1420                 1425 gct caa ctt tcg ata ttt gat atg taa                              4311
Ala Gln Leu Ser Ile Phe Asp Met
        1430             1435

<210> SEQ ID NO 103
<211> LENGTH: 1436
<212> TYPE: PRT
<213> ORGANISM: Staphylococcus aureus

<400> SEQUENCE: 103

Met Thr Glu Gln Gln Lys Phe Lys Val Leu Ala Asp Gln Ile Lys Ile
1               5                   10                  15

Ser Asn Gln Leu Asp Ala Glu Ile Leu Asn Ser Gly Glu Leu Thr Arg
            20                  25                  30

Ile Asp Val Ser Asn Lys Asn Arg Thr Trp Glu Phe His Ile Thr Leu
        35                  40                  45

Pro Gln Phe Leu Ala His Glu Asp Tyr Leu Leu Phe Ile Asn Ala Ile
    50                  55                  60

Glu Gln Glu Phe Lys Asp Ile Ala Asn Val Thr Cys Arg Phe Thr Val
65                  70                  75                  80

Thr Asn Gly Thr Asn Gln Asp Glu His Ala Ile Lys Tyr Phe Gly His
                85                  90                  95

Cys Ile Asp Gln Thr Ala Leu Ser Pro Lys Val Lys Gly Gln Leu Lys
            100                 105                 110

Gln Lys Lys Leu Ile Met Ser Gly Lys Val Leu Lys Val Met Val Ser
        115                 120                 125
```

```
Asn Asp Ile Glu Arg Asn His Phe Asp Lys Ala Cys Asn Gly Ser Leu
    130                 135                 140
Ile Lys Ala Phe Arg Asn Cys Gly Phe Asp Ile Asp Lys Ile Ile Phe
145                 150                 155                 160
Glu Thr Asn Asp Asn Asp Gln Glu Gln Asn Leu Ala Ser Leu Glu Ala
                165                 170                 175
His Ile Gln Glu Glu Asp Glu Gln Ser Ala Arg Leu Ala Thr Glu Lys
            180                 185                 190
Leu Glu Lys Met Lys Ala Glu Lys Ala Lys Gln Gln Asp Asn Asn Glu
        195                 200                 205
Ser Ala Val Asp Lys Cys Gln Ile Gly Lys Pro Ile Gln Ile Glu Asn
    210                 215                 220
Ile Lys Pro Ile Glu Ser Ile Ile Glu Glu Phe Lys Val Ala Ile
225                 230                 235                 240
Glu Gly Val Ile Phe Asp Ile Asn Leu Lys Glu Leu Lys Ser Gly Arg
                245                 250                 255
His Ile Val Glu Ile Lys Val Thr Asp Tyr Thr Asp Ser Leu Val Leu
            260                 265                 270
Lys Met Phe Thr Arg Lys Asn Lys Asp Asp Leu Glu His Phe Lys Ala
        275                 280                 285
Leu Ser Val Gly Lys Trp Val Arg Ala Gln Gly Arg Ile Glu Glu Asp
    290                 295                 300
Thr Phe Ile Arg Asp Leu Val Met Met Met Ser Asp Ile Glu Glu Ile
305                 310                 315                 320
Lys Lys Ala Thr Lys Lys Asp Lys Ala Glu Glu Lys Arg Val Glu Phe
                325                 330                 335
His Leu His Thr Ala Met Ser Gln Met Asp Gly Ile Pro Asn Ile Gly
            340                 345                 350
Ala Tyr Val Lys Gln Ala Ala Asp Trp Gly His Pro Ala Ile Ala Val
        355                 360                 365
Thr Asp His Asn Val Val Gln Ala Phe Pro Asp Ala His Ala Ala Ala
    370                 375                 380
Glu Lys His Gly Ile Lys Met Ile Tyr Gly Met Glu Gly Met Leu Val
385                 390                 395                 400
Asp Asp Gly Val Pro Ile Ala Tyr Lys Pro Gln Asp Val Val Leu Lys
                405                 410                 415
Asp Ala Thr Tyr Val Val Phe Asp Val Glu Thr Thr Gly Leu Ser Asn
            420                 425                 430
Gln Tyr Asp Lys Ile Ile Glu Leu Ala Ala Val Lys Val His Asn Gly
        435                 440                 445
Glu Ile Ile Asp Lys Phe Glu Arg Phe Ser Asn Pro His Glu Arg Leu
    450                 455                 460
Ser Glu Thr Ile Ile Asn Leu Thr His Ile Thr Asp Asp Met Leu Val
465                 470                 475                 480
Asp Ala Pro Glu Ile Glu Glu Val Leu Thr Glu Phe Lys Glu Trp Val
                485                 490                 495
Gly Asp Ala Ile Phe Val Ala His Asn Ala Ser Phe Asp Met Gly Phe
            500                 505                 510
Ile Asp Thr Gly Tyr Glu Arg Leu Gly Phe Gly Pro Ser Thr Asn Gly
        515                 520                 525
Val Ile Asp Thr Leu Glu Leu Ser Arg Thr Ile Asn Thr Glu Tyr Gly
    530                 535                 540
Lys His Gly Leu Asn Phe Leu Ala Lys Lys Tyr Gly Val Glu Leu Thr
```

-continued

```
         545                 550                 555                 560
Gln His His Arg Ala Ile Tyr Asp Thr Glu Ala Thr Ala Tyr Ile Phe
                 565                 570                 575
Ile Lys Met Val Gln Gln Met Lys Glu Leu Gly Val Leu Asn His Asn
                 580                 585                 590
Glu Ile Asn Lys Lys Leu Ser Asn Glu Asp Ala Tyr Lys Arg Ala Arg
                 595                 600                 605
Pro Ser His Val Thr Leu Ile Val Gln Asn Gln Gln Gly Leu Lys Asn
                 610                 615                 620
Leu Phe Lys Ile Val Ser Ala Ser Leu Val Lys Tyr Phe Tyr Arg Thr
625                 630                 635                 640
Pro Arg Ile Pro Arg Ser Leu Leu Asp Glu Tyr Arg Glu Gly Leu Leu
                 645                 650                 655
Val Gly Thr Ala Cys Asp Glu Gly Glu Leu Phe Thr Ala Val Met Gln
                 660                 665                 670
Lys Asp Gln Ser Gln Val Glu Lys Ile Ala Lys Tyr Tyr Asp Phe Ile
                 675                 680                 685
Glu Ile Gln Pro Pro Ala Leu Tyr Gln Asp Leu Ile Asp Arg Glu Leu
                 690                 695                 700
Ile Arg Asp Thr Glu Thr Leu His Glu Ile Tyr Gln Arg Leu Ile His
705                 710                 715                 720
Ala Gly Asp Thr Ala Gly Ile Pro Val Ile Ala Thr Gly Asn Ala His
                 725                 730                 735
Tyr Leu Phe Glu His Asp Gly Ile Ala Arg Lys Ile Leu Ile Ala Ser
                 740                 745                 750
Gln Pro Gly Asn Pro Leu Asn Arg Ser Thr Leu Pro Glu Ala His Phe
                 755                 760                 765
Arg Thr Thr Asp Glu Met Leu Asn Glu Phe His Phe Leu Gly Glu Glu
                 770                 775                 780
Lys Ala His Glu Ile Val Val Lys Asn Thr Asn Glu Leu Ala Asp Arg
785                 790                 795                 800
Ile Glu Arg Val Val Pro Ile Lys Asp Glu Leu Tyr Thr Pro Arg Met
                 805                 810                 815
Glu Gly Ala Asn Glu Glu Ile Arg Glu Leu Ser Tyr Thr Asn Ala Arg
                 820                 825                 830
Lys Leu Tyr Gly Glu Asp Leu Pro Gln Ile Val Ile Asp Arg Leu Glu
                 835                 840                 845
Lys Glu Leu Lys Ser Ile Ile Gly Asn Gly Phe Ala Val Ile Tyr Leu
                 850                 855                 860
Ile Ser Gln Arg Leu Val Lys Lys Ser Leu Asp Asp Gly Tyr Leu Val
865                 870                 875                 880
Gly Ser Arg Gly Ser Val Gly Ser Ser Phe Val Ala Thr Met Thr Glu
                 885                 890                 895
Ile Thr Glu Val Asn Pro Leu Pro Pro His Tyr Ile Cys Pro Asn Cys
                 900                 905                 910
Lys Thr Ser Glu Phe Phe Asn Asp Gly Ser Val Gly Ser Gly Phe Asp
                 915                 920                 925
Leu Pro Asp Lys Thr Cys Glu Thr Cys Gly Ala Pro Leu Ile Lys Glu
                 930                 935                 940
Gly Gln Asp Ile Pro Phe Glu Thr Phe Leu Gly Phe Lys Gly Asp Lys
945                 950                 955                 960
Val Pro Asp Ile Asp Leu Asn Phe Ser Gly Glu Tyr Gln Pro Asn Ala
                 965                 970                 975
```

-continued

His Asn Tyr Thr Lys Val Leu Phe Gly Glu Asp Lys Val Phe Arg Ala
                980                 985                 990
Gly Thr Ile Gly Thr Val Ala Glu Lys Thr Ala Phe Gly Tyr Val Lys
        995                 1000                1005
Gly Tyr Leu Asn Asp Gln Gly Ile His Lys Arg Gly Ala Glu Ile
    1010                1015                1020
Asp Arg Leu Val Lys Gly Cys Thr Gly Val Lys Arg Thr Thr Gly
    1025                1030                1035
Gln His Pro Gly Gly Ile Ile Val Val Pro Asp Tyr Met Asp Ile
    1040                1045                1050
Tyr Asp Phe Thr Pro Ile Gln Tyr Pro Ala Asp Gln Asn Ser
    1055                1060                1065
Ala Trp Met Thr Thr His Phe Asp Phe His Ser Ile His Asp Asn
    1070                1075                1080
Val Leu Lys Leu Asp Ile Leu Gly His Asp Asp Pro Thr Met Ile
    1085                1090                1095
Arg Met Leu Gln Asp Leu Ser Gly Ile Asp Pro Lys Thr Ile Pro
    1100                1105                1110
Val Asp Asp Lys Glu Val Met Gln Ile Phe Ser Thr Pro Glu Ser
    1115                1120                1125
Leu Gly Val Thr Glu Asp Glu Ile Leu Cys Lys Thr Gly Thr Phe
    1130                1135                1140
Gly Val Pro Glu Phe Gly Thr Gly Phe Val Arg Gln Met Leu Glu
    1145                1150                1155
Asp Thr Lys Pro Thr Thr Phe Ser Glu Leu Val Gln Ile Ser Gly
    1160                1165                1170
Leu Ser His Gly Thr Asp Val Trp Leu Gly Asn Ala Gln Glu Leu
    1175                1180                1185
Ile Lys Thr Gly Ile Cys Asp Leu Ser Ser Val Ile Gly Cys Arg
    1190                1195                1200
Asp Asp Ile Met Val Tyr Leu Met Tyr Ala Gly Leu Glu Pro Ser
    1205                1210                1215
Met Ala Phe Lys Ile Met Glu Ser Val Arg Lys Gly Lys Gly Leu
    1220                1225                1230
Thr Glu Glu Met Ile Glu Thr Met Lys Glu Asn Glu Val Pro Asp
    1235                1240                1245
Trp Tyr Leu Asp Ser Cys Leu Lys Ile Lys Tyr Met Phe Pro Lys
    1250                1255                1260
Ala His Ala Ala Ala Tyr Val Leu Met Ala Val Arg Ile Ala Tyr
    1265                1270                1275
Phe Lys Val His His Pro Leu Tyr Tyr Tyr Ala Ser Tyr Phe Thr
    1280                1285                1290
Ile Arg Ala Ser Asp Phe Asp Leu Ile Thr Met Ile Lys Asp Lys
    1295                1300                1305
Thr Ser Ile Arg Asn Thr Val Lys Asp Met Tyr Ser Arg Tyr Met
    1310                1315                1320
Asp Leu Gly Lys Lys Glu Lys Asp Val Leu Thr Val Leu Glu Ile
    1325                1330                1335
Met Asn Glu Met Ala His Arg Gly Tyr Arg Met Gln Pro Ile Ser
    1340                1345                1350
Leu Glu Lys Ser Gln Ala Phe Glu Phe Ile Ile Glu Gly Asp Thr
    1355                1360                1365
Leu Ile Pro Pro Phe Ile Ser Val Pro Gly Leu Gly Glu Asn Val
    1370                1375                1380

Ala Lys Arg Ile Val Glu Ala Arg Asp Asp Gly Pro Phe Leu Ser
    1385                1390                1395

Lys Glu Asp Leu Asn Lys Lys Ala Gly Leu Ser Gln Lys Ile Ile
    1400                1405                1410

Glu Tyr Leu Asp Glu Leu Gly Ser Leu Pro Asn Leu Pro Asp Lys
    1415                1420                1425

Ala Gln Leu Ser Ile Phe Asp Met
    1430                1435

<210> SEQ ID NO 104
<211> LENGTH: 429
<212> TYPE: DNA
<213> ORGANISM: Pseudomonas aeruginosa

<400> SEQUENCE: 104
gtgacccggg tcgatttcta cgtgatcccc agcgccgatc cgtcggcgcg cctgcaggtc      60
gcctgccgcc tggccgagaa ggcctggcgg cagggcatgc aggtctacct gcattgcgcc     120
gacgaggcgc agcgcagcga gttggacggc cgcctgtgga gcttccgcgg cgaggccttc     180
attcctcaca gcctggccga ggaagacgcc gaggcgcccg tcgccctggg cctgggcgag     240
cccccgggga accatcgcga cctgctgatc aacctgaccc tcgaggcccc cggcttcgtc     300
ccgaactttt cgcgggtggc cgaactggtg gtcgaggagc cggcgatccg ccaggcggca     360
cgggataaat tccgcttcta ccgggagcag ggctatcctc tacaggacca tcgcctgccg     420
cgtatctga                                                             429

<210> SEQ ID NO 105
<211> LENGTH: 429
<212> TYPE: DNA
<213> ORGANISM: Pseudomonas aeruginosa
<220> FEATURE:
<221> NAME/KEY: CDS
<222> LOCATION: (1)..(429)

<400> SEQUENCE: 105 gtg acc cgg gtc gat ttc tac gtg atc ccc agc gcc gat ccg tcg gcg      48
Val Thr Arg Val Asp Phe Tyr Val Ile Pro Ser Ala Asp Pro Ser Ala
1               5                   10                  15 cgc ctg cag gtc gcc tgc cgc ctg gcc gag aag gcc tgg cgg cag ggc      96
Arg Leu Gln Val Ala Cys Arg Leu Ala Glu Lys Ala Trp Arg Gln Gly
                20                  25                  30 atg cag gtc tac ctg cat tgc gcc gac gag gcg cag cgc agc gag ttg     144
Met Gln Val Tyr Leu His Cys Ala Asp Glu Ala Gln Arg Ser Glu Leu
            35                  40                  45 gac ggc cgc ctg tgg agc ttc cgc ggc gag gcc ttc att cct cac agc     192
Asp Gly Arg Leu Trp Ser Phe Arg Gly Glu Ala Phe Ile Pro His Ser
        50                  55                  60 ctg gcc gag gaa gac gcc gag gcg ccc gtc gcc ctg ggc ctg ggc gag     240
Leu Ala Glu Glu Asp Ala Glu Ala Pro Val Ala Leu Gly Leu Gly Glu
65                  70                  75                  80 ccc ccg ggg aac cat cgc gac ctg ctg atc aac ctg acc ctc gag gcc     288
Pro Pro Gly Asn His Arg Asp Leu Leu Ile Asn Leu Thr Leu Glu Ala
                85                  90                  95 ccc ggc ttc gtc ccg aac ttt tcg cgg gtg gcc gaa ctg gtg gtc gag     336
Pro Gly Phe Val Pro Asn Phe Ser Arg Val Ala Glu Leu Val Val Glu
                100                 105                 110 gag ccg gcg atc cgc cag gcg gca cgg gat aaa ttc cgc ttc tac cgg     384
Glu Pro Ala Ile Arg Gln Ala Ala Arg Asp Lys Phe Arg Phe Tyr Arg
            115                 120                 125

```
gag cag ggc tat cct cta cag gac cat cgc ctg ccg cgt atc tga         429
Glu Gln Gly Tyr Pro Leu Gln Asp His Arg Leu Pro Arg Ile
        130                 135                 140

<210> SEQ ID NO 106
<211> LENGTH: 142
<212> TYPE: PRT
<213> ORGANISM: Pseudomonas aeruginosa

<400> SEQUENCE: 106

Val Thr Arg Val Asp Phe Tyr Val Ile Pro Ser Ala Asp Pro Ser Ala
1               5                   10                  15

Arg Leu Gln Val Ala Cys Arg Leu Ala Glu Lys Ala Trp Arg Gln Gly
            20                  25                  30

Met Gln Val Tyr Leu His Cys Ala Asp Glu Ala Gln Arg Ser Glu Leu
        35                  40                  45

Asp Gly Arg Leu Trp Ser Phe Arg Gly Glu Ala Phe Ile Pro His Ser
    50                  55                  60

Leu Ala Glu Glu Asp Ala Glu Ala Pro Val Ala Leu Gly Leu Gly Glu
65                  70                  75                  80

Pro Pro Gly Asn His Arg Asp Leu Leu Ile Asn Leu Thr Leu Glu Ala
                85                  90                  95

Pro Gly Phe Val Pro Asn Phe Ser Arg Val Ala Glu Leu Val Val Glu
            100                 105                 110

Glu Pro Ala Ile Arg Gln Ala Ala Arg Asp Lys Phe Arg Phe Tyr Arg
        115                 120                 125

Glu Gln Gly Tyr Pro Leu Gln Asp His Arg Leu Pro Arg Ile
        130                 135                 140
```